United States Patent
Strauch et al.

(10) Patent No.: US 7,479,539 B1
(45) Date of Patent: Jan. 20, 2009

(54) HEDGEHOG FUSION PROTEINS

(75) Inventors: Kathryn Strauch, Bedford, MA (US); Ellen A. Garber, Cambridge, MA (US); Frederick R. Taylor, Milton, MA (US)

(73) Assignee: Curis, Inc., Cambridge, MA (US)

( * ) Notice: Subject to any disclaimer, the term of this patent is extended or adjusted under 35 U.S.C. 154(b) by 934 days.

(21) Appl. No.: 10/129,162

(22) PCT Filed: Nov. 2, 2000

(86) PCT No.: PCT/US00/30405

§ 371 (c)(1),
(2), (4) Date: Mar. 14, 2003

(87) PCT Pub. No.: WO01/34654

PCT Pub. Date: May 17, 2001

Related U.S. Application Data

(60) Provisional application No. 60/164,025, filed on Nov. 5, 1999.

(51) Int. Cl.
| | |
|---|---|
| C07K 14/47 | (2006.01) |
| C07K 16/46 | (2006.01) |
| C07K 19/00 | (2006.01) |
| A61K 38/17 | (2006.01) |
| A61K 39/44 | (2006.01) |

(52) U.S. Cl. .................. 530/350; 530/387.3; 536/23.4; 514/12; 424/134.1

(58) Field of Classification Search ........................ None
See application file for complete search history.

(56) References Cited

U.S. PATENT DOCUMENTS

| 4,710,761 A | 12/1987 | Kapur et al. |
| 4,725,669 A | 2/1988 | Essex et al. |
| 5,116,964 A * | 5/1992 | Capon et al. ............... 536/23.5 |
| 5,759,811 A | 6/1998 | Epstein et al. |
| 5,789,543 A * | 8/1998 | Ingham et al. .............. 530/350 |
| 5,844,079 A | 12/1998 | Ingham et al. |
| 6,444,793 B1 | 9/2002 | Pepinsky et al. |
| 6,897,297 B1 * | 5/2005 | Pepinsky et al. ............ 530/402 |

FOREIGN PATENT DOCUMENTS

| WO | WO 87/02671 | 5/1987 |
| WO | WO 95/23223 | 8/1995 |
| WO | WO 99/28343 | 6/1999 |
| WO | WO 00/25725 | 5/2000 |

OTHER PUBLICATIONS

Wells (Sep. 18, 1990) Biochemistry 29(37): 8509-8517.*

(Continued)

*Primary Examiner*—Elizabeth C. Kemmerer
*Assistant Examiner*—Zachary C Howard
(74) *Attorney, Agent, or Firm*—Ropes & Gray LLP

(57) ABSTRACT

A fusion polypeptide is described having the amino acid sequence X-Y-Z, or portion thereof, comprising the amino acid sequence of a hedgehog (X); Y is an optional linker moiety; and Z is a polypeptide comprising at least a portion of a polypeptide other than hedgehog. It is preferred that X is a human hedgehog. Mutants of hedgehog are also described.

39 Claims, 3 Drawing Sheets

OTHER PUBLICATIONS

Ngo et al. (Mar. 2, 1995) "The Protein Folding Problem and Tertiary Structure Prediction, Chapter 14: Computational Complexity Protein Structure Prediction, and the Levinthal Paradox" pp. 492-495.*
Bork (2000) Genome Research 10:398.*
Skolnick and Fetrow (2000) Trends in Biotech. 18(1): 34.*
Doerks et al. (Jun. 1998) Trends in Genetics 14(6): 248.*
Smith and Zhang (Nov. 1997) Nature Biotechnology 15:1222.*
Brenner (Apr. 1999) Trends in Genetics 15(4): 132.*
Bork and Bairoch (Oct. 1996) Trends in Genetics 12(10): 425.*
Pepinsky et al, 2002, J Pharm Sci. 91(2): 371-387.*
Pepinsky et al. Journal of Biological Chemistry. 22: 14037-14045, published May 28, 1998.*
Katsuura, et al (FEBS Letters. 447: 325-328, published Mar. 26, 1999).*
Faber et al (1995. Yeast. 11: 1331-1344).*
Lehninger et al, 1996 (Principles of Biochemistry, Second Edition, Worth Publishers NY, NY; pp. 114-116 and p. 1000).*
Alcedo, J. et al. The *Drosophila* smoothened Gene Encodes a Seven-Pass Membrane Protein, a Putative Receptor for the Hedgehog Signal. *Cell* 86. 221-232 (1996).
Alexandre, C. et al. Transcriptional activation of hedgehog target genes in *Drosophila* is mediated directly by the *Cubitus interrupts* protein, a member of the GLI family of zinc finger DNA-binding proteins. *Genes & Dev.* 10, 2003-2013 (1996).
Bumcrot, D.A. et al. Preteolytic Processing Yields Two Secreted Forms of Sonic hedgehog. *Mol. Cell Biol.* 15, 2294-2303 (1995).
Chang, D.E. et al. Products, genetic linkage and limb patterning activity of a murine hedgehog gene. *Development* 120, 3339-3353 (1994).
Dominguez, M. et al. Sending and Receiving the Hedgehog Signal: Control by the *Drosophila gli* Protein *Cubitus interruptus*. *Science* 272, 1621-1625 (1996).
Echelard, Y. et al. Sonic Hedgehog, a Member of a Family of Putative Signaling Molecules, is Implicated in the Regulation of CNS Polarity. *Cell* 75, 1417-1417 (1993).
Ekker, S.C. et al. Patterning activities of vertebrate hedgehog proteins in the developing eye and brain. *Curr. Biol.* 5, 944-955 (1995).
Fan, C.-M. et al. Long-Range Sclerotome Induction by Sonic Hedgehog: Direct Role of the Amino-Terminal Cleavage Product and Modulation by the Cyclic AMP Signaling Pathway. *Cell* 81, 457-465 (1995).
Hall, T.M.T. et al. A potential catalytic site revealed by the 1.7-A crystal structure of the amino-terminal signaling domain of Sonic hedgehog. *Nature* 378, 212-216 (378 (1995).
Johnson, R.L. & Tabin, C. The Long and Short of hedgehog Signaling. *Cell* 81, 313-316 (1995).

Katsuura, M. et al. the NH2-terminal region of the active domain of sonic hedgehog is necessary for its signal transduction. *FEBS Letters* 447, 325-328 (1999).
Lee, J.J. et al. Secretion and Localized Transcription Suggest a Role in Positional Signalling for Products of the Segmentation Gene hedgehog. *Cell* 71. 33-50 (1992).
Lee, J.J. et al. Autoproteolysis in hedgehog Protein Biogenesis. *Science* 266, 1528-1536 (1994).
Marigo, V et al. Biochemical evidence that Patched is the Hedgehog receptor. *Nature* 384, 176-179 (1996).
Mohler, J. & Vani, K. Molecular organization and embryonic expression of the hedgehog gene involved in cell-cell communication in segmental patterning of *Drosophila*. *Development* 115, 957-971 (1992).
Pepinsky, B. et al. Identification of a Palmitic Acid-modified Form of Human Sonic hedgehog. *J. Biol. Chem.* 273, 14037-14045 (1998).
Perrimon, N. Serpentine Proteins Slither into the Wingless and Hedgehog Fields. *Cell* 80, 517-520 (1995).
Porter, J.A. et al. Hedgehog Patterning Activity: Role of a Lipophilic Modification Mediated by the Carboxy-Terminal Autoprocessing Domain. *Cell* 86, 21-34 (1995).
Porter, J.A. et al. The product of hedgehog autoproteolytic cleavage active in local and long-range signaling. *Nature* 374, 363-366 (1995).
Porter, J.A. et al. Cholesterol Modification of Hedgehog Signaling Proteins in Animal Development. *Science* 274, 255-258 (1996).
Reis, K.J. et al. Streptococcal Fc Receptors. *J. Immunol.* 132, 3098-3102 (1984).
Roelink, H. et al. Floor Plate and Motor Neuron Induction by vhh-l, a Vertebrate Homolog of hedgehog Expressed by the Notochord *Cell* 76, 761-775 (1994).
Roelink, H. et al. Floor Plate and Motor Neuron Induction by Different Concentrations of the Amino-Terminal Cleavage Product of Sonic Hedgehog Autoproteolysis. *Cell* 81, 445-455 (1995).
Riddle, R.D. et al. Sonic hedgehog Mediates the Polarizing Activity of the ZPA. *Cell* 75, 1401-1416 (1993).
Stone, D.M. et al. The tumour-suppressor gene patched encodes a candidate receptor for Sonic hedgehog. *Nature* 384, 129-134 (1996).
Tabata, T. et al. The *Drosphila* hedgehog gene is expressed specifically in posterior compartment cells and is a target of engrailed regulation. *Genes Dev.* 2635-2645 (1992).
Therond. P.P. et al. Phosphorylation of the fused protein kinase in response to signaling from hedgehog. *PNAS* 93. 4224-4228 (1996).
Williams, K.P. et al. Functional antagonists of sonic hedgehog reveal the importance of the N terminus for activity. *J. Cell Sci.* 112, 4405-4414 (1999).

* cited by examiner

Figure 1 : Alignment of N-terminal fragments of Human Hedgehog Proteins

```
       1
Indian CGPGRVVGSR  RRPPRK-LVP             LAYKQFSPNV  PEKTLGASGR  YEGKIARSSE Sonic  CGPGRGFG-K  RRHPKK-LTP  LAYKQFIPNV  AEKTLGASGR  YEGKISRNSE
Desert CGPGRGPVGR  RRYARKQLVP  LLYKQFVPGV  PERTLGASGP  AEGRVARGSE 51
Indian RFKELTPNYN  PDIIFKDEEN  TGADRLMTQR  CKDRLNSLAI  SVMNQWPGVK
Sonic  RFKELTPNYN  PDIIFKDEEN  TGADRLMTQR  CKDKLNALAI  SVMNQWPGVK
Desert RFRDLVPNYN  PDIIFKDEEN  SGADRLMTER  CKERVNALAI  AVMNMWPGVR 101
Indian LRVTEGWDED  GHHSEESLHY  EGRAVDITTS  DRDRNKYGLL  ARLAVEAGFD
Sonic  LRVTEGWDED  GHHSEESLHY  EGRAVDITTS  DRDRSKYGML  ARLAVEAGFD
Desert LRVTEGWDED  GHHAQDSLHY  EGRALDITTS  DRDRNKYGLL  ARLAVEAGFD 151
Indian WVYYESKAHV  HCSVKSEHSA  AAKTGG      SEQ ID NO: 23
Sonic  WVYYESKAHI  HCSVKAENSV  AAKSGG      SEQ ID NO. 24
Desert WVYYESRNHV  HVSVKADNSL  AVRAGG      SEQ ID NO. 25
```

Gap(s), indicated by -, added to facilitate alignment

Figure 2 : SEQ ID NO: 26 is the consensus sequence of a hedgehog protein suitable for use in developing the conjugated proteins of the invention, antagonist, where "Xaa" indicates amino acids that differ between the Sonic, Indian and Desert hedgehog proteins.

C* G P G R Xaa1 Xaa2 Xaa3 Xaa4 Xaa5

R R Xaa6 Xaa7 Xaa8 K Xaa9 L Xaa10 P

L Xaa11 Y K Q F Xaa12 P Xaa13 V

Xaa14 E K T L G A S G R

Xaa15 E G K Xaa16 Xaa17 R Xaa18 S E

R F K Xaa19 L Xaa20 P N Y N

P D I I F K D E E N

Xaa21 G A D R L M T Xaa22 R

C K Xaa23 Xaa24 Xaa25 N S L A I

Xaa26 V M N Xaa27 W P G V K

L R V T E G W D E D

G H H X2aa8 Xaa29 Xaa30 S L H Y

E G R A V D I T T S

D R D R Xaa31 K Y G Xaa32 L

A R L A V E A G F D

W V Y Y E S Xaa33 Xaa34 H Xaa35

H Xaa36 S V K Xaa37 Xaa38

Xaa39 S Xaa40 A A Xaa41 Xaa42 G G

Where
C* is a cysteine that may be modified, altered or substituted within another moiety or series of moieties as described herein;

| | | |
|---|---|---|
| Xaa1 is either V or G; | Xaa2 is either V, E or P | Xaa3 is either G or V |
| Xaa4 is either S or G; | Xaa5 is either R or K; | Xaa6 is either P, H or Y; |
| Xaa7 is either P or A; | Xaa8 is either R or K; | |
| Xaa9 is any amino acid; | Xaa10 is either V or T; | Xaa11 is either A or L; |
| Xaa12 is either S, I or V; | Xaa13 is either N or G; | Xaa14 is either P or A; |
| Xaa15 is either Y or A; | Xaa16 is either I or V; | Xaa17 is either A or S; |
| Xaa18 is either S, N or G; | Xaa19 is either E or D; | Xaa20 is either T or V; |
| Xaa21 is either T or S; | Xaa22 is either Q or E; | Xaa23 is either D or E; |
| Xaa24 is either R or K; | Xaa25 is either L or V; | Xaa26 is either S or A; |
| Xaa27 is either Q or M; | Xaa28 is either S or A; | Xaa29 is either E or Q; |
| Xaa30 is either E or D; | Xaa31 is either N or S; | Xaa32 is either L or M; |
| Xaa33 is either K or R; | Xaa34 is either A or N; | Xaa35 is either V or I; |
| Xaa36 is either C or V; | Xaa37 is either S or A; | Xaa38 is either E or D; |
| Xaa39 is either H or N; | Xaa40 is either A, V or L; | Xaa41 is either K or R; and |
| Xaa42 is either T, S or A. | | |

KEX2 site for secretion signal processing

KEX2 cleavage site generating N-10 Sonic Hedgehog

```
XhoI
AvaI
TCTCTCGAGAAAAGA TGCGGACCGGGCCAGGGGTTCGGGAAGAGG AGGCACCCCAAAAAGCTGACC
AGAGAGCTCTTTTCT ACGCCTGGCCCGGTCCCCAAGCCCTTCTCC TCCGTGGGGTTTTTCGACTGG
▶ SerLeuGluLysArg CysGlyProGlyArgGlyPheGlyLysArg ArgHisProLysLysLeuThr
                                                                  BbsI
CCTTTAGCCTACAAGCAGTTTATCCCAAATGTGGCCGAGAAGACCCTAGGCGCCAGCGGA
GGAAATCGGATGTTCGTCAAATAGGGTTACACCGGCTCTTCTGGATCCGCGGTCGCCT
▶ ProLeuAlaTyrLysGlnPheIleProAsnValAlaGluLysThrLeuGlyAlaSerGly
```

Figure 3 DNA and protein sequence at junction of alpha factor secretion signal and Sonic Hedgehog protein in pUB55 with relevant KEX2 cleavage sites

US 7,479,539 B1

HEDGEHOG FUSION PROTEINS

RELATED APPLICATIONS

This application is a national stage filing under 35 U.S.C 371 of International Application PCT/US00/30405, filed Nov. 2, 2000, which claims the benefit of priority to U.S. provisional application Ser. No. 60/164,025, filed Nov. 5, 1999.

BACKGROUND OF THE INVENTION

A peptide family which has been the focus of much research, and efforts to improve its administration and bioavailability, is the hedgehog family of proteins. The hedgehog proteins are a family of extracellular signaling proteins that regulate various aspects of embryonic development both in vertebrates and in invertebrates (for reviews see Perrimon, N. (1995) Cell 80, 517-520 and Johnson, R. L., and Tabin, C. (1995) Cell 81, 313-316). The most well-characterized hedgehog protein is Sonic hedgehog (Shh), involved in anterior-posterior patterning, formation of an apical ectodermal ridge, hindgut mesoderm, spinal column, distal limb, rib development, and lung development, and in inducing ventral cell types in the spinal cord, hindbrain and forebrain (see Riddle, R. D., et al. (1993) Cell 75, 1401-1416; Echelard, Y. et al. (1993) Cell 75, 1417-1471; Roelink, H., et al. (1994) Cell 76, 761-775; and Roelink, H., et al. (1995) Cell 81, 445-455).

While the mechanism of action of hedgehog proteins is not understood fully, the most recent biochemical and genetic data suggest that the receptor for Shh is the product of the tumor suppressor gene, patched (Marigo, V., et al. (1996) Nature 384, 176-179; Stone, D. M., et al. (1996) Nature 384, 129-134) and that other proteins; smoothened (Alcedo, J., et al. (1996) Cell 86, 221-232), Cubitus interruptus or its mammalian counterpart gli (Dominguez, M., et al. (1996) Science 272, 1621-1625; Alexandre, C., et al. (1996) Genes & Dev. 10, 2003-2013), and fused (Therond, P. P., et al. (1996) Proc. Natl. Acad. Sci. USA 93, 4224-4228) are involved in the hedgehog signaling pathway.

Human Shh is synthesized as a 45 kDa precursor protein that is cleaved autocatalytically to yield: (I) a 20 kDa N-terminal fragment that is responsible for all known hedgehog signaling activity (SEQ ID NOS. 6 and 24); and (II) a 25 kDa C-terminal fragment that contains the autoprocessing activity (Lee, J. J., et al. (1994) Science 266, 1528-1536; Bumcrot; D. A., et al. (1995) Mol. Cell Biol. 15, 2294-2303; Porter, J. A., et al. (1995) Nature 374, 363-366). The N-terminal fragment of naturally occurring hedgehog consists of amino acid residues 24-197 of the full-length precursor sequence, of which the N-terminal amino acid residue is a cysteine.

The N-terminal fragment remains membrane-associated through the addition of a cholesterol at its C-terminus (Porter, J. A., et al. (1996) Science 274, 255-258; Porter, J. A., et al. (1995) Cell 86, 21-34) and a fatty acid at its N-terminus (Pepinsky et al., (1998) J. Biol. Chem. 273, 14037-14045). These modifications are critical for restricting the tissue localization of the hedgehog signal. The addition of the cholesterol is catalyzed by the C-terminal domain during the processing step.

A major factor limiting the usefulness of proteinaceous substances such as hedgehog for their intended application is that, when given parenterally, they are eliminated from the body within a short time. This can occur as a result of metabolism by proteases or by clearance using normal pathways for protein elimination such as by filtration in the kidneys. The oral route of administration of these substances is even more problematic because in addition to proteolysis in the stomach, the high acidity of the stomach may inactivate them before they reach their intended target tissue. The problems associated with these routes of administration of proteins are well known in the pharmaceutical industry, and various strategies are being used in attempts to solve them.

A great deal of work dealing with protein stabilization has been published. One method of stabilization that has been widely used is the addition of an inert polymer to the protein. Numerous ways of conjugating selected amino acid residues of proteins (e.g., cysteines, lysines, N-terminal residues) with polymeric materials are known, including use of dextrans, polyvinyl pyrrolidones, glycopeptides, polyethylene glycol and polyamino acids. The resulting conjugated polypeptides are reported to retain their biological activities and solubility in water for parenteral applications.

In the case of hedgehog, we have previously discovered that in certain cell types, the protein undergoes proteolytic clipping at various sites in the N-terminal domain. Moreover, these N-terminally clipped forms of hedgehog are inactive in the 10T1/2 assay (in which the cell line 10T1/2 exhibits upregulation of Alkaline phosphatase when cultured for five days in the presence of active Sonic Hedgehog protein). In particular, sonic hedgehog lacking the first 10 amino acids of its N-terminus is inactive and also antagonizes wild-type SHH when both forms are present in the assay. (U.S. Ser. No. 60/106,703). Thus, if one wants to produce a fully active protein that can be further stabilized with a non-hedgehog moiety such as a polymer, one needs to prevent N-terminal proteolytic clipping.

SUMMARY OF THE INVENTION

This invention is based, in part, on our discovery that N-terminal clipping of hedgehog during expression in certain cell types occurs intracellularly and appears to be catalyzed by the KEX2 Golgi protease, or a similar KEX2-like intracellular protease.

The KEX2 recognition sites in Sonic Hedgehog were mutated in order to eliminate this intracellular proteolytic clipping and thus provide a hedgehog protein moiety capable of being linked to a non-hedgehog moiety (e.g., an immunoglobulin domain). These mutant proteins were expressed as the N-terminal domain (codons Cys24-Gly197 of the Sonic Hedgehog coding sequence, corresponding to residues Cys1-Gly174 of mature protein after signal sequence cleavage. Here we report on the stability and hedgehog activity of these mutants and on production of an active form of hedgehog-Fc fusion protein.

Further, we can exploit the advantages of an immunoglobulin hedgehog fusion protein relative to non-fusion forms, whether or not the hedgehog protein is proteolytically clipped at the N-terminus. In particular however, we have developed an hedgehog-Ig fusion composition with increased bioavailability relative to hedgehog lacking the Ig moiety and that further has the salutary properties of being unable to be clipped by intracellular proteases. Thus, modifications can be made to the hedgehog moiety such that the products (hedgehog immunoglobulin fusion proteins) are either agonists or antagonists but retain all or most of their biological activities. The following properties may result: altered pharmacokinetics and pharmacodynamics leading to increased half-life and alterations in tissue distribution (e.g, ability to stay in the vasculature for longer periods of time) Such a formulation is a substantial advance in the pharmaceutical and medical arts and would make a significant contribution to the management of various diseases in which hedgehog has some utility, such as peripheral neuropathies and neurodegenerative diseases. In particular, the ability to remain for longer periods of time in the vasculature allows the hedgehog fusions to potentially cross the blood-brain barrier.

In particular, the invention relates to an isolated polypeptide having the amino acid sequence X-Y-Z, wherein X is a polypeptide having the amino acid sequence, or portion thereof, consisting of the amino acid sequence of hedgehog; Y is an optional linker moiety; and Z is a polypeptide comprising at least a portion of a polypeptide other than hedgehog. Preferably, X is human Sonic, Indian or Desert hedgehog. In the preferred embodiments, Z is at least a portion of a constant region of an immunoglobulin and can be derived from an immunoglobulin of the class selected from IgM, IgG, IgD, IgA, and IgE. If the class is IgG, then it is selected from one of IgG1, IgG2, IgG3 and IgG4. The constant region of human IgM and IgE contain 4 constant regions (CH1, (hinge), CH2, CH3 and CH4, whereas the constant region of human IgG, IgA and IgD contain 3 constant regions (CH1, (hinge), CH2 and CH3. In the most preferred fusion proteins of the invention, the constant region contains at least the hinge, CH2 and CH3 domains.

Another embodiment of the invention is a fusion protein having an amino terminal region consisting of the amino acid sequence of hedgehog or a portion thereof and having a carboxy terminal region comprising at least a portion of a protein other than hedgehog. The carboxy portion is preferably at least a portion of a constant region of an immunoglobulin derived from an immunoglobulin of the class selected from IgM, IgG, IgD, IgA, and IgE. In the most preferred fusion proteins, the constant region contains at least the hinge, CH2 and CH3 domains.

Another embodiment of the invention is a fusion protein whose hedgehog moiety (e.g., X in the formula above) has been mutated to provide for muteins with an altered KEX2 protease recognition site.

Yet another embodiment of the invention is an isolated DNA encoding for the fusion proteins described above. The invention also pertains to a recombinant DNA comprising an isolated DNA encoding the fusion proteins described above and an expression control sequence, wherein the expression control sequence is operatively linked to the DNA. The scope of the invention also includes host cells transformed with the recombinant DNA sequences of the invention.

The invention further pertains to a method of producing a recombinant polypeptide comprising: providing a population of host cells according to the invention; growing the population of cells under conditions whereby the polypeptide encoded by the recombinant DNA is expressed; and isolating the expressed polypeptide.

A further aspect of the invention is a hedgehog fusion protein comprising hedgehog and an additional polypeptide with which it is not natively associated, in substantially purified form, the fusion having a bioavailability that is at least equal to, and preferably greater than, the bioavailability of hedgehog lacking the additional polypeptide.

Yet another aspect of the invention is a pharmaceutical composition comprising a ally effective amount of an hedgehog fusion protein.

BRIEF DESCRIPTION OF THE FIGURES

FIG. 1. N-terminal sequences of Sonic, Indian and Desert Hedgehog

FIG. 2. Consensus Hedgehog Sequence

FIG. 3. N terminal Sequence of Sonic Hedgehog showing clip sites. The amino acid sequence is depicted by SEQ ID NO:105. The sense and anti-sense strands of the DNA sequence are depicted by SEQ ID NO:103 and SEQ ID NO:104, respectively.

DETAILED DESCRIPTION

All references cited in the Detailed Description are incorporated herein by references, unless stipulated otherwise. The following terms are used herein:

I. Definitions

The invention will now be described with reference to the following detailed description of which the following definitions are included:

As used herein, the term hedgehog "antagonist" includes any compound that inhibits hedgehog from binding with its receptor. For the purposes of the invention a hedgehog antagonist also refers to an agent, e.g., a polypeptide such as an anti-hedgehog or anti-patched antibody which can inhibit or block hedgehog and/or patched-mediated binding or which can otherwise modulate hedgehog and/or patched function, e.g., by inhibiting or blocking hedgehog-ligand mediated hedgehog signal transduction. Such an antagonist of the hedgehog/patched interaction is an agent which has one or more of the following properties: (1) it coats, or binds to, a hedgehog on the surface of a hedgehog bearing or secreting cell with sufficient specificity to inhibit a hedgehog-ligand/hedgehog interaction, e.g., the hedgehog/patched interaction; (2) it coats, or binds to, a hedgehog on the surface of a hedgehog-bearing or secreting cell with sufficient specificity to modify, and preferably to inhibit, transduction of a hedgehog-mediated signal e.g., hedgehog/patched-mediated signaling; (3) it coats, or binds to, a hedgehog receptor, (e.g., patched) in or on cells with sufficient specificity to inhibit the hedgehog/patched interaction; (4) it coats, or binds to, a hedgehog receptor (e.g., patched) in or on cells with sufficient specificity to modify, and preferably to inhibit, transduction of hedgehog mediated hedgehog signaling, e.g., patched-mediated hedgehog signaling.

In preferred embodiments the antagonist has one or both of properties 1 and 2. In other preferred embodiments the antagonist has one or both of properties 3 and 4. Moreover, more than one antagonist can be administered to a patient, e.g., an agent which binds to hedgehog can be combined with an agent which binds to patched.

For example, antibody or antibody homolog-containing hedgehog proteins (discussed below) as well as other molecules such as soluble forms of the natural binding proteins for hedgehog are useful. Soluble forms of the natural binding proteins for hedgehog include soluble patched peptides, patched fusion proteins, or bifunctional patched/Ig fusion proteins. For example, a soluble form of patched or a fragment thereof may be administered to bind to hedgehog, and preferably compete for a hedgehog binding site on cells, thereby leading to effects similar to the administration of antagonists such as anti-hedgehog antibodies. In particular, soluble hedgehog mutants that bind patched but do not elicit hedgehog-dependent signaling are included within the scope of the invention Such hedgehog mutants can act as competitive inhibitors of wild type hedgehog protein and are considered "antagonists".

As discussed herein, the hedgehog antagonists that can be fused or otherwise conjugated to, for instance, an antibody homolog such as an immunoglobulin or fragment thereof are not limited to a particular type or structure of hedgehog or patched or other molecule so that, for purposes of the invention, any agent capable of forming a fusion protein and capable of binding to hedgehog antigens and which effectively blocks or coats hedgehog is considered to be an equivalent of the antagonists used in the examples herein.

As used herein, the term "antibody homolog" includes intact antibodies consisting of immunoglobulin light and heavy chains linked via disulfide bonds. The term "antibody homolog" is also intended to encompass a protein comprising one or more polypeptides selected from immunoglobulin light chains, immunoglobulin heavy chains and antigen-binding fragments thereof which are capable of binding to one or more antigens (i.e., hedgehog or patched). The component polypeptides of an antibody homolog composed of more than one polypeptide may optionally be disulfide-bound or otherwise covalently crosslinked. Accordingly, therefore, "antibody homologs" include intact immunoglobulins of types IgA, IgG, IgE, IgD, IgM (as well as subtypes thereof), wherein the light chains of the immunoglobulin may be of types kappa or lambda. Preferred fusion proteins of the invention may include portions of intact antibodies that retain antigen-binding specificity, for example, Fab fragments, Fab' fragments, F(ab')2 fragments, F(v) fragments, heavy chain monomers or dimers, light chain monomers or dimers, dimers consisting of one heavy and one light chain, and the like.

The most preferred fusion proteins comprise a hedgehog moiety fused or otherwise linked to all or part of the hinge and constant regions of an immunoglobulin light chain, heavy chain, or both. Thus, this invention features a molecule which includes: (1) a hedgehog moiety, (2) a second peptide, e.g., one which increases solubility or in vivo life time of the hedgehog moiety, e.g., a member of the immunoglobulin super family or fragment or portion thereof, e.g., a portion or a fragment of IgG, e.g., the human IgG1 heavy chain constant region, e.g., CH2, CH3, and hinge regions; and a toxin moiety.

As used herein, a "humanized antibody homolog" is an antibody homolog, produced by recombinant DNA technology, in which some or all of the amino acids of a human immunoglobulin light or heavy chain that are not required for antigen binding have been substituted for the corresponding amino acids from a nonhuman mammalian immunoglobulin light or heavy chain. A "human antibody homolog" is an antibody homolog in which all the amino acids of an immunoglobulin light or heavy chain (regardless of whether or not they are required for antigen binding) are derived from a human source.

As used herein, the term hedgehog "agonist" includes any compound that activates the hedgehog receptor.

"amino acid"—a monomeric unit of a peptide, polypeptide, or protein. There are twenty amino acids found in naturally occurring peptides, polypeptides and proteins, all of which are L-isomers. The term also includes analogs of the amino acids and D-isomers of the protein amino acids and their analogs.

A hedgehog protein has "biological activity" if it has at least one of the following properties: (i) it has the ability to bind to its receptor, patched or it encodes, upon expression, a polypeptide that has this characteristic; and/or (ii) it may induce alkaline phosphatase activity in C3H10T1/2 cells. The hedgehog protein meeting this functional test of "biological activity" may meet the hedgehog consensus criteria as defined herein in FIG. 2 (SEQ ID NO: 26) but it may also be a mutant form of hedgehog. This term "biological activity" includes antagonists and agonists, as defined herein.

The term "bioavailability" refers to the ability of a compound to be absorbed by the body after administration. For instance, a first compound has greater bioavailability than a second compound if, when both are administered in equal amounts, the first compound is absorbed into the blood to a greater extent than the second compound.

As used herein, the term "covalently coupled" means that the specified moieties of the invention (e.g., immunoglobulin fragment/hedgehog protein) are either directly covalently bonded to one another, or else are indirectly covalently joined to one another through an intervening moiety or moieties, such as a bridge, spacer, or linkage moiety or moieties. The intervening moiety or moieties are called a "coupling group". The term "conjugated" is used interchangeably with "covalently coupled".

"expression control sequence"—a sequence of polynucleotides that controls and regulates expression of genes when operatively linked to those genes.

"expression vector"—a polynucleotide, such as a DNA plasmid or phage (among other common examples) which allows expression of at least one gene when the expression vector is introduced into a host cell. The vector may, or may not, be able to replicate in a cell.

The phrase "extracellular signaling protein" means any protein that is either secreted from a cell, or is associated with the cell membrane, and upon binding to the receptor for that protein on a target cell, triggers a response in the target cell.

An "effective amount" of an agent of the invention is that amount which produces a result or exerts an influence on the particular condition being treated.

"functional equivalent" of an amino acid residue is (i) an amino acid having similar reactive properties as the amino acid residue that was replaced by the functional equivalent; (ii) an amino acid of a ligand of a polypeptide of the invention, the amino acid having similar properties as the amino acid residue that was replaced by the functional equivalent; (iii) a non-amino acid molecule having similar properties as the amino acid residue that was replaced by the functional equivalent.

A first polynucleotide encoding hedgehog protein is "functionally equivalent" compared with a second polynucleotide encoding hedgehog protein if it satisfies at least one of the following conditions:

(a): the "functional equivalent" is a first polynucleotide that hybridizes to the second polynucleotide under standard hybridization conditions and/or is degenerate to the first polynucleotide sequence. Most preferably, it encodes a mutant hedgehog having the activity of an hedgehog protein;

(b) the "functional equivalent" is a first polynucleotide that codes on expression for an amino acid sequence encoded by the second polynucleotide.

The term "hedgehog" includes, but is not limited to, the agents listed herein as well as their functional equivalents. As used herein, the term "functional equivalent" therefore refers to an hedgehog protein or a polynucleotide encoding the hedgehog protein that has the same or an improved beneficial effect on the mammalian recipient as the hedgehog of which it is deemed a functional equivalent. As will be appreciated by one of ordinary skill in the art, a functionally equivalent protein can be produced by recombinant techniques, e.g., by expressing a "functionally equivalent DNA". Accordingly, the instant invention embraces hedgehog proteins encoded by naturally-occurring DNAs, as well as by non-naturally-occurring DNAs which encode the same protein as encoded by the naturally-occurring DNA. Due to the degeneracy of the nucleotide coding sequences, other polynucleotides may be used to encode hedgehog protein. These include all, or portions of the above sequences which are altered by the substitution of different codons that encode the same amino acid residue within the sequence, thus producing a silent change.

Such altered sequences are regarded as equivalents of these sequences. For example, Phe (F) is coded for by two codons, TTC or TTT, Tyr (Y) is coded for by TAC or TAT and His (H) is coded for by CAC or CAT. On the other hand, Trp (W) is coded for by a single codon, TGG. Accordingly, it will be appreciated that for a given DNA sequence encoding a particular hedgehog there will be many DNA degenerate sequences that will code for it. These degenerate DNA sequences are considered within the scope of this invention.

"fusion"—refers to a co-linear linkage of two or more proteins or fragments thereof via their individual peptide backbones through genetic expression of a polynucleotide molecule encoding those proteins. It is preferred that the proteins or fragments thereof be from different sources. Thus, preferred fusion proteins include an hedgehog protein or fragment covalently linked to a second moiety that is not an hedgehog. Specifically, an "hedgehog protein/Ig fusion" is a protein comprising an hedgehog protein of the invention, or fragment thereof linked to an N-terminus of an immunoglobulin chain wherein a portion of the N-terminus of the immunoglobulin is replaced with the hedgehog protein.

The term "fusion" or "fusion protein" refers to a co-linear, covalent linkage of two or more proteins or fragments thereof via their individual peptide backbones, most preferably through genetic expression of a polynucleotide molecule encoding those proteins. It is preferred that the proteins or fragments thereof are from different sources. Thus, preferred fusion proteins include an hedgehog protein or fragment covalently linked to a second moiety that is not a hedgehog protein. Specifically, a "hedgehog/Ig fusion" is a protein comprising a biologically active hedgehog molecule of the invention (i.e., Sonic hedgehog), or a biologically active fragment thereof linked to an N-terminus of an immunoglobulin chain wherein a portion of the N-terminus of the immunoglobulin is replaced with the hedgehog. A species of hedgehog/Ig fusion is an "hedgehog/Fc fusion" which is a protein comprising an hedgehog molecule of the invention (i.e., hedgehog-) linked to at least a part of the constant domain of an immunoglobulin. A preferred Fc fusion comprises a hedgehog mutein of the invention linked to a fragment of an antibody containing the C terminal domain of the heavy immunoglobulin chains. Also, the term "fusion protein" means an hedgehog protein chemically linked via a mono- or heterofunctional molecule to a second moiety that is not an hedgehog protein and is made de novo from purified protein as described below.

"Heterologous promoter"—as used herein is a promoter which is not naturally associated with a gene or a purified nucleic acid.

"Homology"—as used herein is synonymous with the term "identity" and refers to the sequence similarity between two polypeptides, molecules, or between two nucleic acids. When a position in both of the two compared sequences is occupied by the same base or amino acid monomer subunit (for instance, if a position in each of the two DNA molecules is occupied by adenine, or a position in each of two polypeptides is occupied by a lysine), then the respective molecules are homologous at that position. The percentage homology between two sequences is a function of the number of matching or homologous positions shared by the two sequences divided by the number of positions compared×100. For instance, if 6 of 10 of the positions in two sequences are matched or are homologous, then the two sequences are 60% homologous. By way of example, the DNA sequences CTGACT and CAGGTT share 50% homology (3 of the 6 total positions are matched). Generally, a comparison is made when two sequences are aligned to give maximum homology.

Such alignment can be provided using, for instance, the method of Needleman et al., *J. Mol Biol.* 48: 443-453 (1970), implemented conveniently by computer programs described in more detail below. Homologous sequences share identical or similar amino acid residues, where similar residues are conservative substitutions for, or "allowed point mutations" of, corresponding amino acid residues in an aligned reference sequence. In this regard, a "conservative substitution" of a residue in a reference sequence are those substitutions that are physically or functionally similar to the corresponding reference residues, e.g., that have a similar size, shape, electric charge, chemical properties, including the ability to form covalent or hydrogen bonds, or the like. Particularly preferred conservative substitutions are those fulfilling the criteria defined for an "accepted point mutation" in Dayhoff et al., 5: Atlas of Protein Sequence and Structure, 5: Suppl. 3, chapter 22: 354-352, Nat. Biomed. Res. Foundation, Washington, D.C. (1978).

"Homology" and "identity" each refer to sequence similarity between two polypeptide sequences, with identity being a more strict comparison. Homology and identity can each be determined by comparing a position in each sequence which may be aligned for purposes of comparison. When a position in the compared sequence is occupied by the same amino acid residue, then the polypeptides can be referred to as identical at that position; when the equivalent site is occupied by the same amino acid (e.g., identical) or a similar amino acid (e.g., similar in steric and/or electronic nature), then the molecules can be referred to as homologous at that position. A percentage of homology or identity between sequences is a function of the number of matching or homologous positions shared by the sequences. An "unrelated" or "non-homologous" sequence shares less than 40 percent identity, though preferably less than 25 percent identity, with an AR sequence of the present invention.

Various alignment algorithms and/or programs may be used, including FASTA, BLAST or ENTREZ. FASTA and BLAST are available as a part of the GCG sequence analysis package (University of Wisconsin, Madison, Wis.), and can be used with, e.g., default settings. ENTREZ is available through the National Center for Biotechnology Information, National Library of Medicine, National Institutes of Health, Bethesda, Md. In one embodiment, the percent identity of two sequences can be determined by the GCG program with a gap weight of 1, e.g., each amino acid gap is weighted as if it were a single amino acid or nucleotide mismatch between the two sequences.

A "hedgehog protein" of the invention is defined in terms of having at least a portion that consists of the consensus amino acid sequence of FIG. 2 (SEQ ID NO: 26). The term also means a hedgehog polypeptide, or a functional variant of a hedgehog polypeptide, or homolog of a hedgehog polypeptide, or functional variant, which has biological activity.

The term "Hedgehog N-terminal fragment" is used interchangeably with "Hedgehog" and refers to the active mature sequence that is proteolytically cleaved from the hedgehog precursor.

The term "hydrophobic" refers to the tendency of chemical moieties with nonpolar atoms to interact with each other rather than water or other polar atoms. Materials that are "hydrophobic" are, for the most part, insoluble in water. Natural products with hydrophobic properties include lipids, fatty acids, phospholipids, sphingolipids, acylglycerols, waxes, sterols, steroids, terpenes, prostaglandins, thromboxanes, leukotrienes, isoprenoids, retenoids, biotin, and hydrophobic amino acids such as tryptophan, phenylalanine, isoleucine, leucine, valine, methionine, alanine, proline, and tyrosine. A chemical moiety is also hydrophobic or has hydrophobic properties if its physical properties are determined by the presence of nonpolar atoms.

The phrase "internal amino acid" means any amino acid in a peptide sequence that is neither the N-terminal amino acid nor the C-terminal amino acid.

"Isolated" (used interchangeably with "substantially pure")—when applied to nucleic acid i.e., polynucleotide sequences that encode polypeptides, means an RNA or DNA polynucleotide, portion of genomic polynucleotide, cDNA or synthetic polynucleotide which, by virtue of its origin or manipulation: (i) is not associated with all of a polynucleotide with which it is associated in nature (e.g., is present in a host cell as an expression vector, or a portion thereof); or (ii) is linked to a nucleic acid or other chemical moiety other than that to which it is linked in nature; or (iii) does not occur in nature. By "isolated" it is further meant a polynucleotide sequence that is: (i) amplified in vitro by, for example, polymerase chain reaction (PCR); (ii) synthesized chemically; (iii) produced recombinantly by cloning; or (iv) purified, as by cleavage and gel separation.

"Isolated" (used interchangeably with "substantially pure")—when applied to polypeptides means a polypeptide or a portion thereof which, by virtue of its origin or manipulation: (i) is present in a host cell as the expression product of a portion of an expression vector; or (ii) is linked to a protein or other chemical moiety other than that to which it is linked in nature; or (iii) does not occur in nature, for example, a protein that is chemically manipulated by appending, or adding at least one hydrophobic moiety to the protein so that the protein is in a form not found in nature. By "isolated" it is further meant a protein that is: (i) synthesized chemically; or (ii) expressed in a host cell and purified away from associated and contaminating proteins. The term generally means a polypeptide that has been separated from other proteins and nucleic acids with which it naturally occurs. Preferably, the polypeptide is also separated from substances such as antibodies or gel matrices (polyacrylamide) which are used to purify it.

"multivalent protein complex"—refers to a plurality of hedgehog proteins (i.e., one or more). An antibody homology or fragment is attached to at least one of the plurality of hedgehog proteins. The hedgehog protein or the antibody homolog or fragment may be cross-linked or bound to another antibody homolog or fragment. Each protein may be the same or different and each antibody homolog or fragment may be the same or different.

"mutant"—any change in the genetic material of an organism, in particular any change (i.e., deletion, substitution, addition, or alteration) in a wild type polynucleotide sequence or any change in a wild type protein. The term "mutein" is used interchangeably with "mutant".

"N-terminal end"—refers to the first amino acid residue (amino acid number 1) of the mature form of a protein.

"N-terminal cysteine"—refers to the amino acid number 1 as shown in FIGS. 1 and 2 (SEQ ID NOS. 23-26). In certain embodiments of the hedgehog protein, the N-terminal cysteine has been "modified". The term "modified" in this regard refers to chemical modification(s) of the N-terminal cysteine such as linkage thereof to another moiety such as a hydrophobic group and/or replacement of the N-terminal cysteine with another moiety, such as a hydrophobic group.

"operatively linked"—a polynucleotide sequence (DNA, RNA) is operatively linked to an expression control sequence when the expression control sequence controls and regulates the transcription and translation of that polynucleotide sequence. The term "operatively linked" includes having an appropriate start signal (e.g., ATG) in front of the polynucleotide sequence to be expressed, and maintaining the correct reading frame to permit expression of the polynucleotide sequence under the control of the expression control sequence, and production of the desired polypeptide encoded by the polynucleotide sequence.

"protein"—any polymer consisting essentially of any of the 20 amino acids. Although "polypeptide" is often used in reference to relatively large polypeptides, and "peptide" is often used in reference to small polypeptides, usage of these terms in the art overlaps and is varied. The term "protein" as used herein refers to peptides, proteins and polypeptides, unless otherwise noted.

The terms "peptide(s)", "protein(s)" and "polypeptide(s)" are used interchangeably herein. The terms "polynucleotide sequence" and "nucleotide sequence" are also used interchangeably herein "Recombinant," as used herein, means that a protein is derived from recombinant, mammalian expression systems. Since hedgehog is not glycosylated nor contains disulfide bonds, it can be expressed in most prokaryotic and eukaryotic expression systems.

"Spacer" sequence refers to a moiety that may be inserted between an amino acid to be modified with an antibody homolog or fragment and the remainder of the protein. A spacer is designed to provide separation between the modification and the rest of the protein so as to prevent the modification from interfering with protein function and/or make it easier for the modification to link with an antibody homolog moiety or any other moiety.

Thus, "substantially pure nucleic acid" is a nucleic acid which is not immediately contiguous with one or both of the coding sequences with which it is normally contiguous in the naturally occurring genome of the organism from which the nucleic acid is derived. Substantially pure DNA also includes a recombinant DNA which is part of a hybrid gene encoding additional hedgehog sequences.

The phrase "surface amino acid" means any amino acid that is exposed to solvent when a protein is folded in its native form.

"standard hybridization conditions"—salt and temperature conditions substantially equivalent to 0.5×SSC to about 5×SSC and 65° C. for both hybridization and wash. The term "standard hybridization conditions" as used herein is therefore an operational definition and encompasses a range of hybridization conditions. Higher stringency conditions may, for example, include hybridizing with plaque screen buffer (0.2% polyvinylpyrrolidone, 0.2% Ficoll 400; 0.2% bovine serum albumin, 50 mM Tris-HCl (pH 7.5); 1 M NaCl; 0.1% sodium pyrophosphate; 1% SDS); 10% dextran sulfate, and 100 µg/ml denatured, sonicated salmon sperm DNA at 65° C. for 12-20 hours, and washing with 75 mM NaCl/7.5 mM sodium citrate (0.5×SSC)/1% SDS at 65° C. Lower stringency conditions may, for example, include hybridizing with plaque screen buffer, 10% dextran sulfate and 110 µg/ml denatured, sonicated salmon sperm DNA at 55° C. for 12-20 hours, and washing with 300 mM NaCl/30 mM sodium citrate (2.0×SSC)/1% SDS at 55° C. See also Current Protocols in Molecular Biology, John Wiley & Sons, Inc. New York, Sections 6.3.1-6.3.6, (1989).

A "therapeutic composition" as used herein is defined as comprising the proteins of the invention and other biologically compatible ingredients. The therapeutic composition may contain excipients such as water, minerals and carriers such as protein.

"wild type"—the naturally-occurring polynucleotide sequence of an exon of a protein, or a portion thereof, or protein sequence, or portion thereof, respectively, as it normally exists in vivo.

Practice of the present invention will employ, unless indicated otherwise, conventional techniques of cell biology, cell culture, molecular biology, microbiology, recombinant DNA, protein chemistry, and immunology, which are within the skill of the art. Such techniques are described in the literature. Unless stipulated otherwise, all references cited in the Detailed Description are incorporated herein by reference.

II. General Properties of Isolated Hedgehog Proteins

The various naturally-occurring hedgehog proteins from which the subject proteins can be derived are characterized by a signal peptide, a highly conserved N-terminal region (see FIG. 1), and a more divergent C-terminal domain. In addition to signal sequence cleavage in the secretory pathway (Lee, J. J. et al. (1992) Cell 71:33-50; Tabata, T. et al. (1992) Genes Dev. 2635-2645; Chang, D. E. et al. (1994) Development 120:3339-3353), hedgehog precursor proteins naturally undergo an internal autoproteolytic cleavage which depends on conserved sequences in the C-terminal portion (Lee et al. (1994) Science 266:1528-1537; Porter et al. (1995) Nature 374:363-366). This autocleavage leads to a 19 kD N-terminal peptide and a C-terminal peptide of 26-28 kD. The N-terminal peptide stays tightly associated with the surface of cells in which it was synthesized, while the C-terminal peptide is freely diffusible both in vitro and in vivo. Cell surface retention of the N-terminal peptide is dependent on autocleavage, as a truncated form of hedgehog encoded by an RNA which terminates precisely at the normal position of internal cleavage is diffusible in vitro (Porter et al. (1995) supra) and in vivo (Porter, J. A. et al. (1996) Cell 86, 21-34). Biochemical studies have shown that the autoproteolytic cleavage of the hedgehog precursor protein proceeds through an internal thioester intermediate, which subsequently is cleaved in a nucleophilic substitution.

The vertebrate family of hedgehog genes includes at least four members, e.g., paralogs of the single *drosophila* hedgehog gene (reference). Three of these members, herein referred to as Desert hedgehog (Dhh), Sonic hedgehog (Shh) and Indian hedgehog (Ihh), apparently exist in all vertebrates, including fish, birds, and mammals. A fourth member, herein referred to as tiggie-winkle hedgehog (Thh), appears specific to fish. Isolated hedgehog proteins used in the methods of this invention are naturally occurring or recombinant proteins of the hedgehog family and may be obtainable from either invertebrate or from vertebrate sources (see references below). Members of the vertebrate hedgehog protein family share homology with proteins encoded by the *Drosophila* hedgehog (hh) gene (Mohler and Vani, (1992) Development 115, 957-971). Other members continue to be identified.

Mouse and chicken Shh and mouse Ihh genes (see, for example, U.S. Pat. No. 5,789,543) encode glycoproteins which undergo cleavage, yielding an amino terminal fragment of about 20 kDa and a carboxy terminal fragment of about 25 kDa. The most preferred 20 kDa fragment has the consensus sequence SEQ ID NO: 26 which includes the amino acid sequences of SEQ ID NOS: 23-25. Various other fragments that encompass the 20 kDa moiety are considered within the presently claimed invention. Publications disclosing these sequences, as well as their chemical and physical properties, include Hall et al., (1995) Nature 378, 212-216; Ekker et al., (1995) Current Biology 5, 944-955; Fan et al., (1995) Cell 81, 457-465, Chang et al., (1994) Development 120, 3339-3353; Echelard et al., (1993) Cell 75, 1414-1430 34-38); PCT Patent Application WO 95/23223 (Jessell, Dodd, Roelink and Edlund; PCT Patent Publication WO 95/18856 (Ingham, McMahon and Tabin). U.S. Pat. No. 5,759,811 lists the Genbank accession numbers of a complete mRNA sequence encoding human Sonic hedgehog; a partial sequence of human Indian hedgehog mRNA, 5' end; and a partial sequence of human Desert hedgehog mRNA. The hedgehog therapeutic compositions of the subject method can be generated by any of a variety of techniques, including purification of naturally occurring proteins, recombinantly produced proteins and synthetic chemistry. Polypeptide forms of the hedgehog therapeutics are preferably derived from vertebrate hedgehog proteins, e.g., have sequences corresponding to naturally occurring hedgehog proteins, or fragments thereof, from vertebrate organisms. However, it will be appreciated that the hedgehog polypeptide can correspond to a hedgehog protein (or fragment thereof) which occurs in any metazoan organism.

The vertebrate family of hedgehog genes includes at least four members, e.g., paralogs of the single *drosophila* hedgehog gene (SEQ ID No. 19). Three of these members, herein referred to as Desert hedgehog (Dhh), Sonic hedgehog (Shh) and Indian hedgehog (Ihh), apparently exist in all vertebrates, including fish, birds, and mammals. A fourth member, herein referred to as tiggie-winkle hedgehog (Thh), appears specific to fish. According to the appended sequence listing, (see also Table 1) a chicken Shh polypeptide is encoded by SEQ ID No:1; a mouse Dhh polypeptide is encoded by SEQ ID No:2; a mouse Ihh polypeptide is encoded by SEQ ID No:3; a mouse Shh polypeptide is encoded by SEQ ID No:4 a zebrafish Shh polypeptide is encoded by SEQ ID No:5; a human Shh polypeptide is encoded by SEQ ID No:6; a human Ihh polypeptide is encoded by SEQ ID No:7; a human Dhh polypeptide is encoded by SEQ ID No. 8; and a zebrafish Thh is encoded by SEQ ID No. 9.

TABLE 1

Guide to hedgehog sequences in Sequence Listing

| | Nucleotide | Amino Acid |
|---|---|---|
| Chicken Shh | SEQ ID No. 1 | SEQ ID No. 10 |
| Mouse Dhh | SEQ ID No. 2 | SEQ ID No. 11 |
| Mouse Ihh | SEQ ID No. 3 | SEQ ID No. 12 |
| Mouse Shh | SEQ ID No. 4 | SEQ ID No. 13 |
| Zebrafish Shh | SEQ ID No. 5 | SEQ ID No. 14 |
| Human Shh | SEQ ID No. 6 | SEQ ID No. 15 |
| Human Ihh | SEQ ID No. 7 | SEQ ID No. 16 |
| Human Dhh | SEQ ID No. 8 | SEQ ID No. 17 |
| Zebrafish Thh | SEQ ID No. 9 | SEQ ID No. 18 |
| *Drosophila* HH | SEQ ID No. 19 | SEQ ID No. 20 |

In addition to the sequence variation between the various hedgehog homologs, the hedgehog proteins are apparently present naturally in a number of different forms, including a pro-form, a full-length mature form, and several processed fragments thereof. The pro-form includes an N-terminal signal peptide for directed secretion of the extracellular domain, while the full-length mature form lacks this signal sequence.

As described above, further processing of the mature form occurs in some instances to yield biologically active fragments of the protein. For instance, sonic hedgehog undergoes additional proteolytic processing to yield two peptides of approximately 19 kDa and 27 kDa, the 19 kDa fragment corresponding to an proteolytic N-terminal portion of the mature protein.

In addition to the sequence variation between the various hedgehog homologs, the proteins are apparently present naturally in a number of different forms, including a pro-form, a full-length mature form, and several processed fragments thereof. The pro-form includes an N-terminal signal peptide for directed secretion of the extracellular domain, while the full-length mature form lacks this signal sequence.

Family members useful in the methods of the invention include any of the naturally-occurring native hedgehog proteins including allelic, phylogenetic counterparts or other variants thereof, whether naturally-sourced or produced chemically including muteins or mutant proteins, as well as recombinant forms and new, active members of the hedgehog family. Particularly useful hedgehog polypeptides have portions that include all or part of FIGS. 1 and 2 (SEQ ID NOS: 23-26).

Isolated hedgehog polypeptides used in the method of the invention have biological activity. The polypeptides include an amino acid sequence at least 60%, 80%, 90%, 95%, 98%, or 99% homologous to an amino acid sequence from FIGS. 1 and/or 2 (SEQ ID NOS: 23-26). The polypeptide can also include an amino acid sequence essentially the same as an amino acid sequence in FIGS. 1 and/or 2 (SEQ ID NOS: 23-26). The polypeptide is at least 5, 10, 20, 50, 100, or 150 amino acids in length and includes at least 5, preferably at least 10, more preferably at least 20, most preferably at least 50, 100, or 150 contiguous amino acids from FIGS. 1 and/or 2 (SEQ ID NOS: 23-26).

Polypeptides of the invention include those which arise as a result of the existence of multiple genes, alternative transcription events, alternative RNA splicing events, and alternative translational and posttranslational events. The polypeptide can be made entirely by synthetic means or can be expressed in systems, e.g., cultured cells, which result in substantially the same posttranslational modifications present when the protein is expressed in a native cell, or in systems which result in the omission of posttranslational modifications present when expressed in a native cell.

In one embodiment, isolated hedgehog is a hedgehog polypeptide with one or more of the following characteristics:
(i) it has at least 30, 40, 42, 50, 60, 70, 80, 90 or 95% sequence identity with amino acids of SEQ ID NOS: 23-26;
(ii) it has a cysteine or a functional equivalent as the N-terminal end;
(iii) it may induce alkaline phosphatase activity in C3H10T1/2 cells;
(iv) it has an overall sequence identity of at least 50%, preferably at least 60%, more preferably at least 70, 80, 90, or 95%, with a polypeptide of SEQ ID NO; 23-26
(v) it can be isolated from natural sources such as mammalian cells;
(vi) it can bind or interact with patched; and
(vii) it is modified at least one amino acid residue by a polyalkylene glycol polymer attached to the residue or, optionally, via a linker molecule to the amino acid residue.

Preferred nucleic acids encode a polypeptide comprising an amino acid sequence at least 60% homologous or identical, more preferably 70% homologous or identical, and most preferably 80% homologous or identical with an amino acid sequence selected from the group consisting of FIGS. 1 and 2 (SEQ ID NOS: 23-26). Nucleic acids which encode polypeptides at least about 90%, more preferably at least about 95%, and most preferably at least about 98-99% homology or identity with an amino acid sequence represented in one of SEQ ID Nos: 23-26 are also within the scope of the invention.

In another embodiment, the hedgehog protein is a polypeptide encodable by a nucleotide sequence that hybridizes under stringent conditions to a hedgehog coding sequence represented in one or more of SEQ ID NOS: 1-9 or 19. Appropriate stringency conditions which promote DNA hybridization, for example, 6.0× sodium chloride/sodium citrate (SSC) at about 45 degrees C., followed by a wash of 2.0×SSC at 50 degrees C., are known to those skilled in the art or can be found in *Current Protocols in Molecular Biology*, John Wiley & Sons, N.Y. (1989), 6.3.1-6.3.6. For example, the salt concentration in the wash step can be selected from a low stringency of about 2.0×SSC at 50 degrees C. to a high stringency of about 0.2×SSC at 50 degrees C. In addition, the temperature in the wash step can be increased from low stringency conditions at room temperature, about 22 degrees C., to high stringency conditions at about 65 degrees C.

Preferred nucleic acids encode a hedgehog polypeptide comprising an amino acid sequence at least 60% homologous, more preferably 70% homologous and most preferably 80% homologous with an amino acid sequence selected from the group consisting of SEQ ID Nos:8-14. Nucleic acids which encode polypeptides at least about 90%, more preferably at least about 95%, and most preferably at least about 98-99% homology with an amino acid sequence represented in one of SEQ ID Nos:10-18 or 20 are also within the scope of the invention.

Hedgehog polypeptides preferred by the present invention, in addition to native hedgehog proteins, are at least 60% homologous, more preferably 70% homologous and most preferably 80% homologous with an amino acid sequence represented by any of SEQ ID Nos:10-18 or 20. Polypeptides which are at least 90%, more preferably at least 95%, and most preferably at least about 98-99% homologous with a sequence selected from the group consisting of SEQ ID Nos: 10-18 or 20 are also within the scope of the invention.

With respect to fragments of hedgehog polypeptide, preferred hedgehogs moieties include at least 50 amino acid residues of a hedgehog polypeptide, more preferably at least 100, and even more preferably at least 150.

Another preferred hedgehog polypeptide which can be included in the hedgehog therapeutic is an N-terminal fragment of the mature protein having a molecular weight of approximately 19 kDa.

Preferred human hedgehog proteins include N-terminal fragments corresponding approximately to residues 24-197 of SEQ ID No. 15, 28-202 of SEQ ID No. 16, and 23-198 of SEQ ID No. 17. By "corresponding approximately" it is meant that the sequence of interest is at most 20 amino acid residues different in length to the reference sequence, though more preferably at most 5, 10 or 15 amino acid different in length.

Still other preferred hedgehog polypeptides includes an amino acid sequence represented by the formula A-B wherein: (i) A represents all or the portion of the amino acid sequence designated by residues 1-168 of SEQ ID No: 21 or residues 1-167 of SEQ ID NO. 22; and B represents at least one amino acid residue of the amino acid sequence designated by residues 169-221 of SEQ ID No:21; (ii) A represents all or the portion of the amino acid sequence designated by residues 24-193 of SEQ ID No: 15; and B represents at least one amino acid residue of the amino acid sequence designated by residues 194-250 of SEQ ID No: 15; (iii) A represents all or the portion of the amino acid sequence designated by residues 25-193 of SEQ ID No:13; and B represents at least one amino acid residue of the amino acid sequence designated by residues 194-250 of SEQ ID No:13; (iv) A represents all or the portion of the amino acid sequence designated by residues 23-193 of SEQ ID No:11; and B represents at least one amino acid residue of the amino acid sequence designated by residues 194-250 of SEQ ID No:11; (v) A represents all or the portion of the amino acid sequence designated by residues 28-197 of SEQ ID No:12; and B represents at least one amino acid residue of the amino acid sequence designated by residues 198-250 of SEQ ID No:12; (vi) A represents all or the portion of the amino acid sequence designated by residues 29-197 of SEQ ID No:16; and B represents at least one amino acid residue of the amino acid sequence designated by residues 198-250 of SEQ ID No:16; or (vii) A represents all or the portion of the amino acid sequence designated by residues 23-193 of SEQ ID No. 17, and B represents at least one amino acid residue of the amino acid sequence designated by residues 194-250 of SEQ ID No. 17. In certain preferred embodiments, A and B together represent a contiguous polypeptide sequence designated sequence, A represents at least 25, 50, 75, 100, 125 or 150 amino acids of the designated sequence, and B represents at least 5, 10, or 20 amino acid residues of the amino acid sequence designated by corresponding entry in the sequence listing, and A and B together preferably represent a contiguous sequence corresponding to the sequence listing entry. Similar fragments from other hedgehog also contemplated, e.g., fragments which correspond to the preferred fragments from the sequence listing entries which are enumerated above.

Generally, the structure of the a preferred conjugated hedgehog protein of this invention has the general formula: X-Y-Z, where wherein X is a polypeptide having the amino acid sequence, or portion thereof, consisting of the amino acid sequence of hedgehog; Y is an optional linker moiety; and Z is a polypeptide comprising at least a portion of a polypeptide other than hedgehog. Preferably, X is human Sonic, Indian or Desert hedgehog. In the preferred embodiments, Z is at least a portion of a constant region of an immunoglobulin and can be derived from an immunoglobulin of the class selected from IgM, IgG, IgD, IgA, and IgE. If the class is IgG, then it is selected from one of IgG1, IgG2, IgG3 and IgG4. The constant region of human IgM and IgE contain 4 constant regions (CH1, (hinge), CH2, CH3 and CH4, whereas the constant region of human IgG, IgA and IgD contain 3 constant regions (CH1, (hinge), CH2 and CH3). In the most preferred fusion proteins of the invention, the constant region contains at least the hinge, CH2 and CH3 domains.

Another embodiment A-[Sp]-B-[Sp]-X, where A is a non-hedgehog moiety such as an immunoglobulin or fragment thereof; [Sp] is an optional spacer peptide sequence; B is a hedgehog protein (which optionally may be a mutein as described herein); and X is an optional hydrophobic moiety linked (optionally by way of the spacer peptide) to the hedgehog protein B or another residue such as a surface site of the protein.

III. Production of Recombinant Polypeptides

The isolated hedgehog polypeptides described herein can be produced by any suitable method known in the art. Such methods range from direct protein synthetic methods to constructing a DNA sequence encoding isolated polypeptide sequences and expressing those sequences in a suitable transformed host.

In one embodiment of a recombinant method, a DNA sequence is constructed by isolating or synthesizing a DNA sequence encoding a wild type protein of interest. Optionally, the sequence may be mutagenized by site-specific mutagenesis to provide functional analogs thereof. See, e.g., U.S. Pat. No. 4,588,585. Another method of constructing a DNA sequence encoding a polypeptide of interest would be by chemical synthesis using an oligonucleotide synthesizer. Such oligonucleotides may be preferably designed based on the amino acid sequence of the desired polypeptide, and preferably selecting those codons that are favored in the host cell in which the recombinant polypeptide of interest will be produced.

Standard methods may be applied to synthesize an isolated polynucleotide sequence encoding an isolated polypeptide of interest. For example, a complete amino acid sequence may be used to construct a back-translated gene. See Maniatis et al., supra. Further, a DNA oligomer containing a nucleotide sequence coding for the particular isolated polypeptide may be synthesized. For example, several small oligonucleotides coding for portions of the desired polypeptide may be synthesized and then ligated. The individual oligonucleotides typically contain 5' or 3' overhangs for complementary assembly.

Once assembled (by synthesis, site-directed mutagenesis, or by another method), the mutant DNA sequences encoding a particular isolated polypeptide of interest will be inserted into an expression vector and operatively linked to an expression control sequence appropriate for expression of the protein in a desired host. Proper assembly may be confirmed by nucleotide sequencing, restriction mapping, and expression of a biologically active polypeptide in a suitable host. As is well known in the art, in order to obtain high expression levels of a transfected gene in a host, the gene must be operatively linked to transcriptional and translational expression control sequences that are functional in the chosen expression host.

The choice of expression control sequence and expression vector will depend upon the choice of host. A wide variety of expression host/vector combinations may be employed. Useful expression vectors for eukaryotic hosts, include, for example, vectors comprising expression control sequences from SV40, bovine papilloma virus, adenovirus and cytomegalovirus. Useful expression vectors for bacterial hosts include known bacterial plasmids, such as plasmids from *Esherichia coli*, including pCR1, pBR322, pMB9 and their derivatives, wider host range plasmids, such as M13 and filamentous single-stranded DNA phages. Preferred *E. coli* vectors include pL vectors containing the lambda phage pL promoter (U.S. Pat. No. 4,874,702), pET vectors containing the T7 polymerase promoter (Studier et al., Methods in Enzymology 185: 60-89, 1990 1) and the pSP72 vector (Kaelin et al., supra). Useful expression vectors for yeast cells, for example, include the 2 T and centromere plasmids. Further, within each specific expression vector, various sites may be selected for insertion of these DNA sequences. These sites are usually designated by the restriction endonuclease which cuts them. They are well-recognized by those of skill in the art. It will be appreciated that a given expression vector useful in this invention need not have a restriction endonuclease site for insertion of the chosen DNA fragment. Instead, the vector may be joined by the fragment by alternate means.

The expression vector, and the site chosen for insertion of a selected DNA fragment and operative linking to an expression control sequence, is determined by a variety of factors such as: the number of sites susceptible to a particular restriction enzyme, the size of the polypeptide, how easily the polypeptide is proteolytically degraded, and the like. The choice of a vector and insertion site for a given DNA is determined by a balance of these factors.

To provide for adequate transcription of the recombinant constructs of the invention, a suitable promoter/enhancer sequence may preferably be incorporated into the recombinant vector, provided that the promoter/expression control sequence is capable of driving transcription of a nucleotide sequence encoding a hedgehog protein. Any of a wide variety of expression control sequences may be used in these vectors. Such useful expression control sequences include the expression control sequences associated with structural genes of the foregoing expression vectors. Examples of useful expression control sequences include, for example, the early and late promoters of SV40 or adenovirus, the lac system, the trp system, the TAC or TRC system, the major operator and promoter regions of phage lambda, for example pL, the control regions of fd coat protein, the promoter for 3-phosphoglycerate kinase or other glycolytic enzymes, the promoters of acid phosphatase, e.g., Pho5, the promoters of the yeast alpha-mating system and other sequences known to control the expression of genes of prokaryotic or eukaryotic cells and their viruses, and various combinations thereof.

Promoters which may be used to control the expression of immunoglobulin-based fusion protein include, but are not limited to, the SV40 early promoter region (Benoist and Chambon, 1981, Nature 290:304-310), the promoter contained in the 3' long terminal repeat of Rous sarcoma virus (Yamamoto, et al., 1980, Cell 22:787-797), the herpes thymidine kinase promoter (Wagner et al., 1981, Proc. Natl. Acad. Sci. U.S.A. 78:144-1445), the regulatory sequences of the metallothionine gene (Brinster et al., 1982, Nature 296:39-42); plant expression vectors comprising the nopaline synthetase promoter region (Herrera-Estrella et al., Nature 303: 209-213) or the cauliflower mosaic virus 35S RNA promoter (Gardner, et al., 1981, Nucl. Acids Res. 9:2871), and the promoter for the photosynthetic enzyme ribulose biphosphate carboxylase (Herrera-Estrella et al., 1984, Nature 310:115-120); promoter elements from yeast or other fungi such as the Gal 4 promoter, the ADC (alcohol dehydrogenase) promoter, PGK (phosphoglycerol kinase) promoter, alkaline phophatase promoter, and the following animal transcriptional control regions, which exhibit tissue specificity and have been utilized in transgenic animals: elastase I gene control region which is active in pancreatic cells (Swift et al., 1984, Cell 38:639-646; Ornitz et al., 1986, Cold Spring Harbor Symp. Quant. Biol. 50:399-409; MacDonald, 1987, Hepatology 7:425-515); insulin gene enhancers or promoters which are active in pancreatic cells (Hanahan, 1985, Nature 315:115-122); immunoglobulin gene enhancers or promoters which are active in lymphoid cells (Grosschedl et al., 1984, Cell 38:647-658; Adames et al., 1985, Nature 318:533-538; Alexander et al., 1987, Mol. Cell. Biol. 7:1436-1444); the cytomegalovirus early promoter and enhancer regions (Boshart et al., 1985, Cell 41:521-530); mouse mammary tumor virus control region which is active in testicular, breast, lymphoid and mast cells (Leder et al., 1986, Cell 45:485-495); albumin gene control region which is active in liver (Pinkert et al., 1987, Genes and Devel. 1:268-276); alpha-fetoprotein gene control region which is active in liver (Krumlauf et al., 1985, Mol. Cell. Biol. 5:1639-1648; Hammer et al., 1987, Science 235:53-58); alphantitrypsin gene control region which is active in the liver (Kelsey et al, 1987, Genes and Devel. 1:161-171); -globin gene control region which is active in myeloid cells (Mogram et al., 1985, Nature 315:338-340; Kollias et al., 1986, Cell 46:89-94; myelin basic protein gene control region which is active in oligodendrocyte cells in the brain (Readhead et al., 1987, Cell 48:703-712); myosin light chain-2 gene control region which is active in skeletal muscle (Sani, 1985, Nature 314:283-286); and gonadotropic releasing hormone gene control region which is active in the hypothalamus (Mason et al., 1986, Science 234: 1372-1378).

Any suitable host may be used to produce in quantity the isolated hedgehog polypeptides described herein, including bacteria, fungi (including yeasts), plants, insects, mammals, or other appropriate animal cells or cell lines, as well as transgenic animals or plants. More particularly, these hosts may include well known eukaryotic and prokaryotic hosts, such as strains of *E. coli, Pseudomonas, Bacillus, Streptomyces*, fungi, yeast (e.g., *Hansenula*), insect cells such as *Spodoptera frugiperda* (SF9), and High Five™ (see Example 1), animal cells such as Chinese hamster ovary (CHO), mouse cells such as NS/O cells, African green monkey cells COS1, COS 7, BSC 1, BSC 40, and BMT 10, and human cells, as well as plant cells.

It should be understood that not all vectors and expression control sequences will function equally well to express a given isolated polypeptide. Neither will all hosts function equally well with the same expression system. However, one of skill in the art may make a selection among these vectors, expression control systems and hosts without undue experimentation. For example, to produce isolated polypeptide of interest in large-scale animal culture, the copy number of the expression vector must be controlled. Amplifiable vectors are well known in the art. See, for example, Kaufman and Sharp, (1982) Mol. Cell. Biol., 2, 1304-1319 and U.S. Pat. Nos. 4,470,461 and 5,122,464.

Such operative linking of a DNA sequence to an expression control sequence includes the provision of a translation start signal in the correct reading frame upstream of the DNA sequence. If the particular DNA sequence being expressed does not begin with a methionine, the start signal will result in an additional amino acid (methionine) being located at the N-terminus of the product. If a hydrophobic moiety is to be linked to the N-terminal methionyl-containing protein, the protein may be employed directly in the compositions of the invention. Nevertheless, since the preferred N-terminal end of the protein is to consist of a cysteine (or functional equivalent) the methionine must be removed before use. Methods are available in the art to remove such N-terminal methionines from polypeptides expressed with them. For example, certain hosts and fermentation conditions permit removal of substantially all of the N-terminal methionine in vivo. Other hosts require in vitro removal of the N-terminal methionine. Such in vitro and in vivo methods are well known in the art.

Successful incorporation of these polynucleotide constructs into a given expression vector may be identified by three general approaches: (a) DNA-DNA hybridization, (b) presence or absence of "marker" gene functions, and (c) expression of inserted sequences. In the first approach, the presence of the hedgehog gene inserted in an expression vector can be detected by DNA-DNA hybridization using probes comprising sequences that are homologous to the inserted fusion protein gene. In the second approach, the recombinant vector/host system can be identified and selected based upon the presence or absence of certain "marker" gene functions (e.g., thymidine kinase activity, resistance to antibiotics such as G418, transformation phenotype, occlusion body formation in baculovirus, etc.) caused by the insertion of foreign genes in the vector. For example, if the polynucleotide is inserted so as to interrupt a marker gene sequence of the vector, recombinants containing the insert can be identified by the absence of the marker gene function. In the third approach, recombinant expression vectors can be identified by assaying the foreign gene product expressed by the recombinant vector. Such assays can be based, for example, on the physical or functional properties of the gene product in bioassay systems.

The preferred embodiment of the invention contemplates fusion proteins and DNA sequences coding for them. These fusion proteins have an amino-terminal region characterized by the amino acid sequence of hedgehog and a carboxy-terminal region comprising a domain of a protein other than hedgehog-. A preferred generic formula for such a protein is a protein having a primary amino acid sequence X-Y-Z, wherein X is a polypeptide having the amino acid sequence, or portion thereof, consisting of the amino acid sequence of human hedgehog; Y is an optional linker moiety; and Z is a polypeptide comprising at least a portion of a polypeptide other than human hedgehog.

Moiety Z can include, for instance, a plurality of histidine residues or the Fc region of an immunoglobulin, "Fc" defined herein as a fragment of an antibody containing the C terminal domain of the heavy immunoglobulin chains.

In the most preferred fusion proteins, the hedgehog polypeptide is fused to at least a portion of the Fc region of an immunoglobulin. The hedgehog forms the amino-terminal portion, and the Fc region forms the carboxy terminal portion. In these fusion proteins, the Fc region is preferably limited to the constant domain hinge region and the CH2 and CH3 domains. The Fc region in these fusions can also be limited to a portion of the hinge region, the portion being capable of forming intermolecular disulfide bridges, and the CH2 and CH3 domains, or functional equivalents thereof. These constant regions may be derived from any mammalian source (preferably human) and may be derived from any appropriate class and/or isotype, including IgA, IgD, IgM, IgE and IgG1, IgG2, IgG3 and IgG4.

Recombinant nucleic acid molecules which encode the Ig fusions may be obtained by any method known in the art (Maniatis et al., 1982, Molecular Cloning; A Laboratory Manual, Cold Spring Harbor Laboratory, Cold Spring Harbor, N.Y.) or obtained from publicly available clones. Methods for the preparation of genes which encode the heavy or light chain constant regions of immunoglobulins are taught, for example, by Robinson, R. et al., PCT Application, Publication No. WO87-02671. The cDNA sequence encoding the hedgehog molecule or fragment may be directly joined to the cDNA encoding the heavy Ig contant regions or may be joined via a linker sequence. In further embodiments of the invention, a recombinant vector system may be created to accommodate sequences encoding hedgehog in the correct reading frame with a synthetic hinge region. Additionally, it may be desirable to include, as part of the recombinant vector system, nucleic acids corresponding to the 3' flanking region of an immunoglobulin gene including RNA cleavage/polyadenylation sites and downstream sequences. Furthermore, it may be desirable to engineer a signal sequence upstream of the immunoglobulin fusion protein-encoding sequences to facilitate the secretion of the fused molecule from a cell transformed with the recombinant vector.

The present invention provides for dimeric fusion molecules as well as monomeric or multimeric molecules comprising fusion proteins. Such multimers may be generated by using those Fc regions, or portions thereof, of Ig molecules which are usually multivalent such as IgM pentamers or IgA dimers. It is understood that a J chain polypeptide may be needed to form and stabilize IgM pentamers and IgA dimers. Alternatively, multimers of hedgehog fusion proteins may be formed using a protein with an affinity for the Fc region of Ig molecules, such as Protein A. For instance, a plurality of hedgehog/immunoglobulin fusion proteins may be bound to Protein A-agarose beads.

These multivalent forms are useful since they possess multiple hedgehog receptor binding sites. For example, a bivalent soluble hedgehog may consist of two tandem repeats of the amino acids of SEQ ID NO: 24 (or those encoded by nucleic acids of SEQ. ID. NO: 6) (moiety X in the generic formula) separated by a linker region (moiety Y), the repeats bound to at least a portion of an immunoglobulin constant domain (moiety Z). Alternate polyvalent forms may also be constructed, for example, by chemically coupling hedgehog-/Ig fusions to any clinically acceptable carrier molecule, a polymer selected from the group consisting of Ficoll, polyethylene glycol or dextran using conventional coupling techniques. Alternatively, hedgehog may be chemically coupled to biotin, and the biotin-hedgehog Fc conjugate then allowed to bind to avidin, resulting in tetravalent avidin/biotin/hedgehog molecules. Hedgehog/Ig fusions may also be covalently coupled to dinitrophenol (DNP) or trinitrophenol (INP) and the resulting conjugate precipitated with anti-DNP or anti-TNP-IgM, to form decameric conjugates with a valency of 10 for hedgehog receptor binding sites The proteins produced by a transformed host can be purified according to any suitable method. Such standard methods include chromatography (e.g., ion exchange, affinity, and sizing column chromatography), centrifugation, differential solubility, or by any other standard technique for protein purification. For immunoaffinity chromatography (See Example 1), a protein such as Sonic hedgehog may be isolated by binding it to an affinity column comprising of antibodies that were raised against Sonic hedgehog, or a related protein and were affixed to a stationary support. For example, the hedgehog proteins and fragments may be purified by passing a solution thereof through a column having an hedgehog receptor immobilized thereon (see U.S. Pat. No. 4,725,669). The bound hedgehog molecule may then be eluted by treatment with a chaotropic salt or by elution with aqueous acetic acid. The immunoglobulin fusion proteins may be purified by passing a solution containing the fusion protein through a column which contains immobilized protein A or protein G which selectively binds the Fc portion of the fusion protein. See, for example, Reis, K. J., et al., J. Immunol. 132:3098-3102 (1984); PCT Application, Publication No. WO87/00329. The chimeric antibody may then be eluted by treatment with a chaotropic salt or by elution with aqueous acetic acid. Alternatively the hedgehog proteins and immunoglobulin-fusion molecules may be purified on anti-hedgehog, antibody columns, or on anti-immunoglobulin antibody columns to give a substantially pure protein. By the term "substantially pure" is intended that the protein is free of the impurities that are naturally associated therewith. Substantial purity may be evidenced by a single band by electrophoresis. Alternatively, affinity tags such as hexahistidine, maltose binding domain, influenza coat sequence, and glutathione-S-transferase can be attached to the protein to allow easy purification by passage over an appropriate affinity column. Isolated proteins can also be characterized physically using such techniques as proteolysis, nuclear magnetic resonance, and X-ray crystallography.

An example of a useful hedgehog/Ig fusion protein of this invention is that of SEQ ID NO: 83, which is secreted into the cell culture by eukaryotic cells containing the expression plasmid PUB 116 (See Examples). This protein consists of the mature human hedgehog fused to a portion of the hinge region and the CH2 and CH3 constant domains of murine Ig. This contains a sufficient portion of the murine immunoglobulin to be recognized by the Fc binding protein, Protein A.

Other fusion proteins of the invention incorporating human hedgehog are shown in SEQ NOS: 80-82.

The preferred hedgehog proteins of the invention include the novel "junction" DNA sequences which represent the 11 triplet codons on either side of the junction between the hedgehog DNA and the DNA encoding the non-hedgehog moiety.

The DNA "junction" sequences can be used as DNA probes and may be the minimum DNA needed for hybridization under standard conditions to any DNA sequence encoding any hedgehog-/Ig fusion protein. Nevertheless, provided that the whole probe hybridizes to both sides of the junction and both sides of the hedgehog/constant region junction participate in the hybridization, smaller sequences may exist. Furthermore, persons having ordinary skill in the art will understand that DNA sequences larger than these will be suitable for hybridization as well. One of ordinary skill in the art can test if a particular probe is capable of hybridizing on both sides of the junction by labelling the 5' end of either a single strand sense oligonucleotide or a single strand anti-sense oligonucleotide with an appropriately labelled phosphate of ATP using polynucleotide kinase. A sequence of the invention must hybridize to, and thus be labelled by both oligonucleotide probes. It is further understood that the invention encompasses fully degenerate sequences encoding junction sequences.

The most preferred hedgehog fusion proteins contain mutations in the putative KEX2 recognition site (See Table 5)

A. Production of Fragments and Analogs

Fragments of an isolated protein (e.g., fragments of SEQ ID NOS: 23-26) can also be produced efficiently by recombinant methods, by proteolytic digestion, or by chemical synthesis using methods known to those of skill in the art. In recombinant methods, internal or terminal fragments of a polypeptide can be generated by removing one or more nucleotides from one end (for a terminal fragment) or both ends (for an internal fragment) of a DNA sequence which encodes for the isolated hedgehog polypeptide. Expression of the mutagenized DNA produces polypeptide fragments. Digestion with "end nibbling" endonucleases can also generate DNAs which encode an array of fragments. DNAs which encode fragments of a protein can also be generated by random shearing, restriction digestion, or a combination or both. Protein fragments can be generated directly from intact proteins. Peptides can be cleaved specifically by proteolytic enzymes, including, but not limited to plasmin, thrombin, trypsin, chymotrypsin, or pepsin. Each of these enzymes is specific for the type of peptide bond it attacks. Trypsin catalyzes the hydrolysis of peptide bonds in which the carbonyl group is from a basic amino acid, usually arginine or lysine. Pepsin and chymotrypsin catalyse the hydrolysis of peptide bonds from aromatic amino acids, such as tryptophan, tyrosine, and phenylalanine. Alternative sets of cleaved protein fragments are generated by preventing cleavage at a site which is susceptible to a proteolytic enzyme. For instance, reaction of the ε-amino acid group of lysine with ethyltrifluorothioacetate in mildly basic solution yields blocked amino acid residues whose adjacent peptide bond is no longer susceptible to hydrolysis by trypsin. Proteins can be modified to create peptide linkages that are susceptible to proteolytic enzymes. For instance, alkylation of cysteine residues with β-haloethylamines yields peptide linkages that are hydrolyzed by trypsin (Lindley, (1956) Nature 178, 647). In addition, chemical reagents that cleave peptide chains at specific residues can be used. For example, cyanogen bromide cleaves peptides at methionine residues (Gross and Witkip, (1961) J. Am. Chem. Soc. 83, 1510). Thus, by treating proteins with various combinations of modifiers, proteolytic enzymes and/or chemical reagents, the proteins may be divided into fragments of a desired length with no overlap of the fragments, or divided into overlapping fragments of a desired length.

Fragments can also be synthesized chemically using techniques known in the art such as the Merrifield solid phase F moc or t-Boc chemistry. Merrifield, Recent Progress in Hormone Research 23: 451 (1967)

Examples of prior art methods which allow production and testing of fragments and analogs are discussed below. These, or analogous methods may be used to make and screen fragments and analogs of an isolated polypeptide (e.g., hedgehog) which can be shown to have biological activity. An exemplary method to test whether fragments and analogs of hedgehog have biological activity is found in Example 3.

B. Production of Altered DNA and Peptide Sequences: Random Methods

Amino acid sequence variants of a protein can be prepared by random mutagenesis of DNA which encodes the protein or a particular portion thereof. Useful methods include PCR mutagenesis and saturation mutagenesis. A library of random amino acid sequence variants can also be generated by the synthesis of a set of degenerate oligonucleotide sequences. Methods of generating amino acid sequence variants of a given protein using altered DNA and peptides are well-known in the art. The following examples of such methods are not intended to limit the scope of the present invention, but merely serve to illustrate representative techniques. Persons having ordinary skill in the art will recognize that other methods are also useful in this regard.

PCR Mutagenesis: See, for example Leung et al., (1989) Technique 1, 11-15.

Saturation Mutagenesis: One method is described generally in Mayers et al., (1989) Science 229, 242.

Degenerate Oligonucleotide Mutagenesis: See for example Harang, S. A., (1983) Tetrahedron 39, 3; Itakura et al., (1984) Ann. Rev. Biochem. 53, 323 and Itakura et al., Recombinant DNA, Proc. 3rd Cleveland Symposium on Macromolecules, pp. 273-289 (A. G. Walton, ed.), Elsevier, Amsterdam, 1981.

C. Production of Altered DNA and Peptide Sequences: Directed Methods

Non-random, or directed, mutagenesis provides specific sequences or mutations in specific portions of a polynucleotide sequence that encodes an isolated polypeptide, to provide variants which include deletions, insertions, or substitutions of residues of the known amino acid sequence of the isolated polypeptide. The mutation sites may be modified individually or in series, for instance by: (1) substituting first with conserved amino acids and then with more radical choices depending on the results achieved; (2) deleting the target residue; or (3) inserting residues of the same or a different class adjacent to the located site, or combinations of options 1-3.

Clearly, such site-directed methods are one way in which an N-terminal cysteine (or a functional equivalent) can be introduced into a given polypeptide sequence to provide the attachment site for a hydrophobic moiety.

Alanine scanning Mutagenesis: See Cunningham and Wells, (1989) Science 244, 1081-1085).

Oligonucleotide-Mediated Mutagenesis: See, for example, Adelman et al., (1983) DNA 2, 183. We created a functional antagonist using oligonucleotide-directed mutagenesis by engineering an isolated DNA sequence that encodes a functional antagonist that has a mutation of the N-terminal cysteine to another amino residue, preferably a serine residue (SEQ ID NO: 17: Example 7).

Cassette Mutagenesis: See Wells et al., (1985) Gene 34, 315.

Combinatorial Mutagenesis: See, for example, Ladner et al., WO 88/06630

D. Other Variants of Isolated Polypeptides

Included in the invention are isolated molecules that are: allelic variants, natural mutants, induced mutants, and proteins encoded by DNA that hybridizes under high or low stringency conditions to a nucleic acid which encodes a polypeptide such as the N-terminal fragment of Sonic hedgehog (SEQ ID NO: 24) and polypeptides bound specifically by antisera to hedgehog peptides, especially by antisera to an active site or binding site of hedgehog. All variants described herein are expected to: (i) retain the biological function of the original protein and (ii) retain the ability to link to at least one non-hedgehog moiety (e.g, an Ig).

The methods of the invention also feature uses of fragments, preferably biologically active fragments, or analogs of an isolated peptide such as hedgehog. Specifically, a biologically active fragment or analog is one having any in vivo or in vitro activity which is characteristic of the peptide shown in SEQ ID NOS: 10-20 or 23-26 or of other naturally occurring isolated hedgehog. Most preferably, the hydrophobically-modified fragment or analog has at least 10%, preferably 40% or greater, or most preferably at least 90% of the activity of Sonic hedgehog in any in vivo or in vitro assay.

Analogs can differ from naturally occurring isolated protein in amino acid sequence or in ways that do not involve sequence, or both. The most preferred polypeptides of the invention have preferred non-sequence modifications that include in vivo or in vitro chemical derivatization (e.g., of their N-terminal end), as well as possible changes in acetylation, methylation, phosphorylation, amidation, carboxylation, or glycosylation.

Other analogs include a protein such as Sonic hedgehog or its biologically active fragments whose sequences differ from the wild type consensus sequence (e.g., SEQ ID NO: 26) by one or more conservative amino acid substitutions or by one or more non conservative amino acid substitutions, or by deletions or insertions which do not abolish the isolated protein's biological activity. Conservative substitutions typically include the substitution of one amino acid for another with similar characteristics such as substitutions within the following groups: valine, alanine and glycine; leucine and isoleucine; aspartic acid and glutamic acid; asparagine and glutamine; serine and threonine; lysine and arginine; and phenylalanine and tyrosine.

The non-polar hydrophobic amino acids include alanine, leucine, isoleucine, valine, proline, phenylalanine, tryptophan, and methionine. The polar neutral amino acids include glycine, serine, threonine, cysteine, tyrosine, asparagine, and glutamine. The positively charged (basic) amino acids include arginine, lysine, and histidine. The negatively charged (acidic) amino acids include aspartic acid and glutamic acid. Other conservative substitutions can be readily known by workers of ordinary skill, For example, for the amino acid alanine, a conservative substitution can be taken from any one of D-alanine, glycine, beta-alanine, L-cysteine, and D-cysteine. For lysine, a replacement can be any one of D-lysine, arginine, D-arginine, homo-arginine, methionine, D-methionine, ornithine, or D-ornithine.

Other analogs used within the methods of the invention are those with modifications which increase peptide stability. Such analogs may contain, for example, one or more non-peptide bonds (which replace the peptide bonds) in the peptide sequence. Also included are: analogs that include residues other than naturally occurring L-amino acids, such as D-amino acids or non-naturally occurring or synthetic amino acids such as beta or gamma amino acids and cyclic analogs. Incorporation of D- instead of L-amino acids into the isolated hedgehog polypeptide may increase its resistance to proteases. See, U.S. Pat. No. 5,219,990 supra.

The term "fragment", as applied to an isolated hedgehog analog, can be as small as a single amino acid provided that it retains biological activity. It may be at least about 20 residues, more typically at least about 40 residues, preferably at least about 60 residues in length. Fragments can be generated by methods known to those skilled in the art. The ability of a candidate fragment to exhibit isolated hedgehog biological activity can be also assessed by methods known to those skilled in the art as described herein.

Hedgehog Proteins as Antagonists

Isolated hedgehog proteins useful in the present invention may be antagonists such as recombinant fusion proteins containing additional sequences unrelated to hedgehog. Thus, the antagonist polypeptide may also include all or a fragment of an amino acid sequence from SEQ ID NOS: 10-20 or 23-26, fused, in reading frame, to additional amino acid residues. One version of the polypeptides of the invention is a protein having a first polypeptide portion and a hedgehog antagonist portion, the antagonist portion being fused or otherwise linked either 5' or 3' to the first polypeptide portion. Thus, first, additional polypeptide portion has an amino acid sequence unrelated to an antagonist polypeptide. The additional polypeptide portion can be, e.g., any of glutathione-S-transferase, a DNA binding domain, or a polymerase activating domain, a histidine tag. It is most preferably an immunoglobulin or portion thereof, fused or otherwise linked to either the N- or C-terminus of the antagonist portion.

A preferred antagonist has at least the following properties: (i) the isolated protein binds the receptor patched-1 with an affinity that may be less than, but is preferably at least the same as, the binding of mature hedgehog protein to patched-1; and (ii) the isolated protein blocks alkaline phosphatase (AP) induction by mature hedgehog protein when tested in an in vitro CH310T1/2 cell-based AP induction assay. Antagonists of the invention may also have the additional properties of being (iii) unable to induce ptc-1 and gli-1 expression.

Persons having ordinary skill in the art can easily test any putative hedgehog antagonist for these properties. In particular, the mouse embryonic fibroblast line C3H10T1/2 is a mesenchymal stem cell line that is hedgehog responsive (as described in more detail below). Hedgehog treatment of the cells causes an upregulation of gli-1 and patched-1 (known indicators of hedgehog dependent signaling) and also causes induction of alkaline phosphatase activity, an indicator that the cells have differentiated down the chondrocyte/bone osteoblast lineage. Several hedgehog variants are unable to elicit a hedgehog-dependent response on C3H10T1/2 cells, but they competed with mature hedgehog for function and therefore serve as functional antagonists. These functional antagonists are preferred as the hedgehog to which a non-hedgehog (e.g., immunoglobulin) moiety is conjugated. In such a circumstance, it is not necessary to provide for muteins in which the KEX2-like intracellular protease recognition site is disabled. The synthesis and use of such hedgehog antagonist moieties are briefly described below.

A. N-modified Hedgehog Polypeptides as Antagonists

Certain hedgehog variants that contain N-terminal modifications can block hedgehog function because they lack the ability to elicit a hedgehog-dependent response but retain the ability to bind to hedgehog receptor, patched-1. The critical primary amino acid sequence that defines whether a hedgehog polypeptide (i.e., a Sonic, Indian or Desert hedgehog) is a functional hedgehog antagonist is the N-terminal cysteine residue which corresponds to Cys-1 of the mature hedgehog. So long as the hedgehog polypeptide either lacks this N-terminal cysteine completely or contains this N-terminal cysteine in a modified form (e.g. chemically modified or included as part of an N-terminal extension moiety), the resulting polypeptide can act as a functional hedgehog antagonist. In this regard, the fact that an N-terminal cysteine "corresponds to Cys-1" means: (a) the N-terminal cysteine is the Cys-1 of mature Sonic, Indian or Desert hedgehog; or (b) the N-terminal cysteine occupies the same position as Cys-1 of mature Sonic, Indian or Desert hedgehog. Provided that, for example, a Sonic hedgehog has an N-terminal cysteine corresponding to Cys-1 that is altered or otherwise modified as described herein, it can antagonize the action of any other member of the hedgehog family. Therefore, persons having ordinary skill in the art will understand that it is possible to an Indian hedgehog protein that antagonizes the activity of Sonic, Desert or Indian hedgehogs.

Examples of these antagonists with N-terminal modifications are included below and one skilled in the art can alter the disclosed structure of the antagonist, e.g., by producing fragments or analogs, and test the newly produced structures for antagonist activity. These examples in no way limit the structure of any related hedgehog antagonists, but are merely provided for further description. These, or analogous methods, can be used to make and screen fragments and analogs of a antagonist polypeptides. There are several variants that are able to function as antagonists.

1. N-Terminal Extensions

Antagonist polypeptides of the invention may include a hedgehog polypeptide sequence in which the N-terminal cysteine is linked to an N-terminal extension moiety. The isolated antagonist polypeptide can therefore be, as but one example, a recombinant fusion protein having: (a) a first N-terminal polypeptide portion that can be 5' to the hedgehog polypeptide itself, and that contains at least one element (e.g., an amino acid residue) that may be unrelated to hedgehog, linked to (b) an N-terminal cysteine corresponding to Cys-1 of Sonic hedgehog that is part of a hedgehog-antagonist of the invention, or a portion of hedgehog antagonist. This N-terminal extension moiety (e.g., the first N-terminal polypeptide portion) can be a histidine tag, a maltose binding protein, glutathione-S-transferase, a DNA binding domain, or a polymerase activating domain. The functional antagonist may include an N-terminal extension moiety that contains an element which replaces the Cys-1 of mature hedgehog or an N-terminal cysteine that corresponds to Cys-1 of a mature Sonic hedgehog.

2. N-Terminal Deletions

Another variation of a functional antagonist is a hedgehog protein that is missing no greater than about 12 amino acids beginning from that N-terminal cysteine corresponding to Cys-1 of a mature hedgehog. Deletions in more than the about the first 12 contiguous amino acid residues do not generate functional antagonists. Preferably, deletions of about 10 contiguous amino acids will provide suitable functional antagonists. One can, however, remove fewer than 10 contiguous residues and still maintain antagonist function. Moreover, one can delete various combinations of non-contiguous residues provided that there are at least about 3 deleted residues in total.

These structures highlight the importance of the N-terminus of hedgehog proteins for function and indeed, underscore the need to conjugate a hedgehog protein at a site other than the N-terminal cysteine. All of the N-terminal deletion variants were indistinguishable from mature Sonic hedgehog (Shh) in their ability to bind patched-1, but were inactive in the in vitro C3H10T1/2 AP induction assay. All these N-terminal variants are unable to promote hedgehog-dependent signaling.

3. N-Terminal Mutations

Yet another functional antagonist has a mutation of the N-terminal cysteine to another amino acid residue. Any non-hydrophobic amino acid residue may acceptable and persons having ordinary skill in the art following the teachings described herein will be able to perform the mutations and test the effects of such mutations. One example is Shh in which the N-terminal cysteine is replaced with a serine residue. This mutated form is indistinguishable from mature Shh in its ability to bind patched-1, but it blocks AP induction by mature Shh when tested for function in the C3H10T1/2 AP induction assay. Replacements with aspartic acid, alanine and histidine have also shown to serve as antagonists.

4. N-Terminal Cysteine Modifications

Because the primary amino acid sequence of hedgehog contains the Cys-1 that is important for biological activity, certain other modifications will result in inactive antagonist variants of hedgehog protein. Another antagonist is an isolated functional antagonist of a hedgehog polypeptide, comprising a hedgehog polypeptide containing an N-terminal cysteine that corresponds to Cys-1 of a mature Sonic hedgehog, except that the cysteine is in a modified form. Antagonist polypeptides of hedgehog may have non-sequence modifications that include in vivo or in vitro chemical derivatization of their N-terminal cysteine, as well as possible changes in acetylation, methylation, phosphorylation, amidation, or carboxylation. As an example, the functional antagonist can have an N-terminal cysteine in an oxidized form. Thus, a functional antagonist can have an N-terminal cysteine that is effectively modified by including it as part of an N-terminal extension moiety.

B. Other Embodiments

The functional antagonist polypeptides can include amino acid sequences that are at least 60% homologous to a hedgehog protein. The antagonist must exhibit at least the following functional antagonist properties: (i) the isolated protein binds the receptor patched-1 with an affinity that may be less than, but is preferably at least the same as, the binding of mature hedgehog protein to patched-1; and (ii) the isolated protein blocks alkaline phosphatase (AP) induction by mature hedgehog protein when tested in an in vitro CH310T1/2 cell-based AP induction assay.

Antagonists useful in the present invention also include those which arise as a result of the existence of multiple genes, alternative transcription events, alternative RNA splicing events, and alternative translational and posttranslational events. The polypeptide can be made entirely by synthetic means or can be expressed in systems, e.g., cultured cells, which result in substantially the same posttranslational modifications present when the protein is expressed in a native cell, or in systems which result in the omission of posttranslational modifications present when expressed in a native cell.

In a preferred embodiment, isolated antagonist is a polypeptide with one or more of the following characteristics:
(i) it has at least 60, more preferably 90 and most preferably 95% sequence identity with amino acids of SEQ ID NOS: 23-26;
(ii) it either has a modified N-terminal cysteine or lacks an N-terminal cysteine or has an N-terminal cysteine in a position different from the N-terminal cysteine corresponding to Cys-1 of the hedgehog;
(iii) it blocks alkaline phosphatase induction by mature hedgehog in CH310T1/2 cells;
(iv) it binds or interacts with its receptor patched-1 with an affinity that may be less than, but is preferably at least the same as, the binding of mature hedgehog protein to patched-1;
(v) it is unable to induce ptc-1 and gli-1 expression in vitro in CH310T/2 cells; or
(vi) it is unable to induce AP in CH310T1/2 assays.

Agonists of Hedgehog Biological Activity

Other preferred hedgehog polypeptides of the invention are agonists that are derived from several sources of hedgehog protein. In one embodiment, the agonist is not N-terminally clipped (as described above) and contains a mutation in its KEX2-like recognition site. Other embodiments of a hedgehog agonist suitable for use in a fusion protein, moiety, are based, in part, on the discovery disclosed in U.S. Patent Application No. 60/067,423 (Dec. 3, 1997) that human Sonic hedgehog, expressed as a full-length construct in either insect or in mammalian cells, has a hydrophobic palmitoyl group appended to the alpha-amine of the N-terminal cysteine. This is the first example of an extracellular signaling protein being modified in such a manner, and, in contrast to thiol-linked palmitic acid modifications whose attachment is readily reversible, this novel N-linked palmitoyl moiety is likely to be very stable by analogy with myristic acid modifications.

As a direct consequence of this initial discovery, it is known that increasing the hydrophobic nature of a hedgehog signaling protein can increase the protein's biological activity. Thus, the modified hedgehog acts as its own antagonist. In particular, appending a hydrophobic moiety to a signaling protein, such as a hedgehog protein, can enhance the protein's activity, and thus, act as an agonist. The N-terminal cysteine of biologically active proteins not only provides a convenient site for appending a hydrophobic moiety, and thereby modifying the physico-chemical properties of the protein, but modifications to the N-terminal cysteine can also increase the protein's stability. Additionally, addition of a hydrophobic moiety to an internal amino acid residue on the surface of the protein structure enhances the protein's activity. Use of these agonists in conjunction with one or more non-hedgehog conjugates (e.g., an immunoglobulin or fragment thereof) will allow increased bioavailability of the hedgehog agonists in a therapeutic context.

Accordingly, the methods and compositions of the present invention include the use of the conjugated hedgehog agonists due to their increased biological activity and higher patched-1 binding affinity. Moreover, the subject methods can be performed on cells which are provided in culture (in vitro), or on cells in a whole animal (in vivo).

The agonists have at least one of the following properties: (i) the isolated protein binds the receptor patched-1 with an affinity that is at similar to, but is preferably higher than, the binding of mature hedgehog protein to patched-1; or (ii) the isolated protein binds to a hedgehog protein in such a way as to increase the proteins binding affinity to patched-1 when tested in an in vitro CH310T1/2 cell-based AP induction assay. Agonists of the invention may also have the additional properties of being (iii) able to solely induce ptc-1 and gli-1 expression.

A. General Properties of Isolated Hedgehog Proteins Acting as Agonists

The polypeptide portion of the hedgehog compositions of the subject method can be generated by any of a variety of techniques, including purification of naturally occurring proteins, recombinantly produced proteins and synthetic chemistry. Polypeptide forms of the hedgehog proteins are preferably derived from vertebrate hedgehog proteins, e.g., have sequences corresponding to naturally occurring hedgehog proteins, or fragments thereof, from vertebrate organisms. However, it will be appreciated that the hedgehog polypeptide can correspond to a hedgehog protein (or fragment thereof) which occurs in any metazoan organism.

Family members useful in the methods of the invention include any of the naturally-occurring native hedgehog proteins including allelic, phylogenetic counterparts or other variants thereof, whether naturally-sourced or produced chemically including muteins or mutant proteins, as well as recombinant forms and new, active members of the hedgehog family.

The preferred agonists for use in conjugation with a non-hedgehog conjugate (e.g., immunoglobulin or fragment thereof) include a derivitized hedgehog polypeptide sequence as well as other N-terminal and/or C-terminal amino acid sequence or it may include all or a fragment of a hedgehog amino acid sequence. Agonist polypeptides of the invention include those that arise as a result of the existence of multiple genes, alternative transcription events, alternative RNA splicing events, and alternative translational and posttranslational events. The polypeptide can be made entirely by synthetic means or can be expressed in systems, e.g., cultured cells, which result in substantially the same posttranslational modifications present when the protein is expressed in a native cell, or in systems which result in the omission of posttranslational modifications present when expressed in a native cell.

In a preferred embodiment, the agonist to be conjugated is a hedgehog polypeptide with one or more of the following characteristics:
(i) it has at least 30, 40, 42, 50, 60, 70, 80, 90 or 95% sequence identity with a hedgehog sequence;
(ii) it has a cysteine or a functional equivalent as the N-terminal end;
(iii) it may induce alkaline phosphatase activity in C3H10T1/2 cells;
(iv) it has an overall sequence identity of at least 50%, preferably at least 60%, more preferably at least 70, 80, 90, or 95%, with a polypeptide of a hedgehog sequence;
(v) it can be isolated from natural sources such as mammalian cells;
(vi) it can bind or interact with patched; and
(vii) it is hydrophobically-modified (i.e., it has at least one hydrophobic moiety attached to the polypeptide).

Increasing the overall hydrophobic nature of a hedgehog protein increases the biological activity of the protein. The potency of a signaling protein such as hedgehog can be increased by: (a) chemically modifying, such as by adding a hydrophobic moiety to, the sulfhydryl and/or to the alpha-amine of the N-terminal cysteine (see U.S. 60/067,423); (b) replacing the N-terminal cysteine with a hydrophobic amino acid (see U.S. 60/067,423); or (c) replacing the N-terminal cysteine with a different amino acid and then chemically modifying the substituted residue so as to add a hydrophobic moiety at the site of the substitution.

Additionally, modification of a hedgehog protein at an internal residue on the surface of the protein with a hydrophobic moiety by: (a) replacing the internal residue with a hydrophobic amino acid; or (b) replacing the internal residue with a different amino acid and then chemically modifying the substituted residue so as to add a hydrophobic moiety at the site of the substitution will retain or enhance the biological activity of the protein.

Additionally, modification of a protein such as a hedgehog protein at the C-terminus with a hydrophobic moiety by: (a) replacing the C-terminal residue with a hydrophobic amino acid; or (b) replacing the C-terminal residue with a different amino acid and then chemically modifying the substituted residue so as to add a hydrophobic moiety at the site of the substitution, will retain or enhance the biological activity of the protein.

For hydrophobically-modified hedgehog obtained by chemically modifying the soluble, unmodified protein, palmitic acid and other lipids can be added to soluble Shh to create a lipid-modified forms with increased potency in the C3H10T1/2 assay. Another form of protein encompassed by the invention is a protein derivatized with a variety of lipid moieties. The principal classes of lipids that are encompassed within this invention are fatty acids and sterols (e.g., cholesterol). Derivatized proteins of the invention contain fatty acids which are cyclic, acyclic (i.e., straight chain), saturated or unsaturated, mono-carboxylic acids. Exemplary saturated fatty acids have the generic formula: $CH_3(CH_2)_n COOH$. Table 2 below lists examples of some fatty acids that can be derivatized conveniently using conventional chemical methods.

TABLE 2

Exemplary Saturated and Unsaturated Fatty Acids

| Value of n | Common Name |
|---|---|
| Saturated Acids: $CH_3(CH_2)_n COOH$: | |
| 2 | butyric acid |
| 4 | caproic acid |
| 6 | caprylic acid |
| 8 | capric acid |
| 10 | lauric acid |
| 12 | myristic acid* |
| 14 | palmitic acid* |
| 16 | stearic acid* |
| 18 | arachidic acid* |
| 20 | behenic acid |
| 22 | lignoceric acid |
| Unsaturated Acids: | |
| $CH_3CH=CHCOOH$ | crotonic acid |
| $CH_3(CH_2)_3CH=CH(CH_2)_7COOH$ | myristoleic acid* |
| $CH_3(CH_2)_5CH=CH(CH_2)_7COOH$ | palmitoleic acid* |
| $CH_3(CH_2)_7CH=CH(CH_2)_7COOH$ | oleic acid* |
| $CH_3(CH_2)_3(CH_2CH=CH)_2(CH_2)_7COOH$ | linoleic acid |
| $CH_3(CH_2CH=CH)_3(CH_2)_7COOH$ | linolenic acid |
| $CH_3(CH_2)_3(CH_2CH=CH)_4(CH_2)_3COOH$ | arachidonic acid |

The asterisk (*) denotes fatty acids detected in recombinant hedgehog protein secreted from a soluble construct (Pepinsky et at., supra).

Other lipids that can be attached to the protein include branched-chain fatty acids and those of the phospholipid group such as the phosphatidylinositols (i.e., phosphatidylinositol 4-monophosphate and phosphatidylinositol 4,5-biphosphate), phosphatidycholine, phosphatidylethanolamine, phosphatidylserine, and isoprenoids such as farnesyl or geranyl groups. Lipid-modified hedgehog proteins can be purified from either a natural source, or can be obtained by chemically modifying the soluble, unmodified protein.

For protein purified from a natural source, we showed that when full-length human Sonic hedgehog (Shh) was expressed in insect cells and membrane-bound Shh purified from the detergent-treated cells using a combination of SP-Sepharose chromatography and immunoaffinity chromatography, that the purified protein migrated on reducing SDS-PAGE gels as a single sharp band with an apparent mass of 20 kDa. The soluble and membrane-bound Shh proteins were readily distinguishable by reverse phase HPLC, where the tethered forms eluted later in the acetonitrile gradient. We then demonstrated that human Sonic hedgehog is tethered to cell membranes in two forms, one form that contains a cholesterol, and therefore is analogous to the data reported previously for Drosophila hedgehog, and a second novel form that contains both a cholesterol and a palmitic acid modification. Soluble and tethered forms of Shh were analyzed by electrospray mass spectrometry using a triple quadrupole mass spectrometer, equipped with an electrospray ion source as well as by liquid chromatography-mass spectrometry. The identity of the N-terminal peptide from endoproteinase Lys-C digested and hydrophobically modified Shh was confirmed by MALDI PSD mass spectrometric measurement on a MALDI time of flight mass spectrometer. The site of palmitoylation was identified through a combination of peptide mapping and sequence analysis and is at the N-terminus of the protein. Both modified forms were equally as active in the C3H10T1/2 alkaline phosphatase assay, but interestingly both were about 30-times more potent than soluble human Shh lacking the tether(s). The hydrophobic modifications did not significantly affect the apparent binding affinity of Shh for its receptor, patched.

For specific lipid-modified hedgehog obtained by chemically modifying the soluble, unmodified protein, palmitic acid and other lipids can be added to soluble Shh to create a lipid-modified forms with increased potency in the C3H10T1/2 assay. Generally, therefore, the reactive lipid moiety can be in the form of thioesters of saturated or unsaturated carboxylic acids such as a Coenzyme A thioesters. Such materials and their derivatives may include, for example, commercially available Coenzyme A derivatives such as palmitoleoyl Coenzyme A, arachidoyl Coenzyme A, arachidonoyl Coenzyme A, lauroyl Coenzyme A and the like. These materials are readily available from Sigma Chemical Company (St. Louis, Mo., 1998 catalog pp. 303-306).

There are a wide range of hydrophobic moieties with which hedgehog polypeptides can be derivatived. A hydrophobic group can be, for example, a relatively long chain alkyl or cycloalkyl (preferably n-alkyl) group having approximately 7 to 30 carbons. The alkyl group may terminate with a hydroxy or primary amine "tail". To further illustrate, such molecules include naturally-occurring and synthetic aromatic and non-aromatic moieties such as fatty acids, esters and alcohols, other lipid molecules, cage structures such as adamantane and buckminsterfullerenes, and aromatic hydrocarbons such as benzene, perylene, phenanthrene, anthracene, naphthalene, pyrene, chrysene, and naphthacene.

Particularly useful as hydrophobic molecules are alicyclic hydrocarbons, saturated and unsaturated fatty acids and other lipid and phospholipid moieties, waxes, cholesterol, isoprenoids, terpenes and polyalicyclic hydrocarbons including adamantane and buckminsterfullerenes, vitamins, polyethylene glycol or oligoethylene glycol, (C1-C18)-alkyl phosphate diesters, —O—CH2-CH(OH)—O—(C12-C18)-alkyl, and in particular conjugates with pyrene derivatives. The hydrophobic moiety can be a lipophilic dye suitable for use in the invention include, but are not limited to, diphenylhexatriene, Nile Red, N-phenyl-1-naphthylamine, Prodan, Laurodan, Pyrene, Perylene, rhodamine, rhodamine B, tetramethylrhodamine, Texas Red, sulforhodamine, 1,1'-didodecyl-3,3,3',3'tetramethylindocarbocyanine perchlorate, octadecyl rhodamine B and the BODIPY dyes available from Molecular Probes Inc.

Other exemplary lipophilic moieties include aliphatic carbonyl radical groups include 1- or 2-adamantylacetyl, 3-methyladamant-1-ylacetyl, 3-methyl-3-bromo-1-adamantylacetyl, 1-decalinacetyl, camphoracetyl, camphaneacetyl, noradamantylacetyl, norbornaneacetyl, bicyclo[2.2.2.]-oct-5-eneacetyl, 1-methoxybicyclo[2.2.2.]-oct-5-ene-2-carbonyl, cis-5-norbornene-endo-2,3-dicarbonyl, 5-norbornen-2-ylacetyl, (1R)-(–)-myrtentaneacetyl, 2-norbornaneacetyl, anti-3-oxo-tricyclo[2.2.1.0<2,6>]-heptane-7-carbonyl, decanoyl, dodecanoyl, dodecenoyl, tetradecadienoyl, decynoyl or dodecynoyl.

1. Chemical Modifications of the N-Terminal Cysteine of Hedgehog

If an appropriate amino acid is not available at a specific position, site-directed mutagenesis can be used to place a reactive amino acid at that site. Reactive amino acids include cysteine, lysine, histidine, aspartic acid, glutamic acid, serine, threonine, tyrosine, arginine, methionine, and tryptophan. Mutagenesis could also be used to place the reactive amino acid at the N- or C-terminus or at an internal position.

For example, it is possible to chemically modify an N-terminal cysteine of a biologically active protein, such as a hedgehog protein, or eliminate the N-terminal cysteine altogether and still retain the protein's biological activity. The replacement or modification of the N-terminal cysteine of hedgehog with a hydrophobic amino acid results in a protein with increased potency in a cell-based signaling assay. By replacing the cysteine, this approach eliminates the problem of suppressing other unwanted modifications of the cysteine that can occur during the production, purification, formulation, and storage of the protein. The generality of this approach is supported by the finding that three different hydrophobic amino acids, phenylalanine, isoleucine, and methionine, each give a more active form of hedgehog, and thus, an agonist.

This is also important for conjugation with non-hedgehog moieties (e.g., immunoglobulin) as described below in which we introduce two isoleucine residues to the N-terminal cysteine end of Sonic and Desert hedgehog. This effectively allows us to use the thiol of C-terminal cysteine as the reactive site for covalent coupling. Thus, replacement of the N-terminal cysteine with any other hydrophobic amino acid should result in an active protein. Furthermore, since we have found a correlation between the hydrophobicity of an amino acid or chemical modification and the potency of the corresponding modified protein in the C3H10T1/2 assay (e.g. Phe>Met, long chain length fatty acids>short chain length), it could be envisioned that adding more than one hydrophobic amino acid to the hedgehog sequence would increase the potency of the agonist beyond that achieved with a single amino acid addition. Indeed, addition of two consecutive isoleucine residues to the N-terminus of human Sonic hedgehog results in an increase in potency in the C3H10T1/2 assay as compared to the mutant with only a single isoleucine added. Thus, adding hydrophobic amino acids at the N- or C-terminus of a hedgehog protein, in a surface loop, or some combination of positions would be expected to give a more active form of the protein. The substituted amino acid need not be one of the 20 common amino acids. Methods have been reported for substituting unnatural amino acids at specific sites in proteins and this would be advantageous if the amino acid was more hydrophobic in character, resistant to proteolytic attack, or could be used to further direct the hedgehog protein to a particular site in vivo that would make its activity more potent or specific. Unnatural amino acids can be incorporated at specific sites in proteins during in vitro translation, and progress is being reported in creating in vivo systems that will allow larger scale production of such modified proteins.

There are many modifications of the N-terminal cysteine which protect the thiol and append a hydrophobic moiety. One of skill in the art is capable of determining which modification is most appropriate for a particular therapeutic use. Factors affecting such a determination include cost and ease of production, purification and formulation, solubility, stability, potency, pharmacodynamics and kinetics, safety, immunogenicity, and tissue targeting.

2. Chemical Modification of Other Amino Acids.

There are specific chemical methods for the modification of many other amino acids. Therefore, another route for synthesizing a more active form of hedgehog would be to chemically attach a hydrophobic moiety to an amino acid in hedgehog other than to the N-terminal cysteine. If an appropriate amino acid is not available at the desired position, site-directed mutagenesis could be used to place the reactive amino acid at that site in the hedgehog structure, whether at the N- or C-terminus or at another position. Reactive amino acids would include cysteine, lysine, histidine, aspartic acid, glutamic acid, serine, threonine, tyrosine, arginine, methionine, and tryptophan. Thus the goal of creating a better hedgehog agonist could be attained by many chemical means and we do not wish to be restricted by a particular chemistry or site of modification since our results support the generality of this approach.

The hedgehog polypeptide can be linked to the hydrophobic moiety in a number of ways including by chemical coupling means, or by genetic engineering. To illustrate, there are a large number of chemical cross-linking agents that are known to those skilled in the art. For the present invention, the preferred cross-linking agents are heterobifunctional cross-linkers, which can be used to link the hedgehog polypeptide and hydrophobic moiety in a stepwise manner. Heterobifunctional cross-linkers provide the ability to design more specific coupling methods for conjugating to proteins, thereby reducing the occurrences of unwanted side reactions such as homoprotein polymers. A wide variety of heterobifunctional cross-linkers are known in the art. These include: succinimidyl 4-(N-maleimidomethyl)cyclohexane-1-carboxylate (SMCC), m-Maleimidobenzoyl-N-hydroxysuccinimide ester (MBS); N-succinimidyl (4-iodoacetyl)aminobenzoate (SIAB), succinimidyl 4-(p-maleimidophenyl) butyrate (SMPB), 1-ethyl-3-(3-dimethylaminopropyl) carbodiimide hydrochloride (EDC); 4-succinimidyloxycarbonyl-a-methyl-a-(2-pyridyldithio)-toluene (SMPT), N-succinimidyl 3-(2-pyridyldithio) propionate (SPDP), succinimidyl 6-[3-(2-pyridyldithio) propionate] hexanoate (LC-SPDP). Those cross-linking agents having N-hydroxysuccinimide moieties can be obtained as the N-hydroxysulfosuccinimide analogs, which generally have greater water solubility. In addition, those cross-linking agents having disulfide bridges within the linking chain can be synthesized instead as the alkyl derivatives so as to reduce the amount of linker cleavage in vivo.

One particularly useful class of heterobifunctional cross-linkers, included above, contain the primary amine reactive group, N-hydroxysuccinimide (NHS), or its water soluble analog N-hydroxysulfosuccinimide (sulfo-NHS). Primary amines (lysine epsilon groups) at alkaline pH's are unprotonated and react by nucleophilic attack on NHS or sulfo-NHS esters. This reaction results in the formation of an amide bond, and release of NHS or sulfo-NHS as a by-product.

Another reactive group useful as part of a heterobifunctional cross-linker is a thiol reactive group. Common thiol reactive groups include maleimides, halogens, and pyridyl disulfides. Maleimides react specifically with free sulfhydryls (cysteine residues) in minutes, under slightly acidic to neutral (pH 6.5-7.5) conditions. Halogens (iodoacetyl functions) react with —SH groups at physiological pH's. Both of these reactive groups result in the formation of stable thioether bonds.

Testing for Biological Activity

While many bioassays have been used to demonstrate hedgehog activity, the C3H10T1/2 cell line provides a simple system for assessing hedgehog function without the complication of having to work with primary cell cultures or organ explants. The mouse embryonic fibroblast line C3H10T1/2 is a mesenchymal stem cell line that, under defined conditions, can differentiate into adipocytes, chondrocytes, and bone osteoblasts (Taylor, S. M., and Jones, P. A., Cell 17: 771-779 (1979) and Wang, E. A., et al., Growth Factors 9: 57-71 (1993)). Bone morphogenic proteins drive the differentiation of C3H10T1/2 cells into the bone cell lineage and alkaline phosphatase induction has been used as a marker for this process (Wang et al., supra). Shh has a similar effect on C3H10T1/2 cells (Kinto, N. et al., FEBS Letts. 404: 319-323 (1997)) and we routinely use the alkaline phosphatase induction by Shh as a quantitative measure of its in vitro potency. Shh treatment also produces a dose-dependent increase in gli-1 and ptc-1 expression, which can be readily detected by a PCR-based analysis.

Preferred Muteins of the Invention

The active N-terminal signaling domain of human Sonic Hedgehog protein (residues Cys24-197) can be expressed in many cell types (COS, insect cells, *E. coli*, yeast). In Baculovirus and yeast, the protein undergoes proteolytic clipping at various sites between Gly9 and Arg14 (See FIG. 3 for the N terminal sequence of Sonic hedgehog showing the clip sites). In the methylotropic yeast *Pichia pastoris*, strain GS115 (obtained from Invitrogen) this N-terminal clipping occurs exclusively at the Arg33-Arg34 bond, yielding N-10 Sonic Hedgehog protein (residues Arg34-Gly197). This clipping occurs intracellularly and appears to be catalyzed the KEX2 Golgi protease, or a similar KEX2-like intracellular protease.

The N-terminally clipped forms of SHH are inactive in the 10T1/2 assay (See Example 1). N-10 SHH is inactive and also antagonizes wild-type SHH when both forms are present in the assay. Thus, under certain circumstances prevention of N-terminal proteolytic clipping is necessary for production of fully active protein.

Because of the N-terminal clipping, a monomeric form of SHH is expected to contain two protein species, intact SHH and N-10 SHH.

In contrast, a dimeric fusion protein, such as a SHH-Fc (immunoglobulin) protein, is expected to contain 3 species: a species with two intact SHH domains, a species with two clipped domains, and a species with one intact and one clipped SHH domain.

Monomeric SHH could be separated from N-terminally clipped SHH by standard protein purification techniques. A dimeric fusion protein, however, is a more difficult purification problem. In addition, a substantial proportion of N-terminal clipping would more severely reduce the proportion of dimeric molecules containing two intact SHH domains. Thus, efficient production of dimeric fusion proteins is particularly dependent on prevention of the N-terminal clipping.

The KEX2 protease has a recognition sequence at least 3 amino acid residues long of the form:

[Arg or Lys]-Arg-[X] where X is not Pro

This recognition sequence occurs twice in the N-terminal region of Sonic Hedgehog: at Lys9Arg10Arg11 with cleavage between the two Arg residues (cleavage at this site is observed) and at Arg10Arg11His12 with predicted cleavage between Arg and His (cleavage at this site is not observed). We presume that the Lys9Arg10Arg11 site is preferred and cleavage at Arg10Arg11 destroys the Arg10Arg11His12 site.)

The KEX2 recognition sites in Sonic Hedgehog were mutated in order to eliminate this intracellular proteolytic clipping (See Example 1, FIG. 3 and Table 3). These mutant proteins were expressed as the N-terminal domain (codons Cys24-Gly197 of the Sonic Hedgehog coding sequence, corresponding to residues Cys1-Gly174 of mature protein after signal sequence cleavage.

TABLE 3

Summary of Mutations and their properties

| Mutation in Sonic Hedgehog | Sequence of basic Region[1] | Clipping | 10T1/2 activity | Comments |
|---|---|---|---|---|
| Wt | KRRHP | + | + | |
| KRRHP[32-36]RKRHP | RKRHP | + (N-11) | − | Some activity if Palmitoylated |
| KRRHP[32-36]RKRPP | RKRPP | − | − | |
| KRRHP[32-36]KKKHP | KKKHP | − | − | |
| KRRHP[32-36]RQRHP | RQRHP | − | − | Maintains His |
| RKKHP[32-36]RKKHP | RKKHP | − | − | Maintains His |
| Indian-like | GSRKRPPRK GSRKRPPRK[2] | − | + | |
| KRRHP[32-36]QRKHP | QRKHP | −** | + | Maintains central Arg |
| KRRHP[32-36]QRRPP | QRRPP | − | + | Maintains central Arg |

[1]Underlined residues are amino acid substitutions compared to wild type sequence.
[2]Underlined residues are amino acid substitutions compared to wild type Indian Sonic Hedgehog.

IV. UTILITY OF THE INVENTION

The unique property of the preferred immunoglobulin fusion proteins of the invention for therapeutic applications of the present invention is their general biocompatibility. The fusion proteins of the invention are believed not toxic and they are believed non-immunogenic and non-antigenic and do not interfere with the biological activities of the hedgehog protein moiety when conjugated under the conditions described herein. They have long circulation in the blood and are easily excreted from living organisms.

The therapeutic fusions of the present invention may be utilized for the prophylaxis or treatment of any condition or disease state for which a hedgehog or patched protein constituent is efficacious. In addition, the constructs of the present invention may be utilized in diagnosis of constituents, conditions, or disease states in biological systems or specimens, as well as for diagnosis purposes in non-physiological systems.

In therapeutic usage, the present invention contemplates a method of treating an animal subject having or latently susceptible to such condition(s) or disease state(s) and in need of such treatment, comprising administering to such animal an effective amount of a fusion protein of the present invention which is therapeutically effective for said condition or disease state. Subjects to be treated by the fusion proteins of the present invention include mammalian subjects and most preferably human subjects. Depending on the specific condition or disease state to be combated, animal subjects may be administered constructs of the invention at any suitable therapeutically effective and safe dosage, as may readily be determined within the skill of the art, and without undue experimentation.

Generally, the modified proteins described herein are useful for treating the same medical conditions that can be treated with the unmodified forms of the proteins. As but one example of the application of the proteins of this invention in a therapeutic context, modified hedgehog proteins according to the invention can be administered to patients suffering from a variety of neurological conditions. The ability of hedgehog protein to regulate neuronal differentiation during development of the nervous system and also presumably in the adult state indicates that polymer conjugated hedgehog can reasonably be expected to facilitate control of adult neurons with regard to maintenance, functional performance, and aging of normal cells; repair and regeneration processes in lesioned cells; and prevention of degeneration and premature death which results from loss of differentiation in certain pathological conditions. In light of this, the present modified hedgehog compositions, by treatment with a local infusion can prevent and/or reduce the severity of neurological conditions deriving from: (i) acute, subacute, or chronic injury to the nervous system, including traumatic injury, chemical injury, vessel injury, and deficits (such as the ischemia from stroke), together with infectious and tumor-induced injury; (ii) aging of the nervous system including Alzheimer's disease; (iii) chronic neurodegenerative diseases of the nervous system, including Parkinson's disease, Huntington's chorea, amylotrophic lateral sclerosis and the like; and (iv) chronic immunological diseases of the nervous system, including multiple sclerosis. The modified hedgehog proteins may also be injected into the cerebrospinal fluid, e.g., in order to address deficiencies of brain cells, or into the lymph system or blood stream as required to target other tissue or organ system-specific disorders.

Hedgehog compositions of the invention may be used to rescue, for example, various neurons from lesion-induced death as well as guiding reprojection of these neurons after such damage. Such damage can be attributed to conditions that include, but are not limited to, CNS trauma infarction, infection, metabolic disease, nutritional deficiency, and toxic agents (such as cisplatin treatment). Certain hedgehog proteins cause neoplastic or hyperplastic transformed cells to become either post-mitotic or apoptotic. Such compositions may, therefore, be of use in the treatment of, for instance, malignant gliomas, medulloblastomas and neuroectodermal tumors.

Modified proteins of the invention can be used to specifically target medical therapies against cancers and tumors which express the receptor for the protein. Such materials can be made more effective as cancer therapeutics by using them as delivery vehicles for antineoplastic drugs, toxins, and cytocidal radionuclides, such as yttrium 90.

A toxin may also be attached to the modified hedgehog to selectively target and kill hedgehog-responsive cells, such as a tumor expressing hedgehog receptor(s). Other toxins are equally useful, as known to those of skill in the art. Such toxins include, but are not limited to, Pseudomonas exotoxin, Diphtheria toxin, and saporin. This approach should prove successful because hedgehog receptor(s) are expressed in a very limited number of tissues. Another approach to such medical therapies is to use radioisotope labeled, modified protein. Such radiolabeled compounds will preferentially target radioactivity to sites in cells expressing the protein receptor(s), sparing normal tissues. Depending on the radioisotope employed, the radiation emitted from a radiolabeled protein bound to a tumor cell may also kill nearby malignant tumor cells that do not express the protein receptor. A variety of radionuclides may be used.

It is envisioned that subcutaneous delivery will be the primary route for therapeutic administration of the proteins of this invention. Local, intravenous delivery, or delivery through catheter or other surgical tubing may also be envisioned. Alternative routes include tablets and the like, commercially available nebulizers for liquid formulations, and inhalation of lyophilized or aerosolized formulations. Liquid formulations may be utilized after reconstitution from powder formulations.

For neurodegenerative disorders, several animal models are available that are believed to have some clinical predicative value. For Parkinson's disease, models involve the protection, or the recovery in rodents or primates in which the nigral-striatal dopaminergic pathway is damaged either by the systemic administration of MPTP or the local (intracranial) administration of 6-hydroxydopamine [6-OHDA], two selective dopaminergic toxins. Specific models are: MPTP-treated mouse model (Tomac et al., (1995) *Nature* 373, 335-339); MPTP-treated primate (marmoset or Rhesus) model (Gash et al., (1996) *Nature* 380, 252-255) and the unilateral 6-OHDA lesion rat model (Hoffer et al., (1994) *Neuroscience Lett.* 182, 107-111). For ALS, (Amyotrophic lateral sclerosis) models involve treatment of several mice strains that show spontaneous motor neuron degeneration, including the wobbler (Duchen, L. W. and Strich, S. J., (1968), *J. Neurol. Neurosurg. Psychiatry* 31, 535-542) and pmn mice (Kennel et al., (1996) *Neurobiology of Disease* 3, 137-147) and of transgenic mice expressing the human mutated superoxidase dismutase (hSOD) gene that has been linked to familial ALS (Ripps et al., (1995) *Proc. Natl. Acad. Sci, USA,* 92: 689-693). For spinal cord injury, the most common models involve contusion injury to rats, either through a calibrated weight drop, or fluid (hydrodynamic) injury. For Huntington's, models involve protection from excitotoxin (NMDA, quinolinic acid, kainic acid, 3-nitro-propionic acid, APMA) lesion to the striatum in rats (Nicholson, L. et al., (1995) *Neuroscience* 66, 507-521; Beal, M. F. et al., (1993) *J. Neuroscience* 13, 4181-4192). Recently, a model of transgenic mice overexpressing the human trinucleotide expanded repeat in the huntington gene has also been described (Davies, S. et al., (1997) *Cell* 90, 537-548). For multiple sclerosis, EAE in mice and rats is induced by immunization with MBP (myelin basic protein), or passive transfer of T cells activated with MBP (Hebr-Katz, R. (1993) *Int. Rev. Immunol.* 9, 237-285). For Alzheimer's, a relevant murine model is a determination of protection against lesion of the fimbria-fornix in rats (septal lesion), the main nerve bundle supplying the cholinergic innervation of the hippocampus (Borg et al., (1990) *Brain Res.,* 518, 295-298), as well as use of transgenic mice overexpressing the human beta-amyloid gene. For peripheral neuropathies, a relevant model is protection against loss of peripheral nerve conductance caused by chemtherapeutic agents such as taxol, vincristine, and cisplatin in mice and rats (Apfel et al., (1991) *Ann. Neurol.,* 29, 87-90).

The products of the present invention have been found useful in sustaining the half life of hedgehog, and may for example be prepared for therapeutic administration by dissolving in water or acceptable liquid medium. Administration is by either the parenteral, aerosol, or oral route. Fine colloidal suspensions may be prepared for parenteral administration to produce a depot effect, or by the oral route while aerosol formulation may be liquid or dry powder in nature. In the dry, lyophilized state or in solution formulations, the hedgehog protein-polymer conjugates of the present invention should have good storage stability. The thermal stability of conjugated hedgehog protein (data not shown) is advantageous in powder formulation processes that have a dehydration step.

The hedgehog proteins of the invention may be administered per se as well as in the form of pharmaceutically acceptable esters, salts, and other biologically functional derivatives thereof. In such pharmaceutical and medicament formulations, the hedgehog protein preferably is utilized together with one or more pharmaceutically acceptable carrier(s) and optionally any other therapeutic ingredients. The carrier(s) must be pharmaceutically acceptable in the sense of being compatible with the other ingredients of the formulation and not unduly deleterious to the recipient thereof. The hedgehog protein is provided in an amount effective to achieve the desired pharmacological effect, as described above, and in a quantity appropriate to achieve the desired daily dose.

The formulations include those suitable for parenteral as well as non-parenteral administration, and specific administration modalities include oral, rectal, buccal, topical, nasal, ophthalmic, subcutaneous, intramuscular, intravenous, transdermal, intrathecal, intra-articular, intra-arterial, sub-arachnoid, bronchial, lymphatic, vaginal, and intra-uterine administration. Formulations suitable for oral, nasal, and parenteral administration are preferred.

When the hedgehog protein is utilized in a formulation comprising a liquid solution, the formulation advantageously may be administered orally or parenterally. When the hedgehog protein is employed in a liquid suspension formulation or as a powder in a biocompatible carrier formulation, the formulation may be advantageously administered orally, rectally, or bronchially.

When the hedgehog protein is utilized directly in the form of a powdered solid, the hedgehog protein may advantageously be administered orally. Alternatively, it may be administered nasally or bronchially, via nebulization of the powder in a carrier gas, to form a gaseous dispersion of the powder which is inspired by the patient from a breathing circuit comprising a suitable nebulizer device.

The formulations comprising the present invention may conveniently be presented in unit dosage forms and may be prepared by any of the methods well known in the art of pharmacy. Such methods generally include the step of bringing the active ingredient(s) into association with a carrier which constitutes one or more accessory ingredients. Typically, the formulations are prepared by uniformly and intimately bringing the active ingredient(s) into association with a liquid carrier, a finely divided solid carrier, or both, and then, if necessary., shaping the product into dosage forms of the desired formulation.

Formulations of the present invention suitable for oral administration may be presented as discrete units such as capsules, cachets, tablets, or lozenges, each containing a predetermined amount of the active ingredient as a powder or granules; or a suspension in an aqueous liquor or a non-aqueous liquid, such as a syrup, an elixir, an emulsion, or a draught.

A tablet may be made by compression or molding, optionally with one or more accessory ingredients. Compressed tablets may be prepared by compressing in a suitable machine, with the active compound being in a free-flowing form such as a powder or granules which optionally is mixed with a binder, disintegrant, lubricant, inert diluent, surface active agent, or discharging agent. Molded tablets comprised of a mixture of the powdered polymer conjugates with a suitable carrier may be made by molding in a suitable machine.

A syrup may be made by adding the active compound to a concentrated aqueous solution of a sugar, for example sucrose, to which may also be added any accessory ingredient(s). Such accessory ingredient(s) may include flavorings, suitable preservative, agents to retard crystallization of the sugar, and agents to increase the solubility of any other ingredient, such as a polyhydroxy alcohol, for example glycerol or sorbitol.

Formulations suitable for parenteral administration conveniently comprise a sterile aqueous preparation of the active conjugate, which preferably is isotonic with the blood of the recipient (e.g., physiological saline solution). Such formulations may include suspending agents and thickening agents or other microparticulate systems which are designed to target the compound to blood components or one or more organs. The formulations may be presented in unit-dose or multi-dose form.

Nasal spray formulations comprise purified aqueous solutions of the active conjugate with preservative agents and isotonic agents.

Formulations for rectal administration may be presented as a suppository with a suitable carrier such as cocoa butter, hydrogenated fats, or hydrogenated fatty carboxylic acid.

Ophthalmic formulations such as eye drops are prepared by a similar method to the nasal spray, except that the pH and isotonic factors are preferably adjusted to match that of the eye.

Topical formulations comprise the conjugates of the invention dissolved or suspended in one or more media, such as mineral oil, petroleum, polyhydroxy alcohols, or other bases used for topical pharmaceutical formulations.

In addition to the aforementioned ingredients, the formulations of this invention may further include one or more accessory ingredient(s) selected from diluents, buffers, flavoring agents, disintegrants, surface active agents, thickeners, lubricants, preservatives (including antioxidants), and the like.

The following Examples are provided to illustrate the present invention, and should not be construed as limiting thereof. In particular, it will be understood that the in vivo, animal experiments described herein may be varied, so that other modifications and variations of the basic methodology are possible. These modifications and variations to the Examples are to be regarded as being within the spirit and scope of the invention.

EXAMPLE 1

Materials and Methods

Construction of pUB55, expression plasmid for Sonic Hedgehog in *Pichia pastoris*: pUB55 (SEQ ID. NO. 80) contains the N-terminal domain of human Sonic Hedgehog (SEQ ID. MO. 37, Table 4) with the alpha factor PrePro region as the secretion signal. pUB55 was constructed in pCCM73, a derivative of pPIC9 (obtained from Invitrogen, San Diego, Calif.) with the Kanamycin gene (HincII-HincII fragment) of pUC4-K inserted at the Sph1 site of pPIC9. The human Sonic hedgehog coding sequence from Ear1-Not1 was obtained from pEAG543 which has a stop codon and Not1 site engineered following Gly197 in the coding sequence. Plasmid pCCM73 was cut with XhoI and NotI and was ligated with the Ear1-Not1 fragment of pEAG543 (containing the Sonic Hedgehog coding sequence, Table 4) and Oligonucleotides [5' TCG AGA AAA GAT GCG GAC CGG GCA GGG GGT 3': SEQ ID NO: 35 and 5' CGA ACC CCC TGC CCG GTC CGC ATC TTT TC 3': SEQ ID NO: 36] that form a XhoI-Ear1 fragment and create the appropriate coding sequence for placing Sonic hedgehog adjacent to the alpha factor leader sequence in frame.

Construction of KEX2 cleavage site mutations in Sonic Hedgehog: pUB55 was digested with Xho1+Bbs1 and ligated with synthetic oligonucleotides (see Table 5 for oligonucleotides used for each mutation) that replace the XhoI-BbsI fragment which contains the N-terminal coding sequence of Sonic Hedgehog. [Note: although pUB55 has multiple BbsI sites, each has a different 4 base-pair overhang, such that religation of the mixture recreates the pUB55 sequence outside of the novel oligonucleotides included in each ligation reaction.] Novel restriction sites were incorporated into the XhoI-BbsI fragment of each novel mutant.

Expression of Desert Hedgehog in *Pichia pastoris* and construction of KEX2 site mutations: The Desert Hedgehog coding region in plasmid pEAG680 was modified to incorporate a BsrGI and an XmaI site using the Stratagene QuikChange mutagenesis kit. With oligos HOG-711 and HOG-712 for BsrGI, pEAG680 was mutagenized yielding pMMC11. With Oligonucleotides HOG-720 and HOG-721 for XmaI, pMMC11 was mutagenized to yield pMMC13. An expression plasmid for wild-type Desert Hedgehog N-terminal domain was made by subcloning the XmaI-Not1 fragment of pMMC13 to pKS314 at the same sites. [pKS314 contains the Sonic Hedgehog QRRPP mutant coding sequence of pKS310 (Table 5). The XhoI-NotI fragment of pKS310 was subcloned to pWS106, a derivative of pPic9 (Invitrogen) with the NcoI site in the HIS4 region destroyed by mutagenesis. The XmaI site in pKS314 lies within codons 3 and 4 (ProGly) sequence of Sonic Hedgehog. Because the first 4 residues of Sonic and Desert Hedgehog are identical, the Sonic Coding sequence can be used for the Desert Hedgehog constructs.) pKS310 contains a second XmaI site in the Kan gene, and was therefore unsuitable for this series of Desert Hedgehog constructions.]

Mutations in the KEX2 site of Desert Hedgehog were constructed by a three way ligation with (1) the BsrGI-NotI fragment containing the DHH coding region from pMMC13, (2) Oligonucleotides containing the XmaI-BsrGI region of DHH (Oligonucleotides as shown in Table K-2 and K-3) and (3) the plasmid backbone from pKS314 (NotI-XmaI fragment).

Expression of Indian Hedgehog in *Pichia pastoris* and construction of KEX2 site mutations: Plasmid pEAG657 (SEQ ID. NO. 84) is pBluescript with the Indian Hedgehog coding sequence with a stop codon following codon GlyXXX. pEAG658 (SEQ ID. NO. 85) is pBluescript with the Indian Hedgehog coding sequence and a SalI site engineered within residues suitable for fusing the Indian Hedgehog coding sequence with Fc immunoglobulin coding sequences at the hinge region of immunoglobulins. To facilitate subsequent manipulations, SpeI and XmaI sites were introduced to pEAG658 by site-directed mutagenesis. pEAG658 was mutagenized with Oligonucleotides HOG-709 and Hog-710, introducing a SpeI and yielding pMMC10. pMMC10 was subsequently mutagenized with Oligonucleotides HOG-722 and HOG-723, introducing an XmI site and yielding pMMC12. The novel SpeI and XmaI sites were then subcloned to pEAG657 by ligating the small BbsI-DraIII fragment of pEAG657 and the large BbsI-DraIII of pMMC12. An expression plasmid for wild-type Indian Hedgehog in *Pichia pastoris* (pMMC18) was constructed by subcloning the XmaI-NotI fragment of pMMC14 into pKS314 at the same sites. Expression vectors for KEX2 site mutants (pMMC19, RKRPP; and pMMC20, QRRPP) were constructed by ligatiing the SpeI-NotI fragment of pMMC14, the XmaI-NotI backbone of pKS314, and oligonucleotides forming an XmaI-SpeI fragment that contains the KEX2 site mutation (as listed in Tables 5 and 6).

TABLE 4

| DNA sequences of Hedgehog N-terminal domains and Immunogiobulin Fc Regions: | |
|---|---|
| Protein | DNA Sequence |
| human Sonic Hedgehog N-terminal Domain [SEQ ID NO:37] | TGCGGACCGGGCAGGGGGTTCGGGAAGAGGAGGCACCCCA |
| | AAAAGCTGACCCCTTTAGCCTACAAGCAGTTTATCCCCAA |
| | TGTGGCCGAGAAGACCCTAGGCGCCAGCGGAAGGTATGAA |
| | GGGAAGATCTCCAGAAACTCCGAGCGATTTAAGGAACTCA |
| | CCCCCAATTACAACCCCGACATCATATTTAAGGATGAAGA |
| | AAACACCGGAGCGGACAGGCTGATGACTCAGAGGTGTAAG |
| | GACAAGTTGAACGCTTTGGCCATCTCGGTGATGAACCAGT |
| | GGCCAGGAGTGAAACTGCGGGTGACCGAGGGCTGGGACGA |

TABLE 4-continued

DNA sequences of Hedgehog N-terminal domains and Immunoglobulin Fc Regions:

| Protein | DNA Sequence |
|---|---|
| | AGATGGCCACCACTCAGAGGAGTCTCTGCACTACGAGGGC |
| | CGCGCAGTGGACATCACCACGTCTGACCGCGACCGCAGCA |
| | AGTACGGCATGCTGGCCCGCCTGGCGGTGGAGGCCGGCTT |
| | CGACTGGGTGTACTACGAGTCCAAGGCACATATCCACTGC |
| | TCGGTGAAAGCAGAGAACTCGGTGGCGGCCAAATCGGGAG |
| | GC |
| Human Indian Hedgehog N-terminal Domain [SEQ ID NO:38] | TGCGGGCCGGGTCGGGTGGTGGGCAGCCGCCGGCGACCGC |
| | CACGCAAACTCGTGCCGCTCGCCTACAAGCAGTTCAGCCC |
| | CAATGTGCCCGAGAAGACCCTGGGCGCCAGCGGACGCTAT |
| | GAAGGCAAGATCGCTCGCAGCTCCGAGCGCTTCAAGGAGC |
| | TCACCCCCAATTACAATCCAGACATCATCTTCAAGGACGA |
| | GGAGAACACAGGCGCCGACCGCCTCATGACCCAGCGCTGC |
| | AAGGACCGCCTGAACTCGCTGGCTATCTCGGTGATGAACC |
| | AGTGGCCCGGTGTGAAGCTGCGGGTGACCGAGGGCTGGGA |
| | CGAGGACGGCCACCACTCAGAGGAGTCCCTGCATTATGAG |
| | GGCCGCGCGGTGGACATCACCACATCAGACCGCGACCGCA |
| | ATAAGTATGGACTGCTGGCGCGCTTGGCAGTGGAGGCCGG |
| | CTTGACTGGGTGTATTACGAGTCAAAGGCCCACGTGCATT |
| | GCTCCGTCAAGTCCGAGCACTCGGCCGCAGCCAAGACGGG |
| | CGGC |
| Human Desert Hedgehog N-terminal Domain [SEQ ID NO:39] | TGCGGGCCGGGCCGGGGCCGGTTGGCCGGCGCCGCTATG |
| | CGCGCAAGCAGCTCGTGCCGCTACTCTACAAGCAATTTGT |
| | GCCCGGCGTGCCAGAGCGGACCCTGGGCGCCAGTGGGCCA |
| | GCGGAGGGGAGGGTGGCAAGGGGCTCCGAGCGCTTCCGGG |
| | ACCTCGTGCCCAACTACAACCCCGACATCATCTTCAAGGA |
| | TGAGGAGAACAGTGGAGCCGACCGCCTGATGACCGAGCGT |
| | TGTAAGGAGCGGGTGAACGCTTTGGCCATTGCCGTGATGA |
| | ACATGTGGCCCGGAGTGCGCCTACGAGTGACTGAGGGCTG |
| | GGACGAGGACGGCCACCACGCTCAGGATTCACTCCACTAC |
| | GAAGGCCGTGCTTTGGACATCACTACGTCTGACCGCGACC |
| | GCAACAAGTATGGGTTGCTGGCGCGCCTCGCAGTGGAAGC |
| | CGGCTTCGACTGGGTCTACTACGAGTCCCGCAACCACGTC |
| | CACGTGTCGGTCAAAGCTGATAACTCACTGGCGGTCCGGG |
| | CGGGCGGC |
| Fc region of human IgG1 - with Asn-Gln glycosylation site mutation [SEQ ID NO:40] | GTCGACAAAACTCACACATGCCCACCGTGCCCAGCACCTG |
| | AACTCCTGGGGGGACCGTCAGTCTTCCTCTTCCCCCCAAA |
| | ACCCAAGGACACCCTCATGATCTCCCGGACCCCTGAGGTC |

TABLE 4-continued

DNA sequences of Hedgehog N-terminal domains and Immunoglobulin Fc Regions:

| Protein | DNA Sequence |
|---|---|
| | ACATGCGTGGTGGTGGACGTGAGCCACGAAGACCCTGAGG |
| | TCAAGTTCAACTGGTACGTGGACGGCGTGGAGGTGCATAA |
| | TGCCAAGACAAAGCCGcgggaggagcagtaccagagcacg |
| | taccgtgtggTCAGCGTCCTCACCGTCCTGCACCAGGACT |
| | GGCTGAATGGCAAGGAGTACAAGTGCAAGGTCTCCAACAA |
| | AGCCCTCCCAGCCCCCATCGAGAAAACCATCTCCAAAGCC |
| | AAAGGGCAGCCCCGAGAACCACAGGTGTACACCCTGCCCC |
| | CATCCCGGGATGAGCTGACCAAGAACCAGGTCAGCCTGAC |
| | CTGCCTGGTCAAAGGCTTCTATCCCAGCGACATCGCCGTG |
| | GAGTGGGAGAGCAATGGGCAGCCGGAGAACAACTACAAGA |
| | CCACGCCTCCCGTGTTGGACTCCGACGGCTCCTTCTTCCT |
| | CTACAGCAAGCTCACCGTGGACAAGAGCAGGTGGCAGCAG |
| | GGGAACGTCTTCTCATGCTCCGTGATGCATGAGGCTCTGC |
| | ACAACCACTACACGCAGAAGAGCCTCTCCCTGTCTCCCGG |
| | GAAA |
| Fc region of murine IgG1 - with Asn-Gln glycosylation site mutation [SEQ ID NO:41] | GTCGACGTGCCCAGGGATTGTGGTTGTAAGCCTTGCATAT |
| | GTACAGTCCCAGAAGTATCATCTGTCTTCATCTTCCCCCC |
| | AAAGCCCAAGGATGTGCTCACCATTACTCTGACTCCTAAG |
| | GTCACGTGTGTTGTGGTAGACATCAGCAAGGATGATCCCG |
| | AGGTCCAGTTCAGCTGGTTTGTAGATGATGTGGAGGTGCA |
| | CACAGCTCAGACGCAACCaCGGGAaGAGCAGTTCCAAAGC |
| | ACTTTCCGCTCAGTCAGTGAACTTCCCATCATGCACCAGG |
| | ACTGGCTCAATGGCAAGGAGTTCAAATGCAGGGTCAACAG |
| | TGCAGCTTTCCCTGCCCCCATCGAGAAAACCATCTCCAAA |
| | ACCAAAGGCAGACCGAAGGCTCCACAGGTGTACACCATTC |
| | CACCTCCCAAGGAGCAGATGGCCAAGGATAAAGTCAGTCT |
| | GACCTGCATGATAACAGACTTCTTCCCTGAAGACATTACT |
| | GTGGAGTGGCAGTGGAATGGGCAGCCAGCGGAGAACTACA |
| | AGAACACTCAGCCCATCATGGACACAGATGGCTCTTACTT |
| | CGTCTACAGCAAGCTCAATGTGCAGAAGAGCAACTGGGAG |
| | GCAGGAAATACTTTCACCTGCTCTGTGTTACATGAGGGCC |
| | TGCACAACCACCATACTGAGAAGAGCCTCTCCCACTCTCC |
| | TGGTAAA |
| Fc region of murine IgG2a - with Asn-Gln glycosylation site mutation [SEQ ID NO:42] | GTCGACCCCAGAGGGCCCACAATCAAGCCCTGTCCTCCAT |
| | GCAAATGCCCAGCACCTAACCTCTTGGGTGGACCATCCGT |
| | CTTCATCTTCCCTCCAAAGATCAAGGATGTACTCATGATC |
| | TCCCTGAGCCCCATAGTCACATGTGTGGTGGTGGATGTGA |

TABLE 4-continued

DNA sequences of Hedgehog N-terminal domains and Immunoglobulin Fc Regions:

| Protein | DNA Sequence |
|---|---|
| | GCGAGGATGACCCAGATGTCCAGATCAGCTGGTTTGTGAA |
| | CAACGTGGAAGTACACACAGCTCAGACACAAACCCATAGA |
| | GAGGATTACCAAAGTACaCTtCGGGTGGTCAGTGCCCTCC |
| | CCATCCAGCACCAGGACTGGATGAGTGGCAAGGAGTTCAA |
| | ATGCAAGGTCAACAACAAAGACCTCCCAGCGCCCATCGAG |
| | AGAACCAGCACCAGGACTGGATGAGTGGCAAGGAGTTCAA |
| | ATGCATATGTCTTGCCTCCACCAGAAGAAGAGATGACTAA |
| | GAAACAGGTCACTCTGACCTGCATGGTGACAGACTTCATG |
| | CCTGAAGACATTTACGTGGAGTGGACCAACAACGGGGAAA |
| | ACAGAGCTAAACTACAAGAACACTGAACCAGTCCTGGACT |
| | CTGATGGTTCTTACTTCATGTACAGCAAGCTGAGAGTGGA |
| | AAAGAAGAACTGGGTGGAAAGAAATAGCTACTCCTGTTCA |
| | GTGGTCCACGAGGGTCTGCACAATCACCACACGACTAAGA |
| | GCTTCTCCCGGACTCCGGGTAAA |

TABLE 5

KEX2 mutations and the Oligonucleotides for their construction

| Sonic Hedgehog mutations | Oligos used | plasmid name | | |
|---|---|---|---|---|
| wt KRRHP [SEQ ID NO:87] | | | | |
| KRRPP [SEQ ID NO:88] | HOG-402 | pKS285 | | |
| | HOG-403 | | | |
| | HOG-404 | | | |
| | HOG-405 | | | |
| KKKHP [SEQ ID NO:89] | HOG-402 | pKS288 | | |
| | HOG-403 | | | |
| | HOG-409 | | | |
| | HOG410 | | | |
| RQRHP [SEQ ID NO:90] | HOG-465 | pKS301 | | |
| | HOG-466 | | | |
| | HOG-462 | | | |
| | HOG-403 | | | |
| QRKHP [SEQ ID NO:91] | HOG-402 | pKS309 | | |
| | HOG-403 | | | |
| | HOG-565 | | | |
| | HOG-566 | | | |
| QRRPP [SEQ ID NO:92] | HOG-402 | pKS310 | | |
| | HOG-403 | | | |
| | HOG-567 | | | |
| | HOG-568 | | | |
| RKRHP [SEQ ID NO:93] | HOG-402 | pKS287 | | |
| | HOG-403 | | | |
| | HOG-406 | | | |
| | HOG-407 | | | |
| RKKHP [SEQ ID NO:94] | HOG-463 | pKS300 | | |
| | HOG-464 | | | |
| | HOG-462 | | | |
| | HOG-403 | | | |
| INDIAN-LIKE | HOG-402 | pKS289 | | |
| | HOG-403 | | | |
| | HOG-411 | | | |
| | HOG-412 | | | |
| KKRHPKK [SEQ ID NO:95] | HOG-789 | pMMC22 | MMC86 | |
| | HOG-799 | | MMC87 | |
| | HOG-803 | | MMC88 | |
| | HOG-808 | | | |
| RRRHPKK [SEQ ID NO:96] | HOG-791 | pMMC23 | MMC89 | |
| | HOG-799 | | MMC90 | |
| | HOG-804 | | MMC91 | |
| | HOG-808 | | | |
| QQQHPKK [SEQ ID NO:97] | HOG-795 | pMMC25 | MMC99 | |
| | HOG-799 | | MMC100 | |
| | HOG-806 | | MMC101 | |
| | HOG-808 | | | |
| KRRHPQQ [SEQ ID NO:98] | HOG-797 | pMMC26 | MMC96 | |
| | HOG-799 | | MMC97 | |
| | HOG-807 | | MMC98 | |
| | HOG-808 | | | |
| Indian Hedgehog mutations | | | | |
| RKRPP [SEQ ID NO:99] | HOG-743 | pMMC19 | MMC77 | |
| | HOG-744 | | MMC78 | |
| QRRPP [SEQ ID NO:100] | HOG-745 | pMMC20 | MMC79 | |
| | HOG-746 | | MMC80 | |
| Desert Hedgehog mutation | | | | |
| QRRPA [SEQ ID NO:101] | HOG-739 | pMMC16 | MMC49 | |
| | HOG-740 | | MMC50 | |
| | | | MMC51 | |
| RQRYA [SEQ ID NO:102] | HOG-741 | pMMC17 | MMC52 | |
| | HOG-742 | | MMC53 | |
| | | | MMC54 | |

TABLE 6

Sequences of Oligonucleotides used in Plasmid constructions of Table 5

| Name | Sequence |
|---|---|
| HOG-402 [SEQ ID NO:43] | CTGACCCCTTTAGCCTACAAGCAGTTTATCCCCA ATGTGGCCGAGAAGACCC |
| HOG-403 [SEQ ID NO:44] | CCTAGGGTCTTCTCGGCCACATTGGGGATAAACT GCTTGTAGGCTAAAGG |
| HOG-404 [SEQ ID NO:45] | TCGAGAAAAGATGCGGCCCGGGCAGGGGGTTCGG GAAGAGACCTCCCAAAAAG |
| HOG-405 [SEQ ID NO:46] | GGTCAGCTTTTTGGGAGGTCTCTTCCCGAACCCC CTGCCCGGGCCGCATCTTTTC |
| HOG-407 [SEQ ID NO:47] | TCGAGAAAAGATGCGGCCCGGGCAGGGGGTTCGG GAGGAAGAGACACCCCAAAAAG |
| HOG-408 [SEQ ID NO:48] | GGTCAGCTTTTTGGGGTGTCTCTTCCTCCCGAAC CCCCTGCCCGGGCCGCATCTTTTC |
| HOG-409 [SEQ ID NO:49] | TCGAGAAAAGATGCGGCCCGGGCAGGGGGTTCGG GAAGAAGAAGCACCCCAAAAAG |
| HOG-410 [SEQ ID NO:50] | GGTCAGCTTTTTGGGGTGCTTCTTCTTCCCGAAC CCCCTGCCACGGGCCGCATCTTTTC |
| HOG-411 [SEQ ID NO:51] | TCGAGAAAAGATGCGGCCCGGGCAGGGGGTTCGG GTCTAGAAAGAGACCTCCCAGAAAG |
| HOG-412 [SEQ ID NO:52] | GGTCAGCTTTCTGGGAGGTCTCTTtCTAGACCCG AACCCCCTGCCCGGGCCGCATCTTTTC |
| HOG-462 [SEQ ID NO:53] | CTTACCCCTTTAGCCTACAAGCAGTTTATCCCCA ATGTGGCCGAGAAGACCC |
| HOG-463 [SEQ ID NO:54] | TCGAGAAAAGATGCGGCCCGGGCAGGGGGTTCGG GAAGAAGAAGCACCCCAAAAAG |
| HOG-464 [SEQ ID NO:55] | GGTAAGCTTTTTGGGGTGCTTCTTCCTCCCGAAC CCCCTGCCCGGGCCGCATCTTTTC |
| HOG-465 [SEQ ID NO:56] | TCGAGAAAAGATGCGGCCCaGGCAGGGGGTTCGG GAGGCAGAGACACCCCAAAAAG |
| HOG-466 [SEQ ID NO:57] | GGTaAGCTTTTTGGGGTGTCTCTGCCTCCCGAAC CCCCTGCCtGGGCCGCATCTTTTC |
| HOG-565 [SEQ ID NO:58] | TCGAGAAAAGATGCGGCCCGGGCAGGGGGTTCGG GCAGCGGAAGCACCCCAAAAAG |
| HOG-566 [SEQ ID NO:59] | GGTCAGCTTTTTGGGTGCTTCCGCTGCCCGAAC CCCCTGCCCGGGCCGCATCTTTTC |
| HOG-567 [SEQ ID NO:60] | TCGAGAAAAGATGCGGCCCGGGCAGGGGGTTCGG GCAGAGAAGACCACCCCAAAAAG |
| HOG-568 [SEQ ID NO:61] | GGTCAGCTTTTTGGGTGGTCTTCTCTGCCCGAAC CCCCTGCCCGGGCCGCATCTTTTC |
| HOG-739 [SEQ ID NO:62] | CCGGGCCGGGGCCGGTTGGCCAACGCCGGCCGG CGCGCAAGCAGCTCGTGCCGCTACT |
| HOG-740 [SEQ ID NO:63] | GTACAGTAGCGGCACGAGCTGCTTGCGCGCCGGC CGGCGTTGGCCAACCGGCCCCCGGC |
| HOG-741 [SEQ ID NO:64] | CCGGGCCGGGGCCGGTTGGCCGGCAGCGCTATG CGCGCAAGCAGCTGGTGCCGCTACT |
| HOG-742 [SEQ ID NO:65] | GTACAGTAGCGGCACCAGCTGCTTGCGCGCATAG CGCTGCCGGCCAACCGGCCCCCGGC |
| HOG-743 [SEQ ID NO:66] | CCGGGTCGGGTGGTGGGCAGCCGCAAGCGGCCGC CACGCAAA |
| HOG-744 [SEQ ID NO:67] | CTAGTTTGCGTGGCGGCCGCTTGCGGCTGCCCAC CACCCGAC |
| HOG-745 [SEQ ID NO:68] | CCGGGTCGGGTGGTGGGCAGCCAACGTCGACCGC CACGCAAA |
| HOG-746 [SEQ ID NO:69] | CTAGTTTGCGTGGCGGTCGACGTTGGCTGCCCAC CACCCGAC |
| HOG-789 [SEQ ID NO:70] | GCCCGGGCAGGGGGTTCGGGAAGAAGAGGCACCC CAAAAAGCTGACC |
| HOG-791 [SEQ ID NO:71] | GCCCGGGCAGGGGGTTCGGGAGGAGGAGGCACCC CAAAAAGCTGACC |
| HOG-795 [SEQ ID NO:72] | GCCCGGGCAGGGGGTTCGGGCAGCAGCAGCACCC CAAAAAGCTGACC |
| HOG-797 [SEQ ID NO:73] | GCCCGGGCAGGGGGTTCGGGAAGAGGAGGCACCC CCAGCAGCTGACC |
| HOG-799 [SEQ ID NO:74] | CCTTTAGCCTACAAGCAGTTTATCCCCAAGGTGG CCGAGAAGACC |
| HOG-803 [SEQ ID NO:75] | TAAAGGGGTCAGCTTTTTGGGGTGCCTCTTCTTC CCGAACCCCCTGCCCG |
| HOG-804 [SEQ ID NO:76] | TAAAGGGGTCAGCTTTTTGGGGTGCCTCCTCCTC CCGAACCCCCTGCCCG |
| HOG-806 [SEQ ID NO:77] | TAAAGGGGTCAGCTTTTGGGGTGCTGCTGCTGCC CGAACCCCCTGCCCG |
| HOG-807 [SEQ ID NO:78] | TAAAGGGGTCAGCTGCTGGGGGTGCCTCCTCTTC CCGAACCCCCTGCCCG |
| HOG-808 [SEQ ID NO:79] | CTAGGGTCTTCTCGGCCACATTGGGGAGAAACTG CTTGTAGGC |

| Plasmid | DNA sequence |
|---|---|
| PUB55 [SEQ ID | GATCTAACATCCAAAGACGAAAGGTTGAATGAAACCTTTTTG |

TABLE 6-continued

Sequences of Oligonucleotides used in Plasmid constructions of Table 5

NO:80] CCATCCGACATCCACAGGTCCATTCTCACACATAAGTGCCAA
ACGCAACAGGAGGGGATACACTAGCAGCAGACCGTTGCAAAC
GCAGGACCTCCACTCCTCTTCTCCTCAACACCCACTTTTGCC
ATCGAAAAACCAGCCCAGTTATTGGGCTTGATTGGAGCTCGC
TCATTCCAATTCCTTCTATTAGGCTACTAACACCATGACTTT
ATTAGCCTGTCTATCCTGGCCCCCCTGGCGAGGTTCATGTTT
GTTTATTTCCGAATGCAACAAGCTCCGCATTACACCCGAACA
TCACTCCAGATGAGGGCTTTCTGAGTGTGGGGTCAAATAGTT
TCATGTTCCCCAAATGGCCCAAAACTGACAGTTTAAACGCTG
TCTTGGAACCTAATATGACAAAAGCGTGATCTCATCCAAGAT
GAACTAAGTTTGGTTCGTTGAAATGCTAACGGCCAGTTGGTC
AAAAAGAAACTTCCAAAAGTCGCCATACCGTTTGTCTTGTTT
GGTATTGATTGACGAATGCTCAAAAATAATCTCATTAATGCT
TAGCGCAGTCTCTCTATCGCTTCTGAACCCCGGTGCACCTGT
GCCGAAACGCAAATGGGGAAACACCCGCTTTTTGGATGATTA
TGCATTGTCTCCACATTGTATGCTTCCAAGATTCTGGTGGGA
ATACTGCTGATAGCCTAACGTTCATGATCAAAATTTAACTGT
TCTAACCCCTACTTGACAGCAATATATAAACAGAAGGAAGCT
GCCCTGTCTTAAACCTTTTTTTTTATCATCATTATTAGCTTA
CTTTCATAATTGCGACTGGTTCCAATTGACAAGCTTTTGATT
TTAACGACTTTTAACGACAACTTGAGAAGATCAAAAAACAAC
TAATTATTCGAAGGATCCAAACGATGAGATTTCCTTCAATTT
TTACTGCAGTTTTATTCGCAGCATCCTCCGCATTAGCTGCTC
CAGTCAACACTACAACAGAAGATGAAACGGCACAAATTCCGG
CTGAAGCTGTCATCGGTTACTCAGATTTAGAAGGGGATTTCG
TATTGTTTATAAATACTACATGTTGCTGTTTTGCCATTTTCC
AACAGCACAAATAACGGGTTATTGCCAGCATTGCTGCTAAAG
AAGAAGGGGTATCTCTCGAGAAAAGATGCGGACCGGGCAGGG
GGTTCGGGAAGAGGAGGCACCCCAAAAAGCTGACCCCTTTAG
CCTACAAGCAGTTTATCCCCAATGTGGCCGAGAAGACCCTAG
GCGCCAGCGGAAGGTATGAAGGGAAGATCTCCAGAAACTCCG
TATTTAAGGATGAAGAAAACACCGGAGCGATTTAAGGAACTC
ACCCCCAATTACAACCCCGACATCAAGCGGACAGGCTGATGA
CTCAGAGGTGTAAGGACAAGTTGAACGCTTTGGCCATCTCGG
TGATGAACCAGTGGCCAGGAGTGAAACTGCGGGTGACCGAGG
GCTGGGACGAAGATGGCCACCACTCAGAGGAGTCTCTGCACT
ACGAGGGCCGCGCAGTGGACATCACCACGTCTGACCGCGACC
GCAGCAAGTACGGCATGCTGGCCCGCCTGGCGGTGGAGGCCG

GCTTCGACTGGGTGTACTACGAGTCCAAGGCACATATCCACT
GCTCGGTGAAAGCAGAGAACTCGGTGGCGGCCAAATCGGGAG
GCTGATTCGCGGCCGCGAATTAATTCGCCTTAGACATGACTG
TTCCTCAGTTCAAGTTGGGCACTTACGAGAAGACCGGTCTTG
CTAGATTCTAATCAAGAGGATGTCAGAATGCCATTTGCCTGA
GAGATGCAGGCTTCATTTTTGATACTTTTTTATTTGTAACCT
ATAAGTATAGGATTTTTTTGTCATTTTGTTTCTTCTCGTAC
GAGCTTGCTCCTGATCAGCCTATCTCGCAGCTGATGAATATC
TTGTGGTAGGGGTTTGGGAAAATCATTCGAGTTTGATGTTTT
TGTTGGTATTTCCCACTCCTCTTCAGAGTACGAAGATTAAG
TGAGAAGTTCGTTTGTGCAAGCTTATCGATAAGCTTTAATGC
GGTAGTTTATCACAGTTAAATTGCTAACGCAGTCAGGCACCG
TGTATGAAATCTAACAATGCGCTCATCGTCATCCTCGGCACC
GTCACCCTGGATGCTGTAGGCATAGGCTTGGTTATGCCGGTA
CTGCCGGGCCTCTTGCGGGATATCGTCCATTCCGACAGCATC
GCCAGTCACTATGGCGTGCTGCTAGCGCTATATGCGTTGATG
CAATTTCTATGCGCACCCGTTCTCGGAGCACTGTCCGACCGC
TTTGGCCGCCGCCCAGTCCTGCTCGCTTCGCTACTTGGAGCC
ACTATCGACTACGCGATCATGGCGACCACACCCGTCCTGTGG
ATCTATCGAATCTAAATGTAAGTTAAAATCTCTAAATAATTA
AATAAGTCCCAGTTTCTCCATACGAACCTTAACAGCATTGCG
GTGAGCATCTAGACCTTCAACAGCAGCCAGATCCATCACTGC
TTGGCCAATATGTTTCAGTCCCTCAGGAGTTACGTCTTGTGA
AGTGATGAACTTCTGGAAGGTTGCAGTGTTAACTCCGCTGTA
TTGACGGGCATATCCGTACGTTGGCAAAGTGTGGTTGGTACC
GGAGGAGTAATCTCCACAACTCTCTGGAGAGTAGGCACCAAC
AAACACAGATCCAGCGTGTTGTACTTGATCAACATAAGAAGA
AGCATTCTCGATTTGCAGGATCAAGTGTTCAGGAGCGTACTG
ATTGGACATTTCCAAAGCCTGCTCGTAGGTTGCAACCGATAG
GGTTGTAGAGTGTGCAATACACTTGCGTACAATTTCAACCCT
TGGCAACTGCACAGCTTGGTTGTGAACAGCATCTTCAATTCT
GGCAAGCTCCTTGTCTGTCATATCGACAGCCAACAGAATCAC
CTGGGAATCAATACCATGTTCAGCTTGAGCAGAAGGTCTGAG
GCAACGAAATCTGGATCAGCGTATTTATCAGCAATAACTAGA
ACTTCAGAAGGCCCAGCAGGCATGTCAATACTACACAGGGCT
GATGTGTCATTTTGAACCATCATCTTGGCAGCAGTAACGAAC
TGGTTTCCTGGACCAAATATTTTGTCACACTTAGGAACAGTT
TCTGTTCCGTAAGCCATAGCAGCTACTGCCTGGGCGCCTCCT

TABLE 6-continued

Sequences of Oligonucleotides used in Plasmid constructions of Table 5

GCTAGCACGATACACTTAGCACCAACCTTGTGGGCAACGTAG

ATGACTTCTGGGGTAAGGGTACCATCCTTCTTAGGTGGGAGA

TGCAAAAACAATTTCTTTGCAACCAGCAACTTTGGCAGGAAC

ACCCAGCATCAGGGAAGTGGAAGGCAGAATTGCGGTTCCACC

AGGAATATAGAGGCCAACTTTCTCAATAGGTCTTGCAAAACG

AGAGCAGACTACACCAGGGCAAGTCTCAACTTGCAACGTCTC

CGTTAGTTGAGCTTCATGGAATTTCCTGACGTTATCTATAGA

GAGATCAATGGCTCTCTTAACGTTATCTGGCAATTGCATAAG

TTCCTCTGGGAAAGGAGCTTCTAACACAGGTGTCTTCAAAGC

GACTCCATCAAACTTGGCAGTTAGTTCTAAAAGGGCTTTGTC

ACCATTTTGACGAACATTGTCGACAATTGGTTTGACTAATTC

CATAATCTGTTCCGTTTTCTGGATAGGACGACGAAGGGCATC

TTCAATTTCTTGTGAGGAGGCCTTAGAAACGTCAATTTTGCA

CAATTCAATACGACCTTCAGAAGGGACTTCTTTAGGTTTGGA

TTCTTCTTTAGGTTGTTCCTTGGTGTATCCTGGCTTGGCATC

TCCTTTCCTTCTAGTGACCTTTAGGGACTTCATATCCAGGTT

TCTCTCCACCTCGTCCAACGTCACACCGTACTTGGCACATCT

AACTAATGCAAAATAAAATAAGTCAGCACATTCCCAGGCTAT

ATCTTCCTTGGATTTTAGCTTCTGCAAGTTCATCAGCTTCCT

CCCTAATTTTAGCGTTCAAACAAAACTTCGTCGTCAAATAAC

CGTTTGGTATAAGAACCTTCTGGAGCATTGCTCTTACGATCC

CACAAGGTGCTTCCATGGCTCTAAGACCCTTTGATTGGCCAA

AACAGGAAGTGCGTTCCAAGTGACAGAAACCAACACCTGTTT

GTTCAACCACAAATTTCAAGCAGTCTCCATCACAATCCAATT

CGATACCCAGCAACTTTTGAGTTCGTCCAGATGTAGCACCTT

TATACCACAAACCGTGACGACGAGATTGGTAGACTCCAGTTT

GTGTCCTTATAGCCTCCGGAATAGACTTTTTGGACGAGTACA

CCAGGCCAACGAGTAATTAGAAGAGTCAGCCACCAAAGTAGT

GAATAGACCATCGGGGCGGTCAGTAGTCAAAGACGCCAACAA

AATTTCACTGACAGGGAACTTTTTGACATCTTCAGAAAGTTC

GTATTCAGTAGTCAATTGCCGAGCATCAATAATGGGGATTAT

ACCAGAAGCAACAGTGGAAGTCACATCTACCAACTTTGCGGT

CTCAGAAAAAGCATAAACAGTTCTACTACCGCCATTAGTGAA

ACTTTTCAAATCGCCCAGTGGAGAAGAAAAAGGCACAGCGAT

ACTAGCATTAGCGGGCAAGGATGCAACTTTATCAACCAGGGT

CCTATAGATAACCCTAGCGCCTGGGATCATCCTTTGGACAAC

TCTTTCTGCCAAATCTAGGTCCAAAATCACTTCATTGATACC

ATTATTGTACAACTTGAGCAAGTTGTCGATCAGCTCCTCAAA

TABLE 6-continued

Sequences of Oligonucleotides used in Plasmid constructions of Table 5

TTGGTCCTCTGTAACGGATGACTCAACTTGCACATTAACTTG

AAGCTCAGTCGATTGAGTGAACTTGATCAGGTTGTGCAGCTG

GTCAGCAGCATAGGGAAACACGGCTTTTCCTACCAAACTCAA

GGAATTATCAAACTCTGCAACACTTGCGTATGCAGGTAGCAA

GGGAAATGTCATTACTTGAAGTCGGACAGTGAGTGTAGTCTT

GAGAAATTCTGAAGCCGTATTTTTATTATCAGTGAGTCAGTC

ATCAGGAGATCCTCTACGCCGGACGCATCGTGGCCGACCTGC

ACCTGCAGGTCGGCATCACCGGCGCCACAGGTGCGGTTGCTG

GCGCCTATATCGCCGACATCACCGATGGGGAAGATCGGGCTC

GCCACTTCGGGCTCATGAGCGCTTGTTTCGGCGTGGGTATGG

TGGCAGGCCCCGTGGCCGGGGGACTGTTGGGCGCCATCTCCT

TGGACCTGCAGGGGGGGGGGGGAAAGCCACGTTGTGTCTCA

AAATCTCTGATGTTACATTGCACAAGATAAAAATATATCATC

GCGCCATCTCCTTTAAAACTGTCTGCTTACATAAACAGTAAT

ACAAGGGGTGTTATGAGCCATATTCAACGGGAAACGTCTTGC

TCAAGGCCGCGATTAAATTCCAACATGGATGCTGATTTATAT

GGGTATAAATGGGCTCGCGATAATGTCGGGCAATCAGGTGCG

ACAATCTATCGATTGTATGGGAAGCCCGATGCGCCAGAGTTG

TTTCTGAAACATGGCAAAGGTAGCGTTGCCAATGATGTTACA

GATGAGATGGTCAGACTAAACTGGCTGACGGAATTTATGCCT

CTTCCGACCATCAAGCATTTTATCCGTACTCCTGATGATGCA

TGGTTACTCACCACTGCGATCCCCGGGAAAACAGCATTCCAG

GTATTAGAAGAATATCCTGATTCAGGTGAAAATATTGTTGAT

GCGCTGGCAGTGTTCCTGCGCCGGTGCATTCGATTCCTGTTT

GTAATTGTCCTTTTAACAGCGATCGCGTATTTCGTCTCGACT

CAGGCGCAATCACGAATGAATAACGGTTTGGTTGATGCGAGT

GATTTTGATGACGAGCGTAATGGCTGGCCTGTTGAACAAGTC

TGGAAAGAAATGCATAAGCTTTTGCCATTCTCACCGGATTCA

GTCGTCACTCATGGTGATTTCTCACTTGATAACCTTATTTTT

GACGAGGGGAAATTAATAGGTTGTATTGATGTTGGACGAGTC

GGAATCGCAGACCATACCAGGATCTTGCCATCCTATGGAACT

GCCTCGGTGAGTTTTCTCCTTCATTACAGAAACGGCTTTTTC

AAAAATATGGTATTGATAATCCTGATATGAATAAATTGCAGT

TTGATTTGATGCTCGATGAGTTTTTCTAATCAGAATTGGTTA

ATTGGTTGTAACACTGGCAGAGCATTACGCTGACTTGACGGG

ACGGCGGCTTTGTTGAATAAATCGAACTTTTGCTGAGTTGAA

GGATCAGATCACGCATCTTCCCGACAACGCAGACCGTTCCGT

GGCAAAGCAAAAGTTCAAAATCACCAACTGGTCCACCTACAA

TABLE 6-continued

Sequences of Oligonucleotides used in Plasmid constructions of Table 5

CAAAGCTCTCATCAACCGTGGCTCCCTCACTTTCTGGCTGGA
TGATGGGGCGATTCAGGCCTGGTATGAGTCAGCAACACCTTC
TTCACGAGGCAGACCTCAGCGCCCCCCCCCCCTGCAGGTCC
CACGGCGGCGGTGCTCAACGGCCTCAACCTACTACTGGGCTG
CTTCCTAATGCAGGAGTCGCATAAGGGAGAGCGTCGAGTATC
TATGATTGGAAGTATGGGAATGGTGATACCCGCATTCTTCAG
TGTCTTGAGGTCTCCTATCAGATTATGCCCAACTAAAGCAAC
CGGAGGAGGAGATTCATGGTAAATTTCTCTGACTTTTGGTCA
TCAGTAGACTCGAACTGTGAGACTATCTCGGTTATGACAGCA
GAAATGTCCTTCTTGGAGACAGTAAATGAAGTCCCACCAATA
AAGAAATCCTTGTTATCAGGAACAAACTTCTTGTTTCGAACT
TTTTCGGTGCCTTGAACTATAAAATGTAGAGTGGATATGTCG
GGTAGGAATGGAGCGGGCAAATGCTTACCTTCTGGACCTTCA
AGAGGTATGTAGGGTTTGTAGATACTGATGCCAACTTCAGTG
ACAACGTTGCTATTCGTTCAAACCATTCCGAATCCAGAGAAA
TCAAAGTTGTTTGTCTACTATTGATCCAAGCCAGTGCGGTCT
TGAAACTGACAATAGTGTGCTCGTGTTTTGAGGTCATCTTTG
TATGAATAAATCTAGTCTTTGATCTAAATAATCTTGACGAGC
CAAGGCGATAAATACCCAAATCTAAAACTCTTTTAAAACGTT
AAAAGGACAAGTATGTCTGCCTGTATTAAACCCCAAATCAGC
TCGTAGTCTGATCCTCATCAACTTGAGGGGCACTATCTTGTT
TTAGAGAAATTTGCGGAGATGCGATATCGAGAAAAAGGTACG
CTGATTTAAACGTGAAATTTATCTCAAGATCTCTGCCTCGCG
CGTTTCGGTGATGACGGTGAAAACCTCTGACACATGCAGCTC
CCGGAGACGGTCACAGCTTGTCTGTAAGCGGATGCCGGGAGC
AGACAAGCCCGTCAGGGCGCGTCAGCGGGTGTTGGCGGGTGT
CGGGGCGCAGCCATGACCCAGTCACGTAGCGATAGCGGAGTG
TATACTGGCTTAACTATGCGGCATCAGAGCAGATTGTACTGA
GAGTGCACCATATGCGGTGTGAAATACCGCACAGATGCGTAA
GGAGAAAATACCGCATCAGGCGCTCTTCCGCTTCCTCGCTCA
CTGACTCGCTGCGCTGCGGTCGTTCGGCTGCGGCGAGCGGTA
TCAGCTCACTCAAAGGCGGTAATACGGTTATCCACAGAATCA
GGGGATAACGCAGGAAAGAACATGTGAGCAAAAGGCCAGCAA
AAGGCCAGGAACCGTAAAAAGGCCGCGTTGCTGGCGTTTTTC
CATAGGCTCCGCCCCCTGACGAGCATCACAAAAATCGACGC
TCAAGTCAGAGGTGGCGAAACCCGACAGGACTATAAAGATACC
AGGCGTTTCCCCCTGGAAGCTCCCTCGTGCGCTCTCCTGTTC
CGACCCTGCCGCTTACCGGATACCTGTCCGCCTTTCTCCCTT

TABLE 6-continued

Sequences of Oligonucleotides used in Plasmid constructions of Table 5

CGGGAAGCGTGGCGCTTTCTCAATGCTCACGCTGTAGGTATC
TCAGTTCGGTGTAGGTCGTTCGCTCCAAGCTGGGCTGTGTGC
ACGAACCCCCGTTCAGCCCGACCGCTGCGCCTTATCCGGTA
ACTATCGTCTTGAGTCCAACCCGGTAAGACACGACTTATCGC
CACTGGCAGCAGCCACTGGTAACAGGATTAGCAGAGCGAGGT
ATGTAGGCGGTGCTACAGAGTTCTTGAAGTGGTGGCCTAACT
ACGGCTACACTAGAAGGACAGTATTTGGTATCTGCGCTCTGC
TGAAGCCAGTTACCTTCGGAAAAAGAGTTGGTAGCTCTTGAT
CCGGCAAACAAACCACCGCTGGTAGCGGTGGTTTTTTTGTTT
GCAAGCAGCAGATTACGCGCAGAAAAAAAGGATCTCAAGAAG
ATCCTTTGATCTTTTCTACGGGGTCTGACGCTCAGTGGAACG
AAAACTCACGTTAAGGGATTTTGGTCATGAGATTATCAAAAA
GGATCTTCACCTAGATCCTTTTAAATTAAAAATGAAGTTTTA
AATCAATCTAAAGTATATATGAGTAAACTTGGTCTGACAGTT
ACCAATGCTTAATCAGTGAGGCACCTATCTCAGCGATCTGTC
TATTTCGTTCATCCATAGTTGCCTGACTCCCCGTCGTGTAGA
TAACTACGATACGGGAGGGCTTACCATCTGGCCCCAGTGCTG
CAATGATACCGCGAGACCCACGCTCACCGGCTCCAGATTTAT
CAGCAATAAACCAGCCAGCCGGAAGGGCCGAGCGCAGAAGTG
GTCCTGCAACTTTATCCGCCTCCATCCAGTCTATTAATTGTT
GCCGGGAAGCTAGAGTAAGTAGTTCGCCAGTTAATAGTTTGC
GCAACGTTGTTGCCATTGCTGCAGGCATCGTGGTGTCACGCT
CGTCGTTTGGTATGGCTTCATTCAGCTCCGGTTCCCAACGAT
CAAGGCGAGTTACATGATCCCCCATGTTGTGCAAAAAAGCGG
TTAGCTCCTTCGGTCCTCCGATCGTTGTCAGAAGTAAGTTGG
CCGCAGTGTTATCACTCATGGTTATGGCAGCACTGCATAATT
CTCTTACTGTCATGCCATCCGTAAGATGCTTTTCTGTGACTG
GTGAGTACTCAACCAAGTCATTCTGAGAATAGTGTATGCGGC
GACCGAGTTGCTCTTGCCCGGCGTCAACACGGGATAATACCG
CGCCACATAGCAGAACTTTAAAAGTGCTCATCATTGGAAAAC
GTTCTTCGGGGCGAAAACTCTCAAGGATCTTACCGCTGTTGA
GATCCAGTTCGATGTAACCCACTCGTGCACCCAACTGATCTT
CAGCATCTTTTACTTTCACCAGCGTTTCTGGGTGAGCAAAAA
CAGGAAGGCAAAATGCCGCAAAAAAGGGAATAAGGGCGACAC
GGAAATGTTGAATACTCATACTCTTCCTTTTTCAATATTATT
GAAGCATTTATCAGGGTTATTGTCTCATGAGCGGATACATAT
TTGAATGTATTTAGAAAAATAAACAAATAGGGGTTCCGCGCA
CATTTCCCCGAAAAGTGCCACCTGACGTCTAAGAAACCATTA

TABLE 6-continued
Sequences of Oligonucleotides used in Plasmid constructions of Table 5 pUB114
[SEQ ID
NO:81]

```
TTATCATGACATTAACCTATAAAAATAGGCGTATCACGAGGC
CCTTTCGTCTTCAAGAATTAATTCTCATGTTTGACAGCTTAT
CATCGATAAGCTGACTCATGTTGGTATTGTGAAATAGACGCA
GATCGGGAACACTGAAAAATAACAGTTATTATTCGAGATC
GATCTAACATCCAAAGACGAAAGGTTGAATGAACCTTTTTGC
CATCCGACATCCACAGGTCCATTCTCACACATAAGTGCCAAA
CGCAACAGGAGGGGATACACTAGCAGCAGACCGTTGCAAACG
CAGGACCTCCACTCCTCTTCTCCTCAACACCCACTTTTGCCA
TCGAAAAACCAGCCCAGTTATTGGGCTTGATTGGAGCTCGCT
CATTCCAATTCCTTCTATTAGGCTACTAACACCATGACTTTA
TTAGCCTGTCTATCCTGGCCCCCTGGCGAGGTTCATGTTTG
TTTATTTCCGAATGCAACAAGCTCCGCATTACACCCGAACAT
CACTCCAGATGAGGGCTTTCTGAGTGTGGGGTCAAATAGTTT
CATGTTCCCCAAATGGCCCAAAACTGACAGTTTAAACGCTGT
CTTGGAACCTAATATGACAAAAGCGTGATCTCATCCAAGATG
AACTAAGTTTGGTTCGTTGAAATGCTAACGGCCAGTTGGTCA
AAAAGAAACTTCCAAAAGTCGCCATACCGTTTGTCTTGTTTG
GTATTGATTGACGAATGCTCAAAAATAATCTCATTAATGCTT
AGCGCAGTCTCTCTATCGCTTCTGAACCCCGGTGCACCTGTG
CCGAAACGCAAATGGGGAAACACCCGCTTTTTGGATGATTAT
GCATTGTCTCCACATTGTATGCTTCCAAGATTCTGGTGGGAA
TACTGCTGATAGCCTAACGTTCATGATCAAAATTTAACTGTT
CTAACCCCTACTTGACAGCAATATATAAACAGAAGGAAGCTG
CCCTGTCTTAAACCTTTTTTTTATCATCATTATTAGCTTAC
TTTCATAATTGCGACTGGTTCCAATTGACAAGCTTTTGATTT
TAACGACTTTTAACGACAACTTGAGAAGATCAAAAAACAACT
AATTATTCGAAGGATCCAAACGATGAGATTTCCTTCAATTTT
TACTGCAGTTTTATTCGCAGCATCCTCCGCATTAGCTGCTCC
AGTCAACACTACAACAGAAGATGAAACGGCACAAATTCCGGC
TGAAGCTGTCATCGGTTACTCAGATTTAGAAGGGGATTTCGA
TGTTGCTGTTTTGCCATTTTCCAACAGCACAAATAACGGGTT
ATTGTTTATAAATACTACTATTGCCAGCATTGCTGCTAAAGA
AGAAGGGGTATCTCTCGAGAAAAGATGCGGACCGGGCAGGGG
GTTCGGGAAGAGGAGGCACCCCAAAAAGCTGACCCCTTTAGC
CTACAAGCAGTTTATCCCCAATGTGGCCGAGAAGACCCTAGG
CGCCAGCGGAAGGTATGAAGGGAAGATCTCCAGAAACTCCGA
GCGATTTAAGGAACTCACCCCCAATTACAACCCCGACATCAT
ATTTAAGGATGAAGAAAACACCGGAGCGGACAGGCTGATGAC
TCAGAGGTGTAAGGACAAGTTGAACGCTTTGGCCATCTCGGT
GATGAACCAGTGGCCAGGAGTGAAACTGCGGGTGACCGAGGG
CTGGGACGAAGATGGCCACCACTCAGAGGAGTCTCTGCACTA
CGAGGGCCGCGCAGTGGACATCACCACGTCTGACCGCGACCG
CAGCAAGTACGGCATGCTGGCCCGCCTGGCGGTGGAGGCCGG
CTTCGACTGGGTGTACTACGAGTCCAAGGCACATATCCACTG
CTCGGTGAAAGCAGAGAACTCGGTGGCGGCCAAATCGGGAGG
CGTCGACGTGCCCAGGGATTGTGGTTGTAAGCCTTGCATATG
TACAGTCCCAGAAGTATCATCTGTCTTCATCTTCCCCCCAAA
GCCCAAGGATGTGCTCACCATTACTCTGACTCCTAAGGTCAC
GTGTGTTGTGGTAGACATCAGCAAGGATGATCCCGAGGTCCA
GTTCAGCTGGTTTGTAGATGATGTGGAGGTGCACACAGCTCA
GACGCAACCaCGGGAaGAGCAGTTCCAAAGCACTTTCCGCTC
AGTCAGTGAACTTCCCATCATGCACCAGGACTGGCTCAATGG
CAAGGAGTTCAAATGCAGGGTCAACAGTGCAGCTTTCCCTGC
CCCCATCGAGAAACCATCTCCAAAACCAAAGGCAGACCGAA
GGCTCCACAGGTGTACACCATTCCACCTCCCAAGGAGCAGAT
GGCCAAGGATAAAGTCAGTCTGACCTGCATGATAACAGACTT
CTTCCCTGAAGACATTACTGTGGAGTGGCAGTGGAATGGGCA
GCCAGCGGAGAACTACAAGAACACTCAGCCCATCATGGACAC
AGATGGCTCTTACTTCGTCTACAGCAAGCTCAATGTGCAGAA
GAGCAACTGGGAGGCAGGAAATACTTTCACCTGCTCTGTGTT
ACATGAGGGCCTGCACAACCACCATACTGAGAAGAGCCTCTC
CCACTCTCCTGGTAAATGATCCCAGTGTCCTTGGAGCCCTCT
GGTCCTCACAGCGGCCGCGAATTAATTCGCCTTAGACATGAC
TGTTCCTCAGTTCAAGTTGGGCACTTACGAGAAGACCGGTCT
TGCTAGATTCTAATCAAGAGGATGTCAGAATGCCATTTGCCT
GAGAGATGCAGGCTTCATTTTTGATACTTTTTTATTTGTAAC
CTATATAGTATAGGATTTTTTTTGTCATTTTGTTTCTTCTCG
TACGAGCTTGCTCCTGATCAGCCTATCTCGCAGCTGATGAAT
ATCTTGTGGTAGGGTTTGGGAAAATCATTCGAGTTTGATGT
TTTTCTTGGTATTTCCCACTCCTCTTCAGAGTACAGAAGATT
AAGTGAGAAGTTCGTTTGTGCAAGCTTATCGATAAGCTTTAA
TGCGGTAGTTTATCACAGTTAAATTGCTAACGCAGTCAGGCA
CCGTGTATGAAATCTAACAATGCGCTCATCGTCATCCTCGGC
ACCGTCACCCTGGATGCTGTAGGCATAGGCTTGGTTATGCCG
GTACTGCCGGGCCTCTTGCGGGATATCGTCCATTCCGACAGC
ATCGCCAGTCACTATGGCGTGCTGCTAGCGCTATATGCGTTG
```

TABLE 6-continued

Sequences of Oligonucleotides used in Plasmid constructions of Table 5

ATGCAATTTCTATGCGCACCCGTTCTCGGAGCACTGTCCGAC
CGCTTTGGCCGCCGCCCAGTCCTGCTCGCTTCGCTACTTGGA
GCCACTATCGACTACGCGATCATGGCGACCACACCCGTCCTG
TGGATCTATCGAATCTAAATGTAAGTTAAAATCTCTAAATAA
TTAAATAAGTCCCAGTTTCTCCATACGAACCTTAACAGCATT
GCGGTGAGCATCTAGACCTTCAACAGCAGCCAGATCCATCAC
AATATGTTTCAGTCCCTCAGGAGTTACGTCTTGTGAAGTGAT
GAACTTCTGGAAGGTTGCAGTGTTAACTCCGCTGTATTGACG
GGCATATCCGTACGTTGGCAAAGTGTGGTTGGTACCGGAGGA
GTAATCTCCACAACTCTCTGGAGAGTAGGCACCAACAAACAC
AGATCCAGCGTGTTGTACTTGATCAACATAAGAAGAAGCATT
CTCGATTTGCAGGATCAAGTGTTCAGGAGCGTACTGATTGGA
CATTTCCAAAGCCTGCTCGTAGGTTGCAACCGATAGGGTTGT
AGAGTGTGCAATACACTTGCGTACAATTTCAACCCTTGGCAA
CTGCACAGCTTGGTTGTGAACAGCATCTTCAATTCTGGCAAG
CTCCTTGTCTGTCATATCGACAGCCAACAGAATCACCTGGGA
ATCAATACCATGTTCAGCTTGAGCAGAAGGTCTGAGGCAACG
AAATCTGGATCAGCGTATTTATCAGCAATAACTAGAACTTCA
GAAGGCCAGCAGGCATGTCAATACTACACAGGGCTGATGTGT
CATTTTGAACCATCATCTTGGCAGCAGTAACGAACTGGTTTC
CTGGACCAAATATTTTGTCACACTTAGGAACAGTTTCTGTTC
CGTAAGCCATAGCAGCTACTGCCTGGGCGCCTCCTGCTAGCA
CGATACACTTAGCACCAACCTTGTGGGCAACGTAGATGACTT
CTGGGGTAAGGGTACCATCCTTCTTAGGTGGAGATGCAAAAA
CAATTTCTTTGCAACCAGCAACTTTGGCAGGAACACCCAGCA
TCAGGGAAGTGGAAGGCAGAATTGCGGTTCCACCAGGAATAT
GAAGGCCAACTTTCTCAATAGGTCTTGCAAAACGAGAGCAGA
CTACACCAGGGCAAGTCTCAACTTGCAACGTCTCCGTTAGTT
GAGCTTCATGGAATTTCCTGACGTTATCTATAGAGAGATCAA
TGGCTCTCTTAACGTTATCTGGCAATTGCATAAGTTCCTCTG
GGAAAGGAGCTTCTAACAGGTGTCTTCAAAGCGACTCCAT
CAAACTTGGCAGTTAGTTCTAAAAGGGCTTTGTCACCATTTT
GACGAACATTGTCGACAATTGGTTTGACTAATTCCATAATCT
GTTCCGTTTTCTGGATAGGACGACGAAGGGCATCTTCAATTT
CTTGTGAGGAGGCCTTAGAAACGTCAATTTTGCACAATTCAA
TACGACCTTCAGAAGGGACTTCTTTAGGTTTGGATTCTTCTT
TAGGTTGTTCCTTGGTGTATCCTGGCTTGGCATCTCCTTTCC
TTCTAGTGACCTTTAGGGACTTCATATCCAGGTTTCTCTCCA
CCTCGTCCAACGTCACACCGTACTTGGCACATCTAACTAATG
CAAAATAAAATAAGTCAGCACATTCCCAGGCTATATCTTCCT
TGGATTTAGCTTCTGCAAGTTCATCAGCTTCCTCCCTAATTT
TAGCGTTCAAACAAAACTTCGTCGTCAAATAACCGTTTGGTA
TAAGAACCTTCTGGAGCATTGCTCTTACGATCCCACAAGGTG
CTTCCATGGCTCTAAGACCCTTTGATTGGCCAAAACAGGAAG
TGCGTTCCAAGTGACAGAAACCAACACCTGTTTGTTCAACCA
CAAATTTCAAGCAGTCTCCATCACAATCCAATTCGATACCCA
GCAACTTTTGAGTTCGTCCAGATGTAGCACCTTTATACCACA
AACCGTGACGACGAGATTGGTAGACTCCAGTTTGTGTCCTTA
TAGCCTCCGGAATAGACTTTTTGGACGAGTACACCAGGCCCA
ACGAGTAATTAGAAGAGTCAGCCACCAAAGTAGTGAATAGAC
CATCGGGGCGGTCAGTAGTCAAAGACGCCAACAAAATTTCAC
TGACAGGGAACTTTTTGACATCTTCAGAAAGTTCGTATTCAG
TAGTCAATTGCCGAGCATCAATAATGGGGATTATACCAGAAG
CAACAGTGGAAGTCACATCTACCAACTTTGCGGTCTCAGAAA
AAGCATAAACAGTTCTACTACCGCCATTAGTGAAACTTTTCA
AATCGCCCAGTGGAGAAGAAAAAGGCACAGCGATACTAGCAT
TAGCGGGCAAGGATGCAACTTTATCAACCAGGGTCCTATAGA
TAACCCTAGCGCCTGGGATCATCCTTTGGACAACTCTTTCTG
CCAAATCTAGGTCCAAATCACTTCATTGATACCATTATTGT
ACAACTTGAGCAAGTTGTCGATCAGCTCCTCAAATTGGTCCT
CTGTAACGGATGACTCAACTTGCACATTAACTTGAAGCTCAG
TCGATTGAGTGAACTTGATCAGGTTGTGCAGCTGGTCAGCAG
CATAGGGAAACACGGCTTTTGGTACCAAACTCAAGGAATTAT
CAAACTCTGCAACACTTGCGTATGCAGGTAGCAAGGGAAATG
TCATACTTGAAGTCGGACAGTGAGTGTAGTCTTGAGAAATTC
TGAAGCCGTATTTTTATTATCAGTGAGTCAGTCATCAGGAGA
TCCTCTACGCCGGACGCATCGTGGCCGACCTGCAGGTCGGCA
TCACCGGCGCCACAGGTGCGGTTGCTGGCGCCTATATCGCCG
ACATCACCGATGGGGAAGATCGGGCTCGCCACTTCGGGCTCA
TGAGCGCTTGTTCGGCGTGGGTATGGTGGCAGGCCCCGTGGC
CGGGGGACTGTTGGGCGCCATCTCCTTGGACCTGCAGGGGGG
GGGGGGGAAAGCCACGTTGTGTCTCAAAATCTCTGATGTTAC
ATTGCACAAGATAAAATATATCATCATGAACAATAAAACTG
TCTGCTTACATAAACAGTAATACAAGGGGTGTTATGAGCCAT
ATTCAACGGGAAACGTCTTGCTCAAGGCCGCGATTAAATTCC
AACATGGATGCTGATTTATATGGGTATAAATGGGCTCGCGAT

TABLE 6-continued

Sequences of Oligonucleotides used in Plasmid constructions of Table 5

AATGTCGGGCAATCAGGTGCGACAATCTATCGATTGTATGGG

AAGCCCGATGCGCCAGAGTTGTTTCTGAAACATGGCAAAGGT

AGCGTTGCCAATGATGTTACAGATGAGATGGTCAGACTAAAC

TGGCTGACGGAATTTATGCCTCTTCCGACCATCAAGCATTTT

ATCCGTACTCCTGATGATGCATGGTTACTCACCACTGCGATC

CCCGGGAAAACAGCATTCCAGGTATTAGAAGAATATCCTGAT

TCAGGTGAAAATATTGTTGATGCGCTGGCAGTGTTCCTGCGC

CGGTTGCATTCGATTCCTGTTTGTAATTGTCCTTTTAACAGC

GATCGCGTATTTCGTCTCGCTCAGGCGCAATCACGAATGAAT

AACGGTTTGGTTGATGCGAGTGATTTTGATGACGAGCGTAAT

GGCTGGCCTGTTGAACAAGTCTGGAAAGAAATGCATAAGCTT

TTGCCATTCTCACCGGATTCAGTCGTCACTCATGGTGATTTC

TCACTTGATAACCTTATTTTTGACGAGGGGAAATTAATAGGT

TGTATTGATGTTGGACAGAGTCGGAATCGCAGACCGATACCAG

GATCTTGCCCATCCTATGGAACTGCCTCGGTGAGTTTTCTCC

TTCATTACAGAAACGGCTTTTTCAAAAATATGGTATTGATAA

TCCTGATATGAATAAATTGCAGTTTCATTTGATGCTCGATGA

GTTTTTCTAATCAGAATTGGTTAATTGGTTGTAACACTGGCA

GAGCATTACGCTGACTTGACGGGACGGCGGCTTTGTTGAATA

AATCGAACTTTTGCTGAGTTGAAGGATCAGATCACGCATCTC

TCCCGACAACGCAGACCGTTCCGTGGCAAAGCAAAAGTTCAA

AATCACCAACTGGTCCACCTACAACAAAGCTCTCATCAACCG

TGGCTCCCTCACTTTCTGGCTGGATGATGGGGCGATTCAGGC

CTGGTATGAGTCAGCAACACCTTCTTCACGAGGCAGACCTCA

GCGCCCCCCCCCCTGCAGGTCCCACGGCGGCGGTGCTCAAC

GGCCTCAACCTACTACTGGGCTGCTTCCTAATGCAGGAGTCG

CATAAGGGAGAGCGTCGAGTGATCTATGATTGGAAGTATGGG

AATGGTGATACCCGCATTCTTCAGTGTCTTGAGGTCTCCTAT

CAGATTATGCCCAACTAAAGCAACCGGAGGAGGAGATTTCAT

GGTAAATTTCTCTGACTTTTGGTCATCAGTAGACTCGAACTG

TGAGACTATCTCGGTTATGACAGCAGAAATGTCCTTCTTGGA

GACAGTAAATGAAGTCCCACCAATAAAGAAATCCTTGTTATC

AGGAACAAACTTCTTGTTTCGAACTTTTTCGGTGCCTTGAAC

TATAAAATGTAGAGTGGATATGTCGGGTAGGAATGGAGCGGG

CAAATGCTTACCTTCTGGACCTTCAAGAGGTATGTAGGGTTT

GTAGATACTGATGCCAACTTCAGTGACAACGTTGCTATTTCG

TTCAAACCATTCCGAATCCAGAGAAATCAAAGTTGTTTGTCT

ACTATTGATCCAAGCCAGTGCGGTCTTGAAACTGACAATAGT

TABLE 6-continued

Sequences of Oligonucleotides used in Plasmid constructions of Table 5

GTGCTCGTGTTTTGAGGTCATCTTTGTATGAATAAATCTAGT

CTTTGATCTAAATAATCTTGACGAGCCAAGGCGATAAATACC

CAAATCTAAAACTCTTTTAAAACGTTAAAAGGACAAGTATGT

CTGCCTGTATTAAACCCCAAATCAGCTCGTAGTCTGATCCTC

ATCAACTTGAGGGGCACTATCTTGTTTTAGAGAAATTTGCGG

AGATGCGATATCGAGAAAAAGGTACGCTGATTTTAAACGTGA

AATTTATCTCAAGATCTCTGCCTCGCGCGTTTCGGTGATGAC

GGTGAAAACCTCTGACACATGCAGCTCCCGGAGACGGTCACA

GCTTGTCTGTAAGCGGATGCCGGGAGCAGACAAGCCCGTCAG

GGCGCGTCAGCGGGTGTTGGCGGGTGTCGGGGCGCAGCCATG

ACCCAGTCACGTAGCGATAGCGGAGTGTATACTGGCTTAACT

ATGCGGCATCAGAGCAGATTGTACTGAGAGTGCACCATATGC

GGTGTGAAATACCGCACAGATGCGTAAGGAGAAAATACCGCA

TCAGGCGCTCTTCCGCTTCCTCGCTCACTGACTCGCTGCGCT

CGGTGCGTTCGGCTGCGGCGAGCGGTATCAGCTCACTCAAAG

GCGGTAATACGGTTATCCACAGAATCAGGGGATAACGCAGGA

AAGAACATGTGAGCAAAAGGCCAGCAAAAGGCCAGGAACCGT

AAAAAGGCCGCGTTGCTGGCGTTTTTCCATAGGCTCCGCCCC

CCTGACGAGCATCACAAAAATCGACGCTCAAGTCAGAGGTGG

CGAAACCCGACAGGACTATAAAGATACCAGGCGTTTCCCCCT

GGAAGCTCCCTCGTGCGCTCTCCTGTTCCGACCCTGCCGCTT

ACCGGATACCTGTCCGCCTTTCTCCCTTCGGGAAGCGTGGCG

CTTTCTCAATGCTCACGCTGTAGGTATCTCAGTTCGGTGTAG

GTCGTTCGCTCCAAGCTGGGCTGTGTGCACGAACCCCCCGTT

CAGCCCGACCGCTGCGCCTTATCCGGTAACTATCGTCTTGAG

TCCAACCCGGTAAGACACGACTTATCGCCACTGGCAGCAGCC

ACTGGTAACAGGATTAGCAGAGCGAGGTATGTAGGCGGTGCT

ACAGAGTTCTTGAAGTGGTGGCCTAACTACGGCTACACTAGA

AGGACCAGTATTTGGTATCTGCGCTCTGCTGAAGCCAGTTAC

CTTCGGAAAAAGAGTTGGTAGCTCTTGATCCGGCAAACAAAC

CACCGCTGGTAGCGGTGGTTTTTTTGTTTGCAAGCAGCAGAT

TACGCGCAGAAAAAAAGGATCTCAAGAAGATCCTTTGATCTT

TTCTACGGGGTCTGACGCTCAGTGGAACGAAACTCACGTTAA

GGGATTTTGGTCATGAGATTATCAAAAAGGATCTTCACCTAG

ATCCTTTTAAATTAAAAATGAAGTTTTAAATCAATCTAAAGT

ATATATGAGTAAACTTGGTCTGACAGTTACCAATGCTTAAT

CAGTGAGGCACCTATCTCAGCGATCTGTCTATTTCGTTCATC

CATAGTTGCCTGACTCCCCGTCGTGTAGATAACTACGATACG

TABLE 6-continued

Sequences of Oligonucleotides used in Plasmid constructions of Table 5

GGAGGGCTTACCATCTGGCCCCAGTGCTGCAATGATACCGCG
AGACCCACGCTCACGGCTCCAGATTTATCAGCAATAAACCAG
ACCAGCCAGCCGGAAGGGCCGAGCGCAGAAGTGGTCCTGCAA
CTTTATCCGCCTCCATCCAGTCTATTAATTGTTGCCGGAAG
CTAGAGTAAGTAGTTCGCCAGTTAATAGTTTGCGCAACGTTG
TTGCCATTGCTGCAGGCATCGTGGTGTCACGCTCGTCGTTTG
GTATGGCTTCATTCAGCTCCGGTTCCCAACGATCAAGGCGAG
TTACATGATCCCCCATGTTGTGCAAAAAAGCGGTTAGCTCCT
TCGGTCCTCCGATCGTTGTCAGAAGTAAGTTGGCCGCAGTGT
TATCACTCATGGTTATGGCAGCACTGCATAATTCTCTTACTG
TCATGCCATCCGTAAGATGCTTTTCTGTGACTGGTGAGTACT
CAACCAAGTCATTCTGAGAATAGTGTATGCGGCGACCGAGTT
GCTCTTGCCCGGCGTCAACACGGGATAATACCGCGCCACATA
GCAGAACTTTAAAAGTGCTCATCATTGGAAAACGTTCTTCGG
GGCGAAAACTCTCAAGGATCTTACCGCTGTTGAGATCCAGTT
CGATGTAACCCACTCGTGCACCCAACTGATCTTCAGCATCTT
TTACTTTCACCAGCGTTTCTGGGTGAGCAAAAACAGGAAGGC
AAAATGCCGCAAAAAAGGGAATAAGGGCGACACGGAAATGTT
GAATACTCATACTCTTCCTTTTTCAATATTATTGAAGCATTT
ATCAGGGTTATTGTCTCATGAGCGGATACATATTTGAATGTA
TTTAGAAAAATAAACAAATAGGGGTTCCGCGCACATTTCCCC
GAAAAGTGCCACCTGACGTCTAAGAAACCATTATTATCATGA
ACATTAACCTATAAAAATAGGCGTATCACGAGGCCCTTTCGT
CTTCAAGAATTAATTCTCATGTTTGACAGCTTATCATCGATA
AGCTGACTCATGTTGGTATTGTGAAATAGACGCAGATCGGGA
ACACTGAAAAATAACAGTTATTATTCGAGATC pUB 115 [SEQ ID NO: 82] GATCTAACATCCAAAGACGAAAGGTTGAATGAAACCTTTTTG
CCATCCGACATCCACAGGTCCATTCTCACACATAAGTGCCAA
ACGCAACAGGAGGGGATACACTAGCAGCAGACCGTTGCAAAC
GCAGGACCTCCACTCCTCTTCTCCTCAACACCCACTTTTGCC
ATCGAAAACCAGCCCAGTTATTGGGCTTGATTGGAGCTCGCT
CATTCCAATTCCTTCTATTAGGCTACTAACACCATGACTTTA
TTAGCCTGTCTATCCTGGCCCCCCTGGCGAGGTTCATGTTTG
TTTATTTCCGAATGCAACAAGCTCCGCATTACACCCGAACAT
CACTCCAGATGAGGGCTTTCTGAGTGTGGGGTCAAATAGTTT
CATGTTCCCCAAATGGCCCAAAACTGACAGTTTAAACGCTGT
CTTGGAACCTAATATGACAAAAGCGTGATCTCATCCAAGATG
AACTAAGTTTGGTTCGTTGAAATGCTAACGGCCAGTTGGTCA

TABLE 6-continued

Sequences of Oligonucleotides used in Plasmid constructions of Table 5

AAAAGAAACTTCCAAAAGTCGCCATACCGTTTGTCTTGTTTG
GTATTGATTGACGAATGCTCAAAAATAATCTCATTAATGCTT
AGCGCAGTCTCTCTATCGCTTCTGAACCCCGGTGCACCTGTG
CCGAAACGCAAATGGGGAAACACCCGCTTTTTGGATGATTAT
GCATTGTCTCCACATTGTATGCTTCCAAGATTCTGGTGGGAA
TACTGCTGATAGCCTAACGTTCATGATCAAAATTTAACTGTT
CTAACCCCTACTTGACAGCAATATATAAACAGAAGGAAGCTG
CCCTGTCTTAAACCTTTTTTTTATCATCATTATTAGCTTACT
TTCATAATTGCGACTGGTTCCAATTGACAAGCTTTTGATTTT
AACGACTTTTAACGACAACTTGAGAAGATCAAAAAACAACTA
ATTATTCGAAGGATCCAAACGATGAGATTTCCTTCAATTTTT
ACTGCAGTTTTATTCGCAGCATCCTCCGCATTAGCTGCTCCA
GTCAACACTACAACAGAAGATGAAACGGCACAAATTCCGGCT
GAAGCTGTCATCGGTTACTCAGATTTAGAAGGGGATTTCGAT
GTTGCTGTTTTGCCATTTTCCAACAGCACAAATAACGGGTTA
TTGTTTATAAATACTACTATTGCCAGCATTGCTGCTAAAGAA
GAAGGGGTATCTCTCGAGAAAGATGCGGACCGGGCAGGGGG
TTCGGAAGAGGAGGCACCCCAAAAAGCTGACCCCTTTAGCC
TACAAGCAGTTATCCCCAATGTGGCCGAGAAGACCCTAGGCG
CCAGCGGAAGGTATGAAGGGAAGATCTCCAGAAACTCCGAGC
GATTTAAGGAACTCACCCCCAATTACAACCCCGACATCATAT
TTAAGGATGAAGAAAACACCGGAGCGGACAGGCTGATGACTC
AGAGGTGTAAGGACAAGTTGAACGCTTTGGCCATCTCGGTGA
TGAACCAGTGGCCAGGAGTGAAACTGCGGGTGACCGAGGGCT
GGGACGAAGATGGCCACCACTCAGAGGAGTCTCTGCACTACG
AGGGCCGCGCAGTGGACATCACCACGTCTGACCGCGACCGCA
GCAAGTACGGCATGTGGCCCGCCTGGCGGTGGAGGCCGGCT
TCGACTGGGTGTACTACGAGTCCAAGGCACATATCCACTGCT
CGGTGAAAGCAGAGAACTCGGTGGCGGCCAAATCGGGAGGCG
TCGACCCCAGAGGGCCCACAATCAAGCCCTGTCCTCCATGCA
AATGCCCAGCACCTAACCTCTTGGGTGGACCATCCGTCTTCA
TCTTCCCTCCAAAGATCAAGGATGTACTCATGATCTCCCTGA
GCCCCATAGTCACATGTGTGGTGGTGGATGTGAGCGAGGATG
ACCCAGATGTCCAGATCAGCTGGTTTGTGAACAACGTGGAAG
TACACACAGCTCAGACACAAACCCATAGAGAGGATTACCAAA
GTACaCTtCGGGTGGTCAGTGCCCTCCCCATCCAGCACCAGG
ACTGGATGAGTGGCAAGGAGTTCAAATGCAAGGTCAACAACA
AAGACCTCCCAGCGCCCATCGAGAGAACCATCTCAAAACCCA

TABLE 6-continued

Sequences of Oligonucleotides used in Plasmid constructions of Table 5

AAGGGTCAGTAAGAGCTCCACAGGTATATGTCTTGCCTCCAC
CAGAAGAAGAGATGACTAAGAAACAGGTCACTCTGACCTGCA
TGGTGACAGACTTCATGCCTGAAGACATTTACGTGGAGTGGA
CCAACAACGGGAAAACAGAGCTAAACTACAAGAACACTGAAC
CAGTCCTGGACTCTGATGGTTCTTACTTCATGTACAGCAAGC
TGAGAGTGGAAAAGAAGAACTGGGTGGAAAGAAATAGCTACT
CCTGTTCAGTGGTCCACGAGGGTCTGCACAATCACCACACGA
CTAAGAGCTTCTCCCGGACTCCGGGTAAATGAGCTCAGATCG
CACGACATGGATCCTCACATCCCAATCCGCGGCCGCGAATTA
ATTCGCCTTAGACATGACTGTTCCTCAGTTCAAGTTGGGCAC
TTACGAGAAGACCGGTCTTGCTAGATTCTAATCAAGAGGATG
TCAGAATGCCATTTGCCTGAGAGATGCAGGCTTCATTTTTGA
TACTTTTTTATTTGTAACCTGATCAGCCTATCTCGCAGCTGA
TGAATGTTTCTTCTCGTACGAGCTTGCTCCTGATCAGCCTAT
CTCGCAGCTGATGAATATCTTGTGGTAGGGGTTTGGGAAAAT
CATTCGAGTTTGATGTTTTTCTTGGTATTTCCCACTCCTCTT
CAGAGTACAGAAGATTAAGTGAGAAGTTCGTTTGTGCAAGCT
TATCGATAAGCTTTAATGCGGTAGTTTATCACAGTTAAATTG
CTAACGCAGTCAGGCACCGTGTATGAAATCTAACAATGCGCT
CATCGTCATCCTCGGCACCGTCACCCTGGATGCTGTAGGCAT
AGGCTTGGTTATGCCGGTACTGCCGGGCCTCTTGCGGGATAT
CGTCCATTCCGACAGCATCGCCAGTCACTATGGCGTGCTGCT
AGCGCTATATGCGTTGATGCAATTTCTATGCGCACCCGTTCT
CGGAGCACTGTCCGACCGCTTTGGCCGCCGCCCAGTCCTGCT
CGCTTCGCTACTTGGAGCCACTATCGACTACGCGATCATGGC
GACCACACCCGTCCTGTGGATCTATCGAATCTAAATGTAAGT
TAAAATCTCTAAATAATTAAATAAGTCCCAGTTTCTCCATAC
GAACCTTAACAGCATTGCGGTGAGCATCTAGACCTTCAACAG
CAGCCAGATCCATCACTGCTTGGCCAATATGTTTCAGTCCCT
CAGGAGTTACGTCTTGTGAAGTGATGAACTTCTGGAAGGTTG
CAGTGTTAACTCCGCTGTATTGACGGGCATATCCGTACGTTG
GCAAAGTGTGGTTGGTACCGGAGGAGTAATCTCCACAACTCT
CTGGAGAGTAGGCACCAACAAACACAGATCCAGCGTGTTGTA
CTTGATCAACATAAGAAGAAGCATTCTCGATTGCAGGATCAA
GTGTTCAGGAGCGTACTGATTGGACATTTCCAAAGCCTGCTC
GTAGGTTGCAACCGATAGGGTTGTAGAGTGTGCAATACACTT
GCGTACAATTTCAACCCTGGCAACTGCACAGCTTGGTTGTG
AACAGCATCTTCAATTCTGGCAAGCTCCTTGTCTGTCATATC

TABLE 6-continued

Sequences of Oligonucleotides used in Plasmid constructions of Table 5

GACAGCCAACAGAATCACCTGGGAATCAATACCATGTTCAGC
TTGAGCAGAAGGTCTGAGGCAACGAAATCTGGATCAGCGTAT
TTATCAGCAATAACTAGAACTTCAGAAGGCCCAGCAGGCATG
TCAATACTACACAGGGCTGATGTGTCATTTTGAACCATCATC
TTGGCAGCAGTAACGAACTGGTTTCCTGGACCAAATATTTTG
TCACACTTAGGAACAGTTTCTGTTCCGTAAGCCATAGCAGCT
ACTGCCTGGGCGCCTCCTGCTAGCACGATACACTTAGCACCA
ACCTTGTGGGCAACGTAGATGACTTCTGGGGTAAGGGTACCA
TCCTTCTTAGGTGGAGATGCAAAAACAATTTCTTTGCAACCA
GCAACTTTGGCAGGAACACCCAGCATCAGGGAAGTGGAAGGC
AGAATTGCGGTTCCACCAGGAATATAGAGGCCAACTTTCTCA
ATAGGTCTTGCAAAACGAGAGCAGACTACACCAGGGCAAGTC
TCAACTTGCAACGTCTCCGTTAGTTGAGCTTCATGGAATTTC
CTGACGTTATCTATAGAGATCAATGGCTCTTAACGTTATC
TGGCAATTGCATAAGTTCCTCTGGGAAAGGAGCTTCTAACAC
AGGTGTCTTCAAAGCGACTCCATCAAACTTGGCAGTTAGTTC
TAAAAGGGCTTTGTCACCATTTTGACGAACATTGTCGACAAT
TGGTTTGGACTAATTCCATAATCTGTTCCGTTTTCTGGATAG
GACGACGAAGGGCATGTTCAATTTCTTGTGAGGAGGCCTTAG
AAACGTCAATTTTGCACAATTCAATACGACCTTCAGAAGGGA
CTTCTTTAGGTTTGGATTCTTCTTTAGGTTGTTCCTTGGTGT
ATCCTGGCTTGGCATCTCCTTTCCTTCTAGTGACCTTTAGGG
ACTTCATATCCAGGTTTCTCTCCACCTCGTCCAACGTCACAC
CGTACTTGGCACATCTAACTAATGCAAAATAAAATAAGTCAG
CACATTCCCAGGCTATATCTTCCTTGGATTAGCTTCTGCAAG
TTCATCAGCTTCCTCCCTAATTTTAGCGTTCAAACAAAACTT
CGTCGTCAAATAACCGTTTGGTATAAGAACCTTCTGGAGCAT
TGCTCTTACGATCCCACAAGGTGCTTCCATGGCTCTAAGACC
CTTTGATTGGCCAAAACAGGAAGTGCGTTCCAAGTGACAGAA
ACCAACACCTGTTTGTTCAACCACAAATTTCAAGCAGTCTCC
ATCACAATCCAATTCGATACCCAGCAACTTTTGAGTTCGTCC
AGATGTAGCACCTTTATACCACAAACCGTGACGACGAGATTG
GTAGACTCCAGTTTGTGTCCTTATAGCCTCCGGAATAGACTT
TTTGGACGAGTACACCAGGCCCAACGAGTAATTAGAAGAGTC
AGCCACCAAAGTAGTGAATAGACCATCGGGCGGTCAGTAGT
CAAAGACGCCAACAAAATTTCACTGACAGGGAACTTTTTGAC
ATCTTCAGAAAGTTCGTATTCAGTAGTCAATTGCCGAGCATC
AATAATGGGGATTATACCAGAAGCAACAGTGGAAGTCACATC

TABLE 6-continued

Sequences of Oligonucleotides used in Plasmid constructions of Table 5

TACCAACTTTGCGGTCTCAGAAAAAGCATAAACAGTTCTACT

ACCGCCATTAGTGAAACTTTTCAAATCGCCCAGTGGAGAAGA

AAAAGGCACAGCGATACTAGCATTAGCGGGCAAGGATGCAAC

TTTATCAACCAGGGTCCTATAGATAACCCTAGCGCCTGGGAT

CATCCTTTGGACAACTCTTTCTGCCAAATCTAGGTCCAAAAT

CACTTCATTGATACCATTATTGTACAACTTGAGCAAGTTGTC

GATCAGCTCCTCAAATTGGTCCTCTGTAACGGATGACTCAAC

TTGCACATTAACTTGAAGCTCAGTCGATTGAGTGAACTTGAT

CAGGTTGTGCAGCTGGTCAGCAGCATAGGGAAACACGGCTTT

TCCTACCAAACTCAAGGAATTATCAAACTCTGCAACACTTGC

GTATGCAGGTAGCAAGGGAAATGTCATACTTGAAGTCGGACA

GTGAGTGTAGTCTTGAGAAATTCTGAAGCCGTATTTTATTA

TCAGTGAGTCAGTCATCAGGAGATCCTCTACGCCGGACGCAT

CGTGGCCGACCTGCAGGTCGGCATCACCGGCGCCACAGGTGC

GGTTGCTGGCGCCTATATCGCCGACATCACCGATGGGGAAGA

TCGGGCTCGCCACTTCGGGCTCATGAGCGCTTGTTTCGGCGT

GGGTATGGTGGCAGGCCCCGTGGCCGGGGGACTGTTGGGCGC

CATCTCCTTGGACCTGCAGGGGGGGGGGGGGAAAGCCACGTT

GTGTCTCAAAATCTCTGATGTTACATTGCACAAGATAAAAT

ATATCATCATGAACAATAAAACTGTCTGCTTACATAAACAGT

AATACAAGGGGTGTTATGAGCCATATTCAACGGGAAACGTCT

TGCTCAAGGCCGCGATTAAATTCCAACATGGATGCTGATTTA

TATGGGTATAAATGGGCTCGCGATAATGTCGGGCAATCAGGT

GCGACAATCTATCGATTGTATGGGAAGCCCGATGCGCCAGAG

TTGTTTCTGAAACATGGCAAAGGTAGCGTTGCCAATGATGTT

ACAGATGAGATGGTCAGACTAAACTGGCTGACGGAATTTATG

CCTCTTCCGACCATCAAGCATTTTATCCGTACTCCTGATGAT

GCATGGTTACTCACCACTGCGATCCCCGGGAAAACAGCATTC

CAGGTATTAGAAGAATATCCTGATTCAGGTGAAAATATTGTT

GATGCGCTGGCAGTGTTCCTGCGCCGGTTGCATTCGATTCCT

GTTTGTAATTGTCCTTTTAACAGCGATCGCGTATTTCGTCTC

GCTCAGGCGCAATCACGAATGAATAACGGTTTGGTTGATGCG

AGTGATTTTGATGACGAGCGTAATGGCTGGCCTGTTGAACAA

GTCTGGAAAGAAATGCATAAGCTTTTGCCATTCTCACCGGAT

TCAGTCGTCACTCATGGTGATTTCTCACTTGATAACCTTATT

TTTGACGAGGGGAAATTAATAGGTTGTATTGATGTTGGACGA

GTCGGAATCGCAGACCGATACCAGGATCTTGCCATCCTATGG

AACTGCCTCGGTGAGTTTTCTCCTTCATTACAGAAACGGCTT

TABLE 6-continued

Sequences of Oligonucleotides used in Plasmid constructions of Table 5

TTTCAAAAATATGGTATTGATAATCCTGATATGAATAAATTG

CAGTTTCATTTGATGCTCGATGAGTTTTTGTAATCAGAATTG

GTTAATTGGTTGTAACACTGGCAGAGCATTACGCTGACTTGA

CGGGACGGCGGCTTTGTTGAATAAATCGAACTTTTGCTGAGT

TGAAGGATCAGATCACGCATCTTCCCGACAACGCAGACCGTT

CCGTGGCAAAGCAAAAGTTCAAAATCACCAACTGGTCCACCT

ACAACAAAGCTCTCATCAACCGTGGCTCCCTCACTTTCTGGC

TGGATGATGGGGCGATTCAGGCCTGGTATGAGTCAGCAACAC

CTTCTTCACGAGGCAGACCTCAGCGCCCCCCCCCCCTGCAG

GTCCCACGGCGGCGGTGCTCAACGGCCTCAACCTACTACTGG

GCTGCTTCCTAATGCAGGAGTCGCATAAGGGAGAGCGTCGAG

TATCTATGATTGGAAGTATGGGAATGGTGATCCCGCATTCT

TCAGTGTCTTGAGGTCTCCTATCAGATTATGCCCAACTAAAG

CAACCGGAGGAGGAGATTTCATGGTAAATTTCTCTGACTTTT

GGTCATCAGTAGACTCGAACTGTGAGACTATCTCGGTTATGA

CAGCAGAAATGTCCTTCTTGGAGACAGTAAATGAAGTCCCAC

CAATAAAGAAATGGTTGTTATCAGGAACAAACTTCTTGTTTC

GAACTTTTTCGGTGCCTTGAACTATAAAATGTAGAGTGGATA

TGTCGGGTAGGAATGGAGCGGGCAAATGCTTACCTTCTGGAC

CTTCAAGAGGTATGTAGGGTTTGTAGATACTGATGCCAACTT

CAGTGACAACGTTGCTATTTCGTTCAAACCATTCCGAATCCA

GAGAAATCAAAGTTGTTTGTCTACTATTGATCCAAGCCAGTG

CGGTCTTGAAACTGACAATAGTGTGCTCGTGTTTTGAGGTCA

TCTTTGTATGAATAAATCTAGTCTTTGATCTAAATAATCTTG

ACGAGCCAAGGCGATAAATACCCAAATCTAAAACTCTTTTAA

AACGTTAAAAGGACAAGTATGTCTGCCTGTATTAAACCCCAA

ATCAGCTCGTAGTCTGATCCTCATCAACTTGAGGGCACTAT

CTTGTTTTAGAGAAATTTGCGGAGATGCGATATCGAGAAAAA

GGTACGCTGATTTTAAACGTGAAATTTATCTCAAGATCTCTG

CCTCGCGCGTTTCGGTGATGACGGTGAAAACCTCTGACACAT

GCAGCTCCCGGAGACGGTCACAGCTTGTCTGTAAGCGGATGC

CGGGAGCAGACAAGCCCGTCAGGGCGCGTCAGCGGGTGTTGG

CGGGTGTCGGGGCGCAGCCATGACCCAGTCACGTAGCGATAG

CGGAGTGTATACTGGCTTAACTATGCGGCATCAGAGCAGATT

GTACTGAGAGTGCACCATATGCGGTGTGAAATACCGCACAGA

TGCGTAAGGAGAAAATACCGCATCAGGCGCTCTTCCGCTTCC

TCGCTCACTGACTCGCTGCGCTCGGTCGTTCGGCTGCGGCGA

GCGGTATCAGCTCACTCAAAGGCGGTAATACGGTTATCCACA

TABLE 6-continued
Sequences of Oligonucleotides used in Plasmid constructions of Table 5

GAATCAGGGGATAACGCAGGAAAGAACATGTGAGCAAAAGGC

CAGCAAAAGGCCAGGAACCGTAAAAAGGCCGCGTTGCTGGCG

TTTTTCCATAGGCTCCGCCCCCTGACGAGCATCACAAAAAT

CGACGCTCAAGTCAGAGGTGGCGAAACCCGACAGGACTATAA

AGATACCAGGCGTTTCCCCCTGGAAGCTCCCTCGTGCGCTCT

CCTGTTCCGACCCTGCCGCTTACCGGATACCTGTCCGCCTTT

CTCCCTTCGGGAAGCGTGGCTTTCTCAATGCTCACGCTGTAG

GTATCTCAGTTCGGTGTAGGTCGTTCGCTCCAAGCTGGGCTG

TGTGCACGAACCCCCCGTTCAGCCCGACCGCTGCGCCTTATC

CGGTAACTATCGTCTTGAGTCCAACCCGGTAAGACACGACTT

ATCGCCACTGGCAGCAGCCACTGGTAACAGGATTAGCAGAGC

GAGGTATGTAGGCGGTGCTACAGAGTTCTTGAAGTGGTGGCC

TAACTACGGCTACACTAGAAGGACAGTATTTGGTATCTGCGC

TCTGCTGAAGCCAGTTACCTTCGGAAAAAGAGTTGGTAGCTC

TTGATCCGGCAAACAAACCACCGCTGGTAGCGGTGGTTTTTT

GTTTGCAAGCAGCAGATTACGCGCAGAAAAAAAGGATCTCAA

GAAGATCCTTTGATCTTTTCTACGGGGTCTGACGCTCAGTGG

AACGAAAACTCACGTTAAGGGATTTTGGTCATGAGATTATCA

AAAAGGATCTTCACCTAGATCCTTTTAAATTAAAAATGAAGT

TTTAAATCAATCTAAAGTATATATGAGTAAACTTGGTCTGAC

AGTTACCAATGCTTAATCAGTGAGGCACCTATCTCAGCGATC

TGTCTATTTCGTTCATCCATAGTTGCCTGACTCCCCGTCGTG

TAGATAACTACGATACGGGAGGGCTTACCATCTGGCCCCAGT

GCTGCAATGATACCGAGAGACCCACGCTCACCGGCTCCAGAT

TTATCAGCAATAAACCAGCCAGCGGAAGGGCCGAGCGCAGA

AGTGGTCCTGCAACTTTATCCGCCTCCATCCAGTCTATTAAT

TGTTGCCGGGAAGCTAGAGTAAGTAGTTCGCCAGTTAATAGT

TTGCGCAACGTTGTTGCCATTGCTGCAGGCATCGTGGTGTCA

CGCTCGTCGTTTGGTATGGCTTCATTCAGCTCCGGTTCCCAA

CGATCAAGGCGAGTTACATGATCCCCCATGTTGTGCAAAAAA

GCGGTTAGCTCCTTCGGTCCTCCGATCGTTGTCAGAAGTAAG

TTGGCCGCAGTGTTATCACTCATGGTTATGGCAGCACTGCAT

AATTCTCTTACTGTCATGCCATCCGTAAGATGCTTTTCTGT

GACTGGTGAGTACTCAACCAAGTCATTCTGAGAATAGTGTAT

GCGGCGACCGAGTTGCTCTTGCCCGGCGTCAACACGGGATAA

TACCGCGCCACATAGCAGAACTTTAAAAGTGCTCATCATTGG

AAAACGTTCTTCGGGGCGAAAACTCTCAAGGATCTTACCGCT

GTTGAGATCCAGTTCGATGTAACCCACTCGTGCACCCAACTG

ATCTTCAGCATCTTTTACTTTCACCAGCGTTTCTGGGTGAGC

AAAAACAGGAAGGCAAAATGCCGCAAAAAAGGGAATAAGGGC

GACACGGAAATGTTGAATACTCATACTCTTCCTTTTTCAATA

TTATTGAAGCATTTATCAGGGTTATTGTCTCATGAGCGGATA

CATATTTGAATGTATTTAGAAAAATAAACAAATAGGGGTTCC

GCGCACATTTCCCCGAAAAGTGCCACCTGACGTCTAAGAAAC

CATTATTATCATGACATTAACCTATAAAAATAGGCGTATCAC

GAGGCCCTTTCGTCTTCAAGAATTAATTCTCATGTTTGACAG

CTTATCATCGATAAGCTGACTCATGTTGGTATTGTGAAATAG

ACGCAGATCGGGAACACTGAAAAATAACAGTTATTATTCGAG

ATC pUB 116  GATCTAACATCCAAAGACGAAAGGTTGAATGAAACCTTTTTG
[SEQ ID
NO: 83] CCATCCGACATCCACAGGTCCATTCTCACACATAAGTGCCAA

ACGCAACAGGAGGGGATACACTAGCAGCAGACCGTTGCAAAC

GCAGGACCTCCACTCCTCTTCTCCTCAACACCCACTTTTGCC

ATCGAAAACCAGCCCAGTTATTGGGCTTGATTGGAGCTCGC

TCATTCCAATTCCTTCTATTAGGCTACTAACACCATGACTTT

ATTAGCCTGTCTATCCTGGCCCCCCTGGCGAGGTTCATGTTT

GTTTATTTCCGAATGCAACAAGCTCCGCATTACACCCGAACA

TCACTCCAGATGAGGGCTTTCTGAGTGTGGGGTCAAATAGTT

TCATGTTCCCCAAATGGCCCAAAACTGACAGTTTAAACGCTG

TCTTGGAACCTAATATGACAAAAGCGTGATCTCATCCAAGAT

GAACTAAGTTTGGTTCGTTGAAATGCTAACGGCCAGTTGGTC

AAAAAGAAACTTCCAAAAGTCGCCATACCGTTTGTCTTGTTT

GGTATTGATTGACGAATGCTCAAAAATAATCTCATTAATGCT

TAGCGCAGTCTCTCTATCGCTTCTGAACCCCGGTGCACCTGT

GCCGAAACGCAAATGGGAAACACCCGCTTTTTGGATGATTA

TGCATTGTCTCCACATTGTATGCTTCCAAGATTCTGGTGGGA

ATACTGCTGATAGCCTAACGTTCATGATCAAAATTTAACTGT

TCTAACCCCTACTTGACAGCAATATATAAACAGAAGGAAGCT

GCCCTGTCTTAAACCTTTTTTTTTATCATCATTATTAGCTTA

CTTTCATAATTGCGACTGGTTCCAATTGACAAGCTTTTGATT

TTAACGACTTTTAACGACAACTTGAGAAGATCAAAAACAAC

TAATTATTCGAAGGATCCAAAAACGATGAGATTTCCTTCAAT

TTTTACTGCAGTTTTATTCGCAGCATCCTCCGCATTAGCTGC

TCCAGTCAACACTACAACAGAAGATGAAACGGCACAATTCC

GGCTGAAGCTGTCATCGGTTACTCAGATTTAGAAGGGGATTC

GATGTTGCTGTTTTGCCATTTTCCAACAGCACAAATAACGGG

TABLE 6-continued

Sequences of Oligonucleotides used in Plasmid constructions of Table 5

TTATTGTTTATAAATACTACTATTGCCAGCATTGCTGCTAAG

AAGAAGGGGTATCTCTCGAGAAAAGATGCGGACCGGGCAGGG

GGTTCGGGAAGAGGAGGCACCCCAAAAAGCTGACCCCTTTAG

CCTACAAGCAGTTATCCCCAATGTGGCCGAGAAGACCCTAGG

CGCCAGCGGAAGGTATGAAGGGAAGATCTCCAGAAACTCCGA

GCGATTTAAGGAACTCACCCCCAATTACAACCCCGACATCAT

ATTAAGGATGAAGAAAACACCGGAGCGGACAGGCTGATGACT

CAGAGGTGTAAGGACAAGTTGAACGCTTTGGCCATCTCGGTG

ATGAACCAGTGGCCAGGAGTGAAACTGCGGGTGACCGAGGGC

TGGGACGAAGATGGCCACCACTCAGAGGAGTCTCTGCACTAC

GAGGGCCGCGCAGTGGACATCACCACGTCTGACCGCGACCGC

AGCAAGTACGGCATGCTGGCCCGCCTGGCGGTGGAGGCCGGC

TTCGACTGGGTGTACTCGAGTCCAAGGCACATATCCACTGCT

CGGTGAAAGCAGAGAACTCGGTGGCGGCCAAATCGGGAGGCG

TCGACAAAACTCACACATGCCCACCGTGCCCAGCACCTGAAC

TCCTGGGGGGACCGTCAGTCTTCCTCTTCCCCCCAAAACCCA

AGGACACCCTCATGATCTCCCGGACCCCTGAGGTCACATGCG

TGGTGGTGGACGTGAGCCACGAAGACCCTGAGGTCAAGTTCA

ACTGGTACGTGGACGGCGTGGAGGTGCATAATGCCAAGACAA

GCGcgggaggagcagtaccagagcacgtaccgtgtggTCAGC

GTCCTCACCGTCCTGCACCAGGACTGGCTGAATGGCAAGGAG

TACAAGTGCAAGGTCTCCAACAAAGCCCTCCCAGCCCCCATC

GAGAAAACCATCTCCAAAGCCAAAGGGCAGCCCCGAGAACCA

CAGGTGTACACCCTGCCCCCATCCCGGGGATGAGCTGACCAA

GAACCAGGTCAGCCTGACCTGCCTGGTCAAAGGCTTCTATCC

CAGCGACAT CGCCGTGGAGTGGGAGAGCAATGGGCAGCCGG

AGAACAACTACAAGACCACGCCTCCCGTGTTGGACTCCGACG

GCTCCTTCTTCCTCTACAGCAAGCTCACCGTGGACAAGAGCA

GGTGGCAGCAGGGGAACGTCTTCTCATGCTCCGTGATGCATG

AGGCTCTGCACAACCACTACACGCAGAAGAGCCTCTCCCTGT

CTCCCGGGAAATGAGTGCGGCGGCCGCGAATTAATTCGCCTT

AGACATGACTGTTCCTCAGTTCAAGTTGGGCACTTACGAGAA

GACCGGTCTTGCTAGATTCTAATCAAGAGGATGTCAGAATGC

CATTTGCCTGAGAGATGCAGGCTTCATTTTTGATACTTTTTT

ATTTGTAACCTATATAGTATAGGATTTTTTTTGTCATTTTGT

TTCTTCTCGTACGAGCTTGCTCCTGATCAGCCTATCTCGCAG

CTGATGAATATCTTGTGGTAGGGGTTTGGGAAAATCATTCGA

GTTTGATGTTTTCTTGGTATTTCCCACTCCTCTTCAGAGTA

TABLE 6-continued

Sequences of Oligonucleotides used in Plasmid constructions of Table 5

CAGAAGATTAAGTGAGAAGTTCGTTTGTGCAAGCTTATCGAT

AAGCTTTAATGCGGTAGTTTATCACAGTTAAATTGCTAACGC

AGTCAGGCACCGTGTATGAAATCTAACAATGCGCTCATCGTC

ATCCTCGGCACCGTCACCCTGGATGCTGTAGGCATAGGCTTG

GTTATGCCGGTACTGCCGGGCCTCTTGCGGGATATCGTCCAT

TCCGACAGCATCGCCAGTCACTATGGCGTGCTGCTAGCGCTA

TATGCGTTGATGCAATTTCTATGCGCACCCGTTCTCGGAGCA

CTGTCCGACCGCTTTGGCCGCCGCCCAGTCCTGCTCGCTTCG

CTACTTGGAGCCACTATCGACTACGCGATCATGGCGACCACA

CCCGTCCTGTGGATCTATCGAATCTAAATGTAAGTTAAAATC

TCTAAATAATTAAATAAGTCCCAGTTTCTCCATACGAACCTT

AACAGCATTGCGGTGAGCATCTAGACCTTCAACAGCAGCCAG

ATCCATCACTGCTTGGCCAATATGTTCAGTCCCTCAGGAGTT

ACGTCTTGTGAAGTGATGAACTTCTGGAAGGTTGCAGTGTTA

ACTCCGCTGTATTGACGGGCATATCCGTACGTTGGCAAAGTG

TGGTTGGTACCGAGGAGTAATCTCCACAACTCTCTGGAGAG

TAGGCACCAACAAACACAGATCCAGCGTGTTGTACTTGATCA

ACATAAGAAGAAGCATTCTCGATTTGCAGGATCAAGTGTTCA

GGAGCGTACTGATTGGACATTTCCAAAGCCTGCTCGTAGGTT

GCAACCGATAGGGTTGTAGAGTGTGCAATACACTTGCGTACA

ATTTCAACCCTTGGCAACTGCACAGCTTGGTTGTGAACAGCA

TCTTCAATTCTGGCAAGCTCCTTGTCTGTCATATCGACAGCC

AACAGAATCACCTGGGAATCAATACCATGTTCAGCTTGAGCA

GAAGGTCTGAGGCAACGAAATCTGGATCAGCGTATTTATCAG

CAATAACTAGAACTTCAGAAGGCCCAGCAGCATGTCAATACT

ACACAGGGCTGATGTGTCATTTTCAACCATCATCTTGGCAGC

AGTAACGAACTGGTTTCCTGGACCAAATATTTTGTCACACTT

AGGAACAGTTTCTGTTCCGTAAGCCATAGCAGCTACTGCCTG

GGCGCCTCCTGCTAGCACGATACACTTAGCACCAACCTTGTG

GGCAACGTAGATGACTTCTGGGGTAAGGGTACCATCCTTCTT

AGGTGGAGATGCAAAAACAATTTCTTTGCAACCAGCAACTTT

GGCAGGAACACCCAGCATCAGGGAAGTGGAAGGCAGAATTGC

GGTTCCACCAGGAATATAGAGGCCAACTTTCTCAATAGGTCT

TGCAAAACGAGAGCAGACTACACCAGGGCAAGTCTCAACTTG

CAACGTCTCCGTTAGTTGAGCTTCATGGAATTTCCTGACGTT

ATCTATAGAGAGATCAATGGCTCTCTTAACGTTATCTGGCAA

TTGCATAAGTTCCTCTGGGAAAGGAGCTTCTAACACAGGTGT

CTTCAAAGCGACTCCATCAAACTTGGCAGTTAGTTCTAAAAG

TABLE 6-continued

Sequences of Oligonucleotides used in Plasmid constructions of Table 5

GGCTTTGTCACCATTTTGACGAACATTGTCGACAATTGGTTT
GACTAATTCCATAATCTGTTCCGTTTTCTGGATAGGACGACG
AAGGGCATCTTCAATTTCTTGTGAGGAGGCCTTAGAAACGTC
AATTTTGCACAATTCAATACGACCTTCAGAAGGGACTTCTTT
AGGTTTGGATTCTTCTTTAGGTTGTTCCTTGGTGTATCCTGG
CTTGGCATCTCCTTTCCTTCTAGTGACCTTTAGGGACTTCAT
ATCCAGGTTTCTCTCCACCTCGTCCAACGTCACACCGTACTT
GGCACATCTAACTAATGCAAAATAAAATAAGTCAGCACATTC
CCAGGCTATATCTTCCTTGGATTTAGCTTCTGCAAGTTCATC
AGCTTCCTCCCTAATTTTAGCGTTCAAACAAAACTTCGTCGT
CAAATAACCGTTTGGTATAAGAACCTTCTGGAGCATTGCTCT
TACGATCCCACAAGGTGCTTCCATGGCTCTAAGACCCTTTGA
TTGGCCAAAACAGGAAGTGCGTTCCAAGTGACAGAAACCAAC
ACCTGTTTGTTCAACCACAAATTTCAAGCAGTCTCCATCACA
ATCCAATTCGATACCCAGCAACTTTTGAGTTCGTCCAGATGT
AGCACCTTTATACCACAAACCGTGACGACGAGATTGGTAGAC
TCCAGTTTGTGTCCTTATAGCCTCCGGAATAGACTTTTTGGA
CGAGTACACCAGGCCCAACGAGTAATTAGAAGAGTCAGCCAC
CAAAGTAGTGAATAGACCATCGGGGCGGTCAGTAGTCAAAGA
CGCCAACAAAATTTCACTGACAGGGAACTTTTTGACATCTTC
AGAAAGTTCGTATTCAGTAGTCAATTGCCGAGCATCAATAAT
GGGGATTATACCAGAAGCAACAGTGGAAGTCACATCTACCAA
CTTTGCGGTCTCAGAAAAAGCATAAACAGTTCTACTACCGCC
ATTAGTGAAACTTTTCAAATCGCCCAGTGGAGAAGAAAAAGG
CACAGCGATACTAGCATTAGCGGGCAAGGATGCAACTTTATC
AACCAGGGTCCTATAGATAACCCTAGCGCCTGGGATCATCCT
TTGGACAACTCTTTCTGCCAAATCTAGGTCCAAAATCACTTC
ATTGATACCATTATTGTACAACTTGAGCAAGTTGTCGATCAG
CTCCTCAAATTGGTCCTCTGTAACGGATGACTCAACTTGCAC
ATTAACTTGAAGCTCAGTCGATTGAGTGAACTTGATCAGGTT
GTGCAGCTGGTCAGCAGCATAGGGAAACACGGCTTTTCCTAC
CAAACTCAAGGAATTATCAAACTCTGCAACACTTGCGTATGC
AGGTAGCAAGGGAAATGTCATACTTGAAGTCGGACAGTGAGT
GTAGTCTTGAGAAATTCTGAAGCCGTATTTTTATTATCAGTG
AGTCAGTCATCAGGAGATCCTCTACGCCGGACGCATCGTGGC
CGACCTGCAGGTCGGCATCACCGGCGCCACAGGTGCGGTTGC
TGGCGCCTATATCGCCGACATCACCGATGGGGAAGATCGGGC
TCGCCACTTCGGGCTCATGAGCGCTTGTTTCGGCGTGGGTAT

TABLE 6-continued

Sequences of Oligonucleotides used in Plasmid constructions of Table 5

GGTGGCAGGCCCCGTGGCCGGGGGACTGTTGGGCGCCATCTC
CTTGGACCTGCGGGGGGGGGGGGAAAGCCACGTTGTGTCTC
AAAATCTCTGATGTTACATTGCACAAGATAAAAATATATCAT
CATGAACAATAAAACTGTCTGCTTACATAAACAGTAATACAA
GGGGTGTTATGAGCCATATTCAACGGGAAACGTCTTGCTCAA
GGCCGCGATTAAATTCCAACATGGATGCTGATTTATATGGGT
ATAAATGGGCTCGCGATAATGTCGGGCAATCAGGTGCGACAA
TCTATCGATTGTATGGGAAGCCCGATGCGCCAGAGTTGTTTC
TGAAACATGGCAAAGGTAGCGTTGCCAATGATGTTACAGATG
AGATGGTCAGACTAAACTGGCTGACGGAATTTATGCCTCTTC
CGACCATCAAGCATTTTATCCGTACTCCTGATGATGCATGGT
TACTCACCACTGCGATCCCCGGGAAAACAGCATTCCAGGTAT
TAGAAGAATATCCTGATTCAGGTGAAAATATTGTTGATGCGC
TGGCAGTGTTCCTGCGCCGGTTGCATTCGATTCCTGTTTGTA
ATTGTCCTTTTAACAGCGATCGCGTATTTCGTCTCGCTCAGG
CGCAATCACGAATGAATAACGGTTTGGTTGATGCGAGTGATT
TTGATGACGAGCGTAATGGCTGGCCTGTTGAACAAGTCTGGA
AAGAAATGCATAAGCTTTTGCCATTCTCACCGGATTCAGTCG
TCACTCATGGTGATTTCTCACTTGATAACCTTATTTTTGACG
AGGGGAATTAATAGGTTGTATTGATGTTGGACGAGTCGGAAT
CGCAGACCGATACCAGGATCTTGCCATCCTATGGAACTGCCT
CGGTGAGTTTTCTCCTTCATTACAGAAACGGCTTTTTCAAAA
ATATGGTATTGATAATCCTGATATGAATAAATTGCAGTTTCA
TTTGATGCTCGATGAGTTTTTCTAATCAGAATTGGTTAATTG
GTTGTAACACTGGCAGAGCATTACGCTGACTTGACGGGACGG
CGGCTTTGTTGAATAAATCGAACTTTTGCTGAGTTGAAGGAT
CAGATCACGCATCTTCCCGACAACGCAGACCGTTCCGTGGCA
AAGCAAAAGTTCAAAATCACCAACTGGTCCACCTACAACAAA
GCTCTCATCAACCGTGGCTCCCTCACTTTCTGGCTGGATGAT
GGGGCGATTCAGGCCTGGTATGAGTCAGCAACACCTTCTTCA
CGAGGCAGACCTCAGCGCCCCCCCCCCCTGCAGGTCCCACG
GCGGCGGTGCTCAACGGCCTCAACCTACTACTGGGCTGCTTC
CTAATGCAGGAGTCGCATAAGGGAGAGCGTCGAGTATCTATG
ATTGGAAGTATGGGAATGGTGATACCCGCATTCTTCAGTGTC
TTGAGGTCTCCTATCAGATTATGCCCAACTAAAGCAACCGGA
GGAGGAGATTTCATGGTAAATTTCTCTGACTTTTGGTCATCA
GTAGACTCGAACTGTGAGACTATCTCGGTTATGACAGCAGAA
ATGTCCTTCTTGGAGACAGTAAATGAAGTCCCACCAATAAAG

TABLE 6-continued
Sequences of Oligonucleotides used in Plasmid constructions of Table 5

AAATCCTTGTTATCAGGAACAAACTTCTTGTTTCGAACTTTT

TCGGTGCCTTGAACTATAAAATGTAGAGTGGATATGTCGGGT

AGGAATGGAGCGGGCAAATGCTTACCTTCTGGACCTTCAAGA

GGTATGTAGGGTTTGTAGATACTGATGCCAACTTCAGTGACA

ACGTTGCTATTTCGTTCAAACCATTCCGAATCCAGAGAAATC

AAAGTTGTTTGTCTACTATTGATCCAAGCCAGTGCGGTCTTG

AAACTGACAATAGTGTGCTCGTGTTTTGAGGTCATCTTTGTA

TGAATAAATCTAGTCTTTGATCTAAATAATCTTGACGAGCCA

AGGCGATAAATACCCAAATCTAAAACTCTTTTAAAACGTTAA

AAGGACAAGTATGTCTGCCTGTATTAAACCCCAAATCAGCTC

GTAGTCTGATCCTCATCAACTTGAGGGGCACTATCTTGTTTT

AGAGAAATTTGCGGAGATGCGATATCGAGAAAAAGGTACGCT

GATTTTAAACGTGAAATTTATCTCAAGATCTCTGCCTCGCGC

GTTTCGGTGATGACGGTGAAAACCTCTGACACATGCAGCTCC

CGGAGACGGTCACAGCTTGTCTGTAAGCGGATGCCGGGAGCA

GACAAGCCCGTCAGGGCGCGTCAGCGGGTGTTGGCGGGTGTC

GGGGCGCAGCCATGACCCAGTCACGTAGCGATAGCGGAGTGT

ATACTGGCTTAACTATGCGGCATCAGAGCAGATTGTACTGAG

AGTGCACCATATGCGGTGTGAAATACCGCACAGATGCGTAAG

GAGAAAATACCGCATCAGGCGCTCTTCCGCTTCCTCGCTCAC

TGACTCGCTGCGCTCGGTCGTTCGGCTGCGGCGAGCGGTATC

AGCTCACTCAAAGGCGGTAATACGGTTATCCACAGAATCAGG

GGATAACGCAGGAAAGAACATGTGAGCAAAAGGCCAGCAAAA

GGCCAGGAACCGTAAAAAGGCCGCGTTGCTGGCGTTTTTCCA

TAGGCTCCGCCCCCCTGACGAGCATCACAAAAATCGACGCTC

AAGTCAGAGGTGGCGAAACCCGACAGGACTATAAAGATACCA

GGCGTTTCCCCCTGGAAGCTCCCTCGTGCGCTCTCCTGTTCC

GACCCTGCCGCTTACCGGATACCTGTCCGCCTTTCTCCCTTC

GGGAAGCGTGGCGCTTTCTCAATGCTCACGCTGTAGGTATCT

CAGTTCGGTGTAGGTCGTTCGCTCCAAGCTGGGCTGTGTGCA

CGAACCCCCGTTCAGCCCGACCGCTGCGCCTTATCCGGTAAC

TATCGTCTTGAGTCCAACCCGGTAAGACACGACTTATCGCCA

CTGGCAGCAGCCACTGGTAACAGGATTAGCAGAGCGAGGTAT

GTAGGCGGTGCTACAGAGTTCTTGAAGTGGTGGCCTAACTAC

GGCTACACTAGAAGGACAGTATTTGGTATCTGCGCTCTGCTG

AAGCCAGTTACCTTCGGAAAAAGAGTTGGTAGCTCTTGATCC

GGCAAACAAACCACCGCTGGTAGCGGTGGTTTTTTTGTTTGC

AAGCAGCAGATTACGCGCAGAAAAAAAGGATCTCAAGAAGAT

TABLE 6-continued
Sequences of Oligonucleotides used in Plasmid constructions of Table 5

CCTTTGATCTTTTCTACGGGGTCTGACGCTCAGTGGAACGAA

AACTCACGTTAAGGGATTTTGGTCATGAGATTATCAAAAAGG

ATCTTCACCTAGATCCTTTTAAATTAAAAATGAAGTTTTAAA

TCAATCTAAAGTATATATGAGTAAACTTGGTCTGACAGTTAC

CAATGCTTAATCAGTGAGGCACCTATCTCAGCGATCTGTCTA

TTTCGTTCATCCATAGTTGCCTGACTCCCCGTCGTGTAGATA

ACTACGATACGGGAGGGCTTACCATCTGGCCCCAGTGCTGCA

ATGATACCGCGAGACCCACGCTCACCGGCTCCAGATTTATCA

GCAATAAACCAGCCAGCCGGAAGGGCCGAGCGCAGAAGTGGT

CCTGCAACTTTATCCGCCTCCATCCAGTCTATTAATTGTTGC

CGGGAAGCTAGAGTAAGTAGTTCGCCAGTTAATAGTTTGCGC

AACGTTGTTGCCATTGCTGCAGGCATCGTGGTGTCACGCTCG

TCGTTTGGTATGGCTTCATTCAGCTCCGGTTCCCAACGATCA

AGGCGAGTTACATGATCCCCCATGTTGTGCAAAAAAGCGGTT

AGCTCCTTCGGTCCTCCGATCGTTGTCAGAAGTAAGTTGGCC

GCAGTGTTATCACTCATGGTTATGGCAGCACTGCATAATTCT

CTTACTGTCATGCCATCCGTAAGATGCTTTTCTGTGACTGGT

GAGTACTCAACCAAGTCATTCTGAGAATAGTGTATGCGGCGA

CCGAGTTGCTCTTGCCCGGCGTCAACACGGGATAATACCGCG

CCACATAGCAGAACTTTAAAAGTGCTCATCATTGGAAAACGTT

CTTCGGGGCGAAAACTCTCAAGGATCTTACCGCTGTTGAGAT

CCAGTTCGATGTAACCCACTCGTGCACCCAACTGATCTTCAG

CATCTTTTACTTTCACCAGCGTTTCTGGGTGAGCAAAAACAG

GAAGGCAAAATGCCGCAAAAAAGGGAATAAGGGCGACACGGA

AATGTTGAATACTCATACTCTTCCTTTTTCAATATTATTGAA

GCATTTATCAGGGTTATTGTCTCATGAGCGGATACATATTTG

AATGTATTTAGAAAAATAAACAAATAGGGGTTCCGCGCACAT

TTCCCCGAAAAGTGCCACCTGACGTCTAAGAAACCATTATTA

TCATGACATTAACCTATAAAAATAGGCGTATCACGAGGCCCT

TTCGTCTTCAAGAATTAATTCTCATGTTTGACAGCTTATCAT

CGATAAGCTGACTCATGTTGGTATTGTGAAATAGACGCAGAT

CGGGAACACTGAAAATAACAGTTATTATTCGAGATC pEAG657 CTAAATTGTAAGCGTTAATATTTTGTTAAAATTCGCGTTAAA
[SEQ ID
NO; 84] TTTTTGTTAAATCAGCTCATTTTTTAACCAATAGGCCGAAAT

CGGCAAAATCCCTTATAAATCAAAAGAATAGACCGAGATAGG

GTTGAGTGTTGTTCCAGTTTGGAACAAGAGTCCACTATTAAA

GAACGTGGACTCCAACGTCAAAGGGCGAAAAACCGTCTATCA

GGGCGATGGCCCACTACGTGAACCATCACCCTAATCAAGTTT

TABLE 6-continued
Sequences of Oligonucleotides used in Plasmid constructions of Table 5

TTTGGGGTCGAGGTGCCGTAAAGCACTAAATCGGAACCCTAA

AGGGAGCCCCCGATTTAGAGCTTGACGGGGAAAGCCGGCGAA

CGTGGCGAGAAAGGAAGGGAAGAAAGCGAAAGGAGCGGGCGC

TAGGGCGCTGGCAAGTGTAGCGGTCACGCTGCGCGTAACCAC

CACACCCGCCGCGCTTAATGCGCCGCTACAGGGCGCGTCCCA

TTCGCCATTCAGGCTGCGCAACTGTTGGGAAGGGCGATCGGT

GCGGGCCTCTTCGCTATTACGCCAGCTGGCGAAAGGGGGATG

TGCTGCAAGGCGATTAAGTTGGGTAACGCCAGGGTTTTCCCA

GTCACGACGTTGTAAAACGACGGCCAGTGAGCGCGCGTAATA

CGACTCACTATAGGGCGAATTGGGTACCGGGCCCTCTAGATC

CTTTCAGCTCCCTGCCCCGGACATGCCCAGTGGGTGGAAGCT

GCCCTCTTCTAGCAGGAGACGCCCCAGGCGGTAGAGCAGCTG

GGGGTACCAATGCACACCCTCCCCCGGaGTCCAGCTGCCCCA

TGCCAAGCTGTGAAAGAGTATCAGGGGCCAGAAGGCCAACTG

AGCCAGGTGGTGGTCAGCCACGGCCGCGAAGCAGGATGCCAC

CACATCCTCCACCACCAGTGTCCCATGCTTTGTGAGCGGGGC

GTAGGCCCCGAGGGCCACGTGTGTAGAGACAGCTGCCACGCG

GGCAGGCTGCAGGCCTGGCACCCCAGCCACCAGCACGTACTG

GCCAGGCTGCACGTGGCTGGCAAATGTGGCCCGGAAGCGGGC

TGCCGGCTCCGTGTGATTGTCAGCCGTAAAGAGCAGGTGAGC

GGGTGTGAGTGCCAGGCGGCGTGGGGGGTCCTGAGTCTCGAT

GACCTGGAAGGCTCTCAGCCTGTGGGGCTCGCGGTCCAGGAA

AATGAGCACATCGCTGAAGGTGGGGCTCCCATCCTCCCCCAT

GGCCAGCACACGGTCTCCCGGCCTCACGGCTGACAAGGCCAC

ACGCGCCCCACTCTccaggcgtacctgggctgcggccgcgaa tcagccgcccgtcttggCTGCGGCCGAGTGCTCGGACTTGAC

GGAGCAATGCACGTGGGCCTTTGACTCGTAATACACCCAGTC

AAAGCCGGCCTCCACTGCCAAGCGCGCCAGCAGTCCATACTT

ATTGCGGTCGCGGTCTGATGTGGTGATGTCCACCGCGCGGCC

CTCATAATGCAGGGACTCCTCTGAGTGGTGGCCGTCCTCGTC

CCAGCCCTCGGTCACCCGCAGCTTCACACCGGGCCACTGGTT

CATCACCGAGATAGCCAGCGAGTTCAGGCGGTCCTTGCAGCG

CTGGGTCATGAGGCGGTCGGCGCCTGTGTTCTCCTCGTCCTT

GAAGATGATGTCTGGATTGTAATTGGGGGTGAGCTCCTTGAA

GCGCTCGGAGCTGCGAGCGATCTTGCCTTCATAGCGTCCGCT

GGCGCCCAGGGTCTTCTCGGGCACATTGGGGCTGAACTGCTT

GTAGGCGAGCGGCACGAGTTTGCGTGGCGGTCGCCGGCGGCT

GCCCACCACCCGACCCGGCCCGCAGCCCCATGCCGCcGGCAC

CACCAGCAGCAGCAACAGGACCAGGCAGAAGTGCAGTCGGGG

CCGGAGCCGGggcgggagacatggcggccgcgacggtatcgat aagcTTGATATCGAATTCCTGCAGCCCGGGGGATCCACTAGT

TCTAGAGCGGCCGCCACCGCGGTGGAGCTCCAGCTTTTGTTC

CCTTTAGTGAGGGTTAATTGCGCGCTTGGCGTAATCATGGTC

ATAGCTGTTTCCTGTGTGAAATTGTTATCCGCTCACAATTCC

ACACAACATACGAGCCGGAAGCATAAAGTGTAAAGCCTGGGG

TGCCTAATGAGTGAGCTAACTCACATTAATTGCGTTGCGCTC

ACTGCCCGCTTTCCAGTCGGGAAACCTGTCGTGCCAGCTGCA

TTAATGAATCGGCCAACGCGCGGGGAGAGGCGGTTTGCGTAT

TGGGCGCTCTTCCGCTTCCTCGCTCACTGACTCGCTGCGCTC

GGTCGTTCGGCTGCGGCGAGCGGTATCAGCTCACTCAAAGGC

GGTAATACGGTTATCCACAGAATCAGGGGATAACGCAGGAAA

GAACATGTGAGCAAAAGGCCAGCAAAAGGCCAGGAACCGTAA

AAAGGCCGCGTTGCTGGCGTTTTTCCATAGGCTCCGCCCCCC

TGACGAGCATCACAAAAATCGACGCTCAAGTCAGAGGTGGCG

AAACCCGACAGGACTATAAAGATACCAGGCGTTTCCCCCTGG

AAGCTCCCTCGTGCGCTCTCCTGTTCCGACCCTGCCGCTTAC

CGGATACCTGTCCGCCTTTCTCCCTTCGGGAAGCGTGGCGCT

TTCTCATAGCTCACGCTGTAGGTATCTCAGTTCGGTGTAGGT

CGTTCGCTCCAAGCTGGGCTGTGTGCACGAACCCCCCGTTCA

GCCCGACCGCTGCGCCTTATCCGGTAACTATCGTCTTGAGTC

CAACCCGGTAAGACACGACTTATCGCCACTGGCAGCAGCCAC

TGGTAACAGGATTAGCAGAGCGAGGTATGTAGGCGGTGCTAC

AGAGTTCTTGAAGTGGTGGCCTAACTACGGCTACACTAGAAG

GACAGTATTTGGTATCTGCGCTCTGCTGAAGCCAGTTACCTT

CGGAAAAAGAGTTGGTAGCTCTTGATCCGGCAAACAAACCAC

CGCTGGTAGCGGTGGTTTTTTTGTTTGCAAGCAGCAGATTAC

GCGCAGAAAAAAAGGATCTCAAGAAGATCCTTTGATCTTTTC

TACGGGGTCTGACGCTCAGTGGAACGAAAACTCACGTTAAGG

GATTTTGGTCATGAGATTATCAAAAAGGATCTTCACCTAGAT

CCTTTTAAATTAAAAATGAAGTTTTAAATCAATCTAAAGTAT

ATATGAGTAAACTTGGTCTGACAGTTACCAATGCTTAATCAG

TGAGGCACCTATCTCAGCGATCTGTCTATTTCGTTCATCCAT

AGTTGCCTGACTCCCCGTCGTGTAGATAACTACGATACGGGA

GGGCTTACCATCTGGCCCCAGTGCTTGCAATGATACCGCGAG

ACCCACGCTCACCGGCTCCAGATTTATCAGCAATAAACCAGC

CAGCCGGAAGGGCCGAGCGCAGAAGTGGTCCTGCAACTTTAT

TABLE 6-continued
Sequences of Oligonucleotides used in Plasmid constructions of Table 5

|  |  |
|---|---|
|  | CCGCCTCCATCCAGTCTATTAATTGTTGCCGGGAAGCTAGAG |
|  | TAAGTAGTTCGCCAGTTAATAGTTTGCGCAACGTTGTTGCCA |
|  | TTGCTACAGGCATCGTGGTGTCACGCTCGTCGTTTGGTATGG |
|  | CTTCATTCAGCTCCGGTTCCCAACGATCAAGGCGAGTTACAT |
|  | GATCCCCCATGTTGTGCAAAAAAGCGGTTAGCTCCTTCGGTC |
|  | CTCCGATCGTTGTCAGAAGTAAGTTGGCCGCAGTGTTATCAC |
|  | TCATGGTTATGGCAGCACTGCATAATTCTCTTACTGTCATGC |
|  | CATCCGTAAGATGCTTTTCTGTGACTGGTGACGCGTCAACCA |
|  | AGTCATTCTGAGAATAGTGTATGCGGCGACCGAGTTGCTCTT |
|  | GCCCGGCGTCAATACGGGATAATACCGCGCCACATAGCAGAA |
|  | CTTTAAAAGTGCTCATCATTGGAAAACGTTCTTCGGGGCGAA |
|  | AACTCTCAAGGATCTTACCGCTGTTGAGATCCAGTTCGATGT |
|  | AACCCACTCGTGCACCCAACTGATCTTCAGCATCTTTTACTT |
|  | TCACCAGCGTTTCTGGGTGAGCAAAAACAGGAAGGCAAAATG |
|  | CCGCAAAAAAGGGAATAAGGGCGACACGGAAATGTTGAATAC |
|  | TCATACTCTTCCTTTTTCAATATTATTGAAGCATTTATCAGG |
|  | GTTATTGTCTCATGAGCGGATACATATTTGAATGTATTTAGA |
|  | AAAATAAACAAATAGGGGTTCCGCGCACATTTCCCCGAAAAG |
|  | TGCCAC |
| pEAG658 [SEQ ID NO: 85] | CTAAATTGTAAGCGTTAATATTTTGTTAAAATTCGCGTTAAA |
|  | TTTTTGTTAAATCAGCTCATTTTTTAACCAATAGGCCGAAAT |
|  | CGGCAAAATCCCTTATAAATCAAAAGAATAGACCGAGATAGG |
|  | GTTGAGTGTTGTTCCAGTTTGGAACAAGAGTCCACTATTAAA |
|  | GAACGTGGACTCCAACGTCAAAGGGCGAAAAACCGTCTATCA |
|  | GGGCGATGGCCCACTACGTGAACCATCACCCTAATCAAGTTT |
|  | TTTGGGGTCGAGGTGCCGTAAAGCACTAAATCGGAACCCTAA |
|  | AGGGAGCCCCCGATTTAGAGCTTGACGGGGAAAGCCGGCGAA |
|  | CGTGGCGAGAAAGGAAGGGAAGAAAGCGAAAGGAGCGGGCGC |
|  | TAGGGCGCTGGCAAGTGTAGCGGTCACGCTGCGCGTAACCAC |
|  | CACACCCGCCGCGCTTAATGCGCCGCTACAGGGCGCGTCCCA |
|  | TTCGCCATTCAGGCTGCGCAACTGTTGGGAAGGGCGATCGGT |
|  | GCGGGCCTCTTCGCTATTACGCCAGCTGGCGAAAGGGGGATG |
|  | TGCTGCAAGGCGATTAAGTTGGGTAACGCCAGGGTTTTCCCA |
|  | GTCACGACGTTGTAAAACGACGGCCAGTGAGCGCGCGTAATA |
|  | CGACTCACTATAGGGCGAATTGGGTACCGGGCCCTCTAGATC |
|  | CTTTCAGCTCCCTGCCCCGGACATGCCCAGTGGGTGGAAGCT |
|  | GCCCTCTTCTAGCAGGAGACGCCCCAGGCGGTAGAGCAGCTG |
|  | GGGGTACCAATGCACACCCTCCCCCCGGaGTCCAGCTGCCCA |
|  | TGCCAAGCTGTGAAAGAGTCTCAGGGGCCAGAAGGCCAACTG |
|  | AGCCAGGTGGTGGTCAGCCACGGCCGCGAAGCAGGATGCCAC |
|  | CACATCCTCCACCACCAGTGTCCCATGCTTTGTGAGCGGGGC |
|  | GTAGGCCCCAGGGCCACGTGTGTAGAGACAGCTGCCACGCGG |
|  | GCAGGCTGCAGGCCTGGCACCCCAGCCACCAGCACGTACTGG |
|  | CCAGGCTGCACGTGGCTGGCAAATGTGGCCCGGAAGCGGGCT |
|  | GCCGGCTCCGTGTGATTGTCAGCCGTAAAGAGCAGGTGAGCG |
|  | GGTGTGAGTGCCAGGCGGCGTGGGGGGTCCTGAGTCTCGATG |
|  | ACCTGGAAGGCTCTCAGCCTGTGGGCTCGCGGTCCAGGAAA |
|  | ATGAGCACATCGCTGAAGGTGGGGCTCCCATCCTCCCCCATG |
|  | GCCAGCACACGGTCTCCCGGCCTCACGGCTGACAAGGCCACA |
|  | CGCGCCCCACTCTCCAGGCGTACCTgggctccggcagggtcg |
|  | acgccgccgtcttggCTGCGGCCGAGTGCTCGGACTTGACG |
|  | GAGCAATGCACGTGGGCCTTTGACTCGTAATACACCCAGTCA |
|  | AAGCCGGCCTCCACTGCCAAGCGCGCCAGCAGTCCATACTTA |
|  | TTGCGGTCGCGGTCTGATGTGGTGATGTCCACCGCGCGGCCC |
|  | TCATAATGCAGGGACTCCTCTGAGTGGTGGCCGTCCTCGTCC |
|  | CAGCCCTCGGTCACCCGCAGCTTCACACCGGGCCACTGGTTC |
|  | ATCACCGAGATAGCCAGCGAGTTCAGGCGGTCCTTGCAGCGC |
|  | TGGGTCATGAGGCGGTCGGCGCCTGTGTTCTCCTCGTCCTTG |
|  | AAGATGATGTCTGGATTGTAATTGGGGGTGAGCTCCTTGAAG |
|  | CGCTCGGAGCTGCGAGCGATCTTGCCTTCATAGCGTCCGCTG |
|  | GCGCCCAGGGTCTTCTCGGGCACATTGGGGCTGAACTGCTTG |
|  | TAGGCGAGCGGACGAGTTTGCGTGGCGGTCGCCGGCGGCTG |
|  | CCCACCACCGACCCGGCCCGCAGCCCCATGCCGCCGGCACCA |
|  | CCAGCAGCAGCAACAGGACCAGGCAGAAGTGCAGTCGGGGCC |
|  | GGAGCCGggcgggagacatggcggcgcgacggtatcgataag |
|  | cTTGATATCGAATTCCTGCAGCCCGGGGGATCCACTAGTTCT |
|  | AGAGCGGCCGCCACCGCGGTGGAGCTCCAGCTTTTGTTCCCT |
|  | TTAGTGAGGGTTAATTGCGCGCTTGGCGTAATCATGGTCATA |
|  | GCTGTTTCCTGTGTGAAATTGTTATCCGCTCACAATTCCACA |
|  | CAACATACGAGCCGGAAGCATAAAGTGTAAAGCCTGGGGTGC |
|  | CTAATGAGTGAGCTAACTCACATTAATTGCGTTGCGCTCACT |
|  | GCCCGCTTTCCAGTCGGGAAACCTGTCGTGCCAGCTGCATTA |
|  | ATGAATCGGCCAACGCGCGGGGAGAGGCGGTTTGCGTATTGG |
|  | GCGCTCTTCCGCTTCCTCGCTCACTGACTCGCTGCGCTCGGT |
|  | CGTTCGGCTGCGGCGAGCGGTATCAGCTCACTCAAAGGCGGT |
|  | AATACGGTTATCCACAGAATCAGGGGATAACGCAGGAAAGAA |
|  | CATGTGAGCAAAAGGCCAGCAAAAGGCCAGGAACCGTAAAAA |

TABLE 6-continued

Sequences of Oligonucleotides used in Plasmid constructions of Table 5

GGCCGCGTTGCTGGCGTTTTTCCATAGGCTCCGCCCCTGAC

GAGCATCACAAAAATCGACGCTCAAGTCAGAGGTGGCGAAAC

CCGACAGGACTATAAAGATACCAGGCGTTTCCCCCTGGAAGC

TCCCTCGTGCGCTCTCCTGTTCCGACCCTGCCGCTTACCGGA

TACCTGTCCGCCTTTCTCCCTTCGGGAAGCGTGGCGCTTTCT

CATAGCTCACGCTGTAGGTATCTCAGTTCGGTGTAGGTCGTT

CGCTCCAAGCTGGGCTGTGTGCACGAACCCCCCGTTCAGCCC

GACCGCTGCGCCTTATCCGGTAACTATCGTCTTGAGTCCAAC

CCGGTAAGACACGACTTATCGCCACTGGCAGCAGCCACTGGT

AACAGGATTAGCAGAGCGAGGTATGTAGGCGGTGCTACAGAG

TTCTTGAAGTGGTGGCCTAACTACGGCTACACTAGAAGGACA

GTATTTGGTATCTGCGCTCTGCTGAAGCCAGTTACCTTCGGA

AAAAGAGTTGGTAGCTCTTGATCCGGCAAACAAACCACCGCT

GGTAGCGGTGGTTTTTTTGTTTGCAAGCAGCAGATTACGCGC

AGAAAAAAAGGATCTCAAGAAGATCCTTTGATCTTTTCTACG

GGGTCTGACGCTCAGTGGAACGAAAACTCACGTTAAGGGATT

TTGGTCATGAGATTATCAAAAAGGATCTTCACCTAGATCCTT

TTAAATTAAAAATGAAGTTTTAAATCAATCTAAAGTATATAT

GAGTAAACTTGGTCTGACAGTTACCAATGCTTAATCAGTGAG

GCACCTATCTCAGCGATCTGTCTATTCGTTCATCCATAGTTG

CCTGACTCCCGTCGTGTAGATAACTACGATACGGGAGGGCTT

ACCATCTGGCCCCAGTGCTGCAATGATACCGCGAGACCCACG

CTCACCGGCTCCAGATTTATCAGCAATAAACCAGCCAGCCGG

AAGGGCCGAGCGCAGAAGTGGTCCTGCAACTTTATCCGCCTC

CATCCAGTCTATTAATTGTTGCCGGGAAGCTAGAGTAAGTAG

TTCGCCAGTTAATAGTTTGCGCAACGTTGTTGCCATTGCTAC

AGGCATCGTGGTGTCACGCTCGTCGTTTGGTATGGCTTCATT

CAGCTCCGGTTCCCAACGATCAAGGCGAGTTACATGATCCCC

CATGTTGTGCAAAAAAGCGGTTAGCTCCTTCGGTCCTCCGAT

CGTTGTCAGAAGTAAGTTGGCCGCAGTGTTATCACTCATGGT

TATGGCAGCACTGCATAATTCTCTTACTGTCATGCCATCCGT

AAGATGCTTTTCTGTGACTGGTGACGCGTCAACCAAGTCATT

CTGAGAATAGTGTATGCGGCGACCGAGTTGCTCTTGCCCGGC

GTCAATACGGGATAATACCGCGCCACATAGCAGAACTTTAAA

AGTGCTCATCATTGGAAAACGTTCTTCGGGGCGAAAACTCTC

AAGGATCTTACCGCTGTTGAGATCCAGTTCGATGTAACCCAC

TCGTGCACCCAACTGATCTTCAGCATCTTTTACTTTCACCAG

AGTTTCTGGGTGAGCAAAAACAGGAAGGCAAAATGCCGCAAA

TABLE 6-continued

Sequences of Oligonucleotides used in Plasmid constructions of Table 5

AAAGGGAATAAGGGCGACACGGAAATGTTGAATACTCATACT

CTTCCTTTTTCAATATTATTGAAGCATTTATCAGGGTTATTG

TCTCATGAGCGGATACATATTTGAATGTATTTAGAAAAATAA

ACAAATAGGGGTTCCGCGCACATTTCCCCGAAAAGTGCCAC

Construction of Hedgehog-Ig Fusion Proteins

Mutations with activity in the 10T1/2 assay were subcloned to SHH-Fc(muIgG1) plasmid pUB114 (SEQ ID. No.: 81), which has the wild-type SHH domain fused to the CH2 and CH3 regions of murine IgG1.

The Fc region in pUB114 contains a glycosylation site mutation [Asn297Gln, PUB55 and pUB114 plasmids are identical outside of the region coding for the Fc domain fused to SHH. Plasmids identical to pUB114, but containing the human IgG1, or murine IgG2a Fc region are pUB115 (SEQ ID. NO.: 82) and pUB116 (SEQ ID. NO.: 83), respectively. (See also Table 4).

Consequently, mutations in SHH were subcloned to pUB114 from the Sac1 site upstream of SHH in the AOX1 promoter to either the Avr2 site or the Sph1 site (both downstream of the SHH mutations, but upstream of the SHH-Fc fusion joint).

For construction of yeast strains expressing protein, plasmids were digested with Stu1 and transformed into *Pichia pastoris* GS115 by electroporation in 1M Sorbitol (Invitrogen) or by a Li salt transformation procedure (Frozen EZ Yeast Transformation kit, Zymo Research, Orange, Calif.). His+ transformants were selected on MD agar. Colonies were purified on YPD agar and cultured for protein expression in 5 ml BMMY (2% Methanol) medium. BMMY culture supernatants were harvested at 1 or 2 days (1-day harvests were concentrated by TCA precipitation) and were analyzed by SDS-PAGE and Coomassie blue staining to distinguish clipped and unclipped SHH.

Protein Purification

Large scale preparations of protein for purification were prepared as follows: An inoculum in BMGY (late log to stationary phase) was added to 1 L BMGY in a Fernbach flask and incubated at 150 rpm for 2-3 days. The stationary phase BMGY culture was centrifuged and the cell pellet from 1 L was resuspended in BMMY (2% Methanol) and incubated in a Fernbach flask at 30 C for 2-3 days. Pepstatin A (44 microM) was added to BMMY medium for expression of SHH-Fc fusion proteins.

A. Purification of Hedgehog N-Terminal Domain Basic Region Mutants

After removing the *Pichia* cells by centrifugation, the conditioned medium was diluted ten-fold with water to reduce the salt concentration and then re-concentrated using a 3K cutoff spiral filter (Amicon). The concentrate was applied to a CM-Poros®, column (Perseptive Biosystems) equilibrated with 50 mM sodium phosphate, pH 6.0. Elution with a gradient of 0-0.8 M NaCl separated two hedgehog peaks.

The first peak contained a mixture of full-length hedgehog as a disulfide with cysteine or glutathione and clipped hedgehog when a KEX2 proteolytic site was present. The second peak was the full-length disulfide-linked hedgehog homodimer. This second peak of protein was used to assess bioactivity when the first peak contained significant amounts of clipped material.

The peaks were pooled separately, reduced with 10 mM DTT and dialyzed against 5 mM sodium phosphate, pH 5.5, 150 mM NaCl and 0.5 mM DTT. No DTT was used when the N-terminal cysteine of the protein was replaced with other amino acids. This single purification step is sufficient to achieve >95% purity owing to the low level of contaminating proteins in the conditioned medium. Purity was determined by SDS-PAGE on 4-20% gradient gels (Novex) stained with Coomassie Blue. Identity was confirmed by mass spectrometry, and potency was analyzed using a cell-based bioactivity assay (see below).

B. Purification of Hedgehog-Ig Fusion Protein Constructs

Pichia cells were removed from the conditioned medium by centrifugation before application to Protein A Fast Flow® (Pharmacia). Protein from constructs utilizing human IgG1 (SEQ ID NO: 40) or murine IgG2A sequences (SEQ ID NO: 42) were applied directly to the Protein A. Constructs utilizing murine IgG1 sequences were diluted ten-fold with water to reduce the salt concentration, re-concentrated using a 3K cutoff spiral filter (Amicon) and the pH adjusted with the addition of sodium borate buffer, pH 8.5 to a final concentration of 50 mM.

HHIg was eluted with 25 mM sodium phosphate, pH 2.8, and the fractions collected into tubes containing 0.1 volume of 0.5 M sodium phosphate pH 6 to readjust the pH. The Protein A eluant was then diluted eight-fold with 0.5 mM sodium phosphate, pH 6 and applied to a CM-Poros® column (Perseptive Biosystems) equilibrated with 50 mM sodium phosphate, pH 6.0. Elution with a gradient of 0-0.8 M NaCl separated two HHIg peaks.

The first is "one-armed" protein in which one of the HHIg polypeptides of the dimer is proteolytically cleaved at a sequence near the hinge and therefore this dimer contains only one HH N-terminal domain. The second peak is the dimer with two full-length HHIg chains. The peaks were pooled separately, reduced with 10 mM DTT and dialyzed against 5 mM sodium phosphate, pH 5.5, 150 mM NaCl and 0.5 mM DTT. No DTT was used when the N-terminal cysteine of the protein was replaced with other amino acids. These two purification steps achieve >95% purity. Purity was determined by SDS-PAGE on 4-20% gradient gels (Novex) stained with Coomassie Blue. Identity was confirmed by mass spectrometry, and potency was analyzed using a cell-based bioactivity assay (see below).

Mass Spectrometry

The molecular masses of the purified proteins were determined by electrospray ionization mass spectroscopy (ESI-MS) on a Micromass Quattro II triple quadrupole mass spectrometer. Samples were desalted using an on-line Michrom Ultrafast Microprotein Analyzer system with a Reliasil® C4 column (1 mm×5 cm). All electrospray mass spectral data were processed using the Micromass MassLynx data system.

EXAMPLE 2

Pharmacokinetics and Pharmacodynamics

Bioactivity Assay.

Hedgehog proteins were tested for bioactivity in a cell-based assay measuring alkaline phosphatase induction in C3H10T1/2 cells (Pepinsky et al, JBC 273, 14037-14045 (1998)).

Pharmacokinetics.

The hedgehog-Ig fusion proteins shown in Table 3 are compared to wt shh N-terminal domain in a screening pharmacokinetic study in mice as exemplified below. In this study, two female Balb/c mice were intraveneously injected with 50 µg of each protein. Occular bleeds were done at 5 minutes and at 5 or 7 hrs after injection for all proteins. The final bleed was done at 24 hrs after injection.

Serum prepared from all bleeds was frozen immediately on dry ice and stored at −70 C. Hedgehog levels in the serum were determined by a sandwich ELISA where the protein was captured by coated anti-hedgehog mAb 5E1 followed by the secondary antibody (rabbit polyclonal against the 15 N-terminal amino acids of hedgehog) and detection with goat anti rabbit HRP conjugate. Values for various dilutions of the serum samples were backfited from a standard curve made with the specific protein being tested. The standard curves were validated by determining the concentration of known levels of protein spiked into serum.

Results

RKRHP Mutation: This mutation was constructed to test whether the "N-11" clip site could be recognized by KEX2 if the N-10 clip does not occur. As expected, this mutant is expressed as a mixture of both intact and clipped SHH. We have not determined the exact clip site (by N-terminal sequencing of Mass Spectroscopy) but we presume that it occurs by cleavage of the Arg11-His12 bond. This protein is less extensively clipped than wild-type SHH, so we conclude that the N-11 site is indeed a poorer KEX2 site than the N-10 site. The N-11 KEX2 site must be eliminated by mutation to prevent KEX2 clipping of the Sonic Hedgehog protein.

RKRPP Mutation: This mutation destroys both KEX2 sites in the basic region of SHH. We presumed that the conservative substitutions of one basic residue for another [Lys9Arg and Arg10Lys] would not be deleterious to activity. The His12Pro substitution was chosen because the Indian Hedgehog homolog of Sonic Hedgehog has Pro in this position. When the protein was constructed it exhibited no clipping, as expected. When tested in the 10T1/2 assay, the RKRPP mutant protein showed no activity. As this mutation has three amino acid substitutions [Lys9Arg, Arg10Lys, and His 12Pro], we cannot say which substitution(s) destroyed activity. However, Lys9 is an Arg residue in other homologs of Sonic Hedgehog, so it seemed unlikely to be responsible for inactivity. We postulate that the His12Pro mutation is responsible for the inactivity of the protein.

GSRKRPPRK ("Indian-like" Sonic Hedgehog"). The Indian Sonic Hedgehog sequence has only one KEX2 site in the basic region, compared to Sonic Hedgehog, which has two. The Pro for His substitution is responsible for eliminating the second KEX2 site. Another distinction between Sonic and Indian in this region is the insertion of a Ser residue just upstream of the tribasic motif in Indian Hedgehog. We postulate that this Ser addition may compensate for the extra Pro residue in Indian Hedgehog compared to Sonic Hedgehog. Consequently a mutant was constructed that contains both the Ser insertion and the His to Pro mutation. The sequence GSRKRPPRK was substituted for the GKRRHPKK sequence in Sonic Hedgehog. Note that GSRKRPPRK differs from Sonic in five positions (GSRKRPPRK) but differs from the Indian sequence in only one position (GSRKRPPRK). This mutant exhibited no KEX2 clipping and had measurable activity in the 10T1/2 assay, although it is a bit less active than wild-type Sonic Hedgehog.

KKKHP, RKKHP, RQRHP Mutants: These mutants were designed to maintain as much positive charge as possible while maintaining the His12 residue and eliminating the KEX2 recognition sites. All three of these mutants are inactive and thus demonstrate that the three residue Lys9Arg10Arg11 sequence in SHH contains a feature essential for activity. This data also raised the possibility that the His12Pro mutation in the RKRPP mutant may be irrelevant to the loss of activity exhibited by the protein. As the RKRPP and RKRHP mutants differ only in the His12 position, we tested the activity of the unclipped RKRHP mutant protein.

The unclipped RKRHP mutant protein was purified away from the clipped species and tested in the 10T1/2 assay, in which it had no detectable activity. As the RKRHP protein has two of the three substitutions present in the inactive RKRPP mutant, it demonstrates that the apparently conservative Lys9Arg and/or Arg10Lys substitutions are sufficient to eliminate SHH activity in the 10T1/2 assay. QRRPP and QRKHP Mutants: These mutants were constructed in order to destroy the KEX2 site while maintaining the Arg10 residue and maximizing the number of positively charge residues. Both mutants had activity as high as the wild-type protein. We conclude that maintaining the Arg10 residue is critical for Sonic Hedgehog activity.

Conclusions

When the initial HHIg fusion construct with wild-type sonic hedgehog sequence was expressed and purified it was found to be clipped at the R10-R11 bond to give the N-10 protein. Therefore this protein was not suitable for development as an agonist because previous work had established that hedgehog proteins with truncated N-termini act as antagonists (see above). The sequence of the N-10 site suggested it might be the target of proteolysis by a KEX2-like protease that requires three residues K/R-R-X (where X is not proline). This hypothesis was verified by the construction of mutants of this cleavage site sequence which, when expressed and purified, yielded intact protein (Table 7). Most mutants, however, were inactive in the C3H10T1/2 assay, and it was found that an arginine residue must be present at a critical position in the sequence in order to retain activity. The most potent and proteolytically resistant sequence was chosen for the construction of another series of HHIg fusion proteins, some of which also incorporated isoleucine substitutions of the N-terminal cysteine to increase potency and reduce oxidation problems. These fusion proteins have been expressed and purified and shown to be more potent in the C3H10T1/2 assay (Table 8). Pharmacokinetic data in mice demonstrate that the fusion proteins have a substantial increase in serum half-life compared to the Sonic Hedgehog N-terminal domain (Table/9)

TABLE 7

Hedgehog N-terminal domain basic region mutants.

| Basic region sequence | Clipping in basic sequence[a] | Mass spectrum (Found/Predicted) | Potency[b] |
|---|---|---|---|
| KRRH (wild type) | ~70% | 19559/19560 | 1.2-4 µg/ml |
| RKRH | ~20% | 19560/19560 | Inactive |
| RKRP | <5% | 19519/19520 | Inactive |
| RQRH | <10% | 19559/19560 | Inactive |
| RKKH | <5% | 19530/19532 | Inactive |
| SRKRP ("Indian-like") | <10% | 19634/19635 | 3-6 µg/ml |

TABLE 7-continued

Hedgehog N-terminal domain basic region mutants.

| Basic region sequence | Clipping in basic sequence[a] | Mass spectrum (Found/Predicted) | Potency[b] |
|---|---|---|---|
| QRKH | <5% | 19532/19532 | 2 µg/ml |
| QRRP | <5% | 19520/19520 | 1.3 µg/ml |

[a]Estimate based on SDS-PAGE.
[b]Potency is expressed as the concentration of protein required to achieve 50% maximum alkaline phosphatase induction.

TABLE 8

HHIg constructs

| Construct N-terminal domain/ Fc sequence | Clipping in basic sequence[a] | Mass spectrum Found/Predicted | Potency |
|---|---|---|---|
| Wild-type Sonic/ huIgG1 | 80% N-10 | ND[b] | ND |
| Wild-type Sonic/ muIgG1 | ND | ND | ND |
| Wild-type Sonic/ muIgG2a | ND | ND | ND |
| SRKRP Sonic/ muIgG1 | 0% | 45,533/45,533.6 | 1.3 µg/ml |
| QRRP Sonic/ muIgG1 | | | 1.8 µg/ml |
| QRRP Sonic, C24II/ muIgG1 | | | Pending |
| QRRP Sonic, C24III/ muIgG1 | | | Pending |

[a]Determined by N-terminal sequencing.
[b]Not determined

TABLE 9

Preliminary PK Studies in mice with Hedgehog Ig Fusion Proteins

| | % Remaining in Serum | | |
|---|---|---|---|
| Construct | 5 hr | 7 hr | 24 hr |
| Wild type Sonic N-terminal domain | 0.3 | 0.1 | 0 |
| Wild type Sonic/huIgG1 | ND[a] | 4.2 | 0.4 |
| Wild type Sonic/muIgG | | | |
| Exp 1 | ND | 16.4 | 5.5 |
| Exp 2 | 29 | ND | 6.0 |
| Wild type Sonic/muIgG2A | ND | 13.2 | 2.2 |
| SRKRP Sonic/muIgG1 | 23 | ND | 3.2 |

[a]Not determined.

EXAMPLE 3

Comparative Pharmacokinetics and Pharmacodynamics in Primates

Comparative studies are conducted with hedgehog fusion and native hedgehog to determine their relative stability and activity in primates. In these studies, the pharmacokinetics and pharmacodynamics of the hedgehog-fusion in primates is compared to that of native hedgehog and reasonable inferences can be extended to humans.

Animals and Methods

Study Design

This is a parallel group, repeat dose study to evaluate the comparative pharmacokinetics and pharmacodynamics of hedgehog fusion protein and nonfusion hedgehog.

Healthy primates (preferably rhesus monkeys) are used for this study. Prior to dosing, all animals will be evaluated for signs of ill health by a Lab Animal Veterinary on two occasions within 14 days prior to test article administration; one evaluation must be within 24 hours prior to the first test article administration. Only healthy animals will receive the test article. Evaluations will include a general physical examination and pre-dose blood draws for baseline clinical pathology and baseline antibody level to hedgehog-. All animals will be weighed and body temperatures will be recorded within 24 hours prior to test article administrations.

Twelve subjects are enrolled and assigned to groups of three to receive hedgehog as either a fused or a non-fused, but otherwise identical hedgehog. Administration is by either the subcutaneous (SC) or intravenous (IV) routes. Six male animals will receive test article by the IV route (3/treatment) and another 6 male animals will receive test article by the SC route (3/treatment). All animals must be naive to hedgehog treatment. Each animal will be dosed on two occasions; doses will be separated by four weeks. The dose volume will be 1.0 mL/kg.

Blood is drawn for pharmacokinetic testing at 0, 0.083, 0.25, 0.5, 1, 1.5, 2, 4, 6, 8, 12, 24, 48, 72, and 96 hours following each injection. Blood samples for measurements of the hedgehog are drawn at 0, 24, 48, 72, 96, 168, 336, 504 hours following administration of study drug.

Evaluations during the study period include clinical observations performed 30 minutes and 1 hour post-dose for signs of toxicitiy. Daily cageside observations are performed and general appearance, signs of toxicity, discomfort, and changes in behavior will be recorded. Body weights and body temperatures will be recorded at regular intervals through 21 days post-dose.

Assay Methods

Levels of hedgehog in serum are quantitated using a ELISA, as described above.

Pharmacokinetic and Statistical Methods

Rstrip™ software (MicroMath, Inc., Salt Lake City, Utah) is used to fit data to pharmacokinetic models. Geometric mean concentrations are plotted by time for each group. Since assay results are expressed in dilutions, geometric means are considered more appropriate than arithmetic means. Serum hedgehog levels are adjusted for baseline values and non-detectable serum concentrations are set to 5 U/ml, which represents one-half the lower limit of detection.

For IV infusion data, a two compartment IV infusion model is fit to the detectable serum concentrations for each subject, and the SC data are fit to a two compartment injection model.

The following pharmacokinetic parameters are calculated:
(i) observed peak concentration, $C_{max}$ (U/ml);
(ii) area under the curve from 0 to 48 hours, AUC using the trapezoidal rule;
(iii) elimination half-life;

and, from IV infusion data (if IV is employed):
(iv) distribution half-life (h);
(v) clearance (ml/h)
(vi) apparent volume of distribution, Vd (L).

WinNonlin (Version 1.0, Scientific Consulting Inc., Apex, N.C.) software is used to calculate the elimination half-lives after SC and IM injection. For hedgehog, arithmetic means by time are presented for each group. $E_{max}$, the maximum change from baseline, is calculated. $C_{max}$, AUC and $E_{max}$ are submitted to a one-way analysis of variance to compare dosing groups. $C_{max}$ and AUC are logarithmically transformed prior to analysis; geometric means are reported.

What is claimed is:

1. An isolated polypeptide having an amino acid sequence X-Y-Z, wherein

X is a polypeptide comprising the amino acid sequence of a Sonic hedgehog protein, wherein the Sonic hedgehog protein comprises:
  a) an N-terminal 20 kDa fragment of a full-length naturally-occurring Sonic hedgehog sequence, wherein a KEX2 recognition site corresponding to residues 32-36 of a human Shh protein (SEQ ID NO:15) is replaced with a sequence selected from one of SEQ ID NO:88-94 or 99-102 or
  b) an N-terminal 20 kDa fragment of a full-length naturally-occurring Sonic hedgehog sequence wherein the N-terminal cysteine is substituted with phenylalanine, isoleucine, methionine, or two isoleucine residues, and wherein a KEX2 recognition site corresponding to residues 32-36 of a human Shh protein (SEQ ID NO:15) is replaced with a sequence selected from one of SEQ ID NO:88-94 or 99-102;

Y is an optional linker moiety; and

Z is a polypeptide comprising at least a portion of a polypeptide other than hedgehog.

2. The isolated polypeptide of claim 1, wherein the KEX2 recognition site is replaced with a sequence selected from SEQ ID NO: 91, 92, or 93.

3. The isolated polypeptide of claim 1, wherein X is a hedgehog agonist that binds patched-1 with an affinity that is similar to or higher than the binding affinity of a mature naturally-occurring, hedgehog protein to patched-1.

4. The isolated polypeptide of claim 1 or 3, wherein the Sonic hedgehog protein is derivatized with a hydrophobic moiety.

5. The isolated polypeptide of claim 4, wherein Z is at least a portion of a constant region of an immunoglobulin.

6. The isolated polypeptide of claim 5, wherein said at least a portion of the constant region is derived from an immunoglobulin of the class selected from classes IgM, IgG, IgD, IgA, and IgE.

7. The isolated polypeptide of claim 6, wherein the class is IgG.

8. The isolated polypeptide of claim 5, wherein the at least a portion of the constant region comprises at least a hinge, CH2 and CH13 domains.

9. A fusion protein having an amino terminal-region consisting of the amino acid sequence of a Sonic hedgehog protein and having a carboxy terminal region comprising at least a portion of a protein other than hedgehog, wherein the Sonic hedgehog protein comprises:
  a) an N-terminal 20 kDa fragment of a full-length naturally-occurring Sonic hedgehog sequence, wherein a KEX2 recognition site corresponding to residues 32-36 of a human Shh protein (SEQ ID NO:15) is replaced with a sequence selected from one of SEQ ID NO:88-94 or 99-102 or
  b) an N-terminal 20 kDa fragment of a full-length naturally-occurring Sonic hedgehog sequence wherein the N-terminal cysteine is substituted with phenylalanine, isoleucine, methionine, or two isoleucine residues, and wherein a KEX2 recognition site corresponding to residues 32-36 of a human Shh protein (SEQ ID NO: 15) is replaced with a sequence selected from one of SEQ ID NO: 88-94 or 99-102.

10. The fusion protein of claim 9, wherein the mutated KEX2 protease recognition sequence has a sequence selected from SEQ ID NO: 91, 92, or 93.

11. The fusion protein of claim 9, wherein the Sonic hedgehog protein is derivatized.

12. The fusion protein of claim 11, wherein the derivative is selected from a hydrophobic moiety and a polyalkylene glycol polymer.

13. The fusion protein of claim 9, wherein the at least a portion of the protein other than hedgehog is at least a portion of a constant region of an immunoglobulin.

14. The fusion protein of claim 13, wherein said at least a portion of the constant region is derived from an immunoglobulin of the class selected from classes IgM, IgG, IgD, IgA, and IgE.

15. The fusion protein of claim 14, wherein, the class is IgG.

16. The fusion protein of claim 13, wherein the at least a portion of the constant region comprises at least a hinge, CH2 and CH3 domains.

17. A composition comprising the polypeptide of claim 1 or the hedgehog fusion protein of claim 9 and a pharmaceutically acceptable carrier.

18. An isolated polypeptide having the amino acid sequence X-Y-Z, wherein
X is a polypeptide having the amino acid sequence of a Sonic hedgehog protein, wherein the Sonic hedgehog protein comprises an N-terminal 20 kDa fragment of a full-length naturally-occurring Sonic hedgehog sequence wherein the N-terminal cysteine is substituted with phenylalanine, isoleucine, methionine, or two isoleucine residues, and wherein a KEX2 recognition site corresponding to residues 32-36 of a human Shh protein (SEQ ID NO:15) is replaced with a sequence selected from one of SEQ ID NO:88-94 or 99-102;
Y is an optional linker moiety; and
Z is a polypeptide comprising at least a portion of a constant region of an immunoglobulin.

19. The isolated polypeptide of claim 18, wherein X is a hedgehog agonist that binds patched-1 with an affinity that is similar to or higher than the binding affinity of a mature naturally-occurring hedgehog protein to patched-1.

20. The isolated polypeptide of claim 18 or 19, wherein the Sonic hedgehog protein is derivatized with a hydrophobic moiety.

21. The isolated polypeptide of claim 18, wherein said at least a portion of the constant region is derived from an immunoglobulin of the class selected from classes IgM, IgG, IgD, IgA, and IgE.

22. The isolated polypeptide of claim 21, wherein the class is IgG.

23. The isolated polypeptide of claim 18, wherein the at least a portion of the constant region comprises at least a hinge, CH2 and CH3 domains.

24. A fusion protein having an amino terminal region consisting of the amino acid sequence of a Sonic hedgehog protein and having a carboxy terminal region comprising at least a portion of a constant region of an immunoglobulin, wherein the Sonic hedgehog protein comprises an N-terminal 20 kDa fragment of a full-length naturally-occurring Sonic hedgehog sequence wherein the N-terminal cysteine is substituted with phenylalanine, isoleucine, methionine, or two isoleucine residues, and wherein a KEX2 recognition site corresponding to residues 32-36 of a human Shh protein (SEQ ID NO:15) is replaced with a sequence selected from one of SEQ. ID NO:88-94 or 99-102.

25. The protein of claim 24, wherein the Sonic hedgehog protein is derivatized and the derivative is selected from a hydrophobic moiety and a polyalkylene glycol polymer.

26. The protein of claim 24, wherein said at least a portion of the constant region is derived from an immunoglobulin of the class selected from classes IgM, IgG, IgD, IgA, and IgE.

27. The protein of claim 26, wherein the class is IgG.

28. The protein of claim 24, wherein the at least a portion of the constant region comprises at least a hinge, CH2 and CH3 domains.

29. A composition comprising the hedgehog fusion protein of claim 18 or 24 and a pharmaceutically acceptable carrier.

30. An isolated polypeptide having an amino acid sequence X-Y-Z, wherein X is a polypeptide comprising the amino acid sequence of a Sonic hedgehog protein, wherein the Sonic hedgehog protein comprises:
a) an N-terminal 20 kDa fragment of a full-length naturally-occurring Sonic hedgehog sequence, wherein a KEX2 recognition site corresponding to residues 32-36 of a human Shh protein (SEQ ID NO:15) is replaced with the sequence of SEQ ID NO: 92 or
b) an N-terminal 20 kDa fragment of a full-length naturally-occurring Sonic hedgehog sequence wherein the N-terminal cysteine is substituted with phenylalanine, isoleucine, methionine, or two isoleucine residues, and wherein a KEX2 recognition site corresponding to residues 32-36 of a human Shh protein (SEQ ID NO:15) is replaced with the sequence of SEQ ID NO: 92;
Y is an optional linker moiety; and
Z is a polypeptide comprising at least a portion of a polypeptide other than hedgehog.

31. The isolated polypeptide of 30, wherein X is a hedgehog agonist that binds patched-1 with an affinity that is similar to or higher than the binding affinity of a mature naturally-occurring hedgehog protein to patched-1.

32. A composition comprising the polypeptide of claim 30 and a pharmaceutically acceptable carrier.

33. A fusion protein having an amino terminal region consisting of the amino acid sequence of a Sonic hedgehog protein and having a carboxy terminal region comprising at least a portion of a protein other than hedgehog, wherein the Sonic hedgehog protein comprises:
a) an N-terminal 20 kDa fragment of a full-length naturally-occurring Sonic hedgehog sequence, wherein a KEX2 recognition site corresponding to residues 32-36 of a human Shh protein (SEQ ID NO:15) is replaced with the sequence of SEQ ID NO: 92 or
b) an N-terminal 20 kDa fragment of a full-length naturally-occurring Sonic hedgehog sequence wherein the N-terminal cysteine is substituted with phenylalanine, isoleucine, methionine, or two isoleucine residues, and wherein a KEX2 recognition site corresponding to residues 32-36 of a human Shh protein (SEQ ID NO: 15) is replaced with the sequence of SEQ ID NO: 92.

34. A composition comprising the fusion protein of claim 33 and a pharmaceutically acceptable carrier.

35. A isolated polypeptide having the amino acid sequence X-Y-Z, wherein X is a polypeptide having the amino acid sequence of a Sonic hedgehog protein, wherein the Sonic hedgehog protein comprises an N-terminal 20 kDa fragment of a full-length naturally-occurring Sonic hedgehog sequence wherein the N-terminal cysteine is substituted with phenylalanine, isoleucine, methionine, or two isoleucine residues, and wherein a KEX2 recognition site corresponding to residues 32-36 of a human Shh protein (SEQ ID NO:15) is replaced with the sequence of SEQ ID NO: 92;
Y is an optional linker moiety; and
Z is a polypeptide comprising at least a portion of a constant region of an immunoglobulin.

36. The isolated polypeptide of claim 35, wherein X is a hedgehog agonist that binds patched-1 with an affinity that is similar to or higher than the binding affinity of a mature naturally-occurring hedgehog protein to patched-1.

37. A composition comprising the polypeptide of claim 35 and a pharmaceutically acceptable carrier.

38. A fusion protein having an amino terminal region consisting of the amino acid sequence of a Sonic hedgehog protein and having a carboxy terminal region comprising at least a portion of a constant region of an immunoglobulin, wherein the Sonic hedgehog protein comprises an N-terminal 20 kDa fragment of a full-length naturally-occurring Sonic hedgehog sequence wherein the N-terminal cysteine is substituted with phenylalanine, isoleucile, methiodine, or two isoleucine residues, and wherein a KEX2 recognition site corresponding to residues 32-36 of a human Shh protein (SEQ ID NO:15) is replaced with the sequence of SEQ ID NO: 92.

39. A composition comprising the fusion protein of claim 38 and a pharmaceutically acceptable carrier.

\* \* \* \* \*

UNITED STATES PATENT AND TRADEMARK OFFICE
CERTIFICATE OF CORRECTION

PATENT NO. : 7,479,539 B1  Page 1 of 1
APPLICATION NO. : 10/129162
DATED : January 20, 2009
INVENTOR(S) : Strauch et al.

It is certified that error appears in the above-identified patent and that said Letters Patent is hereby corrected as shown below:

In claim 8, column 202, line 44, replace "CH13" with --CH3--;

In claim 38, column 206, line 4, replace "isoleucile" with --isoleucine--;

In claim 38, column 206, line 4, replace "methiodine" with --methionine--.

Signed and Sealed this

Thirty-first Day of March, 2009

JOHN DOLL
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 7,479,539 B1 | Page 1 of 1 |
| APPLICATION NO. | : 10/129162 | |
| DATED | : January 20, 2009 | |
| INVENTOR(S) | : Kathryn Strauch et al. | |

It is certified that error appears in the above-identified patent and that said Letters Patent is hereby corrected as shown below:

On the cover page,

[*] Notice: Subject to any disclaimer, the term of this patent is extended or adjusted under 35 USC 154(b) by (934) days Delete the phrase "by 934 days" and insert -- by 1,122 days --

Signed and Sealed this

Twenty-ninth Day of June, 2010

David J. Kappos
*Director of the United States Patent and Trademark Office*

SEQUENCE LISTING

```
<160> NUMBER OF SEQ ID NOS: 105

<210> SEQ ID NO 1
<211> LENGTH: 1277
<212> TYPE: DNA
<213> ORGANISM: Gallus gallus

<400> SEQUENCE: 1
atggtcgaaa tgctgctgtt gacaagaatt ctcttggtgg gcttcatctg cgctcttta      60 gtctcctctg ggctgacttg tggaccaggc aggggcattg gaaaaaggag gcaccccaaa    120
aagctgaccc cgttagccta taagcagttt attcccaatg tggcagagaa gaccctaggg    180
gccagtggaa gatatgaagg gaagatcaca agaaactccg agagatttaa agaactaacc    240
ccaaattaca accctgacat tatttttaag gatgaagaga cacgggagc tgacagactg     300 atgactcagc gctgcaagga caagctgaat gccctggcga tctcggtgat gaaccagtgg    360 cccgggggtga agctgcgggt gaccgagggc tgggacgagg atggccatca ctccgaggaa   420
tcgctgcact acgagggtcg cgccgtggac atcaccacgt cggatcggga ccgcagcaag    480
tacgaaatgc tggcccgcct cgccgtcgag gccggcttcg actgggtcta ctacgagtcc    540
aaggcgcaca tccactgctc cgtcaaagca gaaaactcag tggcagcgaa atcaggaggc    600
tgcttccctg gctcagccac agtgcacctg gagcatggag gcaccaagct ggtgaaggac    660
ctgagccctg gggaccgcgt gctggctgct gacgcggacg gccggctgct ctacagtgac    720
```

```
ttcctcacct tcctcgaccg gatggacagc tcccgaaagc tcttctacgt catcgagacg    780
cggcagcccc gggcccggct gctactgacg gcggccacc tgctctttgt ggccccccag    840
cacaaccagt cggaggccac agggtccacc agtggccagg cgctcttcgc cagcaacgtg    900
aagcctggcc aacgtgtcta tgtgctgggc gagggcgggc agcagctgct gccggcgtct    960
gtccacagcg tctcattgcg ggaggaggcg tccggagcct acgccccact caccgcccag   1020
ggcaccatcc tcatcaaccg ggtgttggcc tcctgctacg ccgtcatcga ggagcacagt   1080
tgggcccatt gggccttcgc accattccgc ttggctcagg gctgctggc cgccctctgc   1140 ccagatgggg ccatccctac tgccgccacc accaccactg gcatccattg gtactcacgg   1200
ctcctctacc gcatcggcag ctgggtgctg gatggtgacg cgctgcatcc gctgggcatg   1260
gtggcaccgg ccagctg                                                  1277

<210> SEQ ID NO 2
<211> LENGTH: 1190
<212> TYPE: DNA
<213> ORGANISM: Mus musculus

<400> SEQUENCE: 2
atggctctgc cggccagtct gttgcccctg tgctgcttgg cactcttggc actatctgcc     60
cagagctgcg ggccgggccg aggaccggtt ggccggcggc gttatgtgcg caagcaactt    120
gtgcctctgc tatacaagca gtttgtgccc agtatgcccg agcggaccct gggcgcgagt    180
gggccagcgg aggggagggt aacaaggggg tcggagcgct ccgggacct cgtacccaac    240 tacaaccccg acataatctt caaggatgag agaacagcg gcgcagaccg cctgatgaca    300
gagcgttgca aagagcgggt gaacgctcta gccatcgcgg tgatgaacat gtggcccgga    360
gtacgcctac gtgtgactga aggctgggac gaggacggcc accacgcaca ggattcactc    420
cactacgaag gccgtgcctt ggacatcacc acgtctgacc gtgaccgtaa taagtatggt    480
ttgttggcgc gcctagctgt ggaagccgga ttcgactggg tctactacga gtcccgcaac    540
cacatccacg tatcggtcaa agctgataac tcactggcgg tccgagccgg aggctgcttt    600
ccgggaaatg ccacggtgcg cttgcggagc ggcgaacgga aggggctgag ggaactacat    660
cgtggtgact gggtactggc cgctgatgca gcgggccgag tggtacccac gccagtgctg    720
ctcttcctgg accgggatct gcagcgccgc gcctcgttcg tggctgtgga gaccgagcgg    780
cctccgcgca aactgttgct cacaccctgg catctggtgt tcgctgctcg cgggccagcg    840
cctgctccag gtgactttgc accggtgttc gcgcgccgct acgtgctgg cgactcggtg    900 ctggctcccg gcggggacgc gctccagccg gcgcgcgtag cccgcgtggc gcgcgaggaa    960
gccgtgggcg tgttcgcacc gctcactgcg cacgggacgc tgctggtcaa cgacgtcctc   1020
gcctcctgct acgcggttct agagagtcac cagtgggccc accgcgcctt cgccccttg    1080 cggctgctgc acgcgctcgg ggctctgctc cctgggggtg cagtccagcc gactggcatg   1140
cattggtact ctcgcctcct ttaccgcttg gccgaggagt taatgggctg                1190

<210> SEQ ID NO 3
<211> LENGTH: 1281
<212> TYPE: DNA
<213> ORGANISM: Mus musculus

<400> SEQUENCE: 3
atgtctcccg cctggctccg gccccgactg cggttctgtc tgttcctgct gctgctgctt     60
ctggtgccgg cggcgcgggg ctgcgggccg ggccgggtgg tgggcagccg ccggaggccg    120
```

| | |
|---|---|
| cctcgcaagc tcgtgcctct tgcctacaag cagttcagcc ccaacgtgcc ggagaagacc | 180 |
| ctgggcgcca gcgggcgcta cgaaggcaag atcgcgcgca gctctgagcg cttcaaagag | 240 |
| ctcacccca actacaatcc cgacatcatc ttcaaggacg aggagaacac gggtgccgac | 300 |
| cgcctcatga cccagcgctg caaggaccgt ctgaactcac tggccatctc tgtcatgaac | 360 |
| cagtggcctg gtgtgaaact gcgggtgacc gaaggccggg atgaagatgg ccatcactca | 420 |
| gaggagtctt tacactatga gggccgcgcg gtggatatca ccacctcaga ccgtgaccga | 480 |
| aataagtatg gactgctggc gcgcttagca gtggaggccg gcttcgactg ggtgtattac | 540 |
| gagtccaagg cccacgtgca ttgctctgtc aagtctgagc attcggccgc tgccaagaca | 600 |
| ggtggctgct ttcctgccgg agcccaggtg cgcctagaga acggggagcg tgtggccctg | 660 |
| tcagctgtaa agccaggaga ccgggtgctg gccatggggg aggatgggac ccccaccttc | 720 |
| agtgatgtgc ttattttcct ggaccgcgag ccaaaccggc tgagagcttt ccaggtcatc | 780 |
| gagactcagg atcctccgcg tcggctggcg ctcacgcctg cccacctgct cttcattgcg | 840 |
| gacaatcata cagaaccagc agcccacttc cgggccacat tgccagcca tgtgcaacca | 900 |
| ggccaatatg tgctggtatc aggggtacca ggcctccagc ctgctcgggt ggcagctgtc | 960 |
| tccacccacg tggcccttgg gtcctatgct cctctcacaa ggcatgggac acttgtggtg | 1020 |
| gaggatgtgg tggcctcctg ctttgcagct gtggctgacc accatctggc tcagttggcc | 1080 |
| ttctggcccc tgcgactgtt tcccagtttg gcatgggca gctggacccc aagtgagggt | 1140 |
| gttcactcct accctcagat gctctaccgc ctggggcgtc tcttgctaga agagagcacc | 1200 |
| ttccatccac tgggcatgtc tggggcagga agctgaaggg actctaacca ctgccctcct | 1260 |
| ggaactgctg tgcgtggatc c | 1281 |

<210> SEQ ID NO 4
<211> LENGTH: 1313
<212> TYPE: DNA
<213> ORGANISM: Mus musculus

<400> SEQUENCE: 4

| | |
|---|---|
| atgctgctgc tgctggccag atgttttctg gtgatccttg cttcctcgct gctggtgtgc | 60 |
| cccgggctgg cctgtgggcc cggcaggggg tttggaaaga ggcggcaccc caaaaagctg | 120 |
| acccctttag cctacaagca gtttattccc aacgtagccg agaagaccct aggggccagc | 180 |
| ggcagatatg aagggaagat cacaagaaac tccgaacgat taaggaact caccccccaat | 240 |
| tacaaccccg acatcatatt taaggatgag gaaaacacgg gagcagaccg gctgatgact | 300 |
| cagaggtgca agacaagtt aaatgccttg gccatctctg tgatgaacca gtggcctgga | 360 |
| gtgaggctgc gagtgaccga gggctgggat gaggacggcc atcattcaga ggagtctcta | 420 |
| cactatgagg gtcgagcagt ggacatcacc acgtccgacc gggaccgcag caagtacggc | 480 |
| atgctggctc gcctggctgt ggaagcaggt ttcgactggg tctactatga atccaaagct | 540 |
| cacatccact gttctgtgaa agcagagaac tccgtggcgg ccaaatccgg cggctgtttc | 600 |
| ccgggatccg ccaccgtgca cctggagcag gcggcaccaa gctggtgaa ggacttacgt | 660 |
| cccgagacc gcgtgctggc ggctgacgac cagggccggc tgctgtacag cgacttcctc | 720 |
| accttcctgg accgcgacga aggcgccaag aaggtcttct acgtgatcga gacgctggag | 780 |
| ccgcgcgagc gcctgctgct caccgccgcg cacctgctct tcgtggcgcc gcacaacgac | 840 |
| tcggggccca cgcccgggcc aagcgcgctc tttgccagcc gcgtgcgccc cgggcagcgc | 900 |

| | |
|---|---|
| gtgtacgtgg tggctgaacg cggcggggac cgccggctgc tgcccgccgc ggtgcacagc | 960 |
| gtgacgctgc gagaggagga ggcgggcgcg tacgcgccgc tcacgcgcca cggcaccatt | 1020 |
| ctcatcaacc gggtgctcgc ctcgtgctac gctgtcatcg aggagcacag ctgggcacac | 1080 |
| cgggccttcg cgcctttccg cctggcgcac gcgctgctgg ccgcgctggc acccgcccgc | 1140 |
| acggacggcg ggggcggggg cagcatccct gcagcgcaat ctgcaacgga agcgaggggc | 1200 |
| gcggagccga ctgcgggcat ccactggtac tcgcagctgc tctaccacat ggcacctgg | 1260 |
| ctgttggaca gcgagaccat gcatcccttg ggaatggcgg tcaagtccag ctg | 1313 |

<210> SEQ ID NO 5
<211> LENGTH: 1256
<212> TYPE: DNA
<213> ORGANISM: Brachydanio rerio

<400> SEQUENCE: 5

| | |
|---|---|
| atgcggcttt tgacgagagt gctgctggtg tctcttctca ctctgtcctt ggtggtgtcc | 60 |
| ggactggcct gcggtcctgg cagaggctac ggcagaagaa gacatccgaa gaagctgaca | 120 |
| cctctcgcct acaagcagtt catacctaat gtcgcggaga agaccttagg ggccagcggc | 180 |
| agatacgagg gcaagataac gcgcaattcg gagagattta agaacttac tccaaattac | 240 |
| aatcccgaca ttatctttaa ggatgaggag aacacgggag cggacaggct catgacacag | 300 |
| agatgcaaag acaagctgaa ctcgctggcc atctctgtaa tgaaccactg gccaggggtt | 360 |
| aagctgcgtg tgacagaggg ctgggatgag acggtcacc attttgaaga atcactccac | 420 |
| tacgagggaa gagctgttga tattaccacc tctgaccgag acaagagcaa atacgggaca | 480 |
| ctgtctcgcc tagctgtgga ggctggattt gactgggtct attacgagtc caaagcccac | 540 |
| attcattgct ctgtcaaagc agaaaattcg gttgctgcga atctggggg ctgtttccca | 600 |
| ggttcggctc tggtctcgct ccaggacgga ggacagaagg ccgtgaagga cctgaacccc | 660 |
| ggagacaagg tgctggcggc agacagcgcg ggaaacctgg tgttcagcga cttcatcatg | 720 |
| ttcacagacc gagactccac gacgcgacgt gtgttttacg tcatagaaac gcaagaaccc | 780 |
| gttgaaaaga tcaccctcac cgccgctcac ctccttttg tcctcgacaa ctcaacggaa | 840 |
| gatctccaca ccatgaccgc cgcgtatgcc agcagtgtca gagccggaca aaaggtgatg | 900 |
| gttgttgatg atagcggtca gcttaaatct gtcatcgtgc agcggatata cacggaggag | 960 |
| cagcggggct cgttcgcacc agtgactgca catgggacca ttgtggtcga cagaatactg | 1020 |
| gcgtcctgtt acgccgtaat agaggaccag gggcttgcgc atttggcctt cgcgcccgcc | 1080 |
| aggctctatt attacgtgtc atcattcctg tcccccaaaa ctccagcagt cggtccaatg | 1140 |
| cgactttaca acaggagggg gtccactggt actccaggct cctgtcatca aatgggaacg | 1200 |
| tggcttttgg acagcaacat gcttcatcct ttggggatgt cagtaaactc aagctg | 1256 |

<210> SEQ ID NO 6
<211> LENGTH: 1425
<212> TYPE: DNA
<213> ORGANISM: Homo sapiens
<220> FEATURE:
<221> NAME/KEY: modified_base
<222> LOCATION: (1387...1389)
<223> OTHER INFORMATION: n=a, c, g, or t

<400> SEQUENCE: 6

| | |
|---|---|
| atgctgctgc tggcgagatg tctgctgcta gtcctcgtct cctcgctgct ggtatgctcg | 60 |
| ggactggcgt gcggaccggg caggggggttc gggaagagga ggcaccccaa aaagctgacc | 120 |

```
cctttagcct acaagcagtt tatccccaat gtggccgaga agaccctagg cgccagcgga      180
aggtatgaag ggaagatctc cagaaactcc gagcgattta aggaactcac ccccaattac      240
aaccccgaca tcatatttaa ggatgaagaa aacaccggag cggacaggct gatgactcag      300
aggtgtaagg acaagttgaa cgctttggcc atctcggtga tgaaccagtg gccaggagtg      360
aaactgcggg tgaccgaggg ctgggacgaa gatggccacc actcagagga gtctctgcac      420
tacgagggcc gcgcagtgga catcaccacg tctgaccgcg accgcagcaa gtacggcatg      480
ctggcccgcc tggcggtgga ggccggcttc gactgggtgt actacgagtc caaggcacat      540
atccactgct cggtgaaagc agagaactcg gtggcggcca atcgggagg ctgcttcccg       600 ggctcggcca cggtgcacct ggagcagggc ggcaccaagc tggtgaagga cctgagcccc      660
ggggaccgcg tgctggcggc ggacgaccag ggccggctgc tctacagcga cttcctcact      720
ttcctggacc gcgacgacgg cgccaagaag gtcttctacg tgatcgagac gcgggagccg      780
cgcgagcgcc tgctgctcac cgccgcgcac ctgctctttg tggcgccgca caacgactcg      840
gccaccgggg agcccgaggc gtcctcgggc tcggggccgc cttccggggg cgcactgggg      900
cctcgggcgc tgttcgccag ccgcgtgcgc ccgggccagc gcgtgtacgt ggtggccgag      960
cgtgacgggg accgccggct cctgcccgcc gctgtgcaca gcgtgaccct aagcgaggag      1020
gccgcgggcg cctacgcgcc gctcacgcc cagggcacca ttctcatcaa ccgggtgctg       1080
gcctcgtgct acgcggtcat cgaggagcac agctgggcgc accgggcctt cgcgcccttc      1140
cgcctggcgc acgcgctcct ggctgcactg gcgcccgcgc gcacggaccg cggcggggac      1200
agcggcggcg gggaccgcgg ggggcggcgg ggcagagtag ccctaaccgc tccaggtgct      1260
gccgacgctc cgggtgcggg ggccaccgcg ggcatccact ggtactcgca gctgctctac      1320
caaataggca cctggctcct ggacagcgag gccctgcacc cgctgggcat ggcggtcaag      1380
tccagcnnna gccgggggggc cggggagggg gcgcgggagg gggcc                    1425

<210> SEQ ID NO 7
<211> LENGTH: 1622
<212> TYPE: DNA
<213> ORGANISM: Homo sapiens

<400> SEQUENCE: 7
catcagccca ccaggagacc tcgcccgccg ctccccccggg ctccccggcc atgtctcccg      60
cccggctccg gccccgactg cacttctgcc tggtcctgtt gctgctgctg gtggtgcccg     120
cggcatgggg ctgcgggccg ggtcgggtgg tgggcagccg ccgcgaccg ccacgcaaac      180 tcgtgccgct cgcctacaag cagttcagcc ccaatgtgcc cgagaagacc ctgggcgcca     240
gcggacgcta tgaaggcaag atcgctcgca gctccgagcg cttcaaggag ctcaccccca     300
attacaatcc agacatcatc ttcaaggacg aggagaacac aggcgccgac cgcctcatga     360
cccagcgctg caaggaccgc ctgaactcgc tggctatctc ggtgatgaac cagtggcccg     420
gtgtgaagct gcgggtgacc gagggctggg acgaggacgg ccaccactca gaggagtccc     480
tgcattatga gggccgcgcg gtggacatca ccacatcaga ccgcgaccgc aataagtatg     540
gactgctggc gcgcttggca gtggaggccg gctttgactg ggtgtattac gagtcaaagg     600
cccacgtgca ttgctccgtc aagtccgagc actcggccgc agccaagacg ggcggctgct     660
tccctgccgg agcccaggta cgcctggaga gtggggcgcg tgtggccttg tcagccgtga     720
ggccgggaga ccgtgtgctg gccatggggg aggatggga ccccaccttc agcgatgtgc      780
```

```
tcatttttcct ggaccgcgag ccccacaggc tgagagcctt ccaggtcatc gagactcagg      840 acccccacg ccgcctggca ctcacacccg ctcacctgct ctttacggct gacaatcaca        900
cggagccggc agcccgcttc cgggccacat ttgccagcca cgtgcagcct ggccagtacg       960
tgctggtggc tggggtgcca ggcctgcagc ctgcccgcgt ggcagctgtc tctacacacg      1020
tggccctcgg ggcctacgcc ccgctcacaa agcatgggac actggtggtg gaggatgtgg      1080
tggcatcctg cttcgcggcc gtggctgacc accacctggc tcagttggcc ttctggcccc      1140
tgagactctt tcacagcttg catgggca gctggacccc ggggagggt gtgcattggt         1200 acccccagct gctctaccgc ctggggcgtc tcctgctaga agagggcagc ttccacccac      1260
tgggcatgtc cggggcaggg agctgaaagg actccaccgc tgccctcctg gaactgctgt      1320
actgggtcca gaagcctctc agccaggagg gagctggccc tggaagggac ctgagctggg      1380
ggacactggc tcctgccatc tcctctgcca tgaagataca ccattgagac ttgactgggc      1440
aacaccagcg tcccccaccc cgtcgtggt gtagtcatag agctgcaagc tgagctggcg       1500
aggggatggt tgttgacccc tctctcctag agaccttgag gctggcacgg cgactcccaa      1560
ctcagcctgc tctcactacg agttttcata ctctgcctcc cccattggga gggcccattc      1620
cc                                                                    1622

<210> SEQ ID NO 8
<211> LENGTH: 1191
<212> TYPE: DNA
<213> ORGANISM: Homo sapiens

<400> SEQUENCE: 8
atggctctcc tgaccaatct actgcccttg tgctgcttgg cacttctggc gctgccagcc       60
cagagctgcg ggccgggccg ggggccggtt ggccggcgcc gctatgcgcg caagcagctc      120
gtgccgctac tctacaagca atttgtgccc ggcgtgccag agcggaccct gggcgccagt      180
gggccagcgg aggggagggt ggcaaggggc tccgagcgct tccgggacct cgtgcccaac      240
tacaaccccg acatcatctt caaggatgag gagaacagtg gagccgaccg cctgatgacc      300
gagcgttgca aggagagggt gaacgctttg gccattgccg tgatgaacat gtggcccgga      360
gtgcgcctac gagtgactga gggctgggac gaggacggcc accacgctca ggattcactc      420
cactacgaag ccgtgctttt ggacatcact acgtctgacc gcgaccgcaa caagtatggg      480
ttgctggcgc gcctcgcagt ggaagccggc ttcgactggg tctactacga gtcccgcaac      540
cacgtccacg tgtcggtcaa agctgataac tcactggcgg tccgggcggg cggctgcttt      600
ccgggaaatg caactgtgcg cctgtggagc ggcgagcgga aagggctgcg ggaactgcac      660
cgcggagact gggttttggc ggccgatgcg tcaggccggg tggtgcccac gccggtgctg      720
ctcttcctgg accgggactt gcagcgccgg gcttcatttg tggctgtgga gaccgagtgg      780
cctccacgca aactgttgct cacgcccctgg cacctggtgt ttgccgctcg agggccggcg      840
cccgcgccag gcgactttgc accggtgttc gcgcgccggc tacgcgctgg ggactcggtg      900
ctggcgcccg gcggggatgc gcttcggcca gcgcgcgtgg cccgtgtggc gcgggaggaa      960
gccgtgggcg tgttcgcgcc gctcaccgcg cacgggacgc tgctggtgaa cgatgtcctg     1020
gcctcttgct acgcggttct ggagagtcac cagtgggcgc accgcgcttt tgccccttg     1080 agactgctgc acgcgctagg ggcgctgctc cccggcgggg ccgtccagcc gactggcatg     1140
cattggtact ctcggctcct ctaccgctta gcggaggagc tactgggctg a              1191
```

<210> SEQ ID NO 9
<211> LENGTH: 1251
<212> TYPE: DNA
<213> ORGANISM: Brachydanio rerio

<400> SEQUENCE: 9

```
atggacgtaa ggctgcatct gaagcaattt gctttactgt gttttatcag cttgcttctg     60
acgccttgtg gattagcctg tggtcctggt agaggttatg gaaaacgaag acacccaaag    120
aaattaaccc cgttggctta caagcaattc atccccaacg ttgctgagaa aacgcttgga    180
gccagcggca atacgaagg caaaatcaca aggaattcag agagatttaa agagctgatt    240
ccgaattata atcccgatat catctttaag gacgaggaaa acacaaacgc tgacaggctg    300
atgaccaagc gctgtaagga caagttaaat cgttggcca tatccgtcat gaaccactgg    360
cccggcgtga aactgcgcgt cactgaaggc tgggatgagg atggtcacca tttagaagaa    420
tctttgcact atgagggacg ggcagtggac atcactacct cagacaggga taaaagcaag    480
tatgggatgc tatccaggct tgcagtggag gcaggattcg actgggtcta ttatgaatct    540
aaagcccaca tacactgctc tgtcaaagca gaaaattcag tggctgctaa atcaggagga    600
tgttttcctg ggtctgggac ggtgacactt ggtgatggga cgaggaaacc catcaaagat    660
cttaaagtgg gcgaccgggt tttggctgca gacgagaagg gaaatgtctt aataagcgac    720
tttattatgt ttatagacca cgatccgaca acgagaaggc aattcatcgt catcgagacg    780
tcagaacctt tcaccaagct caccctcact gccgcgcacc tagttttcgt tggaaactct    840
tcagcagctt cgggtataac agcaacattt gccagcaacg tgaagcctgg agatacagtt    900
ttagtgtggg aagacacatg cgagagcctc aagagcgtta cagtgaaaag gatttacact    960
gaggagcacg agggctcttt tgcgccagtc accgcgcacg gaaccataat agtggatcag   1020
gtgttggcat cgtgctacgc ggtcattgag aaccacaaat gggcacattg gcttttgcg   1080
ccggtcaggt tgtgtcacaa gctgatgacg tggctttttc cggctcgtga atcaaacgtc   1140
aattttcagg aggatggtat ccactggtac tcaaatatgc tgtttcacat cggctcttgg   1200
ctgctggaca gagactcttt ccatccactc gggattttac acttaagttg a            1251
```

<210> SEQ ID NO 10
<211> LENGTH: 425
<212> TYPE: PRT
<213> ORGANISM: Gallus gallus

<400> SEQUENCE: 10

```
Met Val Glu Met Leu Leu Leu Thr Arg Ile Leu Val Gly Phe Ile
 1               5                  10                  15

Cys Ala Leu Leu Val Ser Ser Gly Leu Thr Cys Gly Pro Gly Arg Gly
            20                  25                  30

Ile Gly Lys Arg Arg His Pro Lys Lys Leu Thr Pro Leu Ala Tyr Lys
        35                  40                  45

Gln Phe Ile Pro Asn Val Ala Glu Lys Thr Leu Gly Ala Ser Gly Arg
    50                  55                  60

Tyr Glu Gly Lys Ile Thr Arg Asn Ser Glu Arg Phe Lys Glu Leu Thr
65                  70                  75                  80

Pro Asn Tyr Asn Pro Asp Ile Ile Phe Lys Asp Glu Glu Asn Thr Gly
                85                  90                  95

Ala Asp Arg Leu Met Thr Gln Arg Cys Lys Asp Lys Leu Asn Ala Leu
            100                 105                 110

Ala Ile Ser Val Met Asn Gln Trp Pro Gly Val Lys Leu Arg Val Thr
```

```
              115                 120                 125
Glu Gly Trp Asp Glu Asp Gly His His Ser Glu Glu Ser Leu His Tyr
            130                 135                 140

Glu Gly Arg Ala Val Asp Ile Thr Thr Ser Asp Arg Asp Arg Ser Lys
145                 150                 155                 160

Tyr Gly Met Leu Ala Arg Leu Ala Val Glu Ala Gly Phe Asp Trp Val
                165                 170                 175

Tyr Tyr Glu Ser Lys Ala His Ile His Cys Ser Val Lys Ala Glu Asn
            180                 185                 190

Ser Val Ala Ala Lys Ser Gly Gly Cys Phe Pro Gly Ser Ala Thr Val
                195                 200                 205

His Leu Glu His Gly Gly Thr Lys Leu Val Lys Asp Leu Ser Pro Gly
            210                 215                 220

Asp Arg Val Leu Ala Ala Asp Ala Asp Gly Arg Leu Leu Tyr Ser Asp
225                 230                 235                 240

Phe Leu Thr Phe Leu Asp Arg Met Asp Ser Ser Arg Lys Leu Phe Tyr
                245                 250                 255

Val Ile Glu Thr Arg Gln Pro Arg Ala Arg Leu Leu Leu Thr Ala Ala
                260                 265                 270

His Leu Leu Phe Val Ala Pro Gln His Asn Gln Ser Glu Ala Thr Gly
            275                 280                 285

Ser Thr Ser Gly Gln Ala Leu Phe Ala Ser Asn Val Lys Pro Gly Gln
            290                 295                 300

Arg Val Tyr Val Leu Gly Glu Gly Gly Gln Gln Leu Leu Pro Ala Ser
305                 310                 315                 320

Val His Ser Val Ser Leu Arg Glu Glu Ala Ser Gly Ala Tyr Ala Pro
                325                 330                 335

Leu Thr Ala Gln Gly Thr Ile Leu Ile Asn Arg Val Leu Ala Ser Cys
            340                 345                 350

Tyr Ala Val Ile Glu Glu His Ser Trp Ala His Trp Ala Phe Ala Pro
            355                 360                 365

Phe Arg Leu Ala Gln Gly Leu Leu Ala Ala Leu Cys Pro Asp Gly Ala
            370                 375                 380

Ile Pro Thr Ala Ala Thr Thr Thr Gly Ile His Trp Tyr Ser Arg
385                 390                 395                 400

Leu Leu Tyr Arg Ile Gly Ser Trp Val Leu Asp Gly Asp Ala Leu His
                405                 410                 415

Pro Leu Gly Met Val Ala Pro Ala Ser
            420                 425

<210> SEQ ID NO 11
<211> LENGTH: 396
<212> TYPE: PRT
<213> ORGANISM: Mus musculus

<400> SEQUENCE: 11

Met Ala Leu Pro Ala Ser Leu Leu Pro Leu Cys Cys Leu Ala Leu Leu
  1               5                  10                  15

Ala Leu Ser Ala Gln Ser Cys Gly Pro Gly Arg Gly Pro Val Gly Arg
                 20                  25                  30

Arg Arg Tyr Val Arg Lys Gln Leu Val Pro Leu Leu Tyr Lys Gln Phe
             35                  40                  45

Val Pro Ser Met Pro Glu Arg Thr Leu Gly Ala Ser Gly Pro Ala Glu
         50                  55                  60
```

```
Gly Arg Val Thr Arg Gly Ser Glu Arg Phe Arg Asp Leu Val Pro Asn
 65                  70                  75                  80

Tyr Asn Pro Asp Ile Ile Phe Lys Asp Glu Asn Ser Gly Ala Asp
             85                  90                  95

Arg Leu Met Thr Glu Arg Cys Lys Glu Arg Val Asn Ala Leu Ala Ile
            100                 105                 110

Ala Val Met Asn Met Trp Pro Gly Val Arg Leu Arg Val Thr Glu Gly
        115                 120                 125

Trp Asp Glu Asp Gly His His Ala Gln Asp Ser Leu His Tyr Glu Gly
    130                 135                 140

Arg Ala Leu Asp Ile Thr Thr Ser Asp Arg Asp Arg Asn Lys Tyr Gly
145                 150                 155                 160

Leu Leu Ala Arg Leu Ala Val Glu Ala Gly Phe Asp Trp Val Tyr Tyr
                165                 170                 175

Glu Ser Arg Asn His Ile His Val Ser Val Lys Ala Asp Asn Ser Leu
            180                 185                 190

Ala Val Arg Ala Gly Gly Cys Phe Pro Gly Asn Ala Thr Val Arg Leu
        195                 200                 205

Arg Ser Gly Glu Arg Lys Gly Leu Arg Glu Leu His Arg Gly Asp Trp
    210                 215                 220

Val Leu Ala Ala Asp Ala Ala Gly Arg Val Val Pro Thr Pro Val Leu
225                 230                 235                 240

Leu Phe Leu Asp Arg Asp Leu Gln Arg Ala Ser Phe Val Ala Val
                245                 250                 255

Glu Thr Glu Arg Pro Pro Arg Lys Leu Leu Thr Pro Trp His Leu
            260                 265                 270

Val Phe Ala Ala Arg Gly Pro Ala Pro Ala Pro Gly Asp Phe Ala Pro
        275                 280                 285

Val Phe Ala Arg Arg Leu Arg Ala Gly Asp Ser Val Leu Ala Pro Gly
        290                 295                 300

Gly Asp Ala Leu Gln Pro Ala Arg Val Ala Arg Val Ala Arg Glu Glu
305                 310                 315                 320

Ala Val Gly Val Phe Ala Pro Leu Thr Ala His Gly Thr Leu Leu Val
                325                 330                 335

Asn Asp Val Leu Ala Ser Cys Tyr Ala Val Leu Glu Ser His Gln Trp
            340                 345                 350

Ala His Arg Ala Phe Ala Pro Leu Arg Leu Leu His Ala Leu Gly Ala
        355                 360                 365

Leu Leu Pro Gly Gly Ala Val Gln Pro Thr Gly Met His Trp Tyr Ser
    370                 375                 380

Arg Leu Leu Tyr Arg Leu Ala Glu Glu Leu Met Gly
385                 390                 395

<210> SEQ ID NO 12
<211> LENGTH: 411
<212> TYPE: PRT
<213> ORGANISM: Mus musculus

<400> SEQUENCE: 12

Met Ser Pro Ala Trp Leu Arg Pro Arg Leu Arg Phe Cys Leu Phe Leu
  1               5                  10                  15

Leu Leu Leu Leu Leu Val Pro Ala Ala Arg Gly Cys Gly Pro Gly Arg
                 20                  25                  30

Val Val Gly Ser Arg Arg Arg Pro Pro Arg Lys Leu Val Pro Leu Ala
             35                  40                  45
```

```
Tyr Lys Gln Phe Ser Pro Asn Val Pro Glu Lys Thr Leu Gly Ala Ser
         50                  55                  60

Gly Arg Tyr Glu Gly Lys Ile Ala Arg Ser Ser Glu Arg Phe Lys Glu
 65                  70                  75                  80

Leu Thr Pro Asn Tyr Asn Pro Asp Ile Ile Phe Lys Asp Glu Glu Asn
                 85                  90                  95

Thr Gly Ala Asp Arg Leu Met Thr Gln Arg Cys Lys Asp Arg Leu Asn
            100                 105                 110

Ser Leu Ala Ile Ser Val Met Asn Gln Trp Pro Gly Val Lys Leu Arg
        115                 120                 125

Val Thr Glu Gly Arg Asp Glu Asp Gly His His Ser Glu Glu Ser Leu
130                 135                 140

His Tyr Glu Gly Arg Ala Val Asp Ile Thr Thr Ser Asp Arg Asp Arg
145                 150                 155                 160

Asn Lys Tyr Gly Leu Leu Ala Arg Leu Ala Val Glu Ala Gly Phe Asp
                165                 170                 175

Trp Val Tyr Tyr Glu Ser Lys Ala His Val His Cys Ser Val Lys Ser
            180                 185                 190

Glu His Ser Ala Ala Lys Thr Gly Gly Cys Phe Pro Ala Gly Ala
        195                 200                 205

Gln Val Arg Leu Glu Asn Gly Glu Arg Val Ala Leu Ser Ala Val Lys
    210                 215                 220

Pro Gly Asp Arg Val Leu Ala Met Gly Glu Asp Gly Thr Pro Thr Phe
225                 230                 235                 240

Ser Asp Val Leu Ile Phe Leu Asp Arg Glu Pro Asn Arg Leu Arg Ala
                245                 250                 255

Phe Gln Val Ile Glu Thr Gln Asp Pro Pro Arg Arg Leu Ala Leu Thr
            260                 265                 270

Pro Ala His Leu Leu Phe Ile Ala Asp Asn His Thr Glu Pro Ala Ala
        275                 280                 285

His Phe Arg Ala Thr Phe Ala Ser His Val Gln Pro Gly Gln Tyr Val
290                 295                 300

Leu Val Ser Gly Val Pro Gly Leu Gln Pro Ala Arg Val Ala Ala Val
305                 310                 315                 320

Ser Thr His Val Ala Leu Gly Ser Tyr Ala Pro Leu Thr Arg His Gly
                325                 330                 335

Thr Leu Val Val Glu Asp Val Val Ala Ser Cys Phe Ala Ala Val Ala
            340                 345                 350

Asp His His Leu Ala Gln Leu Ala Phe Trp Pro Leu Arg Leu Phe Pro
        355                 360                 365

Ser Leu Ala Trp Gly Ser Trp Thr Pro Ser Glu Gly Val His Ser Tyr
370                 375                 380

Pro Gln Met Leu Tyr Arg Leu Gly Arg Leu Leu Glu Glu Ser Thr
385                 390                 395                 400

Phe His Pro Leu Gly Met Ser Gly Ala Gly Ser
                405                 410

<210> SEQ ID NO 13
<211> LENGTH: 437
<212> TYPE: PRT
<213> ORGANISM: Mus musculus

<400> SEQUENCE: 13

Met Leu Leu Leu Leu Ala Arg Cys Phe Leu Val Ile Leu Ala Ser Ser
```

-continued

```
  1               5               10              15
Leu Leu Val Cys Pro Gly Leu Ala Cys Gly Pro Gly Arg Gly Phe Gly
                20              25              30
Lys Arg Arg His Pro Lys Lys Leu Thr Pro Leu Ala Tyr Lys Gln Phe
            35              40              45
Ile Pro Asn Val Ala Glu Lys Thr Leu Gly Ala Ser Gly Arg Tyr Glu
        50              55              60
Gly Lys Ile Thr Arg Asn Ser Glu Arg Phe Lys Glu Leu Thr Pro Asn
65              70              75              80
Tyr Asn Pro Asp Ile Ile Phe Lys Asp Glu Glu Asn Thr Gly Ala Asp
                85              90              95
Arg Leu Met Thr Gln Arg Cys Lys Asp Lys Leu Asn Ala Leu Ala Ile
            100             105             110
Ser Val Met Asn Gln Trp Pro Gly Val Arg Leu Arg Val Thr Glu Gly
        115             120             125
Trp Asp Glu Asp Gly His His Ser Glu Glu Ser Leu His Tyr Glu Gly
        130             135             140
Arg Ala Val Asp Ile Thr Thr Ser Asp Arg Asp Arg Ser Lys Tyr Gly
145             150             155             160
Met Leu Ala Arg Leu Ala Val Glu Ala Gly Phe Asp Trp Val Tyr Tyr
            165             170             175
Glu Ser Lys Ala His Ile His Cys Ser Val Lys Ala Glu Asn Ser Val
            180             185             190
Ala Ala Lys Ser Gly Gly Cys Phe Pro Gly Ser Ala Thr Val His Leu
            195             200             205
Glu Gln Gly Gly Thr Lys Leu Val Lys Asp Leu Arg Pro Gly Asp Arg
        210             215             220
Val Leu Ala Ala Asp Asp Gln Gly Arg Leu Leu Tyr Ser Asp Phe Leu
225             230             235             240
Thr Phe Leu Asp Arg Asp Glu Gly Ala Lys Lys Val Phe Tyr Val Ile
                245             250             255
Glu Thr Leu Glu Pro Arg Glu Arg Leu Leu Leu Thr Ala Ala His Leu
            260             265             270
Leu Phe Val Ala Pro His Asn Asp Ser Gly Pro Thr Pro Gly Pro Ser
        275             280             285
Ala Leu Phe Ala Ser Arg Val Arg Pro Gly Gln Arg Val Tyr Val Val
        290             295             300
Ala Glu Arg Gly Gly Asp Arg Arg Leu Leu Pro Ala Ala Val His Ser
305             310             315             320
Val Thr Leu Arg Glu Glu Glu Ala Gly Ala Tyr Ala Pro Leu Thr Ala
                325             330             335
His Gly Thr Ile Leu Ile Asn Arg Val Leu Ala Ser Cys Tyr Ala Val
            340             345             350
Ile Glu Glu His Ser Trp Ala His Arg Ala Phe Ala Pro Phe Arg Leu
            355             360             365
Ala His Ala Leu Leu Ala Ala Leu Ala Pro Ala Arg Thr Asp Gly Gly
        370             375             380
Gly Gly Gly Ser Ile Pro Ala Ala Gln Ser Ala Thr Glu Ala Arg Gly
385             390             395             400
Ala Glu Pro Thr Ala Gly Ile His Trp Tyr Ser Gln Leu Leu Tyr His
                405             410             415
Ile Gly Thr Trp Leu Leu Asp Ser Glu Thr Met His Pro Leu Gly Met
            420             425             430
```

```
Ala Val Lys Ser Ser
        435

<210> SEQ ID NO 14
<211> LENGTH: 418
<212> TYPE: PRT
<213> ORGANISM: Brachydanio rerio

<400> SEQUENCE: 14

Met Arg Leu Leu Thr Arg Val Leu Val Ser Leu Leu Thr Leu Ser
 1               5                  10                  15

Leu Val Val Ser Gly Leu Ala Cys Gly Pro Gly Arg Gly Tyr Gly
                 20                  25                  30

Arg Arg His Pro Lys Lys Leu Thr Pro Leu Ala Tyr Lys Gln Phe Ile
             35                  40                  45

Pro Asn Val Ala Glu Lys Thr Leu Gly Ala Ser Gly Arg Tyr Glu Gly
     50                  55                  60

Lys Ile Thr Arg Asn Ser Glu Arg Phe Lys Glu Leu Thr Pro Asn Tyr
 65              70                  75                  80

Asn Pro Asp Ile Ile Phe Lys Asp Glu Glu Asn Thr Gly Ala Asp Arg
                 85                  90                  95

Leu Met Thr Gln Arg Cys Lys Asp Lys Leu Asn Ser Leu Ala Ile Ser
                100                 105                 110

Val Met Asn His Trp Pro Gly Val Lys Leu Arg Val Thr Glu Gly Trp
                115                 120                 125

Asp Glu Asp Gly His His Phe Glu Glu Ser Leu His Tyr Glu Gly Arg
    130                 135                 140

Ala Val Asp Ile Thr Thr Ser Asp Arg Asp Lys Ser Lys Tyr Gly Thr
145                 150                 155                 160

Leu Ser Arg Leu Ala Val Glu Ala Gly Phe Asp Trp Val Tyr Tyr Glu
                165                 170                 175

Ser Lys Ala His Ile His Cys Ser Val Lys Ala Glu Asn Ser Val Ala
                180                 185                 190

Ala Lys Ser Gly Gly Cys Phe Pro Gly Ser Ala Leu Val Ser Leu Gln
                195                 200                 205

Asp Gly Gly Gln Lys Ala Val Lys Asp Leu Asn Pro Gly Asp Lys Val
    210                 215                 220

Leu Ala Ala Asp Ser Ala Gly Asn Leu Val Phe Ser Asp Phe Ile Met
225                 230                 235                 240

Phe Thr Asp Arg Asp Ser Thr Thr Arg Arg Val Phe Tyr Val Ile Glu
                245                 250                 255

Thr Gln Glu Pro Val Glu Lys Ile Thr Leu Thr Ala Ala His Leu Leu
                260                 265                 270

Phe Val Leu Asp Asn Ser Thr Glu Asp Leu His Thr Met Thr Ala Ala
                275                 280                 285

Tyr Ala Ser Ser Val Arg Ala Gly Gln Lys Val Met Val Val Asp Asp
    290                 295                 300

Ser Gly Gln Leu Lys Ser Val Ile Val Gln Arg Ile Tyr Thr Glu Glu
305                 310                 315                 320

Gln Arg Gly Ser Phe Ala Pro Val Thr Ala His Gly Thr Ile Val Val
                325                 330                 335

Asp Arg Ile Leu Ala Ser Cys Tyr Ala Val Ile Glu Asp Gln Gly Leu
                340                 345                 350

Ala His Leu Ala Phe Ala Pro Ala Arg Leu Tyr Tyr Tyr Val Ser Ser
```

-continued

```
                355                 360                 365
Phe Leu Ser Pro Lys Thr Pro Ala Val Gly Pro Met Arg Leu Tyr Asn
            370                 375                 380

Arg Arg Gly Ser Thr Gly Thr Pro Gly Ser Cys His Gln Met Gly Thr
385                 390                 395                 400

Trp Leu Leu Asp Ser Asn Met Leu His Pro Leu Gly Met Ser Val Asn
                405                 410                 415

Ser Ser

<210> SEQ ID NO 15
<211> LENGTH: 475
<212> TYPE: PRT
<213> ORGANISM: Homo sapiens
<220> FEATURE:
<221> NAME/KEY: SITE
<222> LOCATION: (463)
<223> OTHER INFORMATION: Xaa=unknown amino acid residue

<400> SEQUENCE: 15

Met Leu Leu Leu Ala Arg Cys Leu Leu Leu Val Leu Val Ser Ser Leu
1               5                   10                  15

Leu Val Cys Ser Gly Leu Ala Cys Gly Pro Gly Arg Gly Phe Gly Lys
                20                  25                  30

Arg Arg His Pro Lys Lys Leu Thr Pro Leu Ala Tyr Lys Gln Phe Ile
            35                  40                  45

Pro Asn Val Ala Glu Lys Thr Leu Gly Ala Ser Gly Arg Tyr Glu Gly
        50                  55                  60

Lys Ile Ser Arg Asn Ser Glu Arg Phe Lys Glu Leu Thr Pro Asn Tyr
65                  70                  75                  80

Asn Pro Asp Ile Ile Phe Lys Asp Glu Glu Asn Thr Gly Ala Asp Arg
                85                  90                  95

Leu Met Thr Gln Arg Cys Lys Asp Lys Leu Asn Ala Leu Ala Ile Ser
            100                 105                 110

Val Met Asn Gln Trp Pro Gly Val Lys Leu Arg Val Thr Glu Gly Trp
        115                 120                 125

Asp Glu Asp Gly His His Ser Glu Glu Ser Leu His Tyr Glu Gly Arg
    130                 135                 140

Ala Val Asp Ile Thr Thr Ser Asp Arg Asp Arg Ser Lys Tyr Gly Met
145                 150                 155                 160

Leu Ala Arg Leu Ala Val Glu Ala Gly Phe Asp Trp Val Tyr Tyr Glu
                165                 170                 175

Ser Lys Ala His Ile His Cys Ser Val Lys Ala Glu Asn Ser Val Ala
            180                 185                 190

Ala Lys Ser Gly Gly Cys Phe Pro Gly Ser Ala Thr Val His Leu Glu
        195                 200                 205

Gln Gly Gly Thr Lys Leu Val Lys Asp Leu Ser Pro Gly Asp Arg Val
    210                 215                 220

Leu Ala Ala Asp Asp Gln Gly Arg Leu Leu Tyr Ser Asp Phe Leu Thr
225                 230                 235                 240

Phe Leu Asp Arg Asp Asp Gly Ala Lys Lys Val Phe Tyr Val Ile Glu
                245                 250                 255

Thr Arg Glu Pro Arg Glu Arg Leu Leu Leu Thr Ala Ala His Leu Leu
            260                 265                 270

Phe Val Ala Pro His Asn Asp Ser Ala Thr Gly Glu Pro Glu Ala Ser
        275                 280                 285
```

Ser Gly Ser Gly Pro Ser Gly Gly Ala Leu Gly Pro Arg Ala Leu
290                 295                 300

Phe Ala Ser Arg Val Arg Pro Gly Gln Arg Val Tyr Val Ala Glu
305                 310                 315                 320

Arg Asp Gly Asp Arg Arg Leu Leu Pro Ala Ala Val His Ser Val Thr
            325                 330                 335

Leu Ser Glu Glu Ala Ala Gly Ala Tyr Ala Pro Leu Thr Ala Gln Gly
            340                 345                 350

Thr Ile Leu Ile Asn Arg Val Leu Ala Ser Cys Tyr Ala Val Ile Glu
            355                 360                 365

Glu His Ser Trp Ala His Arg Ala Phe Ala Pro Phe Arg Leu Ala His
370                 375                 380

Ala Leu Leu Ala Ala Leu Ala Pro Ala Arg Thr Asp Arg Gly Gly Asp
385                 390                 395                 400

Ser Gly Gly Gly Asp Arg Gly Gly Gly Gly Arg Val Ala Leu Thr
            405                 410                 415

Ala Pro Gly Ala Ala Asp Ala Pro Gly Ala Gly Ala Thr Ala Gly Ile
            420                 425                 430

His Trp Tyr Ser Gln Leu Leu Tyr Gln Ile Gly Thr Trp Leu Leu Asp
            435                 440                 445

Ser Glu Ala Leu His Pro Leu Gly Met Ala Val Lys Ser Ser Xaa Ser
450                 455                 460

Arg Gly Ala Gly Gly Gly Ala Arg Glu Gly Ala
465                 470                 475

<210> SEQ ID NO 16
<211> LENGTH: 411
<212> TYPE: PRT
<213> ORGANISM: Homo sapiens

<400> SEQUENCE: 16

Met Ser Pro Ala Arg Leu Arg Pro Arg Leu His Phe Cys Leu Val Leu
1               5                   10                  15

Leu Leu Leu Leu Val Val Pro Ala Ala Trp Gly Cys Gly Pro Gly Arg
                20                  25                  30

Val Val Gly Ser Arg Arg Arg Pro Pro Arg Lys Leu Val Pro Leu Ala
            35                  40                  45

Tyr Lys Gln Phe Ser Pro Asn Val Pro Glu Lys Thr Leu Gly Ala Ser
        50                  55                  60

Gly Arg Tyr Glu Gly Lys Ile Ala Arg Ser Ser Glu Arg Phe Lys Glu
65                  70                  75                  80

Leu Thr Pro Asn Tyr Asn Pro Asp Ile Ile Phe Lys Asp Glu Glu Asn
                85                  90                  95

Thr Gly Ala Asp Arg Leu Met Thr Gln Arg Cys Lys Asp Arg Leu Asn
            100                 105                 110

Ser Leu Ala Ile Ser Val Met Asn Gln Trp Pro Gly Val Lys Leu Arg
        115                 120                 125

Val Thr Glu Gly Trp Asp Glu Asp Gly His His Ser Glu Glu Ser Leu
130                 135                 140

His Tyr Glu Gly Arg Ala Val Asp Ile Thr Thr Ser Asp Arg Asp Arg
145                 150                 155                 160

Asn Lys Tyr Gly Leu Leu Ala Arg Leu Ala Val Glu Ala Gly Phe Asp
                165                 170                 175

Trp Val Tyr Tyr Glu Ser Lys Ala His Val His Cys Ser Val Lys Ser
            180                 185                 190

-continued

Glu His Ser Ala Ala Ala Lys Thr Gly Gly Cys Phe Pro Ala Gly Ala
            195                 200                 205

Gln Val Arg Leu Glu Ser Gly Ala Arg Val Ala Leu Ser Ala Val Arg
    210                 215                 220

Pro Gly Asp Arg Val Leu Ala Met Gly Glu Asp Gly Ser Pro Thr Phe
225                 230                 235                 240

Ser Asp Val Leu Ile Phe Leu Asp Arg Glu Pro His Arg Leu Arg Ala
                245                 250                 255

Phe Gln Val Ile Glu Thr Gln Asp Pro Pro Arg Arg Leu Ala Leu Thr
            260                 265                 270

Pro Ala His Leu Leu Phe Thr Ala Asp Asn His Thr Glu Pro Ala Ala
            275                 280                 285

Arg Phe Arg Ala Thr Phe Ala Ser His Val Gln Pro Gly Gln Tyr Val
        290                 295                 300

Leu Val Ala Gly Val Pro Gly Leu Gln Pro Ala Arg Val Ala Ala Val
305                 310                 315                 320

Ser Thr His Val Ala Leu Gly Ala Tyr Ala Pro Leu Thr Lys His Gly
                325                 330                 335

Thr Leu Val Val Glu Asp Val Val Ala Ser Cys Phe Ala Ala Val Ala
            340                 345                 350

Asp His His Leu Ala Gln Leu Ala Phe Trp Pro Leu Arg Leu Phe His
        355                 360                 365

Ser Leu Ala Trp Gly Ser Trp Thr Pro Gly Glu Gly Val His Trp Tyr
    370                 375                 380

Pro Gln Leu Leu Tyr Arg Leu Gly Arg Leu Leu Glu Glu Gly Ser
385                 390                 395                 400

Phe His Pro Leu Gly Met Ser Gly Ala Gly Ser
                405                 410

<210> SEQ ID NO 17
<211> LENGTH: 396
<212> TYPE: PRT
<213> ORGANISM: Homo sapiens

<400> SEQUENCE: 17

Met Ala Leu Leu Thr Asn Leu Leu Pro Leu Cys Cys Leu Ala Leu Leu
  1               5                  10                  15

Ala Leu Pro Ala Gln Ser Cys Gly Pro Gly Arg Gly Pro Val Gly Arg
                 20                  25                  30

Arg Arg Tyr Ala Arg Lys Gln Leu Val Pro Leu Leu Tyr Lys Gln Phe
             35                  40                  45

Val Pro Gly Val Pro Glu Arg Thr Leu Gly Ala Ser Gly Pro Ala Glu
         50                  55                  60

Gly Arg Val Ala Arg Gly Ser Glu Arg Phe Arg Asp Leu Val Pro Asn
 65                  70                  75                  80

Tyr Asn Pro Asp Ile Ile Phe Lys Asp Glu Glu Asn Ser Gly Ala Asp
                 85                  90                  95

Arg Leu Met Thr Glu Arg Cys Lys Glu Arg Val Asn Ala Leu Ala Ile
                100                 105                 110

Ala Val Met Asn Met Trp Pro Gly Val Arg Leu Arg Val Thr Glu Gly
            115                 120                 125

Trp Asp Glu Asp Gly His His Ala Gln Asp Ser Leu His Tyr Glu Gly
        130                 135                 140

Arg Ala Leu Asp Ile Thr Thr Ser Asp Arg Asp Arg Asn Lys Tyr Gly

```
                145                 150                 155                 160
Leu Leu Ala Arg Leu Ala Val Glu Ala Gly Phe Asp Trp Val Tyr Tyr
                165                 170                 175
Glu Ser Arg Asn His Val His Val Ser Val Lys Ala Asp Asn Ser Leu
                180                 185                 190
Ala Val Arg Ala Gly Gly Cys Phe Pro Gly Asn Ala Thr Val Arg Leu
                195                 200                 205
Trp Ser Gly Glu Arg Lys Gly Leu Arg Glu Leu His Arg Gly Asp Trp
                210                 215                 220
Val Leu Ala Ala Asp Ala Ser Gly Arg Val Val Pro Thr Pro Val Leu
225                 230                 235                 240
Leu Phe Leu Asp Arg Asp Leu Gln Arg Ala Ser Phe Val Ala Val
                245                 250                 255
Glu Thr Glu Trp Pro Pro Arg Lys Leu Leu Leu Thr Pro Trp His Leu
                260                 265                 270
Val Phe Ala Ala Arg Gly Pro Ala Pro Ala Pro Gly Asp Phe Ala Pro
                275                 280                 285
Val Phe Ala Arg Arg Leu Arg Ala Gly Asp Ser Val Leu Ala Pro Gly
                290                 295                 300
Gly Asp Ala Leu Arg Pro Ala Arg Val Ala Arg Val Ala Arg Glu Glu
305                 310                 315                 320
Ala Val Gly Val Phe Ala Pro Leu Thr Ala His Gly Thr Leu Leu Val
                325                 330                 335
Asn Asp Val Leu Ala Ser Cys Tyr Ala Val Leu Glu Ser His Gln Trp
                340                 345                 350
Ala His Arg Ala Phe Ala Pro Leu Arg Leu Leu His Ala Leu Gly Ala
                355                 360                 365
Leu Leu Pro Gly Gly Ala Val Gln Pro Thr Gly Met His Trp Tyr Ser
                370                 375                 380
Arg Leu Leu Tyr Arg Leu Ala Glu Glu Leu Leu Gly
385                 390                 395

<210> SEQ ID NO 18
<211> LENGTH: 416
<212> TYPE: PRT
<213> ORGANISM: Brachydanio rerio

<400> SEQUENCE: 18

Met Asp Val Arg Leu His Leu Lys Gln Phe Ala Leu Leu Cys Phe Ile
1               5                   10                  15
Ser Leu Leu Leu Thr Pro Cys Gly Leu Ala Cys Gly Pro Gly Arg Gly
                20                  25                  30
Tyr Gly Lys Arg Arg His Pro Lys Lys Leu Thr Pro Leu Ala Tyr Lys
            35                  40                  45
Gln Phe Ile Pro Asn Val Ala Glu Lys Thr Leu Gly Ala Ser Gly Lys
        50                  55                  60
Tyr Glu Gly Lys Ile Thr Arg Asn Ser Glu Arg Phe Lys Glu Leu Ile
65                  70                  75                  80
Pro Asn Tyr Asn Pro Asp Ile Ile Phe Lys Asp Glu Glu Asn Thr Asn
                85                  90                  95
Ala Asp Arg Leu Met Thr Lys Arg Cys Lys Asp Lys Leu Asn Ser Leu
                100                 105                 110
Ala Ile Ser Val Met Asn His Trp Pro Gly Val Lys Leu Arg Val Thr
            115                 120                 125
```

-continued

```
Glu Gly Trp Asp Glu Asp Gly His His Leu Glu Glu Ser Leu His Tyr
            130                 135                 140

Glu Gly Arg Ala Val Asp Ile Thr Thr Ser Asp Arg Asp Lys Ser Lys
145                 150                 155                 160

Tyr Gly Met Leu Ser Arg Leu Ala Val Glu Ala Gly Phe Asp Trp Val
                165                 170                 175

Tyr Tyr Glu Ser Lys Ala His Ile His Cys Ser Val Lys Ala Glu Asn
            180                 185                 190

Ser Val Ala Ala Lys Ser Gly Gly Cys Phe Pro Gly Ser Gly Thr Val
            195                 200                 205

Thr Leu Gly Asp Gly Thr Arg Lys Pro Ile Lys Asp Leu Lys Val Gly
    210                 215                 220

Asp Arg Val Leu Ala Ala Asp Glu Lys Gly Asn Val Leu Ile Ser Asp
225                 230                 235                 240

Phe Ile Met Phe Ile Asp His Asp Pro Thr Thr Arg Arg Gln Phe Ile
                245                 250                 255

Val Ile Glu Thr Ser Glu Pro Phe Thr Lys Leu Thr Leu Thr Ala Ala
            260                 265                 270

His Leu Val Phe Val Gly Asn Ser Ser Ala Ala Ser Gly Ile Thr Ala
    275                 280                 285

Thr Phe Ala Ser Asn Val Lys Pro Gly Asp Thr Val Leu Val Trp Glu
290                 295                 300

Asp Thr Cys Glu Ser Leu Lys Ser Val Thr Val Lys Arg Ile Tyr Thr
305                 310                 315                 320

Glu Glu His Glu Gly Ser Phe Ala Pro Val Thr Ala His Gly Thr Ile
                325                 330                 335

Ile Val Asp Gln Val Leu Ala Ser Cys Tyr Ala Val Ile Glu Asn His
            340                 345                 350

Lys Trp Ala His Trp Ala Phe Ala Pro Val Arg Leu Cys His Lys Leu
    355                 360                 365

Met Thr Trp Leu Phe Pro Ala Arg Glu Ser Asn Val Asn Phe Gln Glu
370                 375                 380

Asp Gly Ile His Trp Tyr Ser Asn Met Leu Phe His Ile Gly Ser Trp
385                 390                 395                 400

Leu Leu Asp Arg Asp Ser Phe His Pro Leu Gly Ile Leu His Leu Ser
                405                 410                 415
```

<210> SEQ ID NO 19
<211> LENGTH: 1416
<212> TYPE: DNA
<213> ORGANISM: Drosophila melanogaster
<220> FEATURE:
<221> NAME/KEY: CDS
<222> LOCATION: (1)..(1413)

<400> SEQUENCE: 19

```
atg gat aac cac agc tca gtg cct tgg gcc agt gcc gcc agt gtc acc      48
Met Asp Asn His Ser Ser Val Pro Trp Ala Ser Ala Ala Ser Val Thr
1               5                   10                  15 tgt ctc tcc ctg gga tgc caa atg cca cag ttc cag ttc cag ttc cag      96
Cys Leu Ser Leu Gly Cys Gln Met Pro Gln Phe Gln Phe Gln Phe Gln
                20                  25                  30 ctc caa atc cgc agc gag ctc cat ctc cgc aag ccc gca aga aga acg     144
Leu Gln Ile Arg Ser Glu Leu His Leu Arg Lys Pro Ala Arg Arg Thr
            35                  40                  45 caa acg atg cgc cac att gcg cat acg cag cgt tgc ctc agc agg ctg     192
Gln Thr Met Arg His Ile Ala His Thr Gln Arg Cys Leu Ser Arg Leu
```

-continued

```
              50                  55                  60
acc tct ctg gtg gcc ctg ctg ctg atc gtc ttg ccg atg gtc ttt agc        240
Thr Ser Leu Val Ala Leu Leu Leu Ile Val Leu Pro Met Val Phe Ser
 65                  70                  75                  80 ccg gct cac agc tgc ggt cct ggc cga gga ttg ggt cgt cat agg gcg        288
Pro Ala His Ser Cys Gly Pro Gly Arg Gly Leu Gly Arg His Arg Ala
                     85                  90                  95 cgc aac ctg tat ccg ctg gtc ctc aag cag aca att ccc aat cta tcc        336
Arg Asn Leu Tyr Pro Leu Val Leu Lys Gln Thr Ile Pro Asn Leu Ser
                100                 105                 110 gag tac acg aac agc gcc tcc gga cct ctg gag ggt gtg atc cgt cgg        384
Glu Tyr Thr Asn Ser Ala Ser Gly Pro Leu Glu Gly Val Ile Arg Arg
            115                 120                 125 gat tcg ccc aaa ttc aag gac ctc gtg ccc aac tac aac agg gac atc        432
Asp Ser Pro Lys Phe Lys Asp Leu Val Pro Asn Tyr Asn Arg Asp Ile
        130                 135                 140 ctt ttc cgt gac gag gaa ggc acc gga gcg gat ggc ttg atg agc aag        480
Leu Phe Arg Asp Glu Glu Gly Thr Gly Ala Asp Gly Leu Met Ser Lys
145                 150                 155                 160 cgc tgc aag gag aag cta aac gtg ctg gcc tac tcg gtg atg aac gaa        528
Arg Cys Lys Glu Lys Leu Asn Val Leu Ala Tyr Ser Val Met Asn Glu
                165                 170                 175 tgg ccc ggc atc cgg ctg ctg gtc acc gag agc tgg gac gag gac tac        576
Trp Pro Gly Ile Arg Leu Leu Val Thr Glu Ser Trp Asp Glu Asp Tyr
            180                 185                 190 cat cac ggc cag gag tcg ctc cac tac gag ggc cga gcg gtg acc att        624
His His Gly Gln Glu Ser Leu His Tyr Glu Gly Arg Ala Val Thr Ile
        195                 200                 205 gcc acc tcc gat cgc gac cag tcc aaa tac ggc atg ctc gct cgc ctg        672
Ala Thr Ser Asp Arg Asp Gln Ser Lys Tyr Gly Met Leu Ala Arg Leu
210                 215                 220 gcc gtc gag gct gga ttc gat tgg gtc tcc tac gtc agc agg cgc cac        720
Ala Val Glu Ala Gly Phe Asp Trp Val Ser Tyr Val Ser Arg Arg His
225                 230                 235                 240 atc tac tgc tcc gtc aag tca gat tcg tcg atc agt tcc cac gtg cac        768
Ile Tyr Cys Ser Val Lys Ser Asp Ser Ser Ile Ser Ser His Val His
                245                 250                 255 ggc tgc ttc acg ccg gag agc aca gcg ctg ctg gag agt gga gtc cgg        816
Gly Cys Phe Thr Pro Glu Ser Thr Ala Leu Leu Glu Ser Gly Val Arg
            260                 265                 270 aag ccg ctc ggc gag ctc tct atc gga gat cgt gtt ttg agc atg acc        864
Lys Pro Leu Gly Glu Leu Ser Ile Gly Asp Arg Val Leu Ser Met Thr
        275                 280                 285 gcc aac gga cag gcc gtc tac agc gaa gtg atc ctc ttc atg gac cgc        912
Ala Asn Gly Gln Ala Val Tyr Ser Glu Val Ile Leu Phe Met Asp Arg
290                 295                 300 aac ctc gag cag atg caa aac ttt gtg cag ctg cac acg gac ggt gga        960
Asn Leu Glu Gln Met Gln Asn Phe Val Gln Leu His Thr Asp Gly Gly
305                 310                 315                 320 gca gtg ctc acg gtg acg ccg gct cac ctg gtt agc gtt tgg cag ccg       1008
Ala Val Leu Thr Val Thr Pro Ala His Leu Val Ser Val Trp Gln Pro
                325                 330                 335 gag agc cag aag ctc acg ttt gtg ttt gcg cat cgc atc gag gag aag       1056
Glu Ser Gln Lys Leu Thr Phe Val Phe Ala His Arg Ile Glu Glu Lys
            340                 345                 350 aac cag gtg ctc gta cgg gat gtg gag acg ggc gag ctg agg ccc cag       1104
Asn Gln Val Leu Val Arg Asp Val Glu Thr Gly Glu Leu Arg Pro Gln
        355                 360                 365 cga gtg gtc aag ttg ggc agt gtg cgc agt aag ggc gtg gtc gcg ccg       1152
```

-continued

```
                Arg Val Val Lys Leu Gly Ser Val Arg Ser Lys Gly Val Ala Pro
                    370                 375                 380 ctg acc cgc gag ggc acc att gtg gtc aac tcg gtg gcc gcc agt tgc        1200
Leu Thr Arg Glu Gly Thr Ile Val Val Asn Ser Val Ala Ala Ser Cys
385                 390                 395                 400 tat gcg gtg atc aac agt cag tcg ctg gcc cac tgg gga ctg gct ccc        1248
Tyr Ala Val Ile Asn Ser Gln Ser Leu Ala His Trp Gly Leu Ala Pro
                405                 410                 415 atg cgc ctg ctg tcc acg ctg gag gcg tgg ctg ccc gcc aag gag cag        1296
Met Arg Leu Leu Ser Thr Leu Glu Ala Trp Leu Pro Ala Lys Glu Gln
            420                 425                 430 ttg cac agt tcg ccg aag gtg gtg agc tcg gcg cag cag cag aat ggc        1344
Leu His Ser Ser Pro Lys Val Val Ser Ser Ala Gln Gln Gln Asn Gly
            435                 440                 445 atc cat tgg tat gcc aat gcg ctc tac aag gtc aag gac tac gtg ctg        1392
Ile His Trp Tyr Ala Asn Ala Leu Tyr Lys Val Lys Asp Tyr Val Leu
    450                 455                 460 ccg cag agc tgg cgc cac gat tga                                        1416
Pro Gln Ser Trp Arg His Asp
465                 470
```

<210> SEQ ID NO 20
<211> LENGTH: 471
<212> TYPE: PRT
<213> ORGANISM: Drosophila melanogaster

<400> SEQUENCE: 20

```
Met Asp Asn His Ser Ser Val Pro Trp Ala Ser Ala Ser Val Thr
1               5                   10                  15

Cys Leu Ser Leu Gly Cys Gln Met Pro Gln Phe Gln Phe Gln Phe Gln
                20                  25                  30

Leu Gln Ile Arg Ser Glu Leu His Leu Arg Lys Pro Ala Arg Arg Thr
            35                  40                  45

Gln Thr Met Arg His Ile Ala His Thr Gln Arg Cys Leu Ser Arg Leu
        50                  55                  60

Thr Ser Leu Val Ala Leu Leu Ile Val Leu Pro Met Val Phe Ser
65                  70                  75                  80

Pro Ala His Ser Cys Gly Pro Arg Gly Leu Gly Arg His Arg Ala
                85                  90                  95

Arg Asn Leu Tyr Pro Leu Val Leu Lys Gln Thr Ile Pro Asn Leu Ser
                100                 105                 110

Glu Tyr Thr Asn Ser Ala Ser Gly Pro Leu Gly Val Ile Arg Arg
            115                 120                 125

Asp Ser Pro Lys Phe Lys Asp Leu Val Pro Asn Tyr Asn Arg Asp Ile
        130                 135                 140

Leu Phe Arg Asp Glu Glu Gly Thr Gly Ala Asp Gly Leu Met Ser Lys
145                 150                 155                 160

Arg Cys Lys Glu Lys Leu Asn Val Leu Ala Tyr Ser Val Met Asn Glu
                165                 170                 175

Trp Pro Gly Ile Arg Leu Leu Val Thr Glu Ser Trp Asp Glu Asp Tyr
                180                 185                 190

His His Gly Gln Glu Ser Leu His Tyr Glu Gly Arg Ala Val Thr Ile
            195                 200                 205

Ala Thr Ser Asp Arg Asp Gln Ser Lys Tyr Gly Met Leu Ala Arg Leu
        210                 215                 220

Ala Val Glu Ala Gly Phe Asp Trp Val Ser Tyr Val Ser Arg Arg His
225                 230                 235                 240
```

-continued

```
Ile Tyr Cys Ser Val Lys Ser Asp Ser Ser Ile Ser Ser His Val His
                245                 250                 255

Gly Cys Phe Thr Pro Glu Ser Thr Ala Leu Leu Glu Ser Gly Val Arg
            260                 265                 270

Lys Pro Leu Gly Glu Leu Ser Ile Gly Asp Arg Val Leu Ser Met Thr
        275                 280                 285

Ala Asn Gly Gln Ala Val Tyr Ser Glu Val Ile Leu Phe Met Asp Arg
    290                 295                 300

Asn Leu Glu Gln Met Gln Asn Phe Val Gln Leu His Thr Asp Gly Gly
305                 310                 315                 320

Ala Val Leu Thr Val Thr Pro Ala His Leu Ser Val Trp Gln Pro
                325                 330                 335

Glu Ser Gln Lys Leu Thr Phe Val Phe Ala His Arg Ile Glu Glu Lys
                340                 345                 350

Asn Gln Val Leu Val Arg Asp Val Glu Thr Gly Glu Leu Arg Pro Gln
            355                 360                 365

Arg Val Val Lys Leu Gly Ser Val Arg Ser Lys Gly Val Val Ala Pro
        370                 375                 380

Leu Thr Arg Glu Gly Thr Ile Val Val Asn Ser Val Ala Ala Ser Cys
385                 390                 395                 400

Tyr Ala Val Ile Asn Ser Gln Ser Leu Ala His Trp Gly Leu Ala Pro
                405                 410                 415

Met Arg Leu Leu Ser Thr Leu Glu Ala Trp Leu Pro Ala Lys Glu Gln
                420                 425                 430

Leu His Ser Ser Pro Lys Val Val Ser Ala Gln Gln Gln Asn Gly
                435                 440                 445

Ile His Trp Tyr Ala Asn Ala Leu Tyr Lys Val Lys Asp Tyr Val Leu
    450                 455                 460

Pro Gln Ser Trp Arg His Asp
465                 470

<210> SEQ ID NO 21
<211> LENGTH: 471
<212> TYPE: PRT
<213> ORGANISM: Homo sapiens

<400> SEQUENCE: 21

Met Asp Asn His Ser Ser Val Pro Trp Ala Ser Ala Ala Ser Val Thr
1               5                   10                  15

Cys Leu Ser Leu Gly Cys Gln Met Pro Gln Phe Gln Phe Gln Phe Gln
            20                  25                  30

Leu Gln Ile Arg Ser Glu Leu His Leu Arg Lys Pro Ala Arg Arg Thr
        35                  40                  45

Gln Thr Met Arg His Ile Ala His Thr Gln Arg Cys Leu Ser Arg Leu
    50                  55                  60

Thr Ser Leu Val Ala Leu Leu Ile Val Leu Pro Met Val Phe Ser
65                  70                  75                  80

Pro Ala His Ser Cys Gly Pro Gly Arg Gly Leu Gly Arg His Arg Ala
                85                  90                  95

Arg Asn Leu Tyr Pro Leu Val Leu Lys Gln Thr Ile Pro Asn Leu Ser
            100                 105                 110

Glu Tyr Thr Asn Ser Ala Ser Gly Pro Leu Glu Gly Val Ile Arg Arg
        115                 120                 125

Asp Ser Pro Lys Phe Lys Asp Leu Val Pro Asn Tyr Asn Arg Asp Ile
```

```
                130                 135                 140
Leu Phe Arg Asp Glu Glu Gly Thr Gly Ala Asp Gly Leu Met Ser Lys
145                 150                 155                 160

Arg Cys Lys Glu Lys Leu Asn Val Leu Ala Tyr Ser Val Met Asn Glu
                165                 170                 175

Trp Pro Gly Ile Arg Leu Leu Val Thr Glu Ser Trp Asp Glu Asp Tyr
            180                 185                 190

His His Gly Gln Glu Ser Leu His Tyr Glu Gly Arg Ala Val Thr Ile
            195                 200                 205

Ala Thr Ser Asp Arg Asp Gln Ser Lys Tyr Gly Met Leu Ala Arg Leu
210                 215                 220

Ala Val Glu Ala Gly Phe Asp Trp Val Ser Tyr Val Ser Arg Arg His
225                 230                 235                 240

Ile Tyr Cys Ser Val Lys Ser Asp Ser Ser Ile Ser Ser His Val His
                245                 250                 255

Gly Cys Phe Thr Pro Glu Ser Thr Ala Leu Leu Glu Ser Gly Val Arg
            260                 265                 270

Lys Pro Leu Gly Glu Leu Ser Ile Gly Asp Arg Val Leu Ser Met Thr
            275                 280                 285

Ala Asn Gly Gln Ala Val Tyr Ser Glu Val Ile Leu Phe Met Asp Arg
290                 295                 300

Asn Leu Glu Gln Met Gln Asn Phe Val Gln Leu His Thr Asp Gly Gly
305                 310                 315                 320

Ala Val Leu Thr Val Thr Pro Ala His Leu Val Ser Val Trp Gln Pro
                325                 330                 335

Glu Ser Gln Lys Leu Thr Phe Val Phe Ala His Arg Ile Glu Glu Lys
            340                 345                 350

Asn Gln Val Leu Val Arg Asp Val Glu Thr Gly Glu Leu Arg Pro Gln
            355                 360                 365

Arg Val Val Lys Leu Gly Ser Val Arg Ser Lys Gly Val Val Ala Pro
370                 375                 380

Leu Thr Arg Glu Gly Thr Ile Val Val Asn Ser Val Ala Ala Ser Cys
385                 390                 395                 400

Tyr Ala Val Ile Asn Ser Gln Ser Leu Ala His Trp Gly Leu Ala Pro
                405                 410                 415

Met Arg Leu Leu Ser Thr Leu Glu Ala Trp Leu Pro Ala Lys Glu Gln
            420                 425                 430

Leu His Ser Ser Pro Lys Val Val Ser Ser Ala Gln Gln Gln Asn Gly
            435                 440                 445

Ile His Trp Tyr Ala Asn Ala Leu Tyr Lys Val Lys Asp Tyr Val Leu
450                 455                 460

Pro Gln Ser Trp Arg His Asp
465                 470

<210> SEQ ID NO 22
<211> LENGTH: 221
<212> TYPE: PRT
<213> ORGANISM: Homo sapiens
<220> FEATURE:
<221> NAME/KEY: SITE
<222> LOCATION: (1...221)
<223> OTHER INFORMATION: Xaa=any amino acid

<400> SEQUENCE: 22

Cys Gly Pro Gly Arg Gly Xaa Gly Xaa Arg Arg His Pro Lys Lys Leu
 1               5                  10                  15
```

```
Thr Pro Leu Ala Tyr Lys Gln Phe Ile Pro Asn Val Ala Glu Lys Thr
            20                  25                  30

Leu Gly Ala Ser Gly Arg Tyr Glu Gly Lys Ile Xaa Arg Asn Ser Glu
        35                  40                  45

Arg Phe Lys Glu Leu Thr Pro Asn Tyr Asn Pro Asp Ile Ile Phe Lys
50                  55                  60

Asp Glu Glu Asn Thr Gly Ala Asp Arg Leu Met Thr Gln Arg Cys Lys
65                  70                  75                  80

Asp Lys Leu Asn Xaa Leu Ala Ile Ser Val Met Asn Xaa Trp Pro Gly
                85                  90                  95

Val Xaa Leu Arg Val Thr Glu Gly Trp Asp Glu Asp Gly His His Xaa
            100                 105                 110

Glu Glu Ser Leu His Tyr Glu Gly Arg Ala Val Asp Ile Thr Thr Ser
        115                 120                 125

Asp Arg Asp Xaa Ser Lys Tyr Gly Xaa Leu Xaa Arg Leu Ala Val Glu
130                 135                 140

Ala Gly Phe Asp Trp Val Tyr Tyr Glu Ser Lys Ala His Ile His Cys
145                 150                 155                 160

Ser Val Lys Ala Glu Asn Ser Val Ala Ala Lys Ser Gly Gly Cys Phe
                165                 170                 175

Pro Gly Ser Ala Xaa Val Xaa Leu Xaa Xaa Gly Gly Xaa Lys Xaa Val
            180                 185                 190

Lys Asp Leu Xaa Pro Gly Asp Xaa Val Leu Ala Ala Asp Xaa Xaa Gly
        195                 200                 205

Xaa Leu Xaa Xaa Ser Asp Phe Xaa Xaa Phe Xaa Asp Arg
210                 215                 220

<210> SEQ ID NO 23
<211> LENGTH: 175
<212> TYPE: PRT
<213> ORGANISM: Homo sapiens

<400> SEQUENCE: 23

Cys Gly Pro Gly Arg Val Val Gly Ser Arg Arg Arg Pro Pro Arg Lys
1               5                   10                  15

Leu Val Pro Leu Ala Tyr Lys Gln Phe Ser Pro Asn Val Pro Glu Lys
            20                  25                  30

Thr Leu Gly Ala Ser Gly Arg Tyr Glu Gly Lys Ile Ala Arg Ser Ser
        35                  40                  45

Glu Arg Phe Lys Glu Leu Thr Pro Asn Tyr Asn Pro Asp Ile Ile Phe
50                  55                  60

Lys Asp Glu Glu Asn Thr Gly Ala Asp Arg Leu Met Thr Gln Arg Cys
65                  70                  75                  80

Lys Asp Arg Leu Asn Ser Leu Ala Ile Ser Val Met Asn Gln Trp Pro
                85                  90                  95

Gly Val Lys Leu Arg Val Thr Glu Gly Trp Asp Glu Asp Gly His His
            100                 105                 110

Ser Glu Glu Ser Leu His Tyr Glu Gly Arg Ala Val Asp Ile Thr Thr
        115                 120                 125

Ser Asp Arg Asp Arg Asn Lys Tyr Gly Leu Leu Ala Arg Leu Ala Val
130                 135                 140

Glu Ala Gly Phe Asp Trp Val Tyr Tyr Glu Ser Lys Ala His Val His
145                 150                 155                 160

Cys Ser Val Lys Ser Glu His Ser Ala Ala Ala Lys Thr Gly Gly
```

165          170          175

<210> SEQ ID NO 24
<211> LENGTH: 174
<212> TYPE: PRT
<213> ORGANISM: Homo sapiens

<400> SEQUENCE: 24

Cys Gly Pro Gly Arg Gly Phe Gly Lys Arg Arg His Pro Lys Lys Leu
 1               5                   10                  15

Thr Pro Leu Ala Tyr Lys Gln Phe Ile Pro Asn Val Ala Glu Lys Thr
                20                  25                  30

Leu Gly Ala Ser Gly Arg Tyr Glu Gly Lys Ile Ser Arg Asn Ser Glu
            35                  40                  45

Arg Phe Lys Glu Leu Thr Pro Asn Tyr Asn Pro Asp Ile Ile Phe Lys
    50                  55                  60

Asp Glu Glu Asn Thr Gly Ala Asp Arg Leu Met Thr Gln Arg Cys Lys
65                  70                  75                  80

Asp Lys Leu Asn Ala Leu Ala Ile Ser Val Met Asn Gln Trp Pro Gly
                85                  90                  95

Val Lys Leu Arg Val Thr Glu Gly Trp Asp Glu Asp Gly His His Ser
                100                 105                 110

Glu Glu Ser Leu His Tyr Glu Gly Arg Ala Val Asp Ile Thr Thr Ser
            115                 120                 125

Asp Arg Asp Arg Ser Lys Tyr Gly Met Leu Ala Arg Leu Ala Val Glu
    130                 135                 140

Ala Gly Phe Asp Trp Val Tyr Tyr Glu Ser Lys Ala His Ile His Cys
145                 150                 155                 160

Ser Val Lys Ala Glu Asn Ser Val Ala Ala Lys Ser Gly Gly
                165                 170

<210> SEQ ID NO 25
<211> LENGTH: 783
<212> TYPE: PRT
<213> ORGANISM: Homo sapiens

<400> SEQUENCE: 25

Cys Gly Pro Gly Arg Gly Pro Val Gly Arg Arg Arg Tyr Ala Arg Lys
 1               5                   10                  15

Gln Leu Val Pro Leu Leu Tyr Lys Gln Phe Val Pro Gly Val Pro Glu
                20                  25                  30

Arg Thr Leu Gly Ala Ser Gly Pro Ala Glu Gly Arg Val Ala Arg Gly
            35                  40                  45

Ser Glu Arg Phe Arg Asp Leu Val Pro Asn Tyr Asn Pro Asp Ile Ile
    50                  55                  60

Phe Lys Asp Glu Glu Asn Ser Gly Ala Asp Arg Leu Met Thr Glu Arg
65                  70                  75                  80

Cys Lys Glu Arg Val Asn Ala Leu Ala Ile Ala Val Met Asn Met Trp
                85                  90                  95

Pro Gly Val Arg Leu Arg Val Thr Glu Gly Trp Asp Glu Asp Gly His
                100                 105                 110

His Ala Gln Asp Ser Leu His Tyr Glu Gly Arg Ala Leu Asp Ile Thr
            115                 120                 125

Thr Ser Asp Arg Asp Arg Asn Lys Tyr Gly Leu Leu Ala Arg Leu Ala
    130                 135                 140

Val Glu Ala Gly Phe Asp Trp Val Tyr Tyr Glu Ser Arg Asn His Val

-continued

```
            145                 150                 155                 160
        His Val Ser Val Lys Ala Asp Asn Ser Leu Ala Val Arg Ala Gly Gly
                        165                 170                 175
        Ile Asn Asp Ile Ala Asn Cys Gly Pro Gly Arg Val Val Gly Ser Arg
                        180                 185                 190
        Arg Arg Pro Pro Arg Lys Leu Val Pro Leu Ala Tyr Lys Gln Phe Ser
                        195                 200                 205
        Pro Asn Val Pro Glu Lys Thr Leu Gly Ala Ser Gly Arg Tyr Glu Gly
                        210                 215                 220
        Lys Ile Ala Arg Ser Ser Glu Ser Asn Ile Cys Cys Gly Pro Gly Arg
        225                 230                 235                 240
        Gly Phe Gly Lys Arg Arg His Pro Lys Lys Leu Thr Pro Leu Ala Tyr
                        245                 250                 255
        Lys Gln Phe Ile Pro Asn Val Ala Glu Lys Thr Leu Gly Ala Ser Gly
                        260                 265                 270
        Arg Tyr Glu Gly Lys Ile Ser Arg Asn Ser Glu Asp Glu Ser Glu Arg
                        275                 280                 285
        Thr Cys Gly Pro Gly Arg Gly Pro Val Gly Arg Arg Tyr Ala Arg
                        290                 295                 300
        Lys Gln Leu Val Pro Leu Leu Tyr Lys Gln Phe Val Pro Gly Val Pro
        305                 310                 315                 320
        Glu Arg Thr Leu Gly Ala Ser Gly Pro Ala Glu Gly Arg Val Ala Arg
                        325                 330                 335
        Gly Ser Glu Ile Asn Asp Ile Ala Asn Arg Phe Lys Glu Leu Thr Pro
                        340                 345                 350
        Asn Tyr Asn Pro Asp Ile Ile Phe Lys Asp Glu Glu Asn Thr Gly Ala
                        355                 360                 365
        Asp Arg Leu Met Thr Gln Arg Cys Lys Asp Arg Leu Asn Ser Leu Ala
                        370                 375                 380
        Ile Ser Val Met Asn Gln Trp Pro Gly Val Lys Ser Asn Ile Cys Arg
        385                 390                 395                 400
        Phe Lys Glu Leu Thr Pro Asn Tyr Asn Pro Asp Ile Ile Phe Lys Asp
                        405                 410                 415
        Glu Glu Asn Thr Gly Ala Asp Arg Leu Met Thr Gln Arg Cys Lys Asp
                        420                 425                 430
        Lys Leu Asn Ala Leu Ala Ile Ser Val Met Asn Gln Trp Pro Gly Val
                        435                 440                 445
        Lys Asp Glu Ser Glu Arg Thr Arg Phe Arg Asp Leu Val Pro Asn Tyr
                        450                 455                 460
        Asn Pro Asp Ile Ile Phe Lys Asp Glu Glu Asn Ser Gly Ala Asp Arg
        465                 470                 475                 480
        Leu Met Thr Glu Arg Cys Lys Glu Arg Val Asn Ala Leu Ala Ile Ala
                        485                 490                 495
        Val Met Asn Met Trp Pro Gly Val Arg Ile Asn Asp Ile Ala Asn Leu
                        500                 505                 510
        Arg Val Thr Glu Gly Trp Asp Glu Asp Gly His His Ser Glu Glu Ser
                        515                 520                 525
        Leu His Tyr Glu Gly Arg Ala Val Asp Ile Thr Thr Ser Asp Arg Asp
                        530                 535                 540
        Arg Asn Lys Tyr Gly Leu Leu Ala Arg Leu Ala Val Glu Ala Gly Phe
        545                 550                 555                 560
        Asp Ser Asn Ile Cys Leu Arg Val Thr Glu Gly Trp Asp Glu Asp Gly
                        565                 570                 575
```

```
His His Ser Glu Glu Ser Leu His Tyr Glu Gly Arg Ala Val Asp Ile
            580                 585                 590

Thr Thr Ser Asp Arg Asp Arg Ser Lys Tyr Gly Met Leu Ala Arg Leu
            595                 600                 605

Ala Val Glu Ala Gly Phe Asp Asp Glu Ser Glu Arg Thr Leu Arg Val
        610                 615                 620

Thr Glu Gly Trp Asp Glu Asp Gly His His Ala Gln Asp Ser Leu His
625                 630                 635                 640

Tyr Glu Gly Arg Ala Leu Asp Ile Thr Thr Ser Asp Arg Asp Arg Asn
                645                 650                 655

Lys Tyr Gly Leu Leu Ala Arg Leu Ala Val Glu Ala Gly Phe Asp Ile
            660                 665                 670

Asn Asp Ile Ala Asn Trp Val Tyr Tyr Glu Ser Lys Ala His Val His
            675                 680                 685

Cys Ser Val Lys Ser Glu His Ser Ala Ala Lys Thr Gly Gly Ser
            690                 695                 700

Glu Gln Ile Asp Asn Ser Asn Ile Cys Trp Val Tyr Tyr Glu Ser Lys
705                 710                 715                 720

Ala His Ile His Cys Ser Val Lys Ala Glu Asn Ser Val Ala Ala Lys
                725                 730                 735

Ser Gly Gly Ser Glu Gln Ile Asp Asn Asp Ser Glu Arg Thr Trp
            740                 745                 750

Val Tyr Tyr Glu Ser Arg Asn His Val His Val Ser Val Lys Ala Asp
        755                 760                 765

Asn Ser Leu Ala Val Arg Ala Gly Gly Ser Glu Gln Ile Asp Asn
            770                 775                 780

<210> SEQ ID NO 26
<211> LENGTH: 176
<212> TYPE: PRT
<213> ORGANISM: Homo sapiens
<220> FEATURE:
<221> NAME/KEY: SITE
<222> LOCATION: (1...176)
<223> OTHER INFORMATION: Xaa=any amino acid

<400> SEQUENCE: 26

Xaa Gly Pro Gly Arg Xaa Xaa Xaa Xaa Arg Arg Xaa Xaa Xaa Lys
  1               5                  10                  15

Xaa Leu Xaa Pro Leu Xaa Tyr Lys Gln Phe Xaa Pro Xaa Val Xaa Glu
                20                  25                  30

Lys Thr Leu Gly Ala Ser Gly Arg Xaa Glu Gly Lys Xaa Xaa Arg Xaa
            35                  40                  45

Ser Glu Arg Phe Lys Xaa Leu Xaa Pro Asn Tyr Asn Pro Asp Ile Ile
        50                  55                  60

Phe Lys Asp Glu Glu Asn Xaa Gly Ala Asp Arg Leu Met Thr Xaa Arg
65                  70                  75                  80

Cys Lys Xaa Xaa Xaa Asn Ser Leu Ala Ile Xaa Val Met Asn Xaa Trp
                85                  90                  95

Pro Gly Val Lys Leu Arg Val Thr Glu Gly Trp Asp Glu Asp Gly His
                100                 105                 110

His Xaa Xaa Xaa Ser Leu His Tyr Glu Gly Arg Ala Val Asp Ile Thr
            115                 120                 125

Thr Ser Asp Arg Asp Arg Xaa Lys Tyr Gly Xaa Leu Ala Arg Leu Ala
        130                 135                 140
```

```
Val Glu Ala Gly Phe Asp Trp Val Tyr Tyr Glu Ser Xaa Xaa His Xaa
145                 150                 155                 160

His Xaa Ser Val Lys Xaa Xaa Xaa Ser Xaa Ala Ala Xaa Xaa Gly Gly
            165                 170                 175
```

<210> SEQ ID NO 27
<211> LENGTH: 10
<212> TYPE: PRT
<213> ORGANISM: Homo sapiens

<400> SEQUENCE: 27

```
Lys Arg Arg His Pro Arg Lys Arg His Pro
1               5                   10
```

<210> SEQ ID NO 28
<211> LENGTH: 10
<212> TYPE: PRT
<213> ORGANISM: Homo sapiens

<400> SEQUENCE: 28

```
Lys Arg Arg His Pro Arg Lys Arg Pro Pro
1               5                   10
```

<210> SEQ ID NO 29
<211> LENGTH: 10
<212> TYPE: PRT
<213> ORGANISM: Homo sapiens

<400> SEQUENCE: 29

```
Lys Arg Arg His Pro Lys Lys Lys His Pro
1               5                   10
```

<210> SEQ ID NO 30
<211> LENGTH: 10
<212> TYPE: PRT
<213> ORGANISM: Homo sapiens

<400> SEQUENCE: 30

```
Lys Arg Arg His Pro Arg Gln Arg His Pro
1               5                   10
```

<210> SEQ ID NO 31
<211> LENGTH: 10
<212> TYPE: PRT
<213> ORGANISM: Homo sapiens

<400> SEQUENCE: 31

```
Arg Lys Lys His Pro Arg Lys Lys His Pro
1               5                   10
```

<210> SEQ ID NO 32
<211> LENGTH: 18
<212> TYPE: PRT
<213> ORGANISM: Homo sapiens

<400> SEQUENCE: 32

```
Gly Ser Arg Lys Arg Pro Pro Arg Lys Gly Ser Arg Lys Arg Pro Pro
1               5                   10                  15

Arg Lys
```

<210> SEQ ID NO 33
<211> LENGTH: 10
<212> TYPE: PRT
<213> ORGANISM: Homo sapiens

<400> SEQUENCE: 33

Lys Arg Arg His Pro Gln Arg Lys His Pro
1               5                   10

<210> SEQ ID NO 34
<211> LENGTH: 10
<212> TYPE: PRT
<213> ORGANISM: Homo sapiens

<400> SEQUENCE: 34

Lys Arg Arg His Pro Gln Arg Arg Pro Pro
1               5                   10

<210> SEQ ID NO 35
<211> LENGTH: 30
<212> TYPE: DNA
<213> ORGANISM: Homo sapiens

<400> SEQUENCE: 35
tcgagaaaag atgcggaccg ggcagggggt                                       30

<210> SEQ ID NO 36
<211> LENGTH: 29
<212> TYPE: DNA
<213> ORGANISM: Homo sapiens

<400> SEQUENCE: 36
cgaaccccct gcccggtccg catcttttc                                        29

<210> SEQ ID NO 37
<211> LENGTH: 522
<212> TYPE: DNA
<213> ORGANISM: Homo sapiens

<400> SEQUENCE: 37
tgcggaccgg gcagggggtt cgggaagagg aggcacccca aaaagctgac ccctttagcc      60
tacaagcagt ttatccccaa tgtggccgag aagaccctag cgccagcgg aaggtatgaa     120 gggaagatct ccagaaactc cgagcgattt aaggaactca cccccaatta caaccccgac    180
atcatattta aggatgaaga aaacaccgga gcggacaggc tgatgactca gaggtgtaag    240
gacaagttga acgctttggc catctcggtg atgaaccagt ggccaggagt gaaactgcgg    300
gtgaccgagg gctgggacga agatggccac cactcagagg agtctctgca ctacgagggc    360
cgcgcagtgg acatcaccac gtctgaccgc gaccgcagca agtacggcat gctggcccgc    420
ctggcggtgg aggccggctt cgactgggtg tactacgagt ccaaggcaca tatccactgc    480
tcggtgaaag cagagaactc ggtggcggcc aaatcgggag gc                       522

<210> SEQ ID NO 38
<211> LENGTH: 525
<212> TYPE: DNA
<213> ORGANISM: Homo sapiens

<400> SEQUENCE: 38
tgcgggccgg gtcgggtggt gggcagccgc cggcgaccgc cacgcaaact cgtgccgctc     60
gcctacaagc agttcagccc caatgtgccc gagaagaccc tgggcgccag cggacgctat   120
gaaggcaaga tcgctcgcag ctccgagcgc ttcaaggagc tcacccccaa ttacaatcca   180
gacatcatct tcaaggacga ggagaacaca ggcgccgacc gcctcatgac ccagcgctgc   240

```
aaggaccgcc tgaactcgct ggctatctcg gtgatgaacc agtggcccgg tgtgaagctg    300
cgggtgaccg agggctggga cgaggacggc caccactcag aggagtccct gcattatgag    360
ggccgcgcgg tggacatcac cacatcagac cgcgaccgca ataagtatgg actgctggcg    420
cgcttggcag tggaggccgg cttttgactgg gtgtattacg agtcaaaggc ccacgtgcat    480
tgctccgtca gtccgagca ctcggccgca gccaagacgg gcggc                     525
```

<210> SEQ ID NO 39
<211> LENGTH: 528
<212> TYPE: DNA
<213> ORGANISM: Homo sapiens

<400> SEQUENCE: 39

```
tgcgggccgg gccgggggcc ggttggccgg cgccgctatg cgcgcaagca gctcgtgccg     60
ctactctaca agcaatttgt gcccggcgtg ccagagcgga ccctgggcgc cagtgggcca    120
gcggagggga gggtggcaag gggctccgag cgcttccggg acctcgtgcc caactacaac    180
cccgacatca tcttcaagga tgaggagaac agtggagccg accgcctgat gaccgagcgt    240
tgtaaggagc gggtgaacgc tttggccatt gccgtgatga acatgtggcc cggagtgcgc    300
ctacgagtga ctgagggctg ggacgaggac ggccaccacg ctcaggattc actccactac    360
gaaggccgtg ctttggacat cactacgtct gaccgcgacc gcaacaagta tgggttgctg    420
gcgcgcctcg cagtggaagc cggcttcgac tgggtctact acgagtcccg caaccacgtc    480
cacgtgtcgg tcaaagctga taactcactg gcggtccggg cgggcggc                528
```

<210> SEQ ID NO 40
<211> LENGTH: 684
<212> TYPE: DNA
<213> ORGANISM: Homo sapiens

<400> SEQUENCE: 40

```
gtcgacaaaa ctcacacatg cccaccgtgc ccagcacctg aactcctggg gggaccgtca     60
gtcttcctct tccccccaaa acccaaggac accctcatga tctcccggac ccctgaggtc    120
acatgcgtgg tggtggacgt gagccacgaa gaccctgagg tcaagttcaa ctggtacgtg    180
gacggcgtgg aggtgcataa tgccaagaca aagccgcggg aggagcagta ccagagcacg    240
taccgtgtgg tcagcgtcct caccgtcctg caccaggact ggctgaatgg caaggagtac    300
aagtgcaagg tctccaacaa agccctccca gcccccatcg agaaaaccat ctccaaagcc    360
aaagggcagc cccgagaacc acaggtgtac accctgcccc catcccggga tgagctgacc    420
aagaaccagg tcagcctgac ctgcctggtc aaaggcttct atcccagcga catcgccgtg    480
gagtgggaga gcaatgggca gccggagaac aactacaaga ccacgcctcc cgtgttggac    540
tccgacggct ccttcttcct ctacagcaag ctcaccgtgg acaagagcag gtggcagcag    600
gggaacgtct tctcatgctc cgtgatgcat gaggctctgc acaaccacta cacgcagaag    660
agcctctccc tgtctcccgg gaaa                                          684
```

<210> SEQ ID NO 41
<211> LENGTH: 687
<212> TYPE: DNA
<213> ORGANISM: Mus musculus

<400> SEQUENCE: 41

```
gtcgacgtgc ccagggattg tggttgtaag ccttgcatat gtacagtccc agaagtatca     60
tctgtcttca tcttccccccc aaagcccaag gatgtgctca ccattactct gactcctaag    120
```

```
gtcacgtgtg ttgtggtaga catcagcaag gatgatcccg aggtccagtt cagctggttt    180
gtagatgatg tggaggtgca cacagctcag acgcaaccac gggaagagca gttccaaagc    240
actttccgct cagtcagtga acttcccatc atgcaccagg actggctcaa tggcaaggag    300
ttcaaatgca gggtcaacag tgcagctttc cctgccccca tcgagaaaac catctccaaa    360
accaaaggca gaccgaaggc tccacaggtg tacaccattc cacctcccaa ggagcagatg    420
gccaaggata aagtcagtct gacctgcatg ataacagact tcttccctga agacattact    480
gtggagtggc agtggaatgg gcagccagcg agaaactaca agaacactca gcccatcatg    540
gacacagatg gctcttactt cgtctacagc aagctcaatg tgcagaagag caactgggag    600
gcaggaaata ctttcacctg ctctgtgtta catgagggcc tgcacaacca ccatactgag    660
aagagcctct cccactctcc tggtaaa                                        687

<210> SEQ ID NO 42
<211> LENGTH: 702
<212> TYPE: DNA
<213> ORGANISM: Homo sapiens

<400> SEQUENCE: 42
gtcgacccca gagggcccac aatcaagccc tgtcctccat gcaaatgccc agcacctaac     60
ctcttgggtg gaccatccgt cttcatcttc cctccaaaga tcaaggatgt actcatgatc    120
tccctgagcc ccatagtcac atgtgtggtg gtggatgtga gcgaggatga cccagatgtc    180
cagatcagct ggtttgtgaa caacgtggaa gtacacacag tcagacacaa acccatagaa    240
gaggattacc aaagtacact tcgggtggtc agtgccctcc ccatccagca ccaggactgg    300
atgagtggca aggagttcaa atgcaaggtc aacaacaaag acctcccagc gcccatcgag    360
agaaccatct caaacccaa agggtcagta agagctccac aggtatatgt cttgcctcca    420
ccagaagaag agatgactaa gaaacaggtc actctgacct gcatggtgac agacttcatg    480
cctgaagaca tttacgtgga gtggaccaac aacgggaaaa cagagctaaa ctacaagaac    540
actgaaccag tcctggactc tgatggttct tacttcatgt acagcaagct gagagtggaa    600
aagaagaact gggtggaaag aaatagctac tcctgttcag tggtccacga gggtctgcac    660
aatcaccaca cgactaagag cttctcccgg actccgggta aa                       702

<210> SEQ ID NO 43
<211> LENGTH: 52
<212> TYPE: DNA
<213> ORGANISM: Homo sapiens

<400> SEQUENCE: 43
ctgacccctt tagcctacaa gcagtttatc cccaatgtgg ccgagaagac cc             52

<210> SEQ ID NO 44
<211> LENGTH: 50
<212> TYPE: DNA
<213> ORGANISM: Homo sapiens

<400> SEQUENCE: 44
cctagggtct tctcggccac attggggata aactgcttgt aggctaaagg               50

<210> SEQ ID NO 45
<211> LENGTH: 53
<212> TYPE: DNA
<213> ORGANISM: Homo sapiens
```

<400> SEQUENCE: 45
tcgagaaaag atgcggcccg ggcaggpggt tcgggaagag acctcccaaa aag          53

<210> SEQ ID NO 46
<211> LENGTH: 55
<212> TYPE: DNA
<213> ORGANISM: Homo sapiens

<400> SEQUENCE: 46
ggtcagcttt ttgggaggtc tcttcccgaa cccctgccc gggccgcatc ttttc          55

<210> SEQ ID NO 47
<211> LENGTH: 56
<212> TYPE: DNA
<213> ORGANISM: Homo sapiens

<400> SEQUENCE: 47
tcgagaaaag atgcggcccg ggcaggpggt tcgggaggaa gagacacccc aaaaag        56

<210> SEQ ID NO 48
<211> LENGTH: 58
<212> TYPE: DNA
<213> ORGANISM: Homo sapiens

<400> SEQUENCE: 48
ggtcagcttt ttggggtgtc tcttcctccc gaaccccctg cccgggccgc atctttc       58

<210> SEQ ID NO 49
<211> LENGTH: 56
<212> TYPE: DNA
<213> ORGANISM: Homo sapiens

<400> SEQUENCE: 49
tcgagaaaag atgcggcccg ggcaggpggt tcgggaagaa gaagcacccc aaaaag        56

<210> SEQ ID NO 50
<211> LENGTH: 58
<212> TYPE: DNA
<213> ORGANISM: Homo sapiens

<400> SEQUENCE: 50
ggtcagcttt ttggggtgct tcttcttccc gaaccccctg cccgggccgc atctttc       58

<210> SEQ ID NO 51
<211> LENGTH: 59
<212> TYPE: DNA
<213> ORGANISM: Homo sapiens

<400> SEQUENCE: 51
tcgagaaaag atgcggcccg ggcaggpggt tcgggtctag aaagagacct cccagaaag    59

<210> SEQ ID NO 52
<211> LENGTH: 61
<212> TYPE: DNA
<213> ORGANISM: Homo sapiens

<400> SEQUENCE: 52
ggtcagcttt ctgggaggtc tctttctaga cccgaacccc ctgcccgggc cgcatctttt  60
c                                                                    61

<210> SEQ ID NO 53
<211> LENGTH: 52

-continued

<212> TYPE: DNA
<213> ORGANISM: Homo sapiens

<400> SEQUENCE: 53 cttaccccttt tagcctacaa gcagtttatc cccaatgtgg ccgagaagac cc      52

<210> SEQ ID NO 54
<211> LENGTH: 56
<212> TYPE: DNA
<213> ORGANISM: Homo sapiens

<400> SEQUENCE: 54
tcgagaaaag atgcggcccg ggcaggggt tcgggaagaa gaagcacccc aaaaag    56

<210> SEQ ID NO 55
<211> LENGTH: 58
<212> TYPE: DNA
<213> ORGANISM: Homo sapiens

<400> SEQUENCE: 55
ggtaagcttt tgggtgct tcttcctccc gaaccccctg cccgggccgc atcttttc   58

<210> SEQ ID NO 56
<211> LENGTH: 56
<212> TYPE: DNA
<213> ORGANISM: Homo sapiens

<400> SEQUENCE: 56
tcgagaaaag atgcggccca ggcaggggt tcgggaggca gagacacccc aaaaag    56

<210> SEQ ID NO 57
<211> LENGTH: 58
<212> TYPE: DNA
<213> ORGANISM: Homo sapiens

<400> SEQUENCE: 57
ggtaagcttt ttggggtgtc tctgcctccc gaaccccctg cctggccgc atctttc   58

<210> SEQ ID NO 58
<211> LENGTH: 56
<212> TYPE: DNA
<213> ORGANISM: Homo sapiens

<400> SEQUENCE: 58
tcgagaaaag atgcggcccg ggcaggggt tcgggcagcg gaagcacccc aaaaag    56

<210> SEQ ID NO 59
<211> LENGTH: 58
<212> TYPE: DNA
<213> ORGANISM: Homo sapiens

<400> SEQUENCE: 59
ggtcagcttt ttggggtgct tccgctgccc gaaccccctg cccgggccgc atcttttc 58

<210> SEQ ID NO 60
<211> LENGTH: 56
<212> TYPE: DNA
<213> ORGANISM: Homo sapiens

<400> SEQUENCE: 60
tcgagaaaag atgcggcccg ggcaggggt tcgggcagag aagaccaccc aaaaag    56

<210> SEQ ID NO 61

```
<211> LENGTH: 58
<212> TYPE: DNA
<213> ORGANISM: Homo sapiens

<400> SEQUENCE: 61
ggtcagcttt tgggtggtc ttctctgccc gaaccccctg cccggccgc atcttttc        58

<210> SEQ ID NO 62
<211> LENGTH: 59
<212> TYPE: DNA
<213> ORGANISM: Homo sapiens

<400> SEQUENCE: 62
ccgggccggg ggccggttgg ccaacgccgg ccggcgcgca agcagctcgt gccgctact     59

<210> SEQ ID NO 63
<211> LENGTH: 59
<212> TYPE: DNA
<213> ORGANISM: Homo sapiens

<400> SEQUENCE: 63
gtacagtagc ggcacgagct gcttgcgcgc cggccggcgt tggccaaccg gccccggc     59

<210> SEQ ID NO 64
<211> LENGTH: 59
<212> TYPE: DNA
<213> ORGANISM: Homo sapiens

<400> SEQUENCE: 64
ccgggccggg ggccggttgg ccggcagcgc tatgcgcgca agcagctggt gccgctact     59

<210> SEQ ID NO 65
<211> LENGTH: 59
<212> TYPE: DNA
<213> ORGANISM: Homo sapiens

<400> SEQUENCE: 65
gtacagtagc ggcaccagct gcttgcgcgc atagcgctgc cggccaaccg gccccggc     59

<210> SEQ ID NO 66
<211> LENGTH: 42
<212> TYPE: DNA
<213> ORGANISM: Homo sapiens

<400> SEQUENCE: 66
ccgggtcggg tggtgggcag ccgcaagcgg ccgccacgca aa                       42

<210> SEQ ID NO 67
<211> LENGTH: 42
<212> TYPE: DNA
<213> ORGANISM: Homo sapiens

<400> SEQUENCE: 67
ctagtttgcg tggcggccgc ttgcggctgc ccaccacccg ac                       42

<210> SEQ ID NO 68
<211> LENGTH: 42
<212> TYPE: DNA
<213> ORGANISM: Homo sapiens

<400> SEQUENCE: 68
ccgggtcggg tggtgggcag ccaacgtcga ccgccacgca aa                       42
```

```
<210> SEQ ID NO 69
<211> LENGTH: 42
<212> TYPE: DNA
<213> ORGANISM: Homo sapiens

<400> SEQUENCE: 69
ctagtttgcg tggcggtcga cgttggctgc ccaccacccg ac                    42

<210> SEQ ID NO 70
<211> LENGTH: 47
<212> TYPE: DNA
<213> ORGANISM: Homo sapiens

<400> SEQUENCE: 70
gcccgggcag ggggttcggg aagaagaggc accccaaaaa gctgacc               47

<210> SEQ ID NO 71
<211> LENGTH: 47
<212> TYPE: DNA
<213> ORGANISM: Homo sapiens

<400> SEQUENCE: 71
gcccgggcag ggggttcggg aggaggaggc accccaaaaa gctgacc               47

<210> SEQ ID NO 72
<211> LENGTH: 47
<212> TYPE: DNA
<213> ORGANISM: Homo sapiens

<400> SEQUENCE: 72
gcccgggcag ggggttcggg cagcagcagc accccaaaaa gctgacc               47

<210> SEQ ID NO 73
<211> LENGTH: 47
<212> TYPE: DNA
<213> ORGANISM: Homo sapiens

<400> SEQUENCE: 73
gcccgggcag ggggttcggg aagaggaggc accccagca gctgacc                47

<210> SEQ ID NO 74
<211> LENGTH: 45
<212> TYPE: DNA
<213> ORGANISM: Homo sapiens

<400> SEQUENCE: 74
cctttagcct acaagcagtt tatccccaag gtggccgaga agacc                 45

<210> SEQ ID NO 75
<211> LENGTH: 50
<212> TYPE: DNA
<213> ORGANISM: Homo sapiens

<400> SEQUENCE: 75 taaagggtc agcttttgg ggtgcctctt cttcccgaac cccctgcccg              50

<210> SEQ ID NO 76
<211> LENGTH: 50
<212> TYPE: DNA
<213> ORGANISM: Homo sapiens

<400> SEQUENCE: 76 taaaggggt cagcttttg ggtgcctcct cctcccgaac cccctgcccg              50
```

```
<210> SEQ ID NO 77
<211> LENGTH: 50
<212> TYPE: DNA
<213> ORGANISM: Homo sapiens

<400> SEQUENCE: 77 taaagggtc agcttttgg ggtgctgctg ctgcccgaac cccctgcccg            50

<210> SEQ ID NO 78
<211> LENGTH: 50
<212> TYPE: DNA
<213> ORGANISM: Homo sapiens

<400> SEQUENCE: 78 taaagggtc agctgctggg ggtgcctcct cttcccgaac cccctgcccg            50

<210> SEQ ID NO 79
<211> LENGTH: 43
<212> TYPE: DNA
<213> ORGANISM: Homo sapiens

<400> SEQUENCE: 79
ctagggtctt ctcggccaca ttggggagaa actgcttgta ggc                  43

<210> SEQ ID NO 80
<211> LENGTH: 9776
<212> TYPE: DNA
<213> ORGANISM: Homo sapiens

<400> SEQUENCE: 80
gatctaacat ccaaagacga aaggttgaat gaaaccttt tgccatccga catccacagg    60
tccattctca cacataagtg ccaaacgcaa caggagggga tacactagca gcagaccgtt  120
gcaaacgcag gacctccact cctcttctcc tcaacaccca cttttgccat cgaaaaacca  180
gcccagttat tgggcttgat tggagctcgc tcattccaat tccttctatt aggctactaa  240
caccatgact ttattagcct gtctatcctg gcccccctgg cgaggttcat gtttgtttat  300
ttccgaatgc aacaagctcc gcattacacc cgaacatcac tccagatgag ggctttctga  360 gtgtgggtc aaatagtttc atgttcccca aatggcccaa aactgacagt ttaaacgctg    420
tcttggaacc taatatgaca aaagcgtgat ctcatccaag atgaactaag tttggttcgt  480
tgaaatgcta acggccagtt ggtcaaaaag aaacttccaa aagtcgccat accgtttgtc  540
ttgtttggta ttgattgacg aatgctcaaa aataatctca ttaatgctta gcgcagtctc  600
tctatcgctt ctgaaccccg gtgcacctgt gccgaaacgc aaatgggaa acacccgctt   660 tttggatgat tatgcattgt ctccacattg tatgcttcca agattctggt gggaatactg  720
ctgatagcct aacgttcatg atcaaaattt aactgttcta cccctactt gacagcaata   780 tataaacaga aggaagctgc cctgtcttaa accttttttt ttatcatcat tattagctta  840
ctttcataat tgcgactggt tccaattgac aagcttttga ttttaacgac ttttaacgac  900
aacttgagaa gatcaaaaaa caactaatta ttcgaaggat ccaaacgatg agatttcctt   960
caatttttac tgcagtttta ttcgcagcat cctccgcatt agctgctcca gtcaacacta 1020
caacagaaga tgaaacggca caaattccgg ctgaagctgt catcggttac tcagatttag 1080
aaggggattt cgatgttgct gttttgccat tttccaacag cacaaataac gggttattgt 1140
ttataaatac tactattgcc agcattgctg ctaaagaaga aggggtatct ctcgagaaaa 1200
gatgcggacc gggcaggggg ttcgggaaga ggaggcaccc caaaaagctg acccctttag 1260
```

```
cctacaagca gtttatcccc aatgtggccg agaagaccct aggcgccagc ggaaggtatg    1320
aagggaagat ctccagaaac tccgagcgat ttaaggaact cacccccaat tacaacccg    1380 acatcatatt taaggatgaa gaaaacaccg gagcggacag gctgatgact cagaggtgta    1440
aggacaagtt gaacgctttg gccatctcgg tgatgaacca gtggccagga gtgaaactgc    1500
gggtgaccga gggctgggac gaagatggcc accactcaga ggagtctctg cactacgagg    1560
gccgcgcagt ggacatcacc acgtctgacc gcgaccgcag caagtacggc atgctggccc    1620
gcctggcggt ggaggccggc ttcgactggg tgtactacga gtccaaggca catatccact    1680
gctcggtgaa agcagagaac tcggtggcgg ccaaatcggg aggctgattc gcggccgcga    1740
attaattcgc cttagacatg actgttcctc agttcaagtt gggcacttac gagaagaccg    1800
gtcttgctag attctaatca agaggatgtc agaatgccat ttgcctgaga gatgcaggct    1860
tcatttttga tacttttta tttgtaacct atatagtata ggattttttt tgtcattttg    1920
tttcttctcg tacgagcttg ctcctgatca gcctatctcg cagctgatga atatcttgtg    1980
gtaggggttt gggaaaatca ttcgagtttg atgttttct tggtatttcc cactcctctt    2040
cagagtacag aagattaagt gagaagttcg tttgtgcaag cttatcgata agctttaatg    2100
cggtagttta tcacagttaa attgctaacg cagtcaggca ccgtgtatga aatctaacaa    2160
tgcgctcatc gtcatcctcg gcaccgtcac cctggatgct gtaggcatag gcttggttat    2220
gccggtactg ccgggcctct tgcgggatat cgtccattcc gacagcatcg ccagtcacta    2280
tggcgtgctg ctagcgctat atgcgttgat gcaatttcta tgcgcacccg ttctcggagc    2340
actgtccgac cgctttggcc gccgcccagt cctgctcgct tcgctacttg gagccactat    2400
cgactacgcg atcatggcga ccacacccgt cctgtggatc tatcgaatct aaatgtaagt    2460
taaaatctct aaataattaa ataagtccca gtttctccat acgaacctta acagcattgc    2520
ggtgagcatc tagaccttca acagcagcca gatccatcac tgcttggcca atatgtttca    2580
gtccctcagg agttacgtct tgtgaagtga tgaacttctg gaaggttgca gtgttaactc    2640
cgctgtattg acgggcatat ccgtacgttg gcaaagtgtg gttggtaccg gaggagtaat    2700
ctccacaact ctctggagag taggcaccaa caaacacaga tccagcgtgt tgtacttgat    2760
caacataaga agaagcattc tcgatttgca ggatcaagtg ttcaggagcg tactgattgg    2820
acatttccaa agcctgctcg taggttgcaa ccgatagggt tgtagagtgt gcaatacact    2880
tgcgtacaat ttcaaccctt ggcaactgca cagcttggtt gtgaacagca tcttcaattc    2940
tggcaagctc cttgtctgtc atatcgacag ccaacagaat cacctgggaa tcaataccat    3000
gttcagcttg agcagaaggt ctgaggcaac gaaatctgga tcagcgtatt tatcagcaat    3060
aactagaact tcagaaggcc cagcaggcat gtcaatacta cacagggctg atgtgtcatt    3120
ttgaaccatc atcttggcag cagtaacgaa ctggtttcct ggaccaaata ttttgtcaca    3180
cttaggaaca gtttctgttc cgtaagccat agcagctact gcctgggcgc ctcctgctag    3240
cacgatacac ttagcaccaa ccttgtgggc aacgtagatg acttctgggg taagggtacc    3300
atccttctta ggtggagatg caaaaacaat ttctttgcaa ccagcaactt tggcaggaac    3360
acccagcatc agggaagtgg aaggcagaat tgcggttcca ccaggaatat agaggccaac    3420
tttctcaata ggtcttgcaa aacgagagca gactacacca gggcaagtct caacttgcaa    3480
cgtctccgtt agttgagctt catggaattt cctgacgtta tctatagaga gatcaatggc    3540
tctcttaacg ttatctggca attgcataag ttcctctggg aaaggagctt ctaacacagg    3600
```

```
tgtcttcaaa gcgactccat caaacttggc agttagttct aaaagggctt tgtcaccatt    3660
ttgacgaaca ttgtcgacaa ttggtttgac taattccata atctgttccg ttttctggat    3720
aggacgacga agggcatctt caatttcttg tgaggaggcc ttagaaacgt caattttgca    3780
caattcaata cgaccttcag aagggacttc tttaggtttg gattcttctt taggttgttc    3840
cttggtgtat cctggcttgg catctccttt ccttctagtg acctttaggg acttcatatc    3900
caggtttctc tccacctcgt ccaacgtcac accgtacttg gcacatctaa ctaatgcaaa    3960
ataaaataag tcagcacatt cccaggctat atcttccttg gatttagctt ctgcaagttc    4020
atcagcttcc tccctaattt tagcgttcaa acaaaacttg gtcgtcaaat aaccgtttgg    4080
tataagaacc ttctggagca ttgctcttac gatcccacaa ggtgcttcca tggctctaag    4140
acccttcgat tggccaaaac aggaagtgcg ttcaagtga cagaaaccaa cacctgtttg     4200
ttcaaccaca aatttcaagc agtctccatc acaatccaat tcgatacccca gcaacttttg   4260 agttcgtcca gatgtagcac ctttatacca caaaccgtga cgacgagatt ggtagactcc    4320
agtttgtgtc cttatagcct ccggaataga cttttttggac gagtacacca ggcccaacga   4380
gtaattagaa gagtcagcca ccaaagtagt gaatagacca tcggggcggt cagtagtcaa    4440
agacgccaac aaaatttcac tgacagggaa cttttttgaca tcttcagaaa gttcgtattc    4500
agtagtcaat tgccgagcat caataatggg gattatacca gaagcaacag tggaagtcac    4560
atctaccaac tttgcggtct cagaaaaagc ataaacagtt ctactaccgc cattagtgaa   4620 actttttcaaa tcgcccagtg gagaagaaaa aggcacagcg atactagcat tagcgggcaa   4680
ggatgcaact ttatcaacca gggtcctata gataacccta gcgcctggga tcatcctttg    4740
gacaactctt tctgccaaat ctaggtccaa aatcacttca ttgataccat tattgtacaa    4800
cttgagcaag ttgtcgatca gctcctcaaa ttggtcctct gtaacggatg actcaacttg    4860
cacattaact tgaagctcag tcgattgagt gaacttgatc aggttgtgca gctggtcagc    4920
agcataggga aacacggctt ttcctaccaa actcaaggaa ttatcaaact ctgcaacact    4980
tgcgtatgca ggtagcaagg gaaatgtcat acttgaagtc ggacagtgag tgtagtcttg    5040
agaaattctg aagccgtatt tttattatca gtgagtcagt catcaggaga tcctctacgc    5100
cggacgcatc gtggccgacc tgcaggtcgg catcaccggc gccacaggtg cggttgctgg    5160
cgcctatatc gccgacatca ccgatgggga agatcgggct cgccacttcg ggctcatgag    5220
cgcttgtttc ggcgtgggta tggtggcagg ccccgtggcc gggggactgt gggcgccat    5280 ctccttggac ctgcaggggg gggggggaa agccacgttg tgtctcaaaa tctctgatgt    5340
tacattgcac aagataaaaa tatatcatca tgaacaataa aactgtctgc ttacataaac    5400
agtaatacaa ggggtgttat gagccatatt caacgggaaa cgtcttgctc aaggccgcga    5460
ttaaattcca acatggatgc tgatttatat gggtataaat gggctcgcga taatgtcggg    5520
caatcaggtg cgacaatcta tcgattgtat gggaagcccg atgcgccaga gttgtttctg    5580
aaacatggca aaggtagcgt tgccaatgat gttacagatg atggtcag actaaactgg      5640 ctgacggaat ttatgcctct tccgaccatc aagcatttta tccgtactcc tgatgatgca    5700
tggttactca ccactgcgat ccccgggaaa acagcattcc aggtattaga agaatatcct    5760
gattcaggtg aaaatattgt tgatgcgctg gcagtgttcc tgcgccggtt gcattcgatt    5820
cctgtttgta attgtccttt taacagcgat cgcgtatttc gtctcgctca ggcgcaatca    5880
cgaatgaata acggtttggt tgatgcgagt gattttgatg acgagcgtaa tggctggcct    5940
gttgaacaag tctggaaaga aatgcataag cttttgccat tctcaccgga ttcagtcgtc    6000
```

```
actcatggtg atttctcact tgataacctt attttgacg aggggaaatt aataggttgt    6060
attgatgttg gacgagtcgg aatcgcagac cgataccagg atcttgccat cctatggaac    6120
tgcctcggtg agttttctcc ttcattacag aaacggcttt ttcaaaaata tggtattgat    6180
aatcctgata tgaataaatt gcagtttcat ttgatgctcg atgagttttt ctaatcagaa    6240
ttggttaatt ggttgtaaca ctggcagagc attacgctga cttgacggga cggcggcttt    6300
gttgaataaa tcgaactttt gctgagttga aggatcagat cacgcatctt cccgacaacg    6360
cagaccgttc cgtggcaaag caaaagttca aaatcaccaa ctggtccacc tacaacaaag    6420
ctctcatcaa ccgtggctcc ctcactttct ggctggatga tggggcgatt caggcctggt    6480
atgagtcagc aacaccttct tcacgaggca gacctcagcg ccccccccc cctgcaggtc    6540
ccacggcggc ggtgctcaac ggcctcaacc tactactggg ctgcttccta atgcaggagt    6600
cgcataaggg agagcgtcga gtatctatga ttggaagtat gggaatggtg atacccgcat    6660
tcttcagtgt cttgaggtct cctatcagat tatgcccaac taaagcaacc ggaggaggag    6720
atttcatggt aaatttctct gacttttggt catcagtaga ctcgaactgt gagactatct    6780
cggttatgac agcagaaatg tccttcttgg agacagtaaa tgaagtccca ccaataaaga    6840
aatccttgtt atcaggaaca aacttcttgt ttcgaacttt ttcggtgcct tgaactataa    6900
aatgtagagt ggatatgtcg ggtaggaatg gagcgggcaa atgcttacct tctggacctt    6960
caagaggtat gtagggtttg tagatactga tgccaacttc agtgacaacg ttgctatttc    7020
gttcaaacca ttccgaatcc agagaaatca aagttgtttg tctactattg atccaagcca    7080
gtgcggtctt gaaactgaca atagtgtgct cgtgttttga ggtcatcttt gtatgaataa    7140
atctagtctt tgatctaaat aatcttgacg agccaaggcg ataaataccc aaatctaaaa    7200
ctctttaaa acgttaaaag gacaagtatg tctgcctgta ttaaaccccca aatcagctcg    7260
tagtctgatc ctcatcaact tgaggggcac tatcttgttt tagagaaatt tgcggagatg    7320
cgatatcgag aaaaaggtac gctgatttta aacgtgaaat ttatctcaag atctctgcct    7380
cgcgcgtttc ggtgatgacg gtgaaaacct ctgacacatg cagctcccgg agacggtcac    7440
agcttgtctg taagcggatg ccgggagcag acaagcccgt cagggcgcgt cagcgggtgt    7500
tggcgggtgt cggggcgcag ccatgaccca gtcacgtagc gatagcggag tgtatactgg    7560
cttaactatg cggcatcaga gcagattgta ctgagagtgc accatatgcg gtgtgaaata    7620
ccgcacagat gcgtaaggag aaaataccgc atcaggcgct cttccgcttc ctcgctcact    7680
gactcgctgc gctcggtcgt tcggctgcgg cgagcggtat cagctcactc aaaggcggta    7740
atacggttat ccacagaatc agggggataac gcaggaaaga acatgtgagc aaaaggccag    7800
caaaaggcca ggaaccgtaa aaaggccgcg ttgctggcgt ttttccatag gctccgcccc    7860
cctgacgagc atcacaaaaa tcgacgctca agtcagaggt ggcgaaaccc gacaggacta    7920
taaagatacc aggcgtttcc ccctggaagc tccctcgtgc gctctcctgt tccgaccctg    7980
ccgcttaccg gatacctgtc cgcctttctc ccttcgggaa gcgtggcgct ttctcaatgc    8040
tcacgctgta ggtatctcag ttcggtgtag tcgttcgct ccaagctggg ctgtgtgcac    8100
gaaccccccg ttcagcccga ccgctgcgcc ttatccggta actatcgtct tgagtccaac    8160
ccggtaagac acgacttatc gccactggca gcagccactg gtaacaggat tagcagagcg    8220
aggtatgtag gcggtgctac agagttcttg aagtggtggc ctaactacgg ctacactaga    8280
aggacagtat ttggtatctg cgctctgctg aagccagtta ccttcggaaa aagagttggt    8340
```

-continued

```
agctcttgat ccggcaaaca aaccaccgct ggtagcggtg gttttttttgt ttgcaagcag    8400
cagattacgc gcagaaaaaa aggatctcaa gaagatcctt tgatcttttc tacggggtct    8460
gacgctcagt ggaacgaaaa ctcacgttaa gggattttgg tcatgagatt atcaaaaagg    8520
atcttcacct agatcctttt aaattaaaaa tgaagtttta atcaatcta aagtatatat    8580
gagtaaactt ggtctgacag ttaccaatgc ttaatcagtg aggcacctat ctcagcgatc    8640
tgtctatttc gttcatccat agttgcctga ctccccgtcg tgtagataac tacgatacgg    8700
gagggcttac catctggccc cagtgctgca atgataccgc gagacccacg ctcaccggct    8760
ccagatttat cagcaataaa ccagccagcc ggaagggccg agcgcagaag tggtcctgca    8820
actttatccg cctccatcca gtctattaat tgttgccggg aagctagagt aagtagttcg    8880
ccagttaata gtttgcgcaa cgttgttgcc attgctgcag gcatcgtggt gtcacgctcg    8940
tcgtttggta tggcttcatt cagctccggt tcccaacgat caaggcgagt tacatgatcc    9000
cccatgttgt gcaaaaaagc ggttagctcc ttcggtcctc cgatcgttgt cagaagtaag    9060
ttggccgcag tgttatcact catggttatg gcagcactgc ataattctct tactgtcatg    9120
ccatccgtaa gatgcttttc tgtgactggt gagtactcaa ccaagtcatt ctgagaatag    9180
tgtatgcggc gaccgagttg ctcttgcccg gcgtcaacac gggataatac cgcgccacat    9240
agcagaactt taaaagtgct catcattgga aaacgttctt cggggcgaaa actctcaagg    9300
atcttaccgc tgttgagatc cagttcgatg taacccactc gtgcacccaa ctgatcttca    9360
gcatctttta ctttcaccag cgtttctggg tgagcaaaaa caggaaggca aaatgccgca    9420
aaaaagggaa taagggcgac acggaaatgt tgaatactca tactcttcct ttttcaatat    9480
tattgaagca tttatcaggg ttattgtctc atgagcggat acatatttga atgtatttag    9540
aaaaataaac aaataggggt tccgcgcaca tttccccgaa aagtgccacc tgacgtctaa    9600
gaaaccatta ttatcatgac attaacctat aaaaataggc gtatcacgag gccctttcgt    9660
cttcaagaat taattctcat gtttgacagc ttatcatcga taagctgact catgttggta    9720
ttgtgaaata gacgcagatc gggaacactg aaaaataaca gttattattc gagatc        9776
```

<210> SEQ ID NO 81
<211> LENGTH: 10491
<212> TYPE: DNA
<213> ORGANISM: Homo sapiens

<400> SEQUENCE: 81

```
gatctaacat ccaaagacga aaggttgaat gaaacctttt tgccatccga catccacagg      60
tccattctca cacataagtg ccaaacgcaa caggagggga tacactagca gcagaccgtt     120
gcaaacgcag gacctccact cctcttctcc tcaacaccca cttttgccat cgaaaaacca     180
gcccagttat tgggcttgat tggagctcgc tcattccaat tccttctatt aggctactaa     240
caccatgact ttattagcct gtctatcctg gccccctgg cgaggttcat gtttgtttat     300
ttccgaatgc aacaagctcc gcattacacc cgaacatcac tccagatgag ggctttctga     360
gtgtggggtc aaatagtttc atgttcccca aatggcccaa aactgacagt ttaaacgctg     420
tcttggaacc taatatgaca aaagcgtgat ctcatccaag atgaactaag tttggttcgt     480
tgaaatgcta acggcagtt ggtcaaaaag aaacttccaa aagtcgccat accgtttgtc     540
ttgtttggta ttgattgacg aatgctcaaa ataatctca ttaatgctta gcgcagtctc     600
tctatcgctt ctgaacccg gtgcacctgt gccgaaacgc aaatggggaa acacccgctt     660
tttggatgat tatgcattgt ctccacattg tatgcttcca agattctggt gggaatactg     720
```

```
ctgatagcct aacgttcatg atcaaaattt aactgttcta acccctactt gacagcaata    780
tataaacaga aggaagctgc cctgtcttaa accttttttt tatcatcatt attagcttac    840
tttcataatt gcgactggtt ccaattgaca agcttttgat tttaacgact tttaacgaca    900
acttgagaag atcaaaaaac aactaattat tcgaaggatc caaacgatga gatttccttc    960
aattttttact gcagttttat tcgcagcatc ctccgcatta gctgctccag tcaacactac   1020
aacagaagat gaaacggcac aaattccggc tgaagctgtc atcggttact cagatttaga   1080
agggatttc gatgttgctg ttttgccatt ttccaacagc acaaataacg ggttattgtt    1140
tataaatact actattgcca gcattgctgc taaagaagaa ggggtatctc tcgagaaaag   1200
atgcggaccg ggcaggggt tcgggaagag gaggcacccc aaaaagctga cccctttagc    1260
ctacaagcag tttatcccca atgtggccga aagacccta ggcgccagcg aaggtatga     1320
agggaagatc tccagaaact ccgagcgatt taaggaactc accccaatt acaaccccga    1380
catcatattt aaggatgaag aaaacaccgg agcggacagg ctgatgactc agaggtgtaa   1440
ggacaagttg aacgctttgg ccatctcggt gatgaaccag tggccaggag tgaaactgcg   1500
ggtgaccgag ggctgggacg aagatggcca ccactcagag gagtctctgc actacgaggg   1560
ccgcgcagtg gacatcacca cgtctgaccg cgaccgcagc aagtacggca tgctggcccg   1620
cctggcggtg gaggccggct cgactgggt gtactacgag tccaaggcac atatccactg   1680
ctcggtgaaa gcagagaact cggtggcggc caaatcggga ggcgtcgacg tgcccaggga   1740
ttgtggttgt aagccttgca tatgtacagt cccagaagta tcatctgtct tcatcttccc   1800
cccaaagccc aaggatgtgc tcaccattac tctgactcct aaggtcacgt gtgttgtggt   1860
agacatcagc aaggatgatc ccgaggtcca gttcagctgg tttgtagatg atgtggaggt   1920
gcacacagct cagacgcaac cacgggaaga gcagttccaa agcactttcc gctcagtcag   1980
tgaacttccc atcatgcacc aggactggct caatggcaag gagttcaaat gcagggtcaa   2040
cagtgcagct ttccctgccc ccatcgagaa aaccatctcc aaaaccaaag gcagaccgaa   2100
ggctccacag gtgtacacca ttccacctcc caaggagcag atggccaagg ataaagtcag   2160
tctgacctgc atgataacag acttcttccc tgaagacatt actgtggagt ggcagtggaa   2220
tgggcagcca gcggagaact acaagaacac tcagcccatc atggacacag atggctctta   2280
cttcgtctac agcaagctca atgtgcagaa gagcaactgg gaggcaggaa atactttcac   2340
ctgctctgtg ttacatgagg gcctgcacaa ccaccatact gagaagagcc tctcccactc   2400
tcctggtaaa tgatcccagt gtccttggag ccctctggtc ctacagcggc cgcgaattaa   2460
ttcgccttag acatgactgt tcctcagttc aagttgggca cttacgagaa gaccggtctt   2520
gctagattct aatcaagagg atgtcagaat gccatttgcc tgagagatgc aggcttcatt   2580
tttgatactt ttttatttgt aacctatata gtataggatt ttttttgtca ttttgtttct   2640
tctcgtacga gcttgctcct gatcagccta tctcgcagct gatgaatatc ttgtggtagg   2700
ggtttgggaa aatcattcga gtttgatgtt tttcttggta tttcccactc ctcttcagag   2760
tacagaagat taagtgagaa gttcgtttgt gcaagcttat cgataagctt taatgcggta   2820
gtttatcaca gttaaattgc taacgcagtc aggcaccgtg tatgaaatct aacaatgcgc   2880
tcatcgtcat cctcggcacc gtcaccctgg atgctgtagg cataggcttg gttatgccgg   2940
tactgccggg cctcttgcgg gatatcgtcc attccgacag catcgccagt cactatggcg   3000
tgctgctagc gctatatgcg ttgatgcaat ttctatgcgc acccgttctc ggagcactgt   3060
```

```
ccgaccgctt tggccgccgc ccagtcctgc tcgcttcgct acttggagcc actatcgact   3120
acgcgatcat ggcgaccaca cccgtcctgt ggatctatcg aatctaaatg taagttaaaa   3180
tctctaaata attaaataag tcccagtttc tccatacgaa ccttaacagc attgcggtga   3240
gcatctagac cttcaacagc agccagatcc atcactgctt ggccaatatg tttcagtccc   3300
tcaggagtta cgtcttgtga agtgatgaac ttctggaagg ttgcagtgtt aactccgctg   3360
tattgacggg catatccgta cgttggcaaa gtgtggttgg taccgagga gtaatctcca    3420
caactctctg gagagtaggc accaacaaac acagatccag cgtgttgtac ttgatcaaca   3480
taagaagaag cattctcgat ttgcaggatc aagtgttcag gagcgtactg attggacatt   3540
tccaaagcct gctcgtaggt tgcaaccgat agggttgtag agtgtgcaat acacttgcgt   3600
acaatttcaa cccttggcaa ctgcacagct tggttgtgaa cagcatcttc aattctggca   3660
agctccttgt ctgtcatatc gacagccaac agaatcacct gggaatcaat accatgttca   3720
gcttgagcag aaggtctgag gcaacgaaat ctggatcagc gtatttatca gcaataacta   3780
gaacttcaga aggcccagca ggcatgtcaa tactacacag ggctgatgtg tcattttgaa   3840
ccatcatctt ggcagcagta acgaactggt ttcctggacc aaatattttg tcacacttag   3900
gaacagtttc tgttccgtaa gccatagcag ctactgcctg ggcgcctcct gctagcacga   3960
tacacttagc accaaccttg tgggcaacgt agatgacttc tggggtaagg gtaccatcct   4020
tcttaggtgg agatgcaaaa acaatttctt tgcaaccagc aactttggca ggaacaccca   4080
gcatcaggga agtggaaggc agaattgcgg ttccaccagg aatatagagg ccaactttct   4140
caataggtct tgcaaaacga gagcagacta caccagggca agtctcaact tgcaacgtct   4200
ccgttagttg agcttcatgg aatttcctga cgttatctat agagagatca atggctctct   4260
taacgttatc tggcaattgc ataagttcct ctgggaaagg agcttctaac acaggtgtct   4320
tcaaagcgac tccatcaaac ttggcagtta gttctaaaag gctttgtca ccattttgac    4380
gaacattgtc gacaattggt ttgactaatt ccataatctg ttccgttttc tggataggac   4440
gacgaagggc atcttcaatt tcttgtgagg aggccttaga aacgtcaatt ttgcacaatt   4500
caatacgacc ttcagaaggg acttctttag gtttggattc ttctttaggt tgttccttgg   4560
tgtatcctgg cttggcatct cctttccttc tagtgacctt tagggacttc atatccaggt   4620
ttctctccac ctcgtccaac gtcacaccgt acttggcaca tctaactaat gcaaaataaa   4680
ataagtcagc acattcccag gctatatctt ccttggattt agcttctgca agttcatcag   4740
cttcctccct aattttagcg ttcaaacaaa acttcgtcgt caaataaccg tttggtataa   4800
gaaccttctg gagcattgct cttacgatcc cacaaggtgc ttccatggct ctaagaccct   4860
ttgattggcc aaaacaggaa gtgcgttcca agtgacagaa accaacacct gtttgttcaa   4920
ccacaaattt caagcagtct ccatcacaat ccaattcgat acccagcaac ttttgagttc   4980
gtccagatgt agcaccttta taccacaaac cgtgacgacg agattggtag actccagttt   5040
gtgtccttat agcctccgga atagactttt tggacgagta caccaggccc aacgagtaat   5100
tagaagagtc agccaccaaa gtagtgaata gaccatcggg gcggtcagta gtcaaagacg   5160
ccaacaaaat ttcactgaca gggaaccttt tgacatcttc agaaagttcg tattcagtag   5220
tcaattgccg agcatcaata atggggatta taccagaagc aacagtggaa gtcacatcta   5280
ccaactttgc ggtctcagaa aaagcataaa cagttctact accgccatta gtgaaacttt   5340
tcaaatcgcc cagtgagaa gaaaaaggca cagccgatact agcattagcg ggcaaggatg    5400
caactttatc aaccagggtc ctatagataa ccctagcgcc tgggatcatc ctttggacaa   5460
```

```
ctctttctgc caaatctagg tccaaaatca cttcattgat accattattg tacaacttga   5520
gcaagttgtc gatcagctcc tcaaattggt cctctgtaac ggatgactca acttgcacat   5580
taacttgaag ctcagtcgat tgagtgaact tgatcaggtt gtgcagctgg tcagcagcat   5640
agggaaacac ggcttttcct accaaactca aggaattatc aaactctgca acacttgcgt   5700
atgcaggtag caagggaaat gtcatacttg aagtcggaca gtgagtgtag tcttgagaaa   5760
ttctgaagcc gtattttat tatcagtgag tcagtcatca ggagatcctc tacgccggac    5820
gcatcgtggc cgacctgcag gtcggcatca ccggcgccac aggtgcggtt gctggcgcct   5880
atatcgccga catcaccgat ggggaagatc gggctcgcca cttcgggctc atgagcgctt   5940
gtttcggcgt gggtatggtg gcaggccccg tggccggggg actgttgggc gccatctcct   6000
tggacctgca ggggggggg gggaaagcca cgttgtgtct caaaatctct gatgttacat    6060
tgcacaagat aaaatatat catcatgaac aataaaactg tctgcttaca taaacagtaa    6120
tacaaggggt gttatgagcc atattcaacg ggaaacgtct tgctcaaggc cgcgattaaa   6180
ttccaacatg gatgctgatt tatatgggta taaatgggct cgcgataatg tcggcaatc    6240
aggtgcgaca atctatcgat tgtatgggaa gcccgatgcg ccagagttgt ttctgaaaca   6300
tggcaaaggt agcgttgcca atgatgttac agatgagatg gtcagactaa actggctgac   6360
ggaatttatg cctcttccga ccatcaagca ttttatccgt actcctgatg atgcatggtt   6420
actcaccact gcgatcccg ggaaaacagc attccaggta ttagaagaat atcctgattc    6480
aggtgaaaat attgttgatg cgctggcagt gttcctgcgc cggttgcatt cgattcctgt   6540
ttgtaattgt ccttttaaca gcgatcgcgt atttcgtctc gctcaggcgc aatcacgaat   6600
gaataacggt ttggttgatg cgagtgattt tgatgacgag cgtaatggct ggcctgttga   6660
acaagtctgg aaagaaatgc ataagctttt gccattctca ccggattcag tcgtcactca   6720
tggtgatttc tcacttgata accttatttt tgacgagggg aaattaatag gttgtattga   6780
tgttggacga gtcggaatcg cagaccgata ccaggatctt gccatcctat ggaactgcct   6840
cggtgagttt tctccttcat tacagaaacg gcttttcaa aaatatggta ttgataatcc    6900
tgatatgaat aaattgcagt ttcatttgat gctcgatgag ttttctaat cagaattggt    6960
taattggttg taacactggc agagcattac gctgacttga cgggacggcg gctttgttga   7020
ataaatcgaa cttttgctga gttgaaggat cagatcacgc atcttcccga caacgcagac   7080
cgttccgtgg caaagcaaaa gttcaaaatc accaactggt ccacctacaa caaagctctc   7140
atcaaccgtg gctccctcac tttctggctg gatgatgggg cgattcaggc ctggtatgag   7200
tcagcaacac cttcttcacg aggcagacct cagcgccccc cccccctgc aggtcccacg    7260
gcggcggtgc tcaacggcct caacctacta ctgggctgct tcctaatgca ggagtcgcat   7320
aagggagagc gtcgagtatc tatgattgga agtatgggaa tggtgatacc cgcattcttc   7380
agtgtcttga ggtctcctat cagattatgc ccaactaaag caaccggagg aggagatttc   7440
atggtaaatt tctctgactt ttggtcatca gtagactcga actgtgagac tatctcggtt   7500
atgacagcag aaatgtcctt cttggagaca gtaaatgaag tcccaccaat aaagaaatcc   7560
ttgttatcag gaacaaactt cttgtttcga acttttcgg tgccttgaac tataaaatgt    7620
agagtggata tgtcgggtag gaatggagcg ggcaaatgct taccttctgg accttcaaga   7680
ggtatgtagg gtttgtagat actgatgcca acttcagtga caacgttgct atttcgttca   7740
aaccattccg aatccagaga aatcaaagtt gtttgtctac tattgatcca agccagtgcg   7800
```

```
gtcttgaaac tgacaatagt gtgctcgtgt tttgaggtca tctttgtatg aataaatcta    7860
gtctttgatc taaataatct tgacgagcca aggcgataaa tacccaaatc taaaactctt    7920
ttaaaacgtt aaaaggacaa gtatgtctgc ctgtattaaa ccccaaatca gctcgtagtc    7980
tgatcctcat caacttgagg ggcactatct tgttttagag aaatttgcgg agatgcgata    8040
tcgagaaaaa ggtacgctga ttttaaacgt gaaatttatc tcaagatctc tgcctcgcgc    8100
gtttcggtga tgacggtgaa aacctctgac acatgcagct cccggagacg gtcacagctt    8160
gtctgtaagc ggatgccggg agcagacaag cccgtcaggg cgcgtcagcg ggtgttggcg    8220
ggtgtcgggg cgcagccatg acccagtcac gtagcgatag cggagtgtat actggcttaa    8280
ctatgcggca tcagagcaga ttgtactgag agtgcaccat atgcggtgtg aaataccgca    8340
cagatgcgta aggagaaaat accgcatcag gcgctcttcc gcttcctcgc tcactgactc    8400
gctgcgctcg gtcgttcggc tgcggcgagc ggtatcagct cactcaaagg cggtaatacg    8460
gttatccaca gaatcagggg ataacgcagg aaagaacatg tgagcaaaag gccagcaaaa    8520
ggccaggaac cgtaaaaagg ccgcgttgct ggcgtttttc cataggctcc gcccccctga    8580
cgagcatcac aaaaatcgac gctcaagtca gaggtggcga aacccgacag gactataaag    8640
ataccaggcg tttccccctg gaagctccct cgtgcgctct cctgttccga ccctgccgct    8700
taccggatac ctgtccgcct ttctcccttc gggaagcgtg gcgctttctc aatgctcacg    8760
ctgtaggtat ctcagttcgg tgtaggtcgt tcgctccaag ctgggctgtg tgcacgaacc    8820 cccgttcag cccgaccgct gcgccttatc cggtaactat cgtcttgagt ccaacccggt    8880
aagacacgac ttatcgccac tggcagcagc cactggtaac aggattagca gagcgaggta    8940
tgtaggcggt gctacagagt tcttgaagtg gtggcctaac tacggctaca ctagaaggac    9000
agtatttggt atctgcgctc tgctgaagcc agttaccttc ggaaaaagag ttggtagctc    9060
ttgatccggc aaacaaacca ccgctggtag cggtggtttt tttgtttgca agcagcagat    9120
tacgcgcaga aaaaaggat ctcaagaaga tcctttgatc ttttctacgg ggtctgacgc    9180
tcagtggaac gaaaactcac gttaagggat tttggtcatg agattatcaa aaaggatctt    9240
cacctagatc cttttaaatt aaaaatgaag ttttaaatca atctaaagta tatatgagta    9300
aacttggtct gacagttacc aatgcttaat cagtgaggca cctatctcag cgatctgtct    9360
atttcgttca tccatagttg cctgactccc cgtcgtgtag ataactacga tacgggaggg    9420
cttaccatct ggccccagtg ctgcaatgat accgcgagac ccacgctcac cggctccaga    9480
tttatcagca ataaaccagc cagccggaag ggccgagcgc agaagtggtc ctgcaacttt    9540
atccgcctcc atccagtcta ttaattgttg ccgggaagct agagtaagta gttcgccagt    9600
taatagtttg cgcaacgttg ttgccattgc tgcaggcatc gtggtgtcac gctcgtcgtt    9660
tggtatggct tcattcagct ccggttccca acgatcaagg cgagttacat gatcccccat    9720
gttgtgcaaa aaagcggtta gctccttcgg tcctccgatc gttgtcagaa gtaagttggc    9780
cgcagtgtta tcactcatgg ttatggcagc actgcataat tctcttactg tcatgccatc    9840
cgtaagatgc ttttctgtga ctggtgagta ctcaaccaag tcattctgag aatagtgtat    9900
gcggcgaccg agttgctctt gcccggcgtc aacacgggat aataccgcgc cacatagcag    9960
aactttaaaa gtgctcatca ttggaaaacg ttcttcgggg cgaaaactct caaggatctt   10020
accgctgttg agatccagtt cgatgtaacc cactcgtgca cccaactgat cttcagcatc   10080
ttttactttc accagcgttt ctgggtgagc aaaaacagga aggcaaaatg ccgcaaaaaa   10140
gggaataagg gcgacacgga aatgttgaat actcatactc ttcctttttc aatattattg   10200
```

```
aagcatttat cagggttatt gtctcatgag cggatacata tttgaatgta tttagaaaaa   10260
taaacaaata ggggttccgc gcacatttcc ccgaaaagtg ccacctgacg tctaagaaac   10320
cattattatc atgacattaa cctataaaaa taggcgtatc acgaggccct tcgtcttca    10380 agaattaatt ctcatgtttg acagcttatc atcgataagc tgactcatgt tggtattgtg   10440
aaatagacgc agatcgggaa cactgaaaaa taacagttat tattcgagat c            10491
```

<210> SEQ ID NO 82
<211> LENGTH: 10512
<212> TYPE: DNA
<213> ORGANISM: Homo sapiens

<400> SEQUENCE: 82

```
gatctaacat ccaaagacga aaggttgaat gaaaccttt tgccatccga catccacagg      60
tccattctca cacataagtg ccaaacgcaa caggaggga tacactagca gcagaccgtt     120
gcaaacgcag gacctccact cctcttctcc tcaacaccca cttttgccat cgaaaaacca    180
gcccagttat tgggcttgat tggagctcgc tcattccaat tccttctatt aggctactaa    240
caccatgact ttattagcct gtctatcctg gcccccctgg cgaggttcat gtttgtttat    300
ttccgaatgc aacaagctcc gcattacacc cgaacatcac tccagatgag ggctttctga    360 gtgtgggtc aaatagtttc atgttcccca aatgggccaa aactgacagt ttaaacgctg     420
tcttggaacc taatatgaca aaagcgtgat ctcatccaag atgaactaag tttggttcgt    480
tgaaatgcta acggccagtt ggtcaaaaag aaacttccaa aagtcgccat accgtttgtc    540
ttgtttggta ttgattgacg aatgctcaaa aataatctca ttaatgctta gcgcagtctc    600
tctatcgctt ctgaaccccg gtgcacctgt gccgaaacgc aaatgggaa acacccgctt     660 tttggatgat tatgcattgt ctccacattg tatgcttcca agattctggt gggaatactg    720
ctgatagcct aacgttcatg atcaaaattt aactgttcta acccctactt gacagcaata    780
tataaacaga aggaagctgc cctgtcttaa acctttttt ttatcatcat tattagctta     840 cttctcataat tgcgactggt tccaattgac aagcttttga ttttaacgac ttttaacgac    900
aacttgagaa gatcaaaaaa caactaatta ttcgaaggat ccaaacgatg agatttcctt    960 caattttac tgcagtttta ttcgcagcat cctccgcatt agctgctcca gtcaacacta   1020
caacagaaga tgaaacggca caaattccgg ctgaagctgt catcggttac tcagatttag   1080 aagggggattt cgatgttgct gttttgccat tttccaacag cacaaataac gggttattgt   1140
ttataaatac tactattgcc agcattgctg ctaaagaaga aggggtatct ctcgagaaaa   1200
gatgcggacc gggcaggggg ttcgggaaga ggaggcaccc caaaagctg accccttag      1260 cctacaagca gtttatcccc aatgtggccg agaagaccct aggcgccagc ggaaggtatg   1320
aagggaagat ctccagaaac tccgagcgat taaggaact cacccccaat tacaaccccg    1380
acatcatatt taaggatgaa gaaaacaccg gagcggacag gctgatgact cagaggtgta   1440
aggacaagtt gaacgctttg gccatctcgg tgatgaacca gtggccagga gtgaaactgc   1500
gggtgaccga gggctgggac gaagatggcc accactcaga ggagtctctg cactacgagg   1560
gccgcgcagt ggacatcacc acgtctgacc gcgaccgcag caagtacggc atgctggccc   1620
gcctggcggt ggaggccggc ttcgactggg tgtactacga gtccaaggca catatccact   1680
gctcggtgaa agcagagaac tcggtggcgg ccaaatcggg aggcgtcgac cccgagggc    1740 ccacaatcaa gccctgtcct ccatgcaaat gcccagcacc taacctcttg ggtggaccat   1800
```

```
ccgtcttcat cttccctcca aagatcaagg atgtactcat gatctccctg agccccatag    1860
tcacatgtgt ggtggtggat gtgagcgagg atgacccaga tgtccagatc agctggtttg    1920
tgaacaacgt ggaagtacac acagctcaga cacaaaccca tagagaggat taccaaagta    1980
cacttcgggt ggtcagtgcc ctccccatcc agcaccagga ctggatgagt ggcaaggagt    2040
tcaaatgcaa ggtcaacaac aaagacctcc cagcgcccat cgagagaacc atctcaaaac    2100
ccaaagggtc agtaagagct ccacaggtat atgtcttgcc tccaccagaa gaagagatga    2160
ctaagaaaca ggtcactctg acctgcatgg tgacagactt catgcctgaa gacatttacg    2220
tggagtggac caacaacggg aaaacagagc taaactacaa gaacactgaa ccagtcctgg    2280
actctgatgg ttcttacttc atgtacagca agctgagagt ggaaaagaag aactgggtgg    2340 aaagaaaatag ctactcctgt tcagtggtcc acgagggtct gcacaatcac cacacgacta    2400
agagcttctc ccggactccg ggtaaatgag ctcagatcga ttccatggat cctcacatcc    2460
caatccgcgg ccgcgaatta attcgcctta gacatgactg ttcctcagtt caagttgggc    2520
acttacgaga agaccggtct tgctagattc taatcaagag gatgtcagaa tgccatttgc    2580
ctgagagatg caggcttcat ttttgatact ttttatttg taacctatat agtataggat    2640
tttttttgtc attttgtttc ttctcgtacg agcttgctcc tgatcagcct atctcgcagc    2700
tgatgaatat cttgtggtag gggtttggga aaatcattcg agtttgatgt ttttcttggt    2760
atttcccact cctcttcaga gtacagaaga ttaagtgaga agttcgtttg tgcaagctta    2820
tcgataagct ttaatgcggt agtttatcac agttaaattg ctaacgcagt caggcaccgt    2880
gtatgaaatc taacaatgcg ctcatcgtca tcctcggcac cgtcaccctg gatgctgtag    2940
gcataggctt ggttatgccg gtactgccgg gcctcttgcg ggatatcgtc cattccgaca    3000
gcatcgccag tcactatggc gtgctgctag cgctatatgc gttgatgcaa tttctatgcg    3060
cacccgttct cggagcactg tccgaccgct ttggccgccg cccagtcctg ctcgcttcgc    3120
tacttggagc cactatcgac tacgcgatca tggcgaccac accgtcctg tggatctatc    3180 gaatctaaat gtaagttaaa atctctaaat aattaaataa gtcccagttt ctccatacga    3240
accttaacag cattgcggtg agcatctaga ccttcaacag cagccagatc catcactgct    3300
tggccaatat gtttcagtcc ctcaggagtt acgtcttgtg aagtgatgaa cttctggaag    3360
gttgcagtgt taactccgct gtattgacgg gcatatccgt acgttggcaa agtgtggttg    3420
gtaccggagg agtaatctcc acaactctct ggagagtagg caccaacaaa cacagatcca    3480
gcgtgttgta cttgatcaac ataagaagaa gcattctcga tttgcaggat caagtgttca    3540
ggagcgtact gattggacat ttccaaagcc tgctcgtagg ttgcaaccga tagggttgta    3600
gagtgtgcaa tacacttgcg tacaatttca acccttggca actgcacagc ttggttgtga    3660
acagcatctt caattctggc aagctccttg tctgtcatat cgacagccaa cagaatcacc    3720
tgggaatcaa taccatgttc agcttgagca gaaggtctga ggcaacgaaa tctggatcag    3780
cgtatttatc agcaataact agaacttcag aaggcccagc aggcatgtca atactacaca    3840
gggctgatgt gtcattttga accatcatct tggcagcagt aacgaactgg tttcctggac    3900
caaatatttt gtcacactta ggaacagttt ctgttccgta agccatagca gctactgcct    3960
gggcgcctcc tgctagcacg atacacttag caccaacctt gtgggcaacg tagatgactt    4020
ctggggtaag ggtaccatcc ttcttaggtg gagatgcaaa acaatttct ttgcaaccag    4080 caactttggc aggaacaccc agcatcaggg aagtggaagg cagaattgcg gttccaccag    4140
gaatatagag gccaactttc tcaataggtc ttgcaaaacg agagcagact acaccagggc    4200
```

```
aagtctcaac ttgcaacgtc tccgttagtt gagcttcatg gaatttcctg acgttatcta   4260
tagagagatc aatggctctc ttaacgttat ctggcaattg cataagttcc tctgggaaag   4320
gagcttctaa cacaggtgtc ttcaaagcga ctccatcaaa cttggcagtt agttctaaaa   4380
gggctttgtc accatttga cgaacattgt cgacaattgg tttgactaat tccataatct    4440
gttccgtttt ctggatagga cgacgaaggg catcttcaat ttcttgtgag gaggccttag   4500
aaacgtcaat tttgcacaat tcaatacgac cttcagaagg gacttcttta ggtttggatt   4560
cttctttagg ttgttccttg gtgtatcctg gcttggcatc tcctttcctt ctagtgacct   4620
ttagggactt catatccagg tttctctcca cctcgtccaa cgtcacaccg tacttggcac   4680
atctaactaa tgcaaaataa aataagtcag cacattccca ggctatatct tccttggatt   4740
tagcttctgc aagttcatca gcttcctccc taattttagc gttcaaacaa aacttcgtcg   4800
tcaaataacc gtttggtata agaaccttct ggagcattgc tcttacgatc ccacaaggtg   4860
cttccatggc tctaagaccc tttgattggc caaaacagga agtgcgttcc aagtgacaga   4920
aaccaacacc tgtttgttca accacaaatt tcaagcagtc tccatcacaa tccaattcga   4980
tacccagcaa cttttgagtt cgtccagatg tagcacctt ataccacaaa ccgtgacgac    5040
gagattggta gactccagtt tgtgtcctta tagcctccgg aatagactt ttggacgagt    5100 acaccaggcc caacgagtaa ttagaagagt cagccaccaa agtagtgaat agaccatcgg   5160
ggcggtcagt agtcaaagac gccaacaaaa tttcactgac agggaactt ttgacatctt    5220 cagaaagttc gtattcagta gtcaattgcc gagcatcaat aatggggatt ataccagaag   5280
caacagtgga agtcacatct accaactttg cggtctcaga aaaagcataa acagttctac   5340
taccgccatt agtgaaactt ttcaaatcgc ccagtggaga agaaaaaggc acagcgatac   5400
tagcattagc gggcaaggat gcaactttat caaccagggt cctatagata accctagcgc   5460
ctgggatcat cctttggaca actctttctg ccaaatctag gtccaaaatc acttcattga   5520
taccattatt gtacaacttg agcaagttgt cgatcagctc ctcaaattgg tcctctgtaa   5580
cggatgactc aacttgcaca ttaacttgaa gctcagtcga ttgagtgaac ttgatcaggt   5640
tgtgcagctg gtcagcagca tagggaaaca cggcttttcc taccaaactc aaggaattat   5700
caaactctgc aacacttgcg tatgcaggta gcaagggaaa tgtcatactt gaagtcggac   5760
agtgagtgta gtcttgagaa attctgaagc cgtatttta ttatcagtga gtcagtcatc    5820
aggagatcct ctacgccgga cgcatcgtgg ccgacctgca ggtcggcatc accggcgcca   5880
caggtgcggt tgctggcgcc tatatcgccg acatcaccga tggggaagat cgggctcgcc   5940
acttcgggct catgagcgct tgtttcggcg tgggtatggt ggcaggcccc gtggccgggg   6000
gactgttggg cgccatctcc ttggacctgc aggggggggg ggggaaagcc acgttgtgtc   6060
tcaaaatctc tgatgttaca ttgcacaaga taaaaatata tcatcatgaa caataaaaact  6120 gtctgcttac ataaacagta atacaagggg tgttatgagc catattcaac gggaaacgtc   6180
ttgctcaagg ccgcgattaa attccaacat ggatgctgat ttatatgggt ataaatgggc   6240
tcgcgataat gtcgggcaat caggtgcgac aatctatcga ttgtatggga agcccgatgc   6300
gccagagttg tttctgaaac atggcaaagg tagcgttgcc aatgatgtta cagatgagat   6360
ggtcagacta aactggctga cggaatttat gcctcttccg accatcaagc attttatccg   6420
tactcctgat gatgcatggt tactcaccac tgcgatcccc gggaaaacag cattccaggt   6480
attagaagaa tatcctgatt caggtgaaaa tattgttgat gcgctggcag tgttcctgcg   6540
```

```
ccggttgcat tcgattcctg tttgtaattg tccttttaac agcgatcgcg tatttcgtct   6600
cgctcaggcg caatcacgaa tgaataacgg tttggttgat gcgagtgatt ttgatgacga   6660
gcgtaatggc tggcctgttg aacaagtctg gaaagaaatg cataagcttt tgccattctc   6720
accggattca gtcgtcactc atggtgattt ctcacttgat aaccttattt ttgacgaggg   6780
gaaattaata ggttgtattg atgttggacg agtcggaatc gcagaccgat accaggatct   6840
tgccatccta tggaactgcc tcggtgagtt ttctccttca ttacagaaac ggcttttca    6900 aaaatatggt attgataatc ctgatatgaa taaattgcag tttcatttga tgctcgatga   6960 gttttttctaa tcagaattgg ttaattggtt gtaacactgg cagagcatta cgctgacttg  7020
acgggacggc ggctttgttg aataaatcga acttttgctg agttgaagga tcagatcacg   7080
catcttcccg acaacgcaga ccgttccgtg gcaaagcaaa agttcaaaat caccaactgg   7140
tccacctaca acaaagctct catcaaccgt ggctccctca ctttctggct ggatgatggg   7200
gcgattcagg cctggtatga gtcagcaaca ccttcttcac gaggcagacc tcagcgcccc   7260
cccccccctg caggtcccac ggcggcggtg ctcaacggcc tcaacctact actgggctgc   7320
ttcctaatgc aggagtcgca taagggagag cgtcgagtat ctatgattgg aagtatggga   7380
atggtgatac ccgcattctt cagtgtcttg aggtctccta tcagattatg cccaactaaa   7440
gcaaccggag gaggagattt catggtaaat ttctctgact tttggtcatc agtagactcg   7500
aactgtgaga ctatctcggt tatgacagca gaaatgtcct tcttggagac agtaaatgaa   7560
gtcccaccaa taaagaaatc cttgttatca ggaacaaact tcttgtttcg aacttttcg    7620 gtgccttgaa ctataaaatg tagagtggat atgtcgggta ggaatggagc gggcaaatgc   7680
ttaccttctg gaccttcaag aggtatgtag ggtttgtaga tactgatgcc aacttcagtg   7740
acaacgttgc tatttcgttc aaaccattcc gaatccagag aaatcaaagt tgtttgtcta   7800
ctattgatcc aagccagtgc ggtcttgaaa ctgacaatag tgtgctcgtg ttttgaggtc   7860
atctttgtat gaataaatct agtctttgat ctaaataatc ttgacgagcc aaggcgataa   7920
atacccaaat ctaaaactct tttaaaacgt taaaaggaca agtatgtctg cctgtattaa   7980
accccaaatc agctcgtagt ctgatcctca tcaacttgag gggcactatc ttgttttaga   8040
gaaatttgcg gagatgcgat atcgagaaaa aggtacgctg attttaaacg tgaaatttat   8100
ctcaagatct ctgcctcgcg cgtttcggtg atgacggtga aaacctctga cacatgcagc   8160
tcccggagac ggtcacagct tgtctgtaag cggatgccgg gagcagacaa gcccgtcagg   8220
gcgcgtcagc gggtgttggc gggtgtcggg gcgcagccat gacccagtca cgtagcgata   8280
gcggagtgta tactggctta actatgcggc atcagagcag attgtactga gagtgcacca   8340
tatgcggtgt gaaataccgc acagatgcgt aaggagaaaa taccgcatca ggcgctcttc   8400
cgcttcctcg ctcactgact cgctgcgctc ggtcgttcgg ctgcggcgag cggtatcagc   8460
tcactcaaag gcggtaatac ggttatccac agaatcaggg gataacgcag gaagaacat    8520 gtgagcaaaa ggccagcaaa aggccaggaa ccgtaaaaag gccgcgttgc tggcgttttt   8580
ccataggctc cgcccccctg acgagcatca caaaaatcga cgctcaagtc agaggtggcg   8640
aaacccgaca ggactataaa gataccaggc gtttccccct ggaagctccc tcgtgcgctc   8700
tcctgttccg accctgccgc ttaccggata cctgtccgcc tttctccctt cgggaagcgt   8760
ggcgctttct caatgctcac gctgtaggta tctcagttcg gtgtaggtcg ttcgctccaa   8820
gctgggctgt gtgcacgaac cccccgttca gcccgaccgc tgcgccttat ccggtaacta   8880
tcgtcttgag tccaacccgg taagacacga cttatcgcca ctggcagcag ccactggtaa   8940
```

-continued

| | |
|---|---|
| caggattagc agagcgaggt atgtaggcgg tgctacagag ttcttgaagt ggtggcctaa | 9000 |
| ctacggctac actagaagga cagtatttgg tatctgcgct ctgctgaagc cagttacctt | 9060 |
| cggaaaaaga gttggtagct cttgatccgg caaacaaacc accgctggta gcggtggttt | 9120 |
| ttttgtttgc aagcagcaga ttacgcgcag aaaaaaagga tctcaagaag atcctttgat | 9180 |
| cttttctacg gggtctgacg ctcagtggaa cgaaaactca cgttaaggga ttttggtcat | 9240 |
| gagattatca aaaaggatct tcacctagat ccttttaaat taaaaatgaa gttttaaatc | 9300 |
| aatctaaagt atatatgagt aaacttggtc tgacagttac caatgcttaa tcagtgaggc | 9360 |
| acctatctca gcgatctgtc tatttcgttc atccatagtt gcctgactcc ccgtcgtgta | 9420 |
| gataactacg atacgggagg gcttaccatc tggccccagt gctgcaatga taccgcgaga | 9480 |
| cccacgctca ccggctccag atttatcagc aataaaccag ccagccggaa gggccgagcg | 9540 |
| cagaagtggt cctgcaactt tatccgcctc catccagtct attaattgtt gccgggaagc | 9600 |
| tagagtaagt agttcgccag ttaatagttt gcgcaacgtt gttgccattg ctgcaggcat | 9660 |
| cgtggtgtca cgctcgtcgt ttggtatggc ttcattcagc tccggttccc aacgatcaag | 9720 |
| gcgagttaca tgatccccca tgttgtgcaa aaaagcggtt agctccttcg gtcctccgat | 9780 |
| cgttgtcaga agtaagttgg ccgcagtgtt atcactcatg gttatggcag cactgcataa | 9840 |
| ttctcttact gtcatgccat ccgtaagatg cttttctgtg actggtgagt actcaaccaa | 9900 |
| gtcattctga gaatagtgta tgcggcgacc gagttgctct tgcccggcgt caacacggga | 9960 |
| taataccgcg ccacatagca gaactttaaa agtgctcatc attggaaaac gttcttcggg | 10020 |
| gcgaaaactc tcaaggatct taccgctgtt gagatccagt tcgatgtaac ccactcgtgc | 10080 |
| acccaactga tcttcagcat cttttacttt caccagcgtt tctgggtgag caaaaacagg | 10140 |
| aaggcaaaat gccgcaaaaa agggaataag ggcgacacgg aaatgttgaa tactcatact | 10200 |
| cttcctttt caatattatt gaagcattta tcagggttat tgtctcatga gcggatacat | 10260 |
| atttgaatgt atttagaaaa ataaacaaat aggggttccg cgcacatttc cccgaaaagt | 10320 |
| gccacctgac gtctaagaaa ccattattat catgacatta acctataaaa ataggcgtat | 10380 |
| cacgaggccc tttcgtcttc aagaattaat tctcatgttt gacagcttat catcgataag | 10440 |
| ctgactcatg ttggtattgt gaaatagacg cagatcggga acactgaaaa ataacagtta | 10500 |
| ttattcgaga tc | 10512 |

```
<210> SEQ ID NO 83
<211> LENGTH: 10462
<212> TYPE: DNA
<213> ORGANISM: Homo sapiens

<400> SEQUENCE: 83
```

| | |
|---|---|
| gatctaacat ccaaagacga aaggttgaat gaaacctttt tgccatccga catccacagg | 60 |
| tccattctca cacataagtg ccaaacgcaa caggaggga tacactagca gcagaccgtt | 120 |
| gcaaacgcag gacctccact cctcttctcc tcaacaccca cttttgccat cgaaaaacca | 180 |
| gcccagttat tgggcttgat tggagctcgc tcattccaat tccttctatt aggctactaa | 240 |
| caccatgact ttattagcct gtctatcctg gcccccctgg cgaggttcat gtttgtttat | 300 |
| ttccgaatgc aacaagctcc gcattacacc cgaacatcac tccagatgag ggctttctga | 360 |
| gtgtggggtc aaatagtttc atgttcccca aatggcccaa aactgacagt ttaaacgctg | 420 |
| tcttggaacc taatatgaca aaagcgtgat ctcatccaag atgaactaag tttggttcgt | 480 |

```
tgaaatgcta acggccagtt ggtcaaaaag aaacttccaa aagtcgccat accgtttgtc      540
ttgtttggta ttgattgacg aatgctcaaa aataatctca ttaatgctta gcgcagtctc      600
tctatcgctt ctgaacccccg gtgcacctgt gccgaaacgc aaatgggaa acacccgctt      660 tttggatgat tatgcattgt ctccacattg tatgcttcca agattctggt gggaatactg      720
ctgatagcct aacgttcatg atcaaaattt aactgttcta accccctactt gacagcaata      780 tataaacaga aggaagctgc cctgtcttaa acctttttt ttatcatcat tattagctta       840
ctttcataat tgcgactggt tccaattgac aagcttttga ttttaacgac ttttaacgac      900
aacttgagaa gatcaaaaaa caactaatta ttcgaaggat ccaaacgatg agatttcctt      960 caattttac tgcagtttta ttcgcagcat cctccgcatt agctgctcca gtcaacacta      1020
caacagaaga tgaaacggca caaattccgg ctgaagctgt catcggttac tcagatttag     1080
aaggggattt cgatgttgct gttttgccat tttccaacag cacaaataac gggttattgt     1140
ttataaatac tactattgcc agcattgctg ctaaagaaga aggggtatct ctcgagaaaa     1200
gatgcggacc gggcagggggg ttcgggaaga ggaggcaccc caaaaagctg accccttag    1260 cctacaagca gtttatcccc aatgtggccg agaagaccct aggcgccagc ggaaggtatg    1320
aagggaagat ctccagaaac tccgagcgat ttaaggaact caccccccaat tacaaccccg     1380 acatcatatt taaggatgaa gaaaacaccg gagcggacag gctgatgact cagaggtgta     1440
aggacaagtt gaacgctttg gccatctcgg tgatgaacca gtggccagga gtgaaactgc     1500
gggtgaccga gggctgggac gaagatggcc accactcaga ggagtctctg cactacgagg     1560
gccgcgcagt ggacatcacc acgtctgacc gcgaccgcag caagtacggc atgctggccc     1620
gcctggcggt ggaggccggc ttcgactggg tgtactacga gtccaaggca catatccact     1680
gctcggtgaa agcagagaac tcggtggcgg ccaaatcggg aggcgtcgac aaaactcaca     1740
catgcccacc gtgcccagca cctgaactcc tggggggacc gtcagtcttc ctcttccccc     1800
caaaacccaa ggacaccctc atgatctccc ggacccctga ggtcacatgc gtggtggtgg     1860
acgtgagcca cgaagaccct gaggtcaagt tcaactggta cgtggacggc gtggaggtgc     1920
ataatgccaa gacaaagccg cgggaggagc agtaccagag cacgtaccgt gtggtcagcg     1980
tcctcaccgt cctgcaccag gactggctga atggcaagga gtacaagtgc aaggtctcca     2040
acaaagccct cccagccccc atcgagaaaa ccatctccaa agccaaaggg cagccccgag     2100
aaccacaggt gtacaccctg ccccatccc gggatgagct gaccaagaac caggtcagcc     2160
tgacctgcct ggtcaaaggc ttctatccca gcgacatcgc cgtggagtgg gagagcaatg     2220
ggcagccgga gaacaactac aagaccacgc ctcccgtgtt ggactccgac ggctccttct     2280
tcctctacag caagctcacc gtggacaaga gcaggtggca gcaggggaac gtcttctcat     2340
gctccgtgat gcatgaggct ctgcacaacc actacacgca gaagagcctc tccctgtctc     2400
ccgggaaatg agtgcggcgg ccgcgaatta attcgcctta gacatgactg ttcctcagtt     2460
caagttgggc acttacgaga agaccggtct tgctagattc taatcaagag gatgtcagaa     2520
tgccatttgc ctgagagatg caggcttcat ttttgatact ttttatttg taacctatat      2580 agtataggat tttttttgtc attttgtttc ttctcgtacg agcttgctcc tgatcagcct     2640
atctcgcagc tgatgaatat cttgtggtag gggtttggga aaatcattcg agtttgatgt     2700
ttttcttggt atttcccact cctcttcaga gtacagaaga ttaagtgaga agttcgtttg     2760
tgcaagctta tcgataagct ttaatgcggt agtttatcac agttaaattg ctaacgcagt     2820
caggcaccgt gtatgaaatc taacaatgcg ctcatcgtca tcctcggcac cgtcaccctg     2880
```

```
gatgctgtag gcataggctt ggttatgccg gtactgccgg gcctcttgcg ggatatcgtc    2940
cattccgaca gcatcgccag tcactatggc gtgctgctag cgctatatgc gttgatgcaa    3000
tttctatgcg cacccgttct cggagcactg tccgaccgct ttggccgccg cccagtcctg    3060
ctcgcttcgc tacttggagc cactatcgac tacgcgatca tggcgaccac acccgtcctg    3120
tggatctatc gaatctaaat gtaagttaaa atctctaaat aattaaataa gtcccagttt    3180
ctccatacga accttaacag cattgcggtg agcatctaga ccttcaacag cagccagatc    3240
catcactgct tggccaatat gtttcagtcc ctcaggagtt acgtcttgtg aagtgatgaa    3300
cttctggaag gttgcagtgt taactccgct gtattgacgg gcatatccgt acgttggcaa    3360
agtgtggttg gtaccggagg agtaatctcc acaactctct ggagagtagg caccaacaaa    3420
cacagatcca gcgtgttgta cttgatcaac ataagaagaa gcattctcga tttgcaggat    3480
caagtgttca ggagcgtact gattggacat ttccaaagcc tgctcgtagg ttgcaaccga    3540
tagggttgta gagtgtgcaa tacacttgcg tacaatttca accttggca actgcacagc     3600 ttggttgtga acagcatctt caattctggc aagctccttg tctgtcatat cgacagccaa    3660
cagaatcacc tgggaatcaa taccatgttc agcttgagca aaggtctga ggcaacgaaa     3720 tctggatcag cgtatttatc agcaataact agaacttcag aaggcccagc aggcatgtca    3780
atactacaca gggctgatgt gtcatttga accatcatct tggcagcagt aacgaactgg     3840
tttcctggac caaatatttt gtcacactta ggaacagttt ctgttccgta agccatagca    3900
gctactgcct gggcgcctcc tgctagcacg atacacttag caccaaccttt gtgggcaacg   3960 tagatgactt ctggggtaag ggtaccatcc ttcttaggtg gagatgcaaa aacaatttct    4020
ttgcaaccag caactttggc aggaacaccc agcatcaggg aagtggaagg cagaattgcg    4080
gttccaccag gaatatagag gccaactttc tcaataggtc ttgcaaaacg agagcagact    4140
acaccagggc aagtctcaac ttgcaacgtc tccgttagtt gagcttcatg gaatttcctg    4200
acgttatcta tagagagatc aatggctctc ttaacgttat ctggcaattg cataagttcc    4260
tctgggaaag gagcttctaa cacaggtgtc ttcaaagcga ctccatcaaa cttggcagtt    4320
agttctaaaa gggctttgtc accattttga cgaacattgt cgacaattgg tttgactaat    4380
tccataatct gttccgtttt ctggatagga cgacgaaggg catcttcaat ttcttgtgag    4440
gaggccttag aaacgtcaat tttgcacaat tcaatacgac cttcagaagg gacttcttta    4500
ggtttggatt cttcttttagg ttgttccttg gtgtatcctg gcttggcatc tccttttctt   4560
ctagtgacct ttagggactt catatccagg tttctctcca cctcgtccaa cgtcacaccg    4620
tacttggcac atctaactaa tgcaaaataa aataagtcag cacattccca ggctatatct    4680
tccttggatt tagcttctgc aagttcatca gcttcctccc taattttagc gttcaaacaa    4740
aacttcgtcg tcaaataacc gtttggtata agaaccttct ggagcattgc tcttacgatc    4800
ccacaaggtg cttccatggc tctaagaccc tttgattggc caaaacagga agtgcgttcc    4860
aagtgacaga aaccaacacc tgtttgttca accacaaatt tcaagcagtc tccatcacaa    4920
tccaattcga tacccagcaa cttttgagtt cgtccagatg tagcaccttt ataccacaaa    4980
ccgtgacgac gagattggta gactccagtt tgtgtcctta tagcctccgg aatagacttt    5040
ttggacgagt acaccaggcc caacgagtaa ttagaagagt cagccaccaa agtagtgaat    5100
agaccatcgg ggcggtcagt agtcaaagac gccaacaaaa tttcactgac agggaacttt    5160
ttgacatctt cagaaagttc gtattcagta gtcaattgcc gagcatcaat aatggggatt    5220
```

```
ataccagaag caacagtgga agtcacatct accaactttg cggtctcaga aaaagcataa    5280
acagttctac taccgccatt agtgaaactt ttcaaatcgc ccagtggaga agaaaaaggc    5340
acagcgatac tagcattagc gggcaaggat gcaactttat caaccagggt cctatagata    5400
accctagcgc ctgggatcat cctttggaca actctttctg ccaaatctag gtccaaaatc    5460
acttcattga taccattatt gtacaacttg agcaagttgt cgatcagctc ctcaaattgg    5520
tcctctgtaa cggatgactc aacttgcaca ttaacttgaa gctcagtcga ttgagtgaac    5580
ttgatcaggt tgtgcagctg gtcagcagca tagggaaaca cggcttttcc taccaaactc    5640
aaggaattat caaactctgc aacacttgcg tatgcaggta gcaagggaaa tgtcatactt    5700
gaagtcggac agtgagtgta gtcttgagaa attctgaagc cgtattttta ttatcagtga    5760
gtcagtcatc aggagatcct ctacgccgga cgcatcgtgg ccgacctgca ggtcggcatc    5820
accggcgcca caggtgcggt tgctggcgcc tatatcgccg acatcaccga tggggaagat    5880
cgggctcgcc acttcgggct catgagcgct tgtttcggcg tgggtatggt ggcaggcccc    5940
gtggccgggg gactgttggg cgccatctcc ttggacctgc agggggggg ggggaaagcc    6000 acgttgtgtc tcaaaatctc tgatgttaca ttgcacaaga taaaaatata tcatcatgaa    6060
caataaaact gtctgcttac ataaacagta atacaagggg tgttatgagc catattcaac    6120
gggaaacgtc ttgctcaagg ccgcgattaa attccaacat ggatgctgat ttatatgggt    6180
ataaatgggc tcgcgataat gtcgggcaat caggtgcgac aatctatcga ttgtatggga    6240
agcccgatgc gccagagttg tttctgaaac atggcaaagg tagcgttgcc aatgatgtta    6300
cagatgagat ggtcagacta aactggctga cggaatttat gcctcttccg accatcaagc    6360 atttatccg tactcctgat gatgcatggt tactcaccac tgcgatcccc gggaaaacag    6420
cattccaggt attagaagaa tatcctgatt caggtgaaaa tattgttgat gcgctggcag    6480
tgttcctgcg ccggttgcat tcgattcctg tttgtaattg tccttttaac agcgatcgcg    6540
tatttcgtct cgctcaggcg caatcacgaa tgaataacgg tttggttgat gcgagtgatt    6600
ttgatgacga gcgtaatggc tggcctgttg aacaagtctg gaaagaaatg cataagcttt    6660
tgccattctc accggattca gtcgtcactc atggtgattt ctcacttgat aaccttattt    6720
ttgacgaggg gaaattaata ggttgtattg atgttggacg agtcggaatc gcagaccgat    6780
accaggatct tgccatccta tggaactgcc tcggtgagtt ttctccttca ttacagaaac    6840
ggctttttca aaaatatggt attgataatc ctgatatgaa taaattgcag tttcatttga    6900
tgctcgatga gtttttctaa tcagaattgg ttaattggtt gtaacactgg cagagcatta    6960
cgctgacttg acgggacggc ggctttgttg aataaatcga acttttgctg agttgaagga    7020
tcagatcacg catcttcccg acaacgcaga ccgttccgtg gcaaagcaaa agttcaaaat    7080
caccaactgg tccacctaca acaaagctct catcaaccgt ggctccctca ctttctggct    7140
ggatgatggg gcgattcagg cctggtatga gtcagcaaca ccttcttcac gaggcagacc    7200
tcagcgcccc cccccctg caggtcccac ggcggcggtg ctcaacggcc tcaacctact    7260
actgggctgc ttcctaatgc aggagtcgca taagggagc gtcgagtat ctatgattgg    7320 aagtatggga atggtgatac ccgcattctt cagtgtcttg aggtctccta tcagattatg    7380
cccaactaaa gcaaccggag gaggagattt catggtaaat ttctctgact tttggtcatc    7440
agtagactcg aactgtgaga ctatctcggt tatgacagca gaaatgtcct tcttggagac    7500
agtaaatgaa gtcccaccaa taagaaaatc cttgttatca ggaacaaact tcttgtttcg    7560
aactttttcg gtgccttgaa ctataaaatg tagagtggat atgtcgggta ggaatggagc    7620
```

```
gggcaaatgc ttaccttctg gaccttcaag aggtatgtag ggtttgtaga tactgatgcc    7680
aacttcagtg acaacgttgc tatttcgttc aaaccattcc gaatccagag aaatcaaagt    7740
tgtttgtcta ctattgatcc aagccagtgc ggtcttgaaa ctgacaatag tgtgctcgtg    7800
ttttgaggtc atctttgtat gaataaatct agtctttgat ctaaataatc ttgacgagcc    7860
aaggcgataa atacccaaat ctaaaactct tttaaaacgt taaaaggaca agtatgtctg    7920
cctgtattaa accccaaatc agctcgtagt ctgatcctca tcaacttgag gggcactatc    7980
ttgttttaga gaaatttgcg gagatgcgat atcgagaaaa aggtacgctg attttaaacg    8040
tgaaatttat ctcaagatct ctgcctcgcg cgtttcggtg atgacggtga aaacctctga    8100
cacatgcagc tcccggagac ggtcacagct tgtctgtaag cggatgccgg gagcagacaa    8160
gcccgtcagg gcgcgtcagc gggtgttggc gggtgtcggg gcgcagccat gacccagtca    8220
cgtagcgata gcggagtgta tactggctta actatgcggc atcagagcag attgtactga    8280
gagtgcacca tatgcggtgt gaaataccgc acagatgcgt aaggagaaaa taccgcatca    8340
ggcgctcttc cgcttcctcg ctcactgact cgctgcgctc ggtcgttcgg ctgcggcgag    8400
cggtatcagc tcactcaaag gcggtaatac ggttatccac agaatcaggg gataacgcag    8460
gaaagaacat gtgagcaaaa ggccagcaaa aggccaggaa ccgtaaaaag gccgcgttgc    8520
tggcgttttt ccataggctc cgcccccctg acgagcatca caaaaatcga cgctcaagtc    8580
agaggtggcg aaacccgaca ggactataaa gataccaggc gtttccccct ggaagctccc    8640
tcgtgcgctc tcctgttccg accctgccgc ttaccggata cctgtccgcc tttctccctt    8700
cgggaagcgt ggcgctttct caatgctcac gctgtaggta tctcagttcg gtgtaggtcg    8760
ttcgctccaa gctgggctgt gtgcacgaac cccccgttca gcccgaccgc tgcgccttat    8820
ccggtaacta tcgtcttgag tccaacccgg taagacacga cttatcgcca ctggcagcag    8880
ccactggtaa caggattagc agagcgaggt atgtaggcgg tgctacagag ttcttgaagt    8940
ggtggcctaa ctacggctac actagaagga cagtatttgg tatctgcgct ctgctgaagc    9000
cagttacctt cggaaaaaga gttggtagct cttgatccgg caaacaaacc accgctggta    9060
gcggtggttt ttttgtttgc aagcagcaga ttacgcgcag aaaaaaagga tctcaagaag    9120
atcctttgat cttttctacg gggtctgacg ctcagtggaa cgaaaactca cgttaaggga    9180
ttttggtcat gagattatca aaaaggatct tcacctagat ccttttaaat taaaaatgaa    9240
gttttaaatc aatctaaagt atatatgagt aaacttggtc tgacagttac caatgcttaa    9300
tcagtgaggc acctatctca gcgatctgtc tatttcgttc atccatagtt gcctgactcc    9360
ccgtcgtgta gataactacg atacgggagg gcttaccatc tggccccagt gctgcaatga    9420
taccgcgaga cccacgctca ccggctccag atttatcagc aataaaccag ccagccggaa    9480
gggccgagcg cagaagtggt cctgcaactt tatccgcctc catccagtct attaattgtt    9540
gccgggaagc tagagtaagt agttcgccag ttaatagttt gcgcaacgtt gttgccattg    9600
ctgcaggcat cgtggtgtca cgctcgtcgt ttggtatggc ttcattcagc tccggttccc    9660
aacgatcaag gcgagttaca tgatccccca tgttgtgcaa aaaagcggtt agctccttcg    9720
gtcctccgat cgttgtcaga agtaagttgg ccgcagtgtt atcactcatg gttatggcag    9780
cactgcataa ttctcttact gtcatgccat ccgtaagatg cttttctgtg actggtgagt    9840
actcaaccaa gtcattctga gaatagtgta tgcggcgacc gagttgctct tgcccggcgt    9900
caacacggga taataccgcg ccacatagca gaactttaaa agtgctcatc attggaaaac    9960
```

```
gttcttcggg gcgaaaactc tcaaggatct taccgctgtt gagatccagt tcgatgtaac      10020
ccactcgtgc acccaactga tcttcagcat ctttttacttt caccagcgtt tctgggtgag    10080
caaaaacagg aaggcaaaat gccgcaaaaa agggaataag ggcgacacgg aaatgttgaa     10140
tactcatact cttcctttt caatattatt gaagcattta tcagggttat tgtctcatga      10200
gcggatacat atttgaatgt atttagaaaa ataaacaaat aggggttccg cgcacatttc     10260
cccgaaaagt gccacctgac gtctaagaaa ccattattat catgacatta acctataaaa    10320
ataggcgtat cacgaggccc tttcgtcttc aagaattaat tctcatgttt gacagcttat     10380
catcgataag ctgactcatg ttggtattgt gaaatagacg cagatcggga acactgaaaa    10440
ataacagtta ttattcgaga tc                                              10462
```

<210> SEQ ID NO 84
<211> LENGTH: 4205
<212> TYPE: DNA
<213> ORGANISM: Homo sapiens

<400> SEQUENCE: 84

```
ctaaattgta agcgttaata tttgttaaa attcgcgtta aatttttgtt aaatcagctc         60 atttttaac caataggccg aaatcggcaa atcccttat aaatcaaaag aatagaccga        120 gataggttg agtgttgttc cagtttggaa caagagtcca ctattaaaga acgtggactc       180
caacgtcaaa gggcgaaaaa ccgtctatca gggcgatggc ccactacgtg aaccatcacc     240
ctaatcaagt ttttggggt cgaggtgccg taaagcacta aatcggaacc ctaaagggag      300
cccccgattt agagcttgac ggggaaagcc ggcgaacgtg gcgagaaagg aagggaagaa    360
agcgaaagga gcgggcgcta gggcgctggc aagtgtagcg gtcacgctgc gcgtaaccac    420
cacacccgcc gcgcttaatg cgccgctaca gggcgcgtcc cattcgccat tcaggctgcg    480
caactgttgg gaagggcgat cggtgcgggc ctcttcgcta ttacgccagc tggcgaaagg    540
gggatgtgct gcaaggcgat taagttgggt aacgccaggg ttttcccagt cacgacgttg   600
taaaacgacg ccagtgagc gcgcgtaata cgactcacta tagggcgaat tgggtaccgg    660 gcccctctaga tccttcagc tccctgcccc ggacatgccc agtgggtgga agctgccctc     720
ttctagcagg agacgcccca ggcggtagag cagctggggg taccaatgca cccctcccc   780 cggagtccag ctgccccatg ccaagctgtg aaagagtctc aggggccaga aggccaactg     840
agccaggtgg tggtcagcca cggccgcgaa gcaggatgcc accacatcct ccaccaccag    900
tgtcccatgc tttgtgagcg gggcgtaggc cccgagggcc acgtgtgtag agacagctgc   960
cacgcgggca ggctgcaggc ctggcacccc agccaccagc acgtactggc caggctgcac   1020
gtggctggca aatgtggccc ggaagcgggc tgccggctcc gtgtgattgt cagccgtaaa   1080
gagcaggtga gcgggtgtga gtgccaggcg gcgtgggggg tcctgagtct cgatgacctg    1140
gaaggctctc agcctgtggg gctcgcggtc caggaaaatg agcacatcgc tgaaggtggg   1200
gctcccatcc tcccccatgg ccagcacacg gtctcccggc ctcacggctg acaaggccac    1260
acgcgcccca ctctccaggc gtacctgggc tgcggccgcg aatcagccgc ccgtcttggc   1320
tgcggccgag tgctcggact tgacggagca atgcacgtgg gccttttgact cgtaatacac    1380 ccagtcaaag ccggcctcca ctgccaagcg cgccagcagt ccatacttat tgcggtcgcg   1440
gtctgatgtg gtgatgtcca ccgcgcggcc ctcataatgc agggactcct ctgagtggtg    1500
gccgtcctcg tcccagccct cggtcacccg cagcttcaca ccgggccact ggttcatcac  1560
cgagatagcc agcgagttca ggcggtcctt gcagcgctgg gtcatgaggc ggtcggcgcc  1620
```

-continued

```
tgtgttctcc tcgtccttga agatgatgtc tggattgtaa ttgggggtga gctccttgaa    1680
gcgctcggag ctgcgagcga tcttgccttc atagcgtccg ctggcgccca gggtcttctc    1740
gggcacattg gggctgaact gcttgtaggc gagcggcacg agtttgcgtg gcggtcgccg    1800
gcggctgccc accacccgac ccggcccgca gccccatgcc gccggcacca ccagcagcag    1860
caacaggacc aggcagaagt gcagtcgggg ccggagccgg gcgggagaca tggcggccgc    1920
gacggtatcg ataagcttga tatcgaattc ctgcagcccg gggatccac tagttctaga     1980
gcggccgcca ccgcggtgga gctccagctt ttgttccctt tagtgagggt taattgcgcg    2040
cttggcgtaa tcatggtcat agctgtttcc tgtgtgaaat tgttatccgc tcacaattcc    2100
acacaacata cgagccggaa gcataaagtg taaagcctgg ggtgcctaat gagtgagcta    2160
actcacatta attgcgttgc gctcactgcc cgctttccag tcgggaaacc tgtcgtgcca    2220
gctgcattaa tgaatcggcc aacgcgcggg gagaggcggt ttgcgtattg ggcgctcttc    2280
cgcttcctcg ctcactgact cgctgcgctc ggtcgttcgg ctgcggcgag cggtatcagc    2340
tcactcaaag gcggtaatac ggttatccac agaatcaggg gataacgcag gaaagaacat    2400
gtgagcaaaa ggccagcaaa aggccaggaa ccgtaaaaag gccgcgttgc tggcgttttt    2460
ccataggctc cgcccccctg acgagcatca caaaaatcga cgctcaagtc agaggtggcg    2520
aaacccgaca ggactataaa gataccaggc gtttccccct ggaagctccc tcgtgcgctc    2580
tcctgttccg accctgccgc ttaccggata cctgtccgcc tttctccctt cgggaagcgt    2640
ggcgctttct catagctcac gctgtaggta tctcagttcg gtgtaggtcg ttcgctccaa    2700
gctgggctgt gtgcacgaac ccccgttca gcccgaccgc tgcgcttat ccggtaacta     2760
tcgtcttgag tccaacccgg taagacacga cttatcgcca ctggcagcag ccactggtaa    2820
caggattagc agagcgaggt atgtaggcgg tgctacagag ttcttgaagt ggtggcctaa    2880
ctacggctac actagaagga cagtatttgg tatctgcgct ctgctgaagc cagttacctt    2940
cggaaaaaga gttggtagct cttgatccgg caaacaaacc accgctggta gcggtggttt    3000
ttttgtttgc aagcagcaga ttacgcgcag aaaaaaagga tctcaagaag atcctttgat    3060
cttttctacg gggtctgacg ctcagtggaa cgaaaactca cgttaaggga ttttggtcat    3120
gagattatca aaaaggatct tcacctagat ccttttaaat taaaaatgaa gttttaaatc    3180
aatctaaagt atatatgagt aaacttggtc tgacagttac caatgcttaa tcagtgaggc    3240
acctatctca gcgatctgtc tatttcgttc atccatagtt gcctgactcc ccgtcgtgta    3300
gataactacg atacgggagg gcttaccatc tggccccagt gctgcaatga taccgcgaga    3360
cccacgctca ccggctccag atttatcagc aataaaccag ccagccggaa gggccgagcg    3420
cagaagtggt cctgcaactt tatccgcctc catccagtct attaattgtt gccgggaagc    3480
tagagtaagt agttcgccag ttaatagttt cgcaacgtt gttgccattg ctacaggcat     3540
cgtggtgtca cgctcgtcgt ttggtatggc ttcattcagc tccggttccc aacgatcaag    3600
gcgagttaca tgatccccca tgttgtgcaa aaaagcggtt agctccttcg tcctccgat    3660
cgttgtcaga agtaagttgg ccgcagtgtt atcactcatg gttatggcag cactgcataa    3720
ttctcttact gtcatgccat ccgtaagatg cttttctgtg actggtgacg cgtcaaccaa    3780
gtcattctga gaatagtgta tgcggcgacc gagttgctct tgcccggcgt caatacggga    3840
taataccgcg ccacatagca gaactttaaa agtgctcatc attggaaaac gttcttcggg    3900
gcgaaaactc tcaaggatct taccgctgtt gagatccagt tcgatgtaac ccactcgtgc    3960
```

| | | | | |
|---|---|---|---|---|
| acccaactga | tcttcagcat | cttttacttt | caccagcgtt | tctgggtgag caaaaacagg | 4020 |
| aaggcaaaat | gccgcaaaaa | agggaataag | ggcgacacgg | aaatgttgaa tactcatact | 4080 |
| cttcctttt | caatattatt | gaagcattta | tcagggttat | tgtctcatga gcggatacat | 4140 |
| atttgaatgt | atttagaaaa | ataaacaaat | aggggttccg | cgcacatttc cccgaaaagt | 4200 |
| gccac | | | | | 4205 |

<210> SEQ ID NO 85
<211> LENGTH: 4205
<212> TYPE: DNA
<213> ORGANISM: Homo sapiens

<400> SEQUENCE: 85

| | | | | |
|---|---|---|---|---|
| ctaaattgta | agcgttaata | ttttgttaaa | attcgcgtta | aattttttgtt aaatcagctc | 60 |
| attttttaac | caataggccg | aaatcggcaa | aatcccttat | aaatcaaaag aatagaccga | 120 |
| gatagggttg | agtgttgttc | cagtttggaa | caagagtcca | ctattaaaga acgtggactc | 180 |
| caacgtcaaa | gggcgaaaaa | ccgtctatca | gggcgatggc | ccactacgtg aaccatcacc | 240 |
| ctaatcaagt | tttttggggt | cgaggtgccg | taaagcacta | aatcggaacc ctaaagggag | 300 |
| cccccgattt | agagcttgac | ggggaaagcc | ggcgaacgtg | gcgagaaagg aagggaagaa | 360 |
| agcgaaagga | gcgggcgcta | gggcgctggc | aagtgtagcg | gtcacgctgc gcgtaaccac | 420 |
| cacacccgcc | gcgcttaatg | cgccgctaca | gggcgcgtcc | cattcgccat tcaggctgcg | 480 |
| caactgttgg | gaagggcgat | cggtgcgggc | ctcttcgcta | ttacgccagc tggcgaaagg | 540 |
| gggatgtgct | gcaaggcgat | taagttgggt | aacgccaggg | ttttcccagt cacgacgttg | 600 |
| taaaacgacg | gccagtgagc | gcgcgtaata | cgactcacta tagggcgaat | tgggtaccgg | 660 |
| gccctctaga | tcctttcagc | tccctgcccc | ggacatgccc | agtgggtgga agctgccctc | 720 |
| ttctagcagg | agacgcccca | ggcggtagag | cagctggggg | taccaatgca caccctcccc | 780 |
| cggagtccag | ctgccccatg | ccaagctgtg | aaagagtctc | aggggccaga aggccaactg | 840 |
| agccaggtgg | tggtcagcca | cggccgcgaa | gcaggatgcc | accacatcct ccaccaccag | 900 |
| tgtcccatgc | tttgtgagcg | gggcgtaggc | cccgagggcc | acgtgtgtag agacagctgc | 960 |
| cacgcgggca | ggctgcaggc | ctggcacccc | agccaccagc | acgtactggc caggctgcac | 1020 |
| gtggctggca | aatgtggccc | ggaagcgggc | tgccggctcc | gtgtgattgt cagccgtaaa | 1080 |
| gagcaggtga | gcgggtgtga | gtgccaggcg | gcgtgggggg | tcctgagtct cgatgacctg | 1140 |
| gaaggctctc | agcctgtggg | gctcgcgtc | caggaaaatg | agcacatcgc tgaaggtggg | 1200 |
| gctcccatcc | tcccccatgg | ccagcacacg | gtctcccggc | ctcacggctg acaaggccac | 1260 |
| acgcgcccca | ctctccaggc | gtacctgggc | tccggcaggg | tcgacgccgc ccgtcttggc | 1320 |
| tgcggccgag | tgctcggact | tgacggagca | atgcacgtgg | gcctttgact cgtaatacac | 1380 |
| ccagtcaaag | ccggcctcca | ctgccaagcg | cgccagcagt | ccatacttat tgcggtcgcg | 1440 |
| gtctgatgtg | gtgatgtcca | ccgcgcggcc | ctcataatgc | agggactcct ctgagtggtg | 1500 |
| gccgtcctcg | tcccagccct | cggtcacccg | cagcttcaca | ccgggccact ggttcatcac | 1560 |
| cgagatagcc | agcgagttca | ggcggtcctt | gcagcgctgg | gtcatgaggc ggtcggcgcc | 1620 |
| tgtgttctcc | tcgtccttga | agatgatgtc | tggattgtaa | ttgggggtga gctccttgaa | 1680 |
| gcgctcggag | ctgcgagcga | tcttgccttc | atagcgtccg | ctggcgccca gggtcttctc | 1740 |
| gggcacattg | ggctgaact | gcttgtaggc | gagcggcacg | agtttgcgtg gcggtcgccg | 1800 |
| gcggctgccc | accacccgac | ccggcccgca | gccccatgcc | gccggcacca ccagcagcag | 1860 |

-continued

```
caacaggacc aggcagaagt gcagtcgggg ccggagccgg gcgggagaca tggcggccgc    1920
gacggtatcg ataagcttga tatcgaattc ctgcagcccg gggatccac tagttctaga    1980
gcggccgcca ccgcgtgga gctccagctt ttgttccctt tagtgagggt taattgcgcg    2040
cttggcgtaa tcatggtcat agctgtttcc tgtgtgaaat tgttatccgc tcacaattcc    2100
acacaacata cgagccggaa gcataaagtg taaagcctgg ggtgcctaat gagtgagcta    2160
actcacatta attgcgttgc gctcactgcc cgctttccag tcgggaaacc tgtcgtgcca    2220
gctgcattaa tgaatcggcc aacgcgcggg gagaggcggt ttgcgtattg ggcgctcttc    2280
cgcttcctcg ctcactgact cgctgcgctc ggtcgttcgg ctgcggcgag cggtatcagc    2340
tcactcaaag gcggtaatac ggttatccac agaatcaggg gataacgcag gaaagaacat    2400
gtgagcaaaa ggccagcaaa aggccaggaa ccgtaaaaag gccgcgttgc tggcgttttt    2460
ccataggctc cgcccccctg acgagcatca caaaaatcga cgctcaagtc agaggtggcg    2520
aaacccgaca ggactataaa gataccaggc gtttccccct ggaagctccc tcgtgcgctc    2580
tcctgttccg accctgccgc ttaccggata cctgtccgcc tttctccctt cgggaagcgt    2640
ggcgctttct catagctcac gctgtaggta tctcagttcg gtgtaggtcg ttcgctccaa    2700
gctgggctgt gtgcacgaac cccccgttca gcccgaccgc tgcgccttat ccggtaacta    2760
tcgtcttgag tccaacccgg taagacacga cttatcgcca ctggcagcag ccactggtaa    2820
caggattagc agagcgaggt atgtaggcgg tgctacagag ttcttgaagt ggtggcctaa    2880
ctacggctac actagaagga cagtatttgg tatctgcgct ctgctgaagc cagttacctt    2940
cggaaaaaga gttggtagct cttgatccgg caaacaaacc accgctggta gcggtggttt    3000
ttttgtttgc aagcagcaga ttacgcgcag aaaaaaagga tctcaagaag atcctttgat    3060
cttttctacg gggtctgacg ctcagtggaa cgaaaactca cgttaaggga ttttggtcat    3120
gagattatca aaaaggatct tcacctagat ccttttaaat taaaaatgaa gttttaaatc    3180
aatctaaagt atatatgagt aaacttggtc tgacagttac caatgcttaa tcagtgaggc    3240
acctatctca gcgatctgtc tatttcgttc atccatagtt gcctgactcc ccgtcgtgta    3300
gataactacg atacgggagg gcttaccatc tggccccagt gctgcaatga taccgcgaga    3360
cccacgctca ccggctccag atttatcagc aataaaccag ccagccggaa gggccgagcg    3420
cagaagtggt cctgcaactt tatccgcctc catccagtct attaattgtt gccgggaagc    3480
tagagtaagt agttcgccag ttaatagttt cgcaacgtt gttgccattg ctacaggcat    3540
cgtggtgtca cgctcgtcgt ttggtatggc ttcattcagc tccggttccc aacgatcaag    3600
gcgagttaca tgatccccca tgttgtgcaa aaaagcggtt agctccttcg gtcctccgat    3660
cgttgtcaga agtaagttgg ccgcagtgtt atcactcatg gttatggcag cactgcataa    3720
ttctcttact gtcatgccat ccgtaagatg cttttctgtg actggtgacg cgtcaaccaa    3780
gtcattctga gaatagtgta tgcggcgacc gagttgctct tgcccggcgt caatacggga    3840
taataccgcg ccacatagca gaactttaaa agtgctcatc attggaaaac gttcttcggg    3900
gcgaaaactc tcaaggatct taccgctgtt gagatccagt tcgatgtaac ccactcgtgc    3960
acccaactga tcttcagcat cttttacttt caccagcgtt tctgggtgag caaaaacagg    4020
aaggcaaaat gccgcaaaaa agggaataag ggcgacacgg aaatgttgaa tactcatact    4080
cttcctttt caatattatt gaagcattta tcagggttat tgtctcatga gcggatacat    4140
atttgaatgt atttagaaaa ataaacaaat aggggttccg cgcacatttc cccgaaaagt    4200
```

```
                                        gccac                                4205

<210> SEQ ID NO 86
<211> LENGTH: 126
<212> TYPE: DNA
<213> ORGANISM: Homo sapiens

<400> SEQUENCE: 86
tctctcgaga aaagatgcgg accgggcagg gggttcggga agaggaggca ccccaaaaag      60 ctgaccccctt tagcctacaa gcagtttatc cccaatgtgg ccgagaagac cctaggcgcc    120
agcgga                                                                126

<210> SEQ ID NO 87
<211> LENGTH: 5
<212> TYPE: PRT
<213> ORGANISM: Artificial Sequence
<220> FEATURE:
<223> OTHER INFORMATION: peptide

<400> SEQUENCE: 87

Lys Arg Arg His Pro
 1               5

<210> SEQ ID NO 88
<211> LENGTH: 5
<212> TYPE: PRT
<213> ORGANISM: Artificial Sequence
<220> FEATURE:
<223> OTHER INFORMATION: peptide

<400> SEQUENCE: 88

Lys Arg Arg Pro Pro
 1               5

<210> SEQ ID NO 89
<211> LENGTH: 5
<212> TYPE: PRT
<213> ORGANISM: Artificial Sequence
<220> FEATURE:
<223> OTHER INFORMATION: peptide

<400> SEQUENCE: 89

Lys Lys Lys His Pro
 1               5

<210> SEQ ID NO 90
<211> LENGTH: 5
<212> TYPE: PRT
<213> ORGANISM: Artificial Sequence
<220> FEATURE:
<223> OTHER INFORMATION: peptide

<400> SEQUENCE: 90

Arg Gln Arg His Pro
 1               5

<210> SEQ ID NO 91
<211> LENGTH: 5
<212> TYPE: PRT
<213> ORGANISM: Artificial Sequence
<220> FEATURE:
<223> OTHER INFORMATION: peptide

<400> SEQUENCE: 91

Gln Arg Lys His Pro
```

<210> SEQ ID NO 92
<211> LENGTH: 5
<212> TYPE: PRT
<213> ORGANISM: Artificial Sequence
<220> FEATURE:
<223> OTHER INFORMATION: peptide

<400> SEQUENCE: 92

Gln Arg Arg Pro Pro
1               5

<210> SEQ ID NO 93
<211> LENGTH: 5
<212> TYPE: PRT
<213> ORGANISM: Artificial Sequence
<220> FEATURE:
<223> OTHER INFORMATION: peptide

<400> SEQUENCE: 93

Arg Lys Arg His Pro
1               5

<210> SEQ ID NO 94
<211> LENGTH: 5
<212> TYPE: PRT
<213> ORGANISM: Artificial Sequence
<220> FEATURE:
<223> OTHER INFORMATION: peptide

<400> SEQUENCE: 94

Arg Lys Lys His Pro
1               5

<210> SEQ ID NO 95
<211> LENGTH: 7
<212> TYPE: PRT
<213> ORGANISM: Artificial Sequence
<220> FEATURE:
<223> OTHER INFORMATION: peptide

<400> SEQUENCE: 95

Lys Lys Arg His Pro Lys Lys
1               5

<210> SEQ ID NO 96
<211> LENGTH: 7
<212> TYPE: PRT
<213> ORGANISM: Artificial Sequence
<220> FEATURE:
<223> OTHER INFORMATION: peptide

<400> SEQUENCE: 96

Arg Arg Arg His Pro Lys Lys
1               5

<210> SEQ ID NO 97
<211> LENGTH: 7
<212> TYPE: PRT
<213> ORGANISM: Artificial Sequence
<220> FEATURE:
<223> OTHER INFORMATION: peptide

<400> SEQUENCE: 97

Gln Gln Gln His Pro Lys Lys
1               5

<210> SEQ ID NO 98
<211> LENGTH: 7
<212> TYPE: PRT
<213> ORGANISM: Artificial Sequence
<220> FEATURE:
<223> OTHER INFORMATION: peptide

<400> SEQUENCE: 98

Lys Arg Arg His Pro Gln Gln
1               5

<210> SEQ ID NO 99
<211> LENGTH: 5
<212> TYPE: PRT
<213> ORGANISM: Artificial Sequence
<220> FEATURE:
<223> OTHER INFORMATION: peptide

<400> SEQUENCE: 99

Arg Lys Arg Pro Pro
1               5

<210> SEQ ID NO 100
<211> LENGTH: 5
<212> TYPE: PRT
<213> ORGANISM: Artificial Sequence
<220> FEATURE:
<223> OTHER INFORMATION: peptide

<400> SEQUENCE: 100

Gln Arg Arg Pro Pro
1               5

<210> SEQ ID NO 101
<211> LENGTH: 5
<212> TYPE: PRT
<213> ORGANISM: Artificial Sequence
<220> FEATURE:
<223> OTHER INFORMATION: peptide

<400> SEQUENCE: 101

Gln Arg Arg Pro Ala
1               5

<210> SEQ ID NO 102
<211> LENGTH: 5
<212> TYPE: PRT
<213> ORGANISM: Artificial Sequence
<220> FEATURE:
<223> OTHER INFORMATION: peptide

<400> SEQUENCE: 102

Arg Gln Arg Tyr Ala
1               5

<210> SEQ ID NO 103
<211> LENGTH: 126
<212> TYPE: DNA
<213> ORGANISM: Artificial Sequence
<220> FEATURE:
<223> OTHER INFORMATION: sense strand

<400> SEQUENCE: 103
tctctcgaga aaagatgcgg accgggcagg gggttcggga agaggaggca ccccaaaaag      60
ctgacccctt tagcctacaa gcagtttatc cccaatgtgg ccgagaagac cctaggcgcc     120

-continued

```
agcgga                                                          126

<210> SEQ ID NO 104
<211> LENGTH: 126
<212> TYPE: DNA
<213> ORGANISM: Artificial Sequence
<220> FEATURE:
<223> OTHER INFORMATION: antisense strand

<400> SEQUENCE: 104
agagagctct tttctacgcc tggcccgtcc cccaagccct tctcctccgt ggggtttttc    60
gactggggaa atcggatgtt cgtcaaatag gggttacacc ggctcttctg ggatccgcgg   120
tcgcct                                                             126

<210> SEQ ID NO 105
<211> LENGTH: 44
<212> TYPE: PRT
<213> ORGANISM: Homo sapiens

<400> SEQUENCE: 105

Ser Leu Glu Lys Arg Cys Gly Pro Gly Arg Gly Phe Gly Phe Gly Lys
  1               5                  10                  15

Arg Arg His Pro Lys Lys Leu Thr Pro Leu Ala Tyr Lys Gln Phe Ile
             20                  25                  30

Pro Asn Val Ala Glu Lys Thr Leu Gly Ala Ser Gly
         35                  40
```